US012605185B2

(12) United States Patent
Lee et al.

(10) Patent No.: US 12,605,185 B2
(45) Date of Patent: Apr. 21, 2026

(54) MEDICAL DEVICE INSERTERS AND PROCESSES OF INSERTING AND USING MEDICAL DEVICES

(71) Applicant: ABBOTT DIABETES CARE INC., Alameda, CA (US)

(72) Inventors: Daniel H. Lee, Burlingame, CA (US); Michael R. Love, Pleasanton, CA (US); Louis G. Pace, San Carlos, CA (US); Phillip Yee, San Francisco, CA (US)

(73) Assignee: ABBOTT DIABETES CARE INC., Alameda, CA (US)

(*) Notice: Subject to any disclaimer, the term of this patent is extended or adjusted under 35 U.S.C. 154(b) by 0 days.

(21) Appl. No.: 18/372,319

(22) Filed: Sep. 25, 2023

(65) Prior Publication Data

US 2024/0008779 A1 Jan. 11, 2024

Related U.S. Application Data

(63) Continuation of application No. 18/114,775, filed on Feb. 27, 2023, now abandoned, which is a
(Continued)

(51) Int. Cl.
    *A61B 5/145* (2006.01)
    *A61B 5/00* (2006.01)
    (Continued)

(52) U.S. Cl.
    CPC ........ *A61B 17/3468* (2013.01); *A61B 5/1411* (2013.01); *A61B 5/14503* (2013.01); *A61B 5/14532* (2013.01); *A61B 5/14542* (2013.01); *A61B 5/14546* (2013.01); *A61B 5/150022*

(2013.01); *A61B 5/150259* (2013.01); *A61B 5/150282* (2013.01); *A61B 5/150396* (2013.01); *A61B 5/150419* (2013.01); *A61B 5/150427* (2013.01); *A61B 5/150511* (2013.01);
(Continued)

(58) Field of Classification Search
CPC .............. A61B 5/14503; A61B 5/1451; A61B 5/14532; A61B 5/14865; A61B 5/6833; A61B 17/3468; A61B 5/6848–6849; A61B 2560/063
See application file for complete search history.

(56) References Cited

U.S. PATENT DOCUMENTS 2,402,306 A 6/1946 Turkel
2,752,918 A 7/1956 Uytenbogaart
(Continued)

FOREIGN PATENT DOCUMENTS

AU 2003259741 2/2004
CA 2291105 12/1998
(Continued)

OTHER PUBLICATIONS

AU, 2007309066 Examiner's Report, Jul. 12, 2012.
(Continued)

*Primary Examiner* — Tse W Chen
*Assistant Examiner* — Alice Ling Zou
(74) *Attorney, Agent, or Firm* — ONE LLP

(57) ABSTRACT

An apparatus for insertion of a medical device in the skin of a subject is provided, as well as methods of inserting medical devices.

16 Claims, 69 Drawing Sheets

Related U.S. Application Data continuation of application No. 16/387,023, filed on Apr. 17, 2019, now abandoned, which is a continuation of application No. 14/884,622, filed on Oct. 15, 2015, now Pat. No. 10,292,632, which is a continuation of application No. 13/071,497, filed on Mar. 24, 2011, now Pat. No. 9,186,098.

(60) Provisional application No. 61/411,262, filed on Nov. 8, 2010, provisional application No. 61/361,374, filed on Jul. 2, 2010, provisional application No. 61/345,562, filed on May 17, 2010, provisional application No. 61/317,243, filed on Mar. 24, 2010.

(51) Int. Cl.

| | |
|---|---|
| *A61B 5/15* | (2006.01) |
| *A61B 5/151* | (2006.01) |
| *A61B 5/157* | (2006.01) |
| *A61B 17/34* | (2006.01) |
| *A61M 5/158* | (2006.01) |
| *A61B 5/01* | (2006.01) |
| *A61B 17/00* | (2006.01) |

(52) U.S. Cl.
CPC ...... *A61B 5/15087* (2013.01); *A61B 5/15107* (2013.01); *A61B 5/15113* (2013.01); *A61B 5/15117* (2013.01); *A61B 5/1513* (2013.01); *A61B 5/15186* (2013.01); *A61B 5/1519* (2013.01); *A61B 5/15194* (2013.01); *A61B 5/157* (2013.01); *A61B 5/6848* (2013.01); *A61B 5/6865* (2013.01); *A61B 17/34* (2013.01); *A61M 5/158* (2013.01); *A61B 5/0002* (2013.01); *A61B 5/01* (2013.01); *A61B 5/15016* (2013.01); *A61B 5/150732* (2013.01); *A61B 2017/00384* (2013.01); *A61B 2560/063* (2013.01); *A61M 2005/1585* (2013.01)

(56) References Cited

U.S. PATENT DOCUMENTS

| | | | |
|---|---|---|---|
| 3,123,790 A | 3/1964 | Tyler |
| 3,132,123 A | 5/1964 | Harris, Jr. et al. |
| 3,173,200 A | 3/1965 | Dunmire et al. |
| 3,211,001 A | 10/1965 | Petit |
| 3,260,656 A | 7/1966 | Ross, Jr. |
| 3,517,670 A | 6/1970 | Speelman |
| 3,522,807 A | 8/1970 | Millenbach |
| 3,581,062 A | 5/1971 | Aston |
| 3,653,841 A | 4/1972 | Klein |
| 3,670,727 A | 6/1972 | Reiterman |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |
| 3,949,388 A | 4/1976 | Fuller |
| 3,960,497 A | 6/1976 | Acord et al. |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,033,330 A | 7/1977 | Willis et al. |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danninger et al. |
| 4,172,770 A | 10/1979 | Semersky et al. |
| 4,178,916 A | 12/1979 | McNamara |
| 4,203,446 A | 5/1980 | Hofert et al. |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,245,634 A | 1/1981 | Albisser et al. |
| 4,247,297 A | 1/1981 | Berti et al. |
| 4,294,258 A | 10/1981 | Bernard |
| 4,305,401 A | 12/1981 | Reissmueller et al. |
| 4,308,981 A | 1/1982 | Miura |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,353,888 A | 10/1982 | Sefton |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,392,849 A | 7/1983 | Petre et al. |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,441,968 A | 4/1984 | Emmer et al. |
| 4,450,842 A | 5/1984 | Zick et al. |
| 4,458,686 A | 7/1984 | Clark, Jr. |
| 4,461,691 A | 7/1984 | Frank |
| 4,464,170 A | 8/1984 | Clemens et al. |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatasetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,553,541 A | 11/1985 | Burns |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,592,745 A | 6/1986 | Rex et al. |
| 4,595,011 A | 6/1986 | Phillips |
| 4,619,754 A | 10/1986 | Niki et al. |
| 4,619,793 A | 10/1986 | Lee |
| 4,622,966 A | 11/1986 | Beard |
| 4,627,445 A | 12/1986 | Garcia et al. |
| 4,627,842 A | 12/1986 | Katz |
| 4,627,908 A | 12/1986 | Miller |
| 4,633,878 A | 1/1987 | Bombardieri |
| 4,637,403 A | 1/1987 | Garcia et al. |
| 4,639,062 A | 1/1987 | Taniguchi et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,663,824 A | 5/1987 | Kenmochi |
| 4,665,906 A | 5/1987 | Jervis |
| 4,671,288 A | 6/1987 | Gough |
| 4,675,346 A | 6/1987 | Lin et al. |

(56) References Cited

U.S. PATENT DOCUMENTS

| | | | |
|---|---|---|---|
| 4,679,562 | A | 7/1987 | Luksha |
| 4,680,268 | A | 7/1987 | Clark, Jr. |
| 4,682,602 | A | 7/1987 | Prohaska |
| 4,684,245 | A | 8/1987 | Goldring |
| 4,684,537 | A | 8/1987 | Graetzel et al. |
| 4,685,463 | A | 8/1987 | Williams |
| 4,685,466 | A | 8/1987 | Rau |
| 4,690,675 | A | 9/1987 | Katz |
| 4,698,057 | A | 10/1987 | Joishy |
| 4,703,324 | A | 10/1987 | White |
| 4,703,756 | A | 11/1987 | Gough et al. |
| 4,711,245 | A | 12/1987 | Higgins et al. |
| 4,711,247 | A | 12/1987 | Fishman |
| 4,717,673 | A | 1/1988 | Wrighton et al. |
| 4,721,601 | A | 1/1988 | Wrighton et al. |
| 4,721,677 | A | 1/1988 | Clark, Jr. |
| 4,726,378 | A | 2/1988 | Kaplan |
| 4,726,716 | A | 2/1988 | McGuire |
| 4,729,672 | A | 3/1988 | Takagi |
| 4,731,726 | A | 3/1988 | Allen, III |
| 4,749,985 | A | 6/1988 | Corsberg |
| 4,755,173 | A | 7/1988 | Konopka |
| 4,757,022 | A | 7/1988 | Shults et al. |
| 4,758,323 | A | 7/1988 | Davis et al. |
| 4,759,371 | A | 7/1988 | Franetzki |
| 4,759,828 | A | 7/1988 | Young et al. |
| 4,764,416 | A | 8/1988 | Ueyama et al. |
| 4,776,944 | A | 10/1988 | Janata et al. |
| 4,777,953 | A | 10/1988 | Ash et al. |
| 4,779,618 | A | 10/1988 | Mund et al. |
| 4,781,683 | A | 11/1988 | Wozniak et al. |
| 4,781,798 | A | 11/1988 | Gough |
| 4,784,736 | A | 11/1988 | Lonsdale et al. |
| 4,785,868 | A | 11/1988 | Koenig, Jr. |
| 4,795,707 | A | 1/1989 | Niiyama et al. |
| 4,796,634 | A | 1/1989 | Huntsman et al. |
| 4,805,624 | A | 2/1989 | Yao et al. |
| 4,813,424 | A | 3/1989 | Wilkins |
| 4,815,469 | A | 3/1989 | Cohen et al. |
| 4,817,603 | A | 4/1989 | Turner et al. |
| 4,818,994 | A | 4/1989 | Orth et al. |
| 4,820,399 | A | 4/1989 | Senda et al. |
| 4,822,337 | A | 4/1989 | Newhouse et al. |
| 4,830,959 | A | 5/1989 | McNeil et al. |
| 4,832,797 | A | 5/1989 | Vadgama et al. |
| RE32,947 | E | 6/1989 | Dormer et al. |
| 4,840,893 | A | 6/1989 | Hill et al. |
| 4,847,785 | A | 7/1989 | Stephens |
| 4,848,351 | A | 7/1989 | Finch |
| 4,852,025 | A | 7/1989 | Herpichböhm |
| 4,854,322 | A | 8/1989 | Ash et al. |
| 4,856,648 | A | 8/1989 | Krueger |
| 4,865,038 | A | 9/1989 | Rich et al. |
| 4,871,351 | A | 10/1989 | Feingold |
| 4,871,440 | A | 10/1989 | Nagata et al. |
| 4,874,500 | A | 10/1989 | Madou et al. |
| 4,890,620 | A | 1/1990 | Gough |
| 4,894,137 | A | 1/1990 | Takizawa et al. |
| 4,895,147 | A | 1/1990 | Bodicky et al. |
| 4,897,162 | A | 1/1990 | Lewandowski et al. |
| 4,897,173 | A | 1/1990 | Nankai et al. |
| 4,909,908 | A | 3/1990 | Ross et al. |
| 4,911,794 | A | 3/1990 | Parce et al. |
| 4,917,800 | A | 4/1990 | Lonsdale et al. |
| 4,919,141 | A | 4/1990 | Zier et al. |
| 4,919,767 | A | 4/1990 | Vadgama et al. |
| 4,921,199 | A | 5/1990 | Villaveces |
| 4,923,586 | A | 5/1990 | Katayama et al. |
| 4,924,879 | A | 5/1990 | O'Brien |
| 4,925,268 | A | 5/1990 | Lyer et al. |
| 4,927,516 | A | 5/1990 | Yamaguchi et al. |
| 4,934,369 | A | 6/1990 | Maxwell |
| 4,935,105 | A | 6/1990 | Churchouse |
| 4,935,345 | A | 6/1990 | Guibeau et al. |
| 4,938,860 | A | 7/1990 | Wogoman |
| 4,944,299 | A | 7/1990 | Silvian |
| 4,950,378 | A | 8/1990 | Nagara |
| 4,953,552 | A | 9/1990 | DeMarzo |
| 4,954,129 | A | 9/1990 | Giuliani et al. |
| 4,969,468 | A | 11/1990 | Byers et al. |
| 4,970,145 | A | 11/1990 | Bennetto et al. |
| 4,974,929 | A | 12/1990 | Curry |
| 4,985,142 | A | 1/1991 | Laycock et al. |
| 4,986,271 | A | 1/1991 | Wilkins |
| 4,988,341 | A | 1/1991 | Columbus et al. |
| 4,994,167 | A | 2/1991 | Shults et al. |
| 4,995,402 | A | 2/1991 | Smith et al. |
| 5,000,180 | A | 3/1991 | Kuypers et al. |
| 5,001,054 | A | 3/1991 | Wagner |
| 5,002,054 | A | 3/1991 | Ash et al. |
| 5,006,110 | A | 4/1991 | Garrison et al. |
| 5,013,161 | A | 5/1991 | Zaragoza et al. |
| 5,019,974 | A | 5/1991 | Beckers |
| 5,035,860 | A | 7/1991 | Kleingeld et al. |
| 5,036,860 | A | 8/1991 | Leigh et al. |
| 5,047,044 | A | 9/1991 | Smith et al. |
| 5,050,612 | A | 9/1991 | Matsumura |
| 5,051,688 | A | 9/1991 | Murase et al. |
| 5,055,171 | A | 10/1991 | Peck |
| 5,058,592 | A | 10/1991 | Whisler |
| 5,067,957 | A | 11/1991 | Jervis |
| 5,068,536 | A | 11/1991 | Rosenthal |
| 5,070,535 | A | 12/1991 | Hochmair et al. |
| 5,082,550 | A | 1/1992 | Rishpon et al. |
| 5,082,786 | A | 1/1992 | Nakamoto |
| 5,086,246 | A | 2/1992 | Dymond et al. |
| 5,089,112 | A | 2/1992 | Skotheim et al. |
| 5,095,904 | A | 3/1992 | Seligman et al. |
| 5,101,814 | A | 4/1992 | Palti |
| 5,106,365 | A | 4/1992 | Hernandez |
| 5,108,564 | A | 4/1992 | Szuminsky et al. |
| 5,108,889 | A | 4/1992 | Smith et al. |
| 5,109,850 | A | 5/1992 | Blanco et al. |
| 5,120,420 | A | 6/1992 | Nankai et al. |
| 5,122,925 | A | 6/1992 | Inpyn |
| 5,124,661 | A | 6/1992 | Zelin et al. |
| 5,126,034 | A | 6/1992 | Carter et al. |
| 5,133,856 | A | 7/1992 | Yamaguchi et al. |
| 5,135,003 | A | 8/1992 | Souma |
| 5,135,004 | A | 8/1992 | Adams et al. |
| 5,140,985 | A | 8/1992 | Schroeder et al. |
| 5,141,868 | A | 8/1992 | Shanks et al. |
| 5,161,532 | A | 11/1992 | Joseph |
| 5,162,407 | A | 11/1992 | Turner |
| 5,165,407 | A | 11/1992 | Wilson et al. |
| 5,173,165 | A | 12/1992 | Schmid et al. |
| 5,174,291 | A | 12/1992 | Schoonen et al. |
| 5,190,041 | A | 3/1993 | Palti |
| 5,190,546 | A | 3/1993 | Jervis |
| 5,192,416 | A | 3/1993 | Wang et al. |
| 5,193,545 | A | 3/1993 | Marsoner et al. |
| 5,198,367 | A | 3/1993 | Aizawa et al. |
| 5,202,261 | A | 4/1993 | Musho et al. |
| 5,204,264 | A | 4/1993 | Kaminer et al. |
| 5,205,297 | A | 4/1993 | Montecalvo et al. |
| 5,205,920 | A | 4/1993 | Oyama et al. |
| 5,208,154 | A | 5/1993 | Weaver et al. |
| 5,209,229 | A | 5/1993 | Gilli |
| 5,217,595 | A | 6/1993 | Smith et al. |
| 5,228,449 | A | 7/1993 | Christ et al. |
| 5,229,282 | A | 7/1993 | Yoshioka et al. |
| 5,231,988 | A | 8/1993 | Wernicke et al. |
| 5,234,835 | A | 8/1993 | Nestor et al. |
| 5,238,729 | A | 8/1993 | Debe |
| 5,243,696 | A | 9/1993 | Carr et al. |
| 5,245,314 | A | 9/1993 | Kah et al. |
| 5,246,867 | A | 9/1993 | Lakowicz et al. |
| 5,250,439 | A | 10/1993 | Musho et al. |
| 5,251,126 | A | 10/1993 | Kahn et al. |
| 5,262,035 | A | 11/1993 | Gregg et al. |
| 5,262,305 | A | 11/1993 | Heller et al. |
| 5,264,103 | A | 11/1993 | Yoshioka et al. |
| 5,264,104 | A | 11/1993 | Gregg et al. |
| 5,264,105 | A | 11/1993 | Gregg et al. |

(56) References Cited

U.S. PATENT DOCUMENTS

| | | | |
|---|---|---|---|
| 5,264,106 A | 11/1993 | McAleer et al. |
| 5,267,963 A | 12/1993 | Bachynsky |
| 5,271,815 A | 12/1993 | Wong |
| 5,279,294 A | 1/1994 | Anderson |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,289,497 A | 2/1994 | Jackobson et al. |
| 5,293,546 A | 3/1994 | Tadros et al. |
| 5,293,877 A | 3/1994 | O'Hara et al. |
| 5,299,571 A | 4/1994 | Mastrototaro |
| 5,305,008 A | 4/1994 | Turner et al. |
| 5,318,583 A | 6/1994 | Rabenau et al. |
| 5,320,098 A | 6/1994 | Davidson |
| 5,320,715 A | 6/1994 | Berg |
| 5,320,725 A | 6/1994 | Gregg et al. |
| 5,322,063 A | 6/1994 | Allen et al. |
| 5,333,615 A | 8/1994 | Craelius et al. |
| 5,337,747 A | 8/1994 | Neftel |
| 5,340,722 A | 8/1994 | Wolfbeis et al. |
| 5,342,789 A | 8/1994 | Chick et al. |
| 5,352,348 A | 10/1994 | Young et al. |
| 5,356,420 A | 10/1994 | Czernecki et al. |
| 5,356,786 A | 10/1994 | Heller et al. |
| 5,360,404 A | 11/1994 | Novacek et al. |
| 5,368,028 A | 11/1994 | Palti |
| 5,372,133 A | 12/1994 | Hogen Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,384,547 A | 1/1995 | Lynk et al. |
| 5,387,327 A | 2/1995 | Khan |
| 5,390,670 A | 2/1995 | Centa et al. |
| 5,390,671 A * | 2/1995 | Lord .................. A61B 17/3403 |
| | | 600/347 |
| 5,391,250 A | 2/1995 | Cheney, II et al. |
| 5,394,877 A | 3/1995 | Orr et al. |
| 5,395,504 A | 3/1995 | Saurer et al. |
| 5,400,782 A | 3/1995 | Beaubiah |
| 5,400,794 A | 3/1995 | Gorman |
| 5,402,780 A | 4/1995 | Faasse, Jr. |
| 5,407,431 A | 4/1995 | Botich et al. |
| 5,408,999 A | 4/1995 | Singh et al. |
| 5,410,326 A | 4/1995 | Goldstein |
| 5,411,647 A | 5/1995 | Johnson et al. |
| 5,425,361 A | 6/1995 | Fenzlein et al. |
| 5,425,868 A | 6/1995 | Pedersen |
| 5,431,160 A | 7/1995 | Wilkins |
| 5,431,921 A | 7/1995 | Thombre |
| 5,437,999 A | 8/1995 | Diebold et al. |
| 5,438,983 A | 8/1995 | Falcone |
| 5,462,051 A | 10/1995 | Oka et al. |
| 5,462,645 A | 10/1995 | Albery et al. |
| 5,469,846 A | 11/1995 | Khan |
| 5,472,317 A | 12/1995 | Field et al. |
| 5,482,473 A | 1/1996 | Lord et al. |
| 5,484,403 A | 1/1996 | Yoakum et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,499,243 A | 3/1996 | Hall |
| 5,507,288 A | 4/1996 | Bocker et al. |
| 5,509,410 A | 4/1996 | Hill et al. |
| 5,514,718 A | 5/1996 | Lewis et al. |
| 5,516,832 A | 5/1996 | Kennan et al. |
| 5,527,288 A | 6/1996 | Gross et al. |
| 5,531,878 A | 7/1996 | Vadgama et al. |
| 5,532,686 A | 7/1996 | Urbas et al. |
| 5,533,977 A | 7/1996 | Metcalf et al. |
| 5,536,259 A | 7/1996 | Utterberg |
| 5,543,326 A | 8/1996 | Heller et al. |
| 5,544,196 A | 8/1996 | Tiedmann, Jr. et al. |
| 5,545,191 A | 8/1996 | Mann et al. |
| 5,549,568 A | 8/1996 | Sheilds |
| 5,551,427 A | 9/1996 | Altman |
| 5,555,190 A | 9/1996 | Derby et al. |
| 5,558,638 A | 9/1996 | Evers et al. |
| 5,560,357 A | 10/1996 | Faupei et al. |
| 5,562,713 A | 10/1996 | Silvian |
| 5,564,434 A | 10/1996 | Halperin et al. |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,571,022 A | 11/1996 | Schaarschmidt |
| 5,575,563 A | 11/1996 | Chiu et al. |
| 5,581,206 A | 12/1996 | Chevallier et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halili et al. |
| 5,589,326 A | 12/1996 | Deng et al. |
| 5,593,852 A | 1/1997 | Heller et al. |
| 5,596,150 A | 1/1997 | Arndt et al. |
| 5,597,378 A | 1/1997 | Jervis |
| 5,600,301 A | 2/1997 | Robinson, III |
| 5,601,435 A | 2/1997 | Quy |
| 5,609,575 A | 3/1997 | Larson et al. |
| 5,613,978 A | 3/1997 | Harding |
| 5,617,851 A | 4/1997 | Lipkovker |
| 5,623,933 A | 4/1997 | Amano et al. |
| 5,626,566 A | 5/1997 | Petersen et al. |
| 5,628,310 A | 5/1997 | Rao et al. |
| 5,628,324 A | 5/1997 | Sarbach |
| 5,628,890 A | 5/1997 | Carter et al. |
| 5,632,557 A | 5/1997 | Simons |
| 5,634,468 A | 6/1997 | Platt et al. |
| 5,636,640 A | 6/1997 | Staehlin |
| 5,638,832 A | 6/1997 | Singer et al. |
| 5,640,954 A | 6/1997 | Pfeiffer et al. |
| 5,651,869 A | 7/1997 | Yoshioka et al. |
| 5,653,239 A | 8/1997 | Pompei et al. |
| 5,659,454 A | 8/1997 | Vermesse |
| 5,660,163 A | 8/1997 | Schulman et al. |
| 5,665,071 A | 9/1997 | Wyrick |
| 5,665,222 A | 9/1997 | Heller et al. |
| 5,669,543 A | 9/1997 | Ueno |
| 5,669,890 A | 9/1997 | Grimm |
| 5,670,031 A | 9/1997 | Hintsche et al. |
| 5,673,322 A | 9/1997 | Pepe et al. |
| 5,680,858 A | 10/1997 | Hansen et al. |
| 5,682,233 A | 10/1997 | Brinda |
| 5,695,623 A | 12/1997 | Michel et al. |
| 5,707,502 A | 1/1998 | McCaffrey et al. |
| 5,708,247 A | 1/1998 | McAleer et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,724,030 A | 3/1998 | Urbas et al. |
| 5,726,646 A | 3/1998 | Bane et al. |
| 5,733,044 A | 3/1998 | Rose et al. |
| 5,733,259 A | 3/1998 | Valcke et al. |
| 5,733,262 A | 3/1998 | Paul |
| 5,733,313 A | 3/1998 | Barreras, Sr. et al. |
| 5,735,285 A | 4/1998 | Albert et al. |
| 5,738,220 A | 4/1998 | Geszler |
| 5,741,211 A | 4/1998 | Renirie et al. |
| 5,743,262 A | 4/1998 | Lepper, Jr. et al. |
| 5,746,217 A | 5/1998 | Erickson et al. |
| 5,746,697 A | 5/1998 | Swedlow et al. |
| 5,748,103 A | 5/1998 | Flach et al. |
| 5,749,656 A | 5/1998 | Boehm et al. |
| 5,749,907 A | 5/1998 | Mann |
| 5,758,290 A | 5/1998 | Nealon et al. |
| 5,766,131 A | 6/1998 | Kondo et al. |
| 5,770,028 A | 6/1998 | Maley et al. |
| 5,771,001 A | 6/1998 | Cobb |

(56) References Cited

U.S. PATENT DOCUMENTS

| | | | |
|---|---|---|---|
| 5,771,891 A | 6/1998 | Gozani |
| 5,772,586 A | 6/1998 | Heinonen et al. |
| 5,778,879 A | 7/1998 | Ota et al. |
| 5,779,665 A | 7/1998 | Mastrototaro et al. |
| 5,786,439 A | 7/1998 | Van Antwerp et al. |
| 5,791,344 A | 8/1998 | Schulman et al. |
| 5,798,961 A | 8/1998 | Heyden et al. |
| 5,800,420 A | 9/1998 | Gross et al. |
| 5,804,047 A | 9/1998 | Karube et al. |
| 5,807,375 A | 9/1998 | Gross et al. |
| 5,814,020 A | 9/1998 | Gross |
| 5,820,551 A | 10/1998 | Hill et al. |
| 5,820,570 A | 10/1998 | Erickson et al. |
| 5,820,622 A | 10/1998 | Gross et al. |
| 5,822,715 A | 10/1998 | Worthington et al. |
| 5,823,802 A | 10/1998 | Bartley |
| 5,827,184 A | 10/1998 | Netherly et al. |
| 5,830,064 A | 11/1998 | Bradish et al. |
| 5,833,603 A | 11/1998 | Kovacs et al. |
| 5,840,020 A | 11/1998 | Heinonen et al. |
| 5,842,983 A | 12/1998 | Abel et al. |
| 5,851,197 A | 12/1998 | Marano et al. |
| 5,856,758 A | 1/1999 | Joffe et al. |
| 5,858,001 A | 1/1999 | Tsals et al. |
| 5,865,804 A | 2/1999 | Bachynsky |
| 5,871,494 A | 2/1999 | Simons et al. |
| 5,875,186 A | 2/1999 | Belanger et al. |
| 5,879,311 A | 3/1999 | Duchon et al. |
| 5,885,211 A | 3/1999 | Eppstein et al. |
| 5,891,049 A | 4/1999 | Cyrus et al. |
| 5,899,855 A | 5/1999 | Brown |
| 5,899,856 A | 5/1999 | Schoendorfer et al. |
| 5,914,026 A | 6/1999 | Blubaugh, Jr. et al. |
| 5,918,603 A | 7/1999 | Brown |
| 5,919,141 A | 7/1999 | Money et al. |
| 5,921,963 A | 7/1999 | Erez et al. |
| 5,924,979 A | 7/1999 | Swedlow et al. |
| 5,925,021 A | 7/1999 | Castellano et al. |
| 5,931,814 A | 8/1999 | Alex et al. |
| 5,931,868 A | 8/1999 | Gross |
| 5,935,224 A | 8/1999 | Svancarek et al. |
| 5,938,679 A | 8/1999 | Freeman et al. |
| 5,942,979 A | 8/1999 | Luppino |
| 5,948,006 A | 9/1999 | Mann |
| 5,951,485 A | 9/1999 | Cyrus et al. |
| 5,951,492 A | 9/1999 | Douglas et al. |
| 5,951,521 A | 9/1999 | Mastrototaro et al. |
| 5,951,582 A | 9/1999 | Thorne et al. |
| 5,954,643 A | 9/1999 | Antwerp |
| 5,954,685 A | 9/1999 | Tierny |
| 5,957,854 A | 9/1999 | Besson et al. |
| 5,961,451 A | 10/1999 | Reber et al. |
| 5,964,718 A | 10/1999 | Duchon et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,971,941 A | 10/1999 | Simons et al. |
| 5,972,199 A | 10/1999 | Heller et al. |
| 5,987,353 A | 11/1999 | Khatchatrian et al. |
| 5,993,411 A | 11/1999 | Choi |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,017,335 A | 1/2000 | Burnham |
| 6,022,315 A | 2/2000 | Iliff |
| 6,022,368 A | 2/2000 | Gavronsky et al. |
| 6,024,699 A | 2/2000 | Surwit et al. |
| 6,026,321 A | 2/2000 | Miyata et al. |
| 6,027,459 A | 2/2000 | Shain et al. |
| 6,028,413 A | 2/2000 | Brockmann |
| 6,032,064 A | 2/2000 | Devlin et al. |
| 6,036,924 A | 3/2000 | Simons et al. |
| 6,048,352 A | 4/2000 | Douglas et al. |
| 6,049,727 A | 4/2000 | Crothall |
| 6,052,565 A | 4/2000 | Ishikura et al. |
| 6,054,194 A | 4/2000 | Kane |
| 6,056,718 A | 5/2000 | Funderburk et al. |
| 6,059,946 A | 5/2000 | Yukawa et al. |
| 6,066,243 A | 5/2000 | Anderson et al. |
| 6,068,399 A | 5/2000 | Tseng |
| 6,071,294 A | 6/2000 | Simons et al. |
| 6,071,391 A | 6/2000 | Gotoh et al. |
| 6,083,710 A | 7/2000 | Heller et al. |
| 6,085,342 A | 7/2000 | Marholev et al. |
| 6,088,605 A | 7/2000 | Griffith et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,364 A | 8/2000 | Bok et al. |
| 6,097,480 A | 8/2000 | Kaplan |
| 6,099,484 A | 8/2000 | Douglas et al. |
| 6,102,896 A | 8/2000 | Roser |
| 6,103,033 A | 8/2000 | Say et al. |
| 6,106,484 A | 8/2000 | Terwilliger |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,129,666 A | 10/2000 | DeLuca et al. |
| 6,130,623 A | 10/2000 | MacLellan et al. |
| 6,132,449 A | 10/2000 | Lum et al. |
| 6,134,461 A | 10/2000 | Say et al. |
| 6,141,573 A | 10/2000 | Kurnik et al. |
| 6,143,164 A | 11/2000 | Heller et al. |
| 6,144,837 A | 11/2000 | Quy |
| 6,144,871 A | 11/2000 | Saito et al. |
| 6,144,922 A | 11/2000 | Douglas et al. |
| 6,149,626 A | 11/2000 | Bachynsky et al. |
| 6,157,850 A | 12/2000 | Diab et al. |
| 6,159,147 A | 12/2000 | Lichter et al. |
| 6,159,181 A | 12/2000 | Crossman et al. |
| 6,161,095 A | 12/2000 | Brown |
| 6,162,611 A | 12/2000 | Heller et al. |
| 6,168,606 B1 | 1/2001 | Levin et al. |
| 6,175,752 B1 | 1/2001 | Say et al. |
| 6,186,982 B1 | 2/2001 | Gross et al. |
| 6,192,891 B1 | 2/2001 | Gravel et al. |
| 6,197,040 B1 | 3/2001 | LeVaughn et al. |
| 6,198,946 B1 | 3/2001 | Shin et al. |
| 6,200,265 B1 | 3/2001 | Walsh et al. |
| 6,203,495 B1 | 3/2001 | Bardy et al. |
| 6,212,416 B1 | 4/2001 | Ward et al. |
| 6,213,972 B1 | 4/2001 | Butterfield et al. |
| 6,219,574 B1 | 4/2001 | Cormier et al. |
| 6,223,283 B1 | 4/2001 | Chaiken et al. |
| 6,231,531 B1 | 5/2001 | Lum et al. |
| 6,233,471 B1 | 5/2001 | Berner et al. |
| 6,237,394 B1 | 5/2001 | Harris et al. |
| 6,248,067 B1 | 6/2001 | Causey, III et al. |
| 6,254,536 B1 | 7/2001 | DeVito |
| 6,254,586 B1 | 7/2001 | Mann et al. |
| 6,264,810 B1 | 7/2001 | Stol et al. |
| 6,270,455 B1 | 8/2001 | Brown |
| 6,275,717 B1 | 8/2001 | Gross et al. |
| 6,283,761 B1 | 9/2001 | Joao |
| 6,283,982 B1 | 9/2001 | Levaughn et al. |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,298,255 B1 | 10/2001 | Cordero et al. |
| 6,299,347 B1 | 10/2001 | Pompei |
| 6,299,757 B1 | 10/2001 | Feldman et al. |
| 6,302,866 B1 | 10/2001 | Marggi |
| 6,304,766 B1 | 10/2001 | Colvin, Jr. |
| 6,306,104 B1 | 10/2001 | Cunningham et al. |
| 6,306,141 B1 | 10/2001 | Jervis |
| 6,309,884 B1 | 10/2001 | Cooper et al. |

(56)                References Cited

U.S. PATENT DOCUMENTS

| | | |
|---|---|---|
| 6,314,317 B1 | 11/2001 | Willis |
| 6,329,161 B1 | 12/2001 | Heller et al. |
| 6,331,244 B1 | 12/2001 | Lewis et al. |
| 6,336,269 B1 | 1/2002 | Eldridge et al. |
| 6,338,790 B1 | 1/2002 | Feldman et al. |
| 6,341,232 B1 | 1/2002 | Conn et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,364,890 B1 | 4/2002 | Lum et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,368,339 B1 | 4/2002 | Amplatz |
| 6,377,828 B1 | 4/2002 | Chaiken et al. |
| 6,377,829 B1 | 4/2002 | Al-Ali |
| 6,377,894 B1 | 4/2002 | Deweese et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,409,740 B1 | 6/2002 | Kuhr et al. |
| 6,413,393 B1 | 7/2002 | Van Antwerp et al. |
| 6,416,471 B1 | 7/2002 | Kumar et al. |
| 6,418,332 B1 | 7/2002 | Mastrototaro et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,433,743 B1 | 8/2002 | Massy et al. |
| 6,435,017 B1 | 8/2002 | Nowicki, Jr. et al. |
| 6,437,679 B1 | 8/2002 | Roques |
| 6,438,414 B1 | 8/2002 | Conn et al. |
| 6,440,068 B1 | 8/2002 | Brown et al. |
| 6,442,413 B1 | 8/2002 | Silver |
| 6,445,374 B2 | 9/2002 | Albert et al. |
| 6,451,025 B1 | 9/2002 | Jervis |
| 6,458,109 B1 | 10/2002 | Henley et al. |
| 6,461,496 B1 | 10/2002 | Feldman et al. |
| 6,471,689 B1 | 10/2002 | Joseph et al. |
| 6,472,220 B1 | 10/2002 | Simons et al. |
| 6,478,736 B1 | 11/2002 | Mault |
| 6,482,176 B1 | 11/2002 | Wich |
| 6,484,045 B1* | 11/2002 | Holker ............... A61B 5/14865 |
| | | 600/347 |
| 6,484,046 B1 | 11/2002 | Say et al. |
| 6,493,069 B1 | 12/2002 | Nagashimada et al. |
| 6,494,830 B1 | 12/2002 | Wessel |
| 6,496,729 B2 | 12/2002 | Thompson |
| 6,497,655 B1 | 12/2002 | Linberg et al. |
| 6,503,381 B1 | 1/2003 | Gotoh et al. |
| 6,510,344 B1 | 1/2003 | Halpern |
| 6,514,460 B1 | 2/2003 | Fendrock |
| 6,514,689 B2 | 2/2003 | Han et al. |
| 6,514,718 B2 | 2/2003 | Heller et al. |
| 6,520,326 B2 | 2/2003 | McIvor et al. |
| 6,522,927 B1 | 2/2003 | Bishay et al. |
| 6,533,805 B1 | 3/2003 | Jervis |
| 6,537,242 B1 | 3/2003 | Palmer |
| 6,540,891 B1 | 4/2003 | Stewart et al. |
| 6,544,212 B2 | 4/2003 | Galley et al. |
| 6,546,268 B1 | 4/2003 | Ishikawa et al. |
| 6,549,796 B2 | 4/2003 | Sohrab |
| 6,551,494 B1 | 4/2003 | Heller et al. |
| 6,551,496 B1 | 4/2003 | Moles et al. |
| 6,554,795 B2 | 4/2003 | Bagaoisan et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,572,566 B2 | 6/2003 | Effenhauser |
| 6,574,490 B2 | 6/2003 | Abbink et al. |
| 6,574,510 B2 | 6/2003 | Von Arx et al. |
| 6,575,895 B1 | 6/2003 | Blair |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,602,268 B2 | 8/2003 | Kuhr et al. |
| 6,603,995 B1 | 8/2003 | Carter |
| 6,604,050 B2 | 8/2003 | Trippel et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,607,543 B2 | 8/2003 | Purcell et al. |
| 6,608,562 B1 | 8/2003 | Kimura et al. |
| 6,610,012 B2 | 8/2003 | Mault |
| 6,611,206 B2 | 8/2003 | Eshelman et al. |
| 6,613,015 B2 | 9/2003 | Sandstrom et al. |
| 6,616,819 B1 | 9/2003 | Liamos et al. |
| 6,618,934 B1 | 9/2003 | Feldman et al. |
| 6,627,154 B1 | 9/2003 | Goodman et al. |
| 6,631,281 B1 | 10/2003 | Kastle |
| 6,633,772 B2 | 10/2003 | Ford et al. |
| 6,635,014 B2 | 10/2003 | Starkweather et al. |
| 6,635,167 B1 | 10/2003 | Batman et al. |
| 6,637,611 B2 | 10/2003 | Luch |
| 6,641,533 B2 | 11/2003 | Causey, III et al. |
| 6,645,359 B1 | 11/2003 | Bhullar et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,662,439 B1 | 12/2003 | Bhullar |
| 6,666,849 B1 | 12/2003 | Marshall et al. |
| 6,668,196 B1 | 12/2003 | Villegas et al. |
| 6,671,534 B2 | 12/2003 | Putz |
| 6,675,030 B2 | 1/2004 | Ciurczak et al. |
| 6,676,290 B1 | 1/2004 | Lu |
| 6,676,816 B2 | 1/2004 | Mao et al. |
| 6,682,546 B2 | 1/2004 | Amplatz |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,699,188 B2 | 3/2004 | Wessel |
| 6,702,857 B2 | 3/2004 | Brauker et al. |
| 6,706,159 B2 | 3/2004 | Moerman et al. |
| 6,721,582 B2 | 4/2004 | Trepagnier et al. |
| 6,730,025 B1 | 5/2004 | Platt |
| 6,730,072 B2 | 5/2004 | Shawgo et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,735,479 B2 | 5/2004 | Fabian et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,743,635 B2 | 6/2004 | Neel et al. |
| 6,746,582 B2 | 6/2004 | Heller et al. |
| 6,748,445 B1 | 6/2004 | Darcey et al. |
| 6,749,740 B2 | 6/2004 | Liamos et al. |
| 6,758,810 B2 | 7/2004 | Lebel et al. |
| 6,758,835 B2 | 7/2004 | Close et al. |
| 6,764,581 B1 | 7/2004 | Forrow et al. |

(56)                  References Cited

U.S. PATENT DOCUMENTS

| 6,767,440 B1 | 7/2004 | Bhullar et al. |
| 6,770,030 B1 | 8/2004 | Schaupp et al. |
| 6,773,671 B1 | 8/2004 | Lewis et al. |
| 6,781,522 B2 | 8/2004 | Sleva et al. |
| 6,790,178 B1 | 9/2004 | Mault et al. |
| 6,804,558 B2 | 10/2004 | Haller et al. |
| 6,804,561 B2 | 10/2004 | Stover |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,814,844 B2 | 11/2004 | Bhullar et al. |
| 6,830,551 B1 | 12/2004 | Uchigaki et al. |
| 6,837,858 B2 | 1/2005 | Cunningham et al. |
| 6,837,885 B2 | 1/2005 | Koblish et al. |
| 6,837,988 B2 | 1/2005 | Leong et al. |
| 6,849,052 B2 | 2/2005 | Uchigaki et al. |
| 6,850,790 B2 | 2/2005 | Berner et al. |
| 6,850,859 B1 | 2/2005 | Schuh |
| 6,854,882 B2 | 2/2005 | Chen |
| 6,862,465 B2 | 3/2005 | Shults et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,923,764 B2 | 8/2005 | Aceti et al. |
| 6,925,393 B1 | 8/2005 | Kalatz et al. |
| 6,931,327 B2 | 8/2005 | Goode, Jr. et al. |
| 6,932,892 B2 | 8/2005 | Chen |
| 6,932,894 B2 | 8/2005 | Mao et al. |
| 6,936,006 B2 | 8/2005 | Sabra |
| 6,937,222 B2 | 8/2005 | Numao |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman IV et al. |
| 6,954,662 B2 | 10/2005 | Freger et al. |
| 6,958,705 B2 | 10/2005 | Lebel et al. |
| 6,959,211 B2 | 10/2005 | Rule et al. |
| 6,960,192 B1 | 11/2005 | Flaherty et al. |
| 6,968,294 B2 | 11/2005 | Gutta et al. |
| 6,971,274 B2 | 12/2005 | Olin |
| 6,971,999 B2 | 12/2005 | Py et al. |
| 6,973,706 B2 | 12/2005 | Say et al. |
| 6,974,437 B2 | 12/2005 | Lebel et al. |
| 6,975,893 B2 | 12/2005 | Say et al. |
| 6,983,867 B1 | 1/2006 | Fugere |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,005,857 B2 | 2/2006 | Stiene et al. |
| 7,009,511 B2 | 3/2006 | Mazar et al. |
| 7,010,356 B2 | 3/2006 | Jog et al. |
| 7,015,817 B2 | 3/2006 | Copley et al. |
| 7,016,713 B2 | 3/2006 | Gardner et al. |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,743 B2 | 4/2006 | Mann et al. |
| 7,025,774 B2 | 4/2006 | Freeman et al. |
| 7,027,848 B2 | 4/2006 | Robinson et al. |
| 7,027,859 B1 | 4/2006 | McNichols et al. |
| 7,027,931 B1 | 4/2006 | Jones et al. |
| 7,029,444 B2 | 4/2006 | Shin et al. |
| 7,041,057 B1 | 5/2006 | Faupel et al. |
| 7,041,068 B2 | 5/2006 | Freeman et al. |
| 7,041,468 B2 | 5/2006 | Drucker et al. |
| 7,043,305 B2 | 5/2006 | Kenknight et al. |
| 7,046,153 B2 | 5/2006 | Oja et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,073,246 B2 | 7/2006 | Bhullar et al. |
| 7,074,307 B2 | 7/2006 | Simpson et al. |
| 7,081,195 B2 | 7/2006 | Simpson et al. |
| 7,082,334 B2 | 7/2006 | Boute et al. |
| 7,097,637 B2 | 8/2006 | Triplett et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,120,483 B2 | 10/2006 | Russel et al. |
| 7,123,950 B2 | 10/2006 | Mannheimer |
| 7,124,027 B1 | 10/2006 | Ernst et al. |
| 7,125,382 B2 | 10/2006 | Zhou et al. |
| 7,131,984 B2 | 11/2006 | Sato et al. |
| 7,134,999 B2 | 11/2006 | Brauker et al. |
| 7,136,689 B2 | 11/2006 | Shults et al. |
| 7,144,384 B2 | 12/2006 | Gorman et al. |
| 7,146,202 B2 | 12/2006 | Ward et al. |
| 7,154,398 B2 | 12/2006 | Chen et al. |
| 7,155,290 B2 | 12/2006 | Von Arx et al. |
| 7,167,818 B2 | 1/2007 | Brown |
| 7,169,600 B2 | 1/2007 | Hoss et al. |
| 7,171,274 B2 | 1/2007 | Starkweather et al. |
| 7,174,199 B2 | 2/2007 | Berner et al. |
| 7,179,226 B2 | 2/2007 | Crothall et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,220,387 B2 | 5/2007 | Flaherty et al. |
| 7,223,276 B2 | 5/2007 | List et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,228,162 B2 | 6/2007 | Ward et al. |
| 7,228,182 B2 | 6/2007 | Healy et al. |
| 7,237,712 B2 | 7/2007 | DeRocco et al. |
| 7,267,665 B2 | 9/2007 | Steil et al. |
| 7,276,029 B2 | 10/2007 | Goode, Jr. et al. |
| 7,276,146 B2 | 10/2007 | Wilsey |
| 7,276,147 B2 | 10/2007 | Wilsey |
| 7,278,983 B2 | 10/2007 | Ireland et al. |
| 7,286,894 B1 | 10/2007 | Grant et al. |
| 7,287,318 B2 | 10/2007 | Bhullar et al. |
| 7,291,497 B2 | 11/2007 | Holmes et al. |
| 7,295,867 B2 | 11/2007 | Berner et al. |
| 7,297,151 B2 | 11/2007 | Boecker et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,324,850 B2 | 1/2008 | Persen et al. |
| 7,329,239 B2 | 2/2008 | Safabash et al. |
| 7,335,294 B2 | 2/2008 | Heller et al. |
| 7,340,287 B2 | 3/2008 | Mason et al. |
| 7,340,309 B2 | 3/2008 | Miazga et al. |
| 7,344,500 B2 | 3/2008 | Talbot et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,384,397 B2 | 6/2008 | Zhang et al. |
| 7,386,937 B2 | 6/2008 | Bhullar et al. |
| 7,387,010 B2 | 6/2008 | Sunshine et al. |
| 7,399,277 B2 | 7/2008 | Saidara et al. |

(56)  References Cited

U.S. PATENT DOCUMENTS

| | | | |
|---|---|---|---|
| 7,400,111 B2 | 7/2008 | Batman et al. |
| 7,401,111 B1 | 7/2008 | Batman et al. |
| 7,402,153 B2 | 7/2008 | Steil et al. |
| 7,404,796 B2 | 7/2008 | Ginsberg |
| 7,407,493 B2 | 8/2008 | Cane |
| 7,408,132 B2 | 8/2008 | Wambsganss et al. |
| 7,416,541 B2 | 8/2008 | Yuzhakov et al. |
| 7,419,573 B2 | 9/2008 | Gundel |
| 7,424,318 B2 | 9/2008 | Brister et al. |
| 7,429,255 B2 | 9/2008 | Thompson |
| 7,433,727 B2 | 10/2008 | Ward |
| 7,448,996 B2 | 11/2008 | Khanuja et al. |
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,476,827 B1 | 1/2009 | Bhullar et al. |
| 7,481,819 B2 | 1/2009 | Koeppel et al. |
| 7,492,254 B2 | 2/2009 | Bandy et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,545,272 B2 | 6/2009 | Goodnow et al. |
| 7,547,281 B2 | 6/2009 | Hayes et al. |
| 7,565,197 B2 | 7/2009 | Haubrich et al. |
| 7,568,619 B2 | 8/2009 | Todd et al. |
| 7,569,030 B2 | 8/2009 | Lebel et al. |
| 7,574,266 B2 | 8/2009 | Dudding et al. |
| 7,582,059 B2 | 9/2009 | Funderburk et al. |
| 7,583,990 B2 | 9/2009 | Goode, Jr. et al. |
| 7,585,287 B2 | 9/2009 | Bresina et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,604,592 B2 | 10/2009 | Freeman et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,643,798 B2 | 1/2010 | Ljung |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,660,615 B2 | 2/2010 | VanAntwerp et al. |
| 7,666,149 B2 | 2/2010 | Simons et al. |
| 7,668,596 B2 | 2/2010 | Von Arx et al. |
| 7,682,338 B2 | 3/2010 | Griffin |
| 7,697,967 B2 | 4/2010 | Stafford |
| 7,699,775 B2 | 4/2010 | Desai et al. |
| 7,699,807 B2 | 4/2010 | Faust et al. |
| 7,701,052 B2 | 4/2010 | Borland et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,729,737 B2 | 6/2010 | Ward |
| 7,731,657 B2 | 6/2010 | Stafford |
| 7,731,691 B2 | 6/2010 | Cote et al. |
| 7,736,310 B2 | 6/2010 | Taub et al. |
| 7,736,344 B2 | 6/2010 | Moberg et al. |
| 7,741,734 B2 | 6/2010 | Joannopoulos et al. |
| 7,763,042 B2 | 7/2010 | Iio et al. |
| 7,766,829 B2 | 8/2010 | Sloan et al. |
| 7,768,387 B2 | 8/2010 | Fennell et al. |
| 7,771,352 B2 | 8/2010 | Shults et al. |
| 7,774,145 B2 | 8/2010 | Brauker et al. |
| 7,775,444 B2 | 8/2010 | DeRocco et al. |
| 7,778,680 B2 | 8/2010 | Goode, Jr. et al. |
| 7,779,332 B2 | 8/2010 | Karr et al. |
| 7,780,827 B1 | 8/2010 | Bhullar et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,811,231 B2 | 10/2010 | Jin et al. |
| 7,813,809 B2 | 10/2010 | Strother et al. |
| 7,822,454 B1 | 10/2010 | Alden et al. |
| 7,826,981 B2 | 11/2010 | Goode, Jr. et al. |
| 7,831,310 B2 | 11/2010 | Lebel et al. |
| 7,833,151 B2 | 11/2010 | Khait et al. |
| 7,833,170 B2 | 11/2010 | Matsumoto et al. |
| 7,837,633 B2 | 11/2010 | Conway et al. |
| 7,842,046 B1 | 11/2010 | Nakao |
| 7,846,132 B2 | 12/2010 | Gravesen et al. |
| 7,850,652 B2 | 12/2010 | Liniger et al. |
| 7,860,574 B2 | 12/2010 | Von Arx et al. |
| 7,866,026 B1 | 1/2011 | Wang et al. |
| 7,867,244 B2 | 1/2011 | Lathrop et al. |
| 7,873,299 B2 | 1/2011 | Berner et al. |
| 7,882,611 B2 | 2/2011 | Shah et al. |
| 7,883,464 B2 | 2/2011 | Stafford |
| 7,883,473 B2 | 2/2011 | LeVaughn et al. |
| 7,885,697 B2 | 2/2011 | Brister et al. |
| 7,889,069 B2 | 2/2011 | Fifolt et al. |
| 7,896,844 B2 | 3/2011 | Thalmann et al. |
| 7,899,511 B2 | 3/2011 | Shults et al. |
| 7,899,545 B2 | 3/2011 | John |
| 7,905,833 B2 | 3/2011 | Brister et al. |
| 7,912,655 B2 | 3/2011 | Power et al. |
| 7,912,674 B2 | 3/2011 | Killoren Clark et al. |
| 7,914,450 B2 | 3/2011 | Goode, Jr. et al. |
| 7,914,460 B2 | 3/2011 | Melker et al. |
| 7,916,013 B2 | 3/2011 | Stevenson |
| 7,920,906 B2 | 4/2011 | Goode, Jr. et al. |
| 7,920,907 B2 | 4/2011 | McGarraugh et al. |
| 7,938,797 B2 | 5/2011 | Estes |
| 7,941,200 B2 | 5/2011 | Weinart et al. |
| 7,946,984 B2 | 5/2011 | Brister et al. |
| 7,946,985 B2 | 5/2011 | Mastrototaro et al. |
| 7,955,258 B2 | 6/2011 | Goscha et al. |
| 7,955,297 B2 | 6/2011 | Radmer et al. |
| 7,970,448 B2 | 6/2011 | Shults et al. |
| 7,970,449 B2 | 6/2011 | Ward |
| 7,972,296 B2 | 7/2011 | Braig et al. |
| 7,974,672 B2 | 7/2011 | Shults et al. |
| 7,976,467 B2 | 7/2011 | Young et al. |
| 7,978,063 B2 | 7/2011 | Baldus et al. |
| 7,985,203 B2 | 7/2011 | Haueter et al. |
| 7,985,222 B2 | 7/2011 | Gall et al. |
| 7,996,158 B2 | 8/2011 | Hayter et al. |
| 7,999,674 B2 | 8/2011 | Kamen |
| 8,000,918 B2 | 8/2011 | Fjield et al. |
| 8,005,524 B2 | 8/2011 | Brauker et al. |
| 8,010,174 B2 | 8/2011 | Goode, Jr. et al. |
| 8,010,256 B2 | 8/2011 | Oowada |
| 8,016,774 B2 | 9/2011 | Freeman et al. |
| 8,028,837 B2 | 10/2011 | Gerstle et al. |
| 8,029,441 B2 | 10/2011 | Mazza et al. |
| 8,029,442 B2 | 10/2011 | Funderburk et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |

(56) References Cited

U.S. PATENT DOCUMENTS

| | | | |
|---|---|---|---|
| 8,103,471 B2 | 1/2012 | Hayter |
| 8,111,042 B2 | 2/2012 | Bennett |
| 8,112,240 B2 | 2/2012 | Fennell |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Docks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,140,312 B2 | 3/2012 | Hayter et al. |
| 8,150,321 B2 | 4/2012 | Winter et al. |
| 8,150,516 B2 | 4/2012 | Levine et al. |
| 8,160,670 B2 | 4/2012 | Quyang et al. |
| 8,160,900 B2 | 4/2012 | Taub et al. |
| 8,172,805 B2 | 5/2012 | Mogensen et al. |
| 8,175,673 B2 | 5/2012 | Say et al. |
| 8,179,266 B2 | 5/2012 | Hermle |
| 8,180,423 B2 | 5/2012 | Mang et al. |
| 8,192,394 B2 | 6/2012 | Estes et al. |
| 8,216,138 B1 | 7/2012 | McGaraugh et al. |
| 8,221,332 B2 | 7/2012 | Robbins et al. |
| 8,224,410 B2 | 7/2012 | Hadvary et al. |
| 8,239,166 B2 | 8/2012 | Hayter et al. |
| 8,255,026 B1 | 8/2012 | Al-Ali |
| 8,260,558 B2 | 9/2012 | Hayter et al. |
| 8,262,618 B2 | 9/2012 | Scheurer |
| 8,282,549 B2 | 10/2012 | Brauker et al. |
| 8,333,714 B2 | 12/2012 | Stafford |
| 8,346,335 B2 | 1/2013 | Harper et al. |
| 8,346,337 B2 | 1/2013 | Heller et al. |
| 8,373,544 B2 | 2/2013 | Pitt-Plady |
| 8,374,668 B1 | 2/2013 | Hayter et al. |
| 8,376,945 B2 | 2/2013 | Hayter et al. |
| 8,377,271 B2 | 2/2013 | Mao et al. |
| 8,382,671 B2 | 2/2013 | Anthony et al. |
| 8,398,664 B2 | 3/2013 | Lamps et al. |
| 8,409,093 B2 | 4/2013 | Bugler |
| 8,409,145 B2 | 4/2013 | Raymond et al. |
| 8,439,838 B2 | 5/2013 | Mogensen et al. |
| 8,444,560 B2 | 5/2013 | Hayter et al. |
| 8,461,985 B2 | 6/2013 | Fennell et al. |
| 8,469,986 B2 | 6/2013 | Schraga |
| 8,512,243 B2 | 8/2013 | Stafford |
| 8,515,518 B2 | 8/2013 | Ouyang et al. |
| 8,515,519 B2 | 8/2013 | Brister et al. |
| 8,538,512 B1 | 9/2013 | Bibian et al. |
| 8,545,403 B2 | 10/2013 | Peyser et al. |
| 8,560,038 B2 | 10/2013 | Hayter et al. |
| 8,562,567 B2 | 10/2013 | Gundberg |
| 8,571,808 B2 | 10/2013 | Hayter |
| 8,583,205 B2 | 11/2013 | Budiman et al. |
| 8,585,591 B2 | 11/2013 | Sloan et al. |
| 8,597,570 B2 | 12/2013 | Terashima et al. |
| 8,600,681 B2 | 12/2013 | Hayter et al. |
| 8,602,991 B2 | 12/2013 | Stafford |
| 8,612,163 B2 | 12/2013 | Hayter et al. |
| 8,615,282 B2 | 12/2013 | Brister et al. |
| 8,617,069 B2 | 12/2013 | Bernstein et al. |
| 8,617,071 B2 | 12/2013 | Say et al. |
| 8,622,903 B2 | 1/2014 | Jin et al. |
| 8,628,498 B2 | 1/2014 | Safabach et al. |
| 8,641,674 B2 | 2/2014 | Bobroff et al. |
| 8,652,043 B2 | 2/2014 | Drucker et al. |
| 8,682,408 B2 | 3/2014 | Boock et al. |
| 8,682,615 B2 | 3/2014 | Hayter et al. |
| 8,684,930 B2 | 4/2014 | Feldman et al. |
| 8,692,655 B2 | 4/2014 | Zimman et al. |
| 8,710,993 B2 | 4/2014 | Hayter et al. |
| 8,747,363 B2 | 6/2014 | Nielsen et al. |
| 8,750,955 B2 | 6/2014 | Brister et al. |
| 8,771,183 B2 | 7/2014 | Sloan |
| 8,797,163 B2 | 8/2014 | Finkenzeller |
| 8,808,515 B2 | 8/2014 | Feldman et al. |
| 8,834,366 B2 | 9/2014 | Hayter et al. |
| 8,845,536 B2 | 9/2014 | Brauker et al. |
| 8,870,822 B2 | 10/2014 | Thalmann et al. |
| 8,880,138 B2 | 11/2014 | Cho |
| 8,945,056 B2 | 2/2015 | Lio et al. |
| 8,961,413 B2 | 2/2015 | Teller et al. |
| 9,007,781 B2 | 4/2015 | Moein et al. |
| 9,014,774 B2 | 4/2015 | Mao et al. |
| 9,031,630 B2 | 5/2015 | Hoss et al. |
| 9,060,719 B2 | 6/2015 | Hayter et al. |
| 9,060,805 B2 | 6/2015 | Goodnow et al. |
| 9,066,697 B2 | 6/2015 | Peyser et al. |
| 9,101,302 B2 | 8/2015 | Mace et al. |
| 9,186,098 B2 | 11/2015 | Lee et al. |
| 9,215,992 B2 | 12/2015 | Donnay et al. |
| 9,241,631 B2 | 1/2016 | Valdes et al. |
| 9,259,175 B2 | 2/2016 | Stafford |
| 9,265,453 B2 | 2/2016 | Curry et al. |
| 9,289,179 B2 | 3/2016 | Hayter et al. |
| 9,295,786 B2 | 3/2016 | Gottlieb et al. |
| 9,357,951 B2 | 6/2016 | Simpson et al. |
| 9,398,872 B2 | 7/2016 | Hayter et al. |
| 9,402,544 B2 | 8/2016 | Yee et al. |
| 9,402,570 B2 | 8/2016 | Pace et al. |
| 9,439,586 B2 | 9/2016 | Bugler |
| 9,451,910 B2 | 9/2016 | Brister et al. |
| 9,474,479 B2 | 10/2016 | Pusey et al. |
| 9,480,421 B2 | 11/2016 | Stafford |
| 9,483,608 B2 | 11/2016 | Hayter et al. |
| 9,504,471 B2 | 11/2016 | Vaitekunas et al. |
| 9,558,325 B2 | 1/2017 | Hayter et al. |
| 9,566,384 B2 | 2/2017 | Gyrn et al. |
| 9,636,068 B2 | 5/2017 | Yee et al. |
| 9,668,682 B2 | 6/2017 | Brister et al. |
| 9,743,876 B2 | 8/2017 | Gelfand et al. |
| 9,808,574 B2 | 11/2017 | Yodfat et al. |
| 9,814,414 B2 | 11/2017 | Brister et al. |
| 10,213,139 B2 | 2/2019 | Rao et al. |
| 10,292,632 B2 | 5/2019 | Lee et al. |
| 10,342,489 B2 | 7/2019 | Stafford |
| 10,772,547 B1 | 9/2020 | Lee et al. |
| 10,820,842 B2 | 11/2020 | Harper |
| 10,827,954 B2 | 11/2020 | Hoss et al. |
| 10,874,338 B2 | 12/2020 | Stafford |
| 10,881,340 B2 | 1/2021 | Curry et al. |
| 10,881,341 B1 | 1/2021 | Curry et al. |
| 10,945,647 B2 | 3/2021 | Mazza et al. |
| 10,945,649 B2 | 3/2021 | Lee et al. |
| 10,952,653 B2 | 3/2021 | Harper |
| 10,959,654 B2 | 3/2021 | Curry et al. |
| 10,966,644 B2 | 4/2021 | Stafford |
| 10,973,443 B2 | 4/2021 | Funderburk et al. |
| 10,980,461 B2 | 4/2021 | Simpson et al. |
| 11,000,213 B2 | 5/2021 | Kamath et al. |
| 11,000,216 B2 | 5/2021 | Curry et al. |
| 11,006,870 B2 | 5/2021 | Yee et al. |
| 11,006,871 B2 | 5/2021 | Yee et al. |
| 11,013,440 B2 | 5/2021 | Lee et al. |
| 11,051,724 B2 | 7/2021 | Pace et al. |
| 11,064,917 B2 | 7/2021 | Simpson et al. |
| 11,116,430 B2 | 9/2021 | Funderburk et al. |
| 11,141,084 B2 | 10/2021 | Funderburk et al. |
| 11,166,656 B2 | 11/2021 | Yee et al. |
| 11,179,068 B2 | 11/2021 | Pace et al. |
| 11,197,625 B1 | 12/2021 | Schleicher et al. |
| 11,202,591 B2 | 12/2021 | Yee et al. |
| 11,213,229 B2 | 1/2022 | Yee et al. |
| 11,246,519 B2 | 2/2022 | Donnay et al. |
| 11,266,335 B2 | 3/2022 | Donnay et al. |
| 11,298,056 B2 | 4/2022 | Harper |

(56) References Cited

U.S. PATENT DOCUMENTS

| | | |
|---|---|---|
| 11,298,058 B2 | 4/2022 | Stafford |
| 11,510,625 B2 | 11/2022 | Gray et al. |
| 2001/0016682 A1 | 8/2001 | Berner et al. |
| 2001/0034479 A1 | 10/2001 | Ring et al. |
| 2001/0037060 A1 | 11/2001 | Thompson et al. |
| 2001/0037366 A1 | 11/2001 | Webb et al. |
| 2001/0039387 A1 | 11/2001 | Rutynowski et al. |
| 2001/0044608 A1 | 11/2001 | Odell et al. |
| 2001/0047127 A1 | 11/2001 | New et al. |
| 2001/0056262 A1 | 12/2001 | Cabiri et al. |
| 2002/0002344 A1 | 1/2002 | Douglas et al. |
| 2002/0010390 A1 | 1/2002 | Guice et al. |
| 2002/0013522 A1 | 1/2002 | Lav et al. |
| 2002/0013538 A1 | 1/2002 | Teller |
| 2002/0016534 A1 | 2/2002 | Trepagnier et al. |
| 2002/0016568 A1 | 2/2002 | Lebel et al. |
| 2002/0019022 A1 | 2/2002 | Dunn et al. |
| 2002/0019584 A1 | 2/2002 | Schulze et al. |
| 2002/0019586 A1 | 2/2002 | Teller et al. |
| 2002/0019606 A1 | 2/2002 | Lebel et al. |
| 2002/0022855 A1 | 2/2002 | Bobroff et al. |
| 2002/0023852 A1 | 2/2002 | McIvor et al. |
| 2002/0029058 A1 | 3/2002 | LeVaughn et al. |
| 2002/0032386 A1 | 3/2002 | Sackner et al. |
| 2002/0039026 A1 | 4/2002 | Stroth et al. |
| 2002/0042090 A1 | 4/2002 | Heller et al. |
| 2002/0045808 A1 | 4/2002 | Ford et al. |
| 2002/0049482 A1 | 4/2002 | Fabian et al. |
| 2002/0050250 A1 | 5/2002 | Peterson et al. |
| 2002/0055711 A1 | 5/2002 | Lavi et al. |
| 2002/0057993 A1 | 5/2002 | Maisey et al. |
| 2002/0065454 A1 | 5/2002 | Lebel et al. |
| 2002/0066764 A1 | 6/2002 | Perry et al. |
| 2002/0072720 A1 | 6/2002 | Hague et al. |
| 2002/0072784 A1 | 6/2002 | Sheppard et al. |
| 2002/0074162 A1 | 6/2002 | Su et al. |
| 2002/0076966 A1 | 6/2002 | Carron et al. |
| 2002/0077599 A1 | 6/2002 | Wojcik |
| 2002/0082487 A1 | 6/2002 | Kollias et al. |
| 2002/0084196 A1 | 7/2002 | Liamos et al. |
| 2002/0091796 A1 | 7/2002 | Higginson et al. |
| 2002/0093969 A1 | 7/2002 | Lin et al. |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0111832 A1 | 8/2002 | Judge |
| 2002/0117639 A1 | 8/2002 | Paolini et al. |
| 2002/0118528 A1 | 8/2002 | Su et al. |
| 2002/0119711 A1 | 8/2002 | VanAntwerp et al. |
| 2002/0120186 A1 | 8/2002 | Keimel |
| 2002/0124017 A1 | 9/2002 | Mault |
| 2002/0128594 A1 | 9/2002 | Das et al. |
| 2002/0130042 A1 | 9/2002 | Moerman et al. |
| 2002/0133066 A1 | 9/2002 | Miller et al. |
| 2002/0147135 A1 | 10/2002 | Schnell |
| 2002/0150959 A1 | 10/2002 | Lejeune et al. |
| 2002/0151770 A1 | 10/2002 | Noll et al. |
| 2002/0151796 A1 | 10/2002 | Koulik |
| 2002/0151816 A1 | 10/2002 | Rich et al. |
| 2002/0154050 A1 | 10/2002 | Krupp et al. |
| 2002/0161288 A1 | 10/2002 | Shin et al. |
| 2002/0161290 A1 | 10/2002 | Chance |
| 2002/0161338 A1 | 10/2002 | Peterson |
| 2002/0164836 A1 | 11/2002 | Ho |
| 2002/0165462 A1 | 11/2002 | Westbrook et al. |
| 2002/0169369 A1 | 11/2002 | Ward et al. |
| 2002/0169439 A1 | 11/2002 | Flaherty et al. |
| 2002/0169635 A1 | 11/2002 | Shillingburg |
| 2002/0183604 A1 | 12/2002 | Gowda et al. |
| 2002/0185128 A1 | 12/2002 | Theobald |
| 2002/0185130 A1 | 12/2002 | Wright et al. |
| 2002/0188748 A1 | 12/2002 | Blackwell et al. |
| 2002/0197522 A1 | 12/2002 | Lawrence et al. |
| 2002/0198444 A1 | 12/2002 | Ughigaki et al. |
| 2002/0198543 A1 | 12/2002 | Burdulis et al. |
| 2003/0004403 A1 | 1/2003 | Drinan et al. |
| 2003/0020477 A1 | 1/2003 | Goldstein |
| 2003/0023189 A1 | 1/2003 | Kuo |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0028184 A1 | 2/2003 | Lebel et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0055380 A1 | 3/2003 | Flaherty |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0069509 A1 | 4/2003 | Matzinger et al. |
| 2003/0069510 A1 | 4/2003 | Semler |
| 2003/0076792 A1 | 4/2003 | Theimer |
| 2003/0077642 A1 | 4/2003 | Fritsch et al. |
| 2003/0078481 A1 | 4/2003 | McIvor et al. |
| 2003/0078560 A1 | 4/2003 | Miller et al. |
| 2003/0083686 A1 | 5/2003 | Freeman et al. |
| 2003/0088166 A1 | 5/2003 | Say et al. |
| 2003/0097092 A1 | 5/2003 | Flaherty |
| 2003/0100040 A1 | 5/2003 | Bonnecaze et al. |
| 2003/0100821 A1 | 5/2003 | Heller et al. |
| 2003/0109775 A1 | 6/2003 | O'Neil et al. |
| 2003/0114897 A1 | 6/2003 | Von Arx et al. |
| 2003/0114898 A1 | 6/2003 | Von Arx et al. |
| 2003/0119457 A1 | 6/2003 | Standke |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0135127 A1 | 7/2003 | Sackner et al. |
| 2003/0135333 A1 | 7/2003 | Aceti et al. |
| 2003/0144579 A1 | 7/2003 | Buss |
| 2003/0144581 A1 | 7/2003 | Conn et al. |
| 2003/0144608 A1 | 7/2003 | Kojima et al. |
| 2003/0153900 A1 | 8/2003 | Aceti et al. |
| 2003/0155656 A1 | 8/2003 | Chiu et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0188427 A1 | 10/2003 | Say et al. |
| 2003/0199744 A1 | 10/2003 | Buse et al. |
| 2003/0199790 A1 | 10/2003 | Boecker et al. |
| 2003/0199910 A1 | 10/2003 | Boecker et al. |
| 2003/0204290 A1 | 10/2003 | Sadler et al. |
| 2003/0208113 A1 | 11/2003 | Mault et al. |
| 2003/0208114 A1 | 11/2003 | Ackerman |
| 2003/0212317 A1 | 11/2003 | Kovatchev et al. |
| 2003/0212379 A1 | 11/2003 | Bylund et al. |
| 2003/0212579 A1 | 11/2003 | Brown et al. |
| 2003/0216621 A1 | 11/2003 | Alpert et al. |
| 2003/0216630 A1 | 11/2003 | Jersey-Willuhn et al. |
| 2003/0217966 A1 | 11/2003 | Tapsak et al. |
| 2003/0225361 A1 | 12/2003 | Sabra |
| 2003/0225373 A1 | 12/2003 | Bobroff et al. |
| 2003/0236489 A1 | 12/2003 | Jacobson et al. |
| 2004/0002682 A1 | 1/2004 | Kovelman et al. |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0017300 A1 | 1/2004 | Kotzin et al. |
| 2004/0030226 A1 | 2/2004 | Quy |
| 2004/0030531 A1 | 2/2004 | Miller et al. |
| 2004/0030581 A1 | 2/2004 | Levin et al. |
| 2004/0034289 A1 | 2/2004 | Teller et al. |
| 2004/0039255 A1 | 2/2004 | Simonsen et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0060818 A1 | 4/2004 | Feldman et al. |
| 2004/0061232 A1 | 4/2004 | Shah et al. |
| 2004/0063435 A1 | 4/2004 | Sakamoto et al. |
| 2004/0064068 A1 | 4/2004 | DeNuzzio et al. |

(56)                References Cited

U.S. PATENT DOCUMENTS

| | | |
|---|---|---|
| 2004/0064133 A1 | 4/2004 | Miller et al. |
| 2004/0072357 A1 | 4/2004 | Steine et al. |
| 2004/0073266 A1 | 4/2004 | Haefner et al. |
| 2004/0078215 A1 | 4/2004 | Dahlin et al. |
| 2004/0096959 A1 | 5/2004 | Steine et al. |
| 2004/0100376 A1 | 5/2004 | Lye et al. |
| 2004/0105411 A1 | 6/2004 | Boatwright et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0111017 A1 | 6/2004 | Say et al. |
| 2004/0116847 A1 | 6/2004 | Wall |
| 2004/0116865 A1 | 6/2004 | Bengtsson |
| 2004/0116866 A1 | 6/2004 | Gorman et al. |
| 2004/0117204 A1 | 6/2004 | Mazar et al. |
| 2004/0119169 A1 | 6/2004 | Hanawa |
| 2004/0122353 A1 | 6/2004 | Shahmirian et al. |
| 2004/0122489 A1 | 6/2004 | Mazar et al. |
| 2004/0133089 A1 | 7/2004 | Kilcoyne et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |
| 2004/0135684 A1 | 7/2004 | Steinthal et al. |
| 2004/0138544 A1 | 7/2004 | Ward et al. |
| 2004/0138588 A1 | 7/2004 | Saikley et al. |
| 2004/0138688 A1 | 7/2004 | Giraud |
| 2004/0140211 A1 | 7/2004 | Broy et al. |
| 2004/0142403 A1 | 7/2004 | Hetzel et al. |
| 2004/0146909 A1 | 7/2004 | Duong et al. |
| 2004/0147872 A1 | 7/2004 | Thompson |
| 2004/0147996 A1 | 7/2004 | Miazga et al. |
| 2004/0152366 A1 | 8/2004 | Schultz et al. |
| 2004/0152622 A1 | 8/2004 | Keith et al. |
| 2004/0158207 A1 | 8/2004 | Hunn et al. |
| 2004/0162521 A1* | 8/2004 | Bengtsson ............ A61B 5/1518 604/173 |
| 2004/0162678 A1 | 8/2004 | Hetzel et al. |
| 2004/0167801 A1 | 8/2004 | Say et al. |
| 2004/0171910 A1 | 9/2004 | Moore-Steele |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204673 A1 | 10/2004 | Flaherty |
| 2004/0204687 A1 | 10/2004 | Mogensen et al. |
| 2004/0204744 A1 | 10/2004 | Penner et al. |
| 2004/0204868 A1 | 10/2004 | Maynard et al. |
| 2004/0206625 A1 | 10/2004 | Bhullar et al. |
| 2004/0206916 A1 | 10/2004 | Colvin, Jr. et al. |
| 2004/0210122 A1 | 10/2004 | Sleburg |
| 2004/0221057 A1 | 11/2004 | Darcey et al. |
| 2004/0223876 A1 | 11/2004 | Kirollos et al. |
| 2004/0223985 A1 | 11/2004 | Dunfield et al. |
| 2004/0225199 A1 | 11/2004 | Evanyk et al. |
| 2004/0225262 A1 | 11/2004 | Fathallah et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0240426 A1 | 12/2004 | Wu et al. |
| 2004/0249253 A1 | 12/2004 | Racchini et al. |
| 2004/0249999 A1 | 12/2004 | Connolly et al. |
| 2004/0254433 A1 | 12/2004 | Bandis et al. |
| 2004/0254434 A1 | 12/2004 | Goodnow et al. |
| 2004/0258564 A1 | 12/2004 | Charlton |
| 2004/0260224 A1 | 12/2004 | Binder et al. |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0006122 A1 | 1/2005 | Burnette |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0038465 A1 | 2/2005 | Shraga |
| 2005/0038680 A1 | 2/2005 | McMahon |
| 2005/0043598 A1 | 2/2005 | Goode et al. |
| 2005/0049179 A1 | 3/2005 | Davidson et al. |
| 2005/0051427 A1 | 3/2005 | Brauker et al. |
| 2005/0051440 A1 | 3/2005 | Simpson et al. |
| 2005/0056552 A1 | 3/2005 | Simpson et al. |
| 2005/0065464 A1 | 3/2005 | Talbot et al. |
| 2005/0070774 A1 | 3/2005 | Addison et al. |
| 2005/0070819 A1 | 3/2005 | Poux et al. |
| 2005/0085872 A1 | 4/2005 | Yanagihara et al. |
| 2005/0090607 A1 | 4/2005 | Tapsak et al. |
| 2005/0090850 A1 | 4/2005 | Thoes et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0096520 A1 | 5/2005 | Maekawa et al. |
| 2005/0096587 A1 | 5/2005 | Santini, Jr. et al. |
| 2005/0101912 A1 | 5/2005 | Faust et al. |
| 2005/0101932 A1 | 5/2005 | Cote et al. |
| 2005/0103624 A1 | 5/2005 | Bhullar et al. |
| 2005/0104457 A1 | 5/2005 | Jordan et al. |
| 2005/0106713 A1 | 5/2005 | Phan et al. |
| 2005/0112169 A1 | 5/2005 | Brauker et al. |
| 2005/0112544 A1 | 5/2005 | Xu et al. |
| 2005/0113648 A1 | 5/2005 | Yang et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0131347 A1 | 6/2005 | Marano-Ford et al. |
| 2005/0134731 A1 | 6/2005 | Lee et al. |
| 2005/0137488 A1 | 6/2005 | Henry et al. |
| 2005/0137530 A1 | 6/2005 | Campbell et al. |
| 2005/0143635 A1 | 6/2005 | Kamath et al. |
| 2005/0149066 A1 | 7/2005 | Stafford |
| 2005/0151976 A1 | 7/2005 | Toma |
| 2005/0154271 A1 | 7/2005 | Rasdal et al. |
| 2005/0154410 A1 | 7/2005 | Conway et al. |
| 2005/0159678 A1 | 7/2005 | Taniike et al. |
| 2005/0161346 A1 | 7/2005 | Simpson et al. |
| 2005/0165404 A1 | 7/2005 | Miller |
| 2005/0171442 A1 | 8/2005 | Shirasaki et al. |
| 2005/0173245 A1 | 8/2005 | Feldman et al. |
| 2005/0176136 A1 | 8/2005 | Burd et al. |
| 2005/0177398 A1 | 8/2005 | Watanabe et al. |
| 2005/0181010 A1 | 8/2005 | Hunter et al. |
| 2005/0182306 A1 | 8/2005 | Sloan |
| 2005/0182358 A1 | 8/2005 | Heit et al. |
| 2005/0187442 A1 | 8/2005 | Cho et al. |
| 2005/0187720 A1 | 8/2005 | Goode et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0197793 A1 | 9/2005 | Baker |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0215871 A1 | 9/2005 | Feldman et al. |
| 2005/0221504 A1 | 10/2005 | Petruno et al. |
| 2005/0222518 A1 | 10/2005 | Dib |
| 2005/0222599 A1 | 10/2005 | Czernecki et al. |

(56)                 References Cited

U.S. PATENT DOCUMENTS

| | | |
|---|---|---|
| 2005/0236277 A9 | 10/2005 | Imran et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode et al. |
| 2005/0245799 A1 | 11/2005 | Brauker et al. |
| 2005/0245839 A1 | 11/2005 | Stivoric et al. |
| 2005/0245844 A1 | 11/2005 | Mace et al. |
| 2005/0245904 A1 | 11/2005 | Estes et al. |
| 2005/0247319 A1 | 11/2005 | Berger |
| 2005/0251033 A1 | 11/2005 | Scarantino et al. |
| 2005/0261563 A1 | 11/2005 | Zhou et al. |
| 2005/0267325 A1 | 12/2005 | Bouchier et al. |
| 2005/0267327 A1 | 12/2005 | Lizuka et al. |
| 2005/0269214 A1 | 12/2005 | Lee |
| 2005/0277164 A1 | 12/2005 | Drucker et al. |
| 2005/0277912 A1 | 12/2005 | John |
| 2005/0281234 A1 | 12/2005 | Kawamura et al. |
| 2005/0283114 A1 | 12/2005 | Bresina et al. |
| 2005/0283208 A1 | 12/2005 | Von Arx et al. |
| 2005/0283209 A1 | 12/2005 | Katoozi et al. |
| 2005/0284758 A1 | 12/2005 | Funke et al. |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0004272 A1 | 1/2006 | Shah et al. |
| 2006/0004303 A1 | 1/2006 | Weidenhaupt et al. |
| 2006/0006141 A1 | 1/2006 | Ufer et al. |
| 2006/0009727 A1 | 1/2006 | O'Mahony et al. |
| 2006/0010098 A1 | 1/2006 | Goodnow et al. |
| 2006/0012464 A1 | 1/2006 | Nitzan et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1* | 1/2006 | Brister .............. A61B 17/3468 |
| | | 600/345 |
| 2006/0020300 A1 | 1/2006 | Nghiem et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0030789 A1 | 2/2006 | Allen |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0040793 A1 | 2/2006 | Martens et al. |
| 2006/0041276 A1 | 2/2006 | Chan |
| 2006/0042080 A1 | 3/2006 | Say et al. |
| 2006/0047220 A1 | 3/2006 | Sakata et al. |
| 2006/0049359 A1 | 3/2006 | Busta et al. |
| 2006/0058588 A1 | 3/2006 | Zdeblick |
| 2006/0064035 A1 | 3/2006 | Wang et al. |
| 2006/0068208 A1 | 3/2006 | Tapsak et al. |
| 2006/0079740 A1 | 4/2006 | Silver et al. |
| 2006/0081469 A1 | 4/2006 | Lee |
| 2006/0086624 A1 | 4/2006 | Tapsak et al. |
| 2006/0091006 A1 | 5/2006 | Wang et al. |
| 2006/0094944 A1 | 5/2006 | Chuang |
| 2006/0095014 A1 | 5/2006 | Ethelfeld |
| 2006/0116607 A1 | 6/2006 | Nakamura et al. |
| 2006/0129173 A1 | 6/2006 | Wilkinson |
| 2006/0129733 A1 | 6/2006 | Solbelman |
| 2006/0135908 A1 | 6/2006 | Liniger et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0155210 A1 | 7/2006 | Beckman et al. |
| 2006/0155317 A1 | 7/2006 | List |
| 2006/0161194 A1 | 7/2006 | Freeman et al. |
| 2006/0161664 A1 | 7/2006 | Motoyama |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0181695 A1 | 8/2006 | Sage |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0189939 A1 | 8/2006 | Gonnelli et al. |
| 2006/0193375 A1 | 8/2006 | Lee et al. |
| 2006/0195029 A1 | 8/2006 | Shults et al. |
| 2006/0195133 A1 | 8/2006 | Freeman et al. |
| 2006/0200020 A1 | 9/2006 | Brister et al. |
| 2006/0200022 A1 | 9/2006 | Brauker et al. |
| 2006/0200181 A1 | 9/2006 | Fukuzawa et al. |
| 2006/0200970 A1 | 9/2006 | Brister et al. |
| 2006/0200981 A1 | 9/2006 | Bhullar et al. |
| 2006/0200982 A1 | 9/2006 | Bhullar et al. |
| 2006/0202805 A1 | 9/2006 | Schulman et al. |
| 2006/0202859 A1 | 9/2006 | Mastrototaro et al. |
| 2006/0211921 A1 | 9/2006 | Brauker et al. |
| 2006/0220839 A1 | 10/2006 | Fifolt et al. |
| 2006/0222566 A1 | 10/2006 | Brauker et al. |
| 2006/0222866 A1 | 10/2006 | Nakamura et al. |
| 2006/0224108 A1 | 10/2006 | Brauker et al. |
| 2006/0224109 A1 | 10/2006 | Steil et al. |
| 2006/0224141 A1 | 10/2006 | Rush et al. |
| 2006/0224171 A1 | 10/2006 | Sakata et al. |
| 2006/0226985 A1 | 10/2006 | Goodnow et al. |
| 2006/0229512 A1 | 10/2006 | Petisce et al. |
| 2006/0233839 A1 | 10/2006 | Jacquet |
| 2006/0247508 A1 | 11/2006 | Fennell |
| 2006/0247710 A1 | 11/2006 | Goetz et al. |
| 2006/0247895 A1 | 11/2006 | Liamos et al. |
| 2006/0248398 A1 | 11/2006 | Neel et al. |
| 2006/0253085 A1 | 11/2006 | Geismar et al. |
| 2006/0253086 A1 | 11/2006 | Moberg et al. |
| 2006/0258929 A1 | 11/2006 | Goode, Jr. et al. |
| 2006/0258939 A1 | 11/2006 | Pesach et al. |
| 2006/0258959 A1 | 11/2006 | Sode |
| 2006/0264785 A1 | 11/2006 | Dring et al. |
| 2006/0264888 A1 | 11/2006 | Moberg et al. |
| 2006/0270922 A1 | 11/2006 | Brauker et al. |
| 2006/0270923 A1 | 11/2006 | Brauker et al. |
| 2006/0271013 A1 | 11/2006 | Triplett et al. |
| 2006/0272652 A1 | 12/2006 | Stocker et al. |
| 2006/0273759 A1 | 12/2006 | Reggiardo |
| 2006/0276714 A1 | 12/2006 | Holt et al. |
| 2006/0276724 A1 | 12/2006 | Freeman et al. |
| 2006/0276771 A1 | 12/2006 | Galley et al. |
| 2006/0281985 A1 | 12/2006 | Ward et al. |
| 2006/0282042 A1 | 12/2006 | Walters et al. |
| 2006/0287591 A1 | 12/2006 | Ocvirk et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0016129 A1 | 1/2007 | Liniger et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027384 A1 | 2/2007 | Brister et al. |
| 2007/0027385 A1 | 2/2007 | Brister et al. |
| 2007/0027507 A1 | 2/2007 | Burdett et al. |
| 2007/0030154 A1 | 2/2007 | Aiki et al. |
| 2007/0032706 A1 | 2/2007 | Kamath et al. |
| 2007/0032717 A1 | 2/2007 | Brister et al. |
| 2007/0032718 A1 | 2/2007 | Shults et al. |

(56) References Cited

U.S. PATENT DOCUMENTS

| | | |
|---|---|---|
| 2007/0033074 A1 | 2/2007 | Nitzan et al. |
| 2007/0038044 A1 | 2/2007 | Dobbles et al. |
| 2007/0045902 A1 | 3/2007 | Brauker et al. |
| 2007/0049865 A1 | 3/2007 | Radmer et al. |
| 2007/0055799 A1 | 3/2007 | Koehler et al. |
| 2007/0056858 A1 | 3/2007 | Chen et al. |
| 2007/0059196 A1 | 3/2007 | Brister et al. |
| 2007/0060801 A1 | 3/2007 | Neinast |
| 2007/0060814 A1 | 3/2007 | Stafford |
| 2007/0060869 A1 | 3/2007 | Tolle et al. |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0088377 A1 | 4/2007 | Levaughn et al. |
| 2007/0090511 A1 | 4/2007 | Borland et al. |
| 2007/0093704 A1 | 4/2007 | Brister et al. |
| 2007/0093754 A1 | 4/2007 | Mogensen et al. |
| 2007/0093786 A1 | 4/2007 | Goldsmith et al. |
| 2007/0095661 A1 | 5/2007 | Wang et al. |
| 2007/0100218 A1 | 5/2007 | Sweitzer et al. |
| 2007/0100222 A1 | 5/2007 | Mastrototaro et al. |
| 2007/0106133 A1 | 5/2007 | Satchwell et al. |
| 2007/0106135 A1 | 5/2007 | Sloan et al. |
| 2007/0108048 A1 | 5/2007 | Wang et al. |
| 2007/0110124 A1 | 5/2007 | Shiraki et al. |
| 2007/0111196 A1 | 5/2007 | Alarcon et al. |
| 2007/0123819 A1 | 5/2007 | Mernoe et al. |
| 2007/0124002 A1 | 5/2007 | Estes et al. |
| 2007/0129621 A1 | 6/2007 | Kellogg et al. |
| 2007/0135696 A1 | 6/2007 | Ward |
| 2007/0135774 A1 | 6/2007 | Turner et al. |
| 2007/0149873 A1 | 6/2007 | Say et al. |
| 2007/0149875 A1 | 6/2007 | Ouyang et al. |
| 2007/0153705 A1 | 7/2007 | Rosar et al. |
| 2007/0156033 A1 | 7/2007 | Causey, III et al. |
| 2007/0156094 A1 | 7/2007 | Safabash et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173711 A1 | 7/2007 | Shah et al. |
| 2007/0173741 A1 | 7/2007 | Deshmukh et al. |
| 2007/0173761 A1 | 7/2007 | Kanderian, Jr. et al. |
| 2007/0179349 A1 | 8/2007 | Hoyme et al. |
| 2007/0179352 A1 | 8/2007 | Randlov et al. |
| 2007/0179406 A1 | 8/2007 | DeNuzzio et al. |
| 2007/0191701 A1 | 8/2007 | Feldman et al. |
| 2007/0191702 A1 | 8/2007 | Yodfat et al. |
| 2007/0197889 A1 | 8/2007 | Brister et al. |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203539 A1 | 8/2007 | Stone et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213611 A1 | 9/2007 | Simpson et al. |
| 2007/0219480 A1 | 9/2007 | Kamen et al. |
| 2007/0219496 A1 | 9/2007 | Kamen et al. |
| 2007/0222609 A1 | 9/2007 | Duron et al. |
| 2007/0227911 A1 | 10/2007 | Wang et al. |
| 2007/0228071 A1 | 10/2007 | Kamen et al. |
| 2007/0231846 A1 | 10/2007 | Cosentino et al. |
| 2007/0232877 A1 | 10/2007 | He |
| 2007/0232878 A1 | 10/2007 | Kovatchev et al. |
| 2007/0232879 A1 | 10/2007 | Brister et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244368 A1 | 10/2007 | Bayloff et al. |
| 2007/0244379 A1 | 10/2007 | Boock et al. |
| 2007/0244383 A1 | 10/2007 | Talbot et al. |
| 2007/0244398 A1 | 10/2007 | Lo et al. |
| 2007/0249922 A1 | 10/2007 | Peyser et al. |
| 2007/0253021 A1 | 11/2007 | Mehta et al. |
| 2007/0255116 A1 | 11/2007 | Mehta et al. |
| 2007/0255125 A1 | 11/2007 | Moberg et al. |
| 2007/0255302 A1 | 11/2007 | Koeppel et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |
| 2008/0004512 A1 | 1/2008 | Funderburk et al. |
| 2008/0004515 A1 | 1/2008 | Jennewine et al. |
| 2008/0004573 A1 | 1/2008 | Kaufmann et al. |
| 2008/0004601 A1 | 1/2008 | Jennewine et al. |
| 2008/0004904 A1 | 1/2008 | Tran |
| 2008/0009304 A1 | 1/2008 | Fry |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0018433 A1 | 1/2008 | Pitt-Pladdy |
| 2008/0021543 A1 | 1/2008 | Shrivastava |
| 2008/0021666 A1 | 1/2008 | Goode, Jr. et al. |
| 2008/0027296 A1 | 1/2008 | Hadvary et al. |
| 2008/0027474 A1 | 1/2008 | Curry et al. |
| 2008/0029391 A1 | 2/2008 | Mao et al. |
| 2008/0030369 A1 | 2/2008 | Mann et al. |
| 2008/0031941 A1 | 2/2008 | Pettersson |
| 2008/0033254 A1 | 2/2008 | Kamath et al. |
| 2008/0033268 A1 | 2/2008 | Stafford |
| 2008/0033273 A1 | 2/2008 | Zhou et al. |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0046038 A1 | 2/2008 | Hill et al. |
| 2008/0055070 A1 | 3/2008 | Bange et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0058830 A1 | 3/2008 | Cole et al. |
| 2008/0059227 A1 | 3/2008 | Clapp |
| 2008/0060955 A1 | 3/2008 | Goodnow |
| 2008/0061961 A1 | 3/2008 | John |
| 2008/0062055 A1 | 3/2008 | Cunningham et al. |
| 2008/0064437 A1 | 3/2008 | Chambers et al. |
| 2008/0064937 A1 | 3/2008 | McGarraugh et al. |
| 2008/0064941 A1 | 3/2008 | Funderburk et al. |
| 2008/0064943 A1 | 3/2008 | Talbot et al. |
| 2008/0064944 A1 | 3/2008 | VanAntwerp et al. |
| 2008/0065646 A1 | 3/2008 | Zhang et al. |
| 2008/0066305 A1 | 3/2008 | Wang et al. |
| 2008/0067627 A1 | 3/2008 | Boeck et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0071580 A1 | 3/2008 | Marcus |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0092911 A1 | 4/2008 | Schulman et al. |
| 2008/0097246 A1 | 4/2008 | Stafford |
| 2008/0097289 A1 | 4/2008 | Steil et al. |
| 2008/0097908 A1 | 4/2008 | Dicks et al. |
| 2008/0099332 A1 | 5/2008 | Scott et al. |
| 2008/0102441 A1 | 5/2008 | Chen et al. |
| 2008/0108942 A1 | 5/2008 | Brister et al. |
| 2008/0112848 A1 | 5/2008 | Huffstodt et al. |

(56)          References Cited

U.S. PATENT DOCUMENTS

| | | |
|---|---|---|
| 2008/0114228 A1 | 5/2008 | Mccluskey et al. |
| 2008/0114280 A1 | 5/2008 | Stafford |
| 2008/0119705 A1 | 5/2008 | Patel et al. |
| 2008/0119707 A1 | 5/2008 | Stafford |
| 2008/0119710 A1 | 5/2008 | Reggiardo et al. |
| 2008/0125636 A1 | 5/2008 | Ward et al. |
| 2008/0127052 A1 | 5/2008 | Rostoker |
| 2008/0129486 A1 | 6/2008 | Jeckelmann et al. |
| 2008/0133059 A1 | 6/2008 | Trippel et al. |
| 2008/0133702 A1 | 6/2008 | Sharma et al. |
| 2008/0139910 A1 | 6/2008 | Mastrototaro et al. |
| 2008/0146904 A1 | 6/2008 | Hunn |
| 2008/0148873 A1 | 6/2008 | Wang |
| 2008/0154205 A1 | 6/2008 | Wojcik |
| 2008/0154286 A1 | 6/2008 | Abbott et al. |
| 2008/0154513 A1 | 6/2008 | Kovatchev et al. |
| 2008/0161664 A1 | 7/2008 | Mastrototaro et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0167578 A1 | 7/2008 | Bryer et al. |
| 2008/0172205 A1 | 7/2008 | Breton et al. |
| 2008/0177149 A1 | 7/2008 | Weinart et al. |
| 2008/0177165 A1 | 7/2008 | Blomquist et al. |
| 2008/0179187 A1 | 7/2008 | Ouyang |
| 2008/0182537 A1 | 7/2008 | Manku et al. |
| 2008/0183060 A1 | 7/2008 | Steil et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0188796 A1 | 8/2008 | Steil et al. |
| 2008/0189051 A1 | 8/2008 | Goode, Jr. et al. |
| 2008/0194926 A1 | 8/2008 | Goh et al. |
| 2008/0194934 A1 | 8/2008 | Ray et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0208113 A1 | 8/2008 | Damiano et al. |
| 2008/0214481 A1 | 9/2008 | Challoner et al. |
| 2008/0214900 A1 | 9/2008 | Fennell et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0215035 A1 | 9/2008 | Yodfat et al. |
| 2008/0228051 A1 | 9/2008 | Shults et al. |
| 2008/0228054 A1 | 9/2008 | Shults et al. |
| 2008/0234561 A1 | 9/2008 | Roesicke et al. |
| 2008/0234992 A1 | 9/2008 | Ray et al. |
| 2008/0235469 A1 | 9/2008 | Drew |
| 2008/0242961 A1 | 10/2008 | Brister et al. |
| 2008/0242962 A1 | 10/2008 | Roesicke et al. |
| 2008/0242963 A1 | 10/2008 | Essenpreis et al. |
| 2008/0243051 A1 | 10/2008 | DeStefano |
| 2008/0252459 A1 | 10/2008 | Butler et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255440 A1 | 10/2008 | Eilerson et al. |
| 2008/0255808 A1 | 10/2008 | Hayter |
| 2008/0256048 A1 | 10/2008 | Hayter |
| 2008/0262300 A1 | 10/2008 | Reynolds et al. |
| 2008/0262469 A1 | 10/2008 | Brister et al. |
| 2008/0267823 A1 | 10/2008 | Wang et al. |
| 2008/0269584 A1 | 10/2008 | Shekalim |
| 2008/0269673 A1 | 10/2008 | Butoi et al. |
| 2008/0269683 A1 | 10/2008 | Bikovsky |
| 2008/0269687 A1 | 10/2008 | Chong et al. |
| 2008/0269714 A1 | 10/2008 | Mastrototaro et al. |
| 2008/0275313 A1 | 11/2008 | Brister et al. |
| 2008/0275327 A1 | 11/2008 | Faarbaek et al. |
| 2008/0278333 A1 | 11/2008 | Fennell et al. |
| 2008/0281178 A1 | 11/2008 | Chuang et al. |
| 2008/0281179 A1 | 11/2008 | Fennell et al. |
| 2008/0283396 A1 | 11/2008 | Wang et al. |
| 2008/0287755 A1 | 11/2008 | Sass et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0300572 A1 | 12/2008 | Rankers et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0308523 A1 | 12/2008 | Krulevitch et al. |
| 2008/0312518 A1 | 12/2008 | Jina et al. |
| 2008/0312601 A1 | 12/2008 | Cane |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0312859 A1 | 12/2008 | Skyggebjerg et al. |
| 2008/0319085 A1 | 12/2008 | Wright et al. |
| 2008/0319295 A1 | 12/2008 | Bernstein et al. |
| 2008/0319296 A1 | 12/2008 | Bernstein et al. |
| 2008/0319414 A1 | 12/2008 | Yodfat et al. |
| 2008/0319416 A1 | 12/2008 | Yodfat et al. |
| 2009/0005659 A1 | 1/2009 | Kollias et al. |
| 2009/0005665 A1 | 1/2009 | Hayter et al. |
| 2009/0005666 A1 | 1/2009 | Shin et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0006133 A1 | 1/2009 | Weinart et al. |
| 2009/0012376 A1 | 1/2009 | Agus |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0020502 A1 | 1/2009 | Bhullar et al. |
| 2009/0028824 A1 | 1/2009 | Chiang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0036915 A1 | 2/2009 | Karbowniczek et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048499 A1 | 2/2009 | Glejbol |
| 2009/0048503 A1 | 2/2009 | Dalal et al. |
| 2009/0048563 A1 | 2/2009 | Ethelfeld et al. |
| 2009/0054737 A1 | 2/2009 | Magar et al. |
| 2009/0054745 A1 | 2/2009 | Jennewine et al. |
| 2009/0054747 A1 | 2/2009 | Fennell |
| 2009/0054748 A1 | 2/2009 | Feldman et al. |

(56)         References Cited

U.S. PATENT DOCUMENTS

| | | |
|---|---|---|
| 2009/0054753 A1 | 2/2009 | Robinson et al. |
| 2009/0054866 A1 | 2/2009 | Teisen-Simony et al. |
| 2009/0055149 A1 | 2/2009 | Hayter et al. |
| 2009/0058635 A1 | 3/2009 | LaLonde et al. |
| 2009/0062633 A1 | 3/2009 | Brauker et al. |
| 2009/0062635 A1 | 3/2009 | Brauker et al. |
| 2009/0062767 A1 | 3/2009 | Van Antwerp et al. |
| 2009/0063187 A1 | 3/2009 | Johnson et al. |
| 2009/0063402 A1 | 3/2009 | Hayter |
| 2009/0069658 A1 | 3/2009 | Say et al. |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub |
| 2009/0088787 A1 | 4/2009 | Koike et al. |
| 2009/0093687 A1 | 4/2009 | Telfort et al. |
| 2009/0099436 A1 | 4/2009 | Brister et al. |
| 2009/0099521 A1 | 4/2009 | Gravesen et al. |
| 2009/0102678 A1 | 4/2009 | Mazza et al. |
| 2009/0105554 A1 | 4/2009 | Stahmann et al. |
| 2009/0105560 A1 | 4/2009 | Solomon |
| 2009/0105568 A1 | 4/2009 | Bugler |
| 2009/0105569 A1* | 4/2009 | Stafford ............... A61B 5/6833 |
| | | 600/365 |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0108992 A1 | 4/2009 | Shafer |
| 2009/0112123 A1 | 4/2009 | Freeman et al. |
| 2009/0112478 A1 | 4/2009 | Mueller, Jr. et al. |
| 2009/0118592 A1 | 5/2009 | Klitgaard |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0124979 A1 | 5/2009 | Raymond et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149728 A1 | 6/2009 | Van Antwerp et al. |
| 2009/0150186 A1 | 6/2009 | Cohen et al. |
| 2009/0150454 A1 | 6/2009 | Gejdos et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0171182 A1 | 7/2009 | Stafford |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0198186 A1 | 8/2009 | Mernoe et al. |
| 2009/0198215 A1 | 8/2009 | Chong et al. |
| 2009/0203981 A1 | 8/2009 | Brauker et al. |
| 2009/0204340 A1 | 8/2009 | Feldman et al. |
| 2009/0204341 A1 | 8/2009 | Brauker et al. |
| 2009/0210249 A1 | 8/2009 | Rasch-Menges et al. |
| 2009/0212766 A1 | 8/2009 | Olson et al. |
| 2009/0216100 A1 | 8/2009 | Ebner et al. |
| 2009/0216103 A1 | 8/2009 | Brister et al. |
| 2009/0216215 A1 | 8/2009 | Thalmann et al. |
| 2009/0234200 A1 | 9/2009 | Husheer |
| 2009/0240120 A1 | 9/2009 | Mensinger et al. |
| 2009/0240121 A1 | 9/2009 | Bickoff |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorenson |
| 2009/0253973 A1 | 10/2009 | Bashan et al. |
| 2009/0259118 A1 | 10/2009 | Feldman et al. |
| 2009/0259201 A1 | 10/2009 | Hwang et al. |
| 2009/0259202 A1 | 10/2009 | Leeflang et al. |
| 2009/0267765 A1 | 10/2009 | Greene et al. |
| 2009/0270765 A1 | 10/2009 | Ghesquire et al. |
| 2009/0277242 A1 | 11/2009 | Crane et al. |
| 2009/0281406 A1 | 11/2009 | McGarraugh et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0292184 A1 | 11/2009 | Funderburk et al. |
| 2009/0292185 A1 | 11/2009 | Funderburk et al. |
| 2009/0294277 A1 | 12/2009 | Thomas et al. |
| 2009/0298182 A1 | 12/2009 | Schulat et al. |
| 2009/0299152 A1 | 12/2009 | Taub et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299167 A1 | 12/2009 | Seymour |
| 2009/0299276 A1 | 12/2009 | Brauker et al. |
| 2009/0299301 A1 | 12/2009 | Gottleib et al. |
| 2010/0004597 A1 | 1/2010 | Gryn et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0014626 A1 | 1/2010 | Fennell et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022863 A1 | 1/2010 | Mogensen et al. |
| 2010/0022988 A1 | 1/2010 | Wochner et al. |
| 2010/0025238 A1 | 2/2010 | Gottlieb et al. |
| 2010/0030038 A1 | 2/2010 | Brauker et al. |
| 2010/0030053 A1 | 2/2010 | Goode, Jr. et al. |
| 2010/0030111 A1 | 2/2010 | Perriere |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0036281 A1 | 2/2010 | Doi |
| 2010/0041971 A1 | 2/2010 | Goode, Jr. et al. |
| 2010/0045465 A1 | 2/2010 | Brauker et al. |
| 2010/0049014 A1 | 2/2010 | Funderburk et al. |
| 2010/0049024 A1 | 2/2010 | Saint et al. |
| 2010/0049129 A1 | 2/2010 | Yokoi et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0069728 A1 | 3/2010 | Funderburk et al. |
| 2010/0076283 A1 | 3/2010 | Simpson et al. |
| 2010/0076379 A1 | 3/2010 | Matusch |
| 2010/0081905 A1 | 4/2010 | Bommakanti et al. |

(56)                References Cited

U.S. PATENT DOCUMENTS

| | | | |
|---|---|---|---|
| 2010/0081906 A1 | 4/2010 | Hayter et al. |
| 2010/0081908 A1 | 4/2010 | Dobbles et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0094251 A1 | 4/2010 | Estes et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100113 A1 | 4/2010 | Iio et al. |
| 2010/0105999 A1 | 4/2010 | Dixon et al. |
| 2010/0106088 A1 | 4/2010 | Yodfat et al. |
| 2010/0113897 A1 | 5/2010 | Brenneman et al. |
| 2010/0119693 A1 | 5/2010 | Tapsak et al. |
| 2010/0119881 A1 | 5/2010 | Patel et al. |
| 2010/0121167 A1 | 5/2010 | McGarraugh et al. |
| 2010/0121169 A1 | 5/2010 | Petisce et al. |
| 2010/0137695 A1 | 6/2010 | Yodfat et al. |
| 2010/0141656 A1 | 6/2010 | Krieftewirth |
| 2010/0145229 A1 | 6/2010 | Perez et al. |
| 2010/0145377 A1 | 6/2010 | Lai et al. |
| 2010/0146300 A1 | 6/2010 | Brown |
| 2010/0152548 A1 | 6/2010 | Koski |
| 2010/0152554 A1 | 6/2010 | Steine et al. |
| 2010/0152674 A1 | 6/2010 | Kavazov et al. |
| 2010/0160757 A1 | 6/2010 | Weinart et al. |
| 2010/0160759 A1 | 6/2010 | Celentano et al. |
| 2010/0160760 A1 | 6/2010 | Shults et al. |
| 2010/0161269 A1 | 6/2010 | Kamath et al. |
| 2010/0168538 A1 | 7/2010 | Keenan et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168545 A1 | 7/2010 | Kamath et al. |
| 2010/0168546 A1 | 7/2010 | Kamath et al. |
| 2010/0168547 A1 | 7/2010 | Kamath et al. |
| 2010/0168660 A1 | 7/2010 | Galley et al. |
| 2010/0168677 A1 | 7/2010 | Gabriel et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode, Jr. et al. |
| 2010/0174266 A1 | 7/2010 | Estes |
| 2010/0179399 A1 | 7/2010 | Goode, Jr. et al. |
| 2010/0179400 A1 | 7/2010 | Brauker et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179405 A1 | 7/2010 | Goode, Jr. et al. |
| 2010/0179407 A1 | 7/2010 | Goode, Jr. et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode, Jr. et al. |
| 2010/0185073 A1 | 7/2010 | Goode, Jr. et al. |
| 2010/0185074 A1 | 7/2010 | Goode, Jr. et al. |
| 2010/0185075 A1 | 7/2010 | Brister et al. |
| 2010/0185175 A1 | 7/2010 | Kamen et al. |
| 2010/0190435 A1 | 7/2010 | Cook et al. |
| 2010/0191082 A1 | 7/2010 | Brister et al. |
| 2010/0191087 A1 | 7/2010 | Talbot et al. |
| 2010/0191472 A1 | 7/2010 | Doniger et al. |
| 2010/0198033 A1 | 8/2010 | Krulevitch et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0198042 A1 | 8/2010 | Sloan et al. |
| 2010/0198142 A1 | 8/2010 | Sloan et al. |
| 2010/0198314 A1 | 8/2010 | Wei |
| 2010/0204557 A1 | 8/2010 | Kiaie et al. |
| 2010/0204653 A1 | 8/2010 | Gryn et al. |
| 2010/0212583 A1 | 8/2010 | Brister et al. |
| 2010/0213057 A1 | 8/2010 | Feldman et al. |
| 2010/0213080 A1 | 8/2010 | Celentano et al. |
| 2010/0214104 A1 | 8/2010 | Goode, Jr. et al. |
| 2010/0217105 A1 | 8/2010 | Yodfat et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228111 A1 | 9/2010 | Friman et al. |
| 2010/0228497 A1 | 9/2010 | Kamath et al. |
| 2010/0230285 A1 | 9/2010 | Hoss et al. |
| 2010/0235439 A1 | 9/2010 | Goodnow et al. |
| 2010/0240975 A1 | 9/2010 | Goode, Jr. et al. |
| 2010/0240976 A1 | 9/2010 | Goode, Jr. et al. |
| 2010/0256471 A1 | 10/2010 | Say et al. |
| 2010/0259543 A1 | 10/2010 | Tarassenko et al. |
| 2010/0261987 A1 | 10/2010 | Kamath et al. |
| 2010/0262183 A1 | 10/2010 | Abbott et al. |
| 2010/0262201 A1 | 10/2010 | He et al. |
| 2010/0267161 A1 | 10/2010 | Wu et al. |
| 2010/0274107 A1 | 10/2010 | Boock et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0312176 A1 | 12/2010 | Lauer et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0324403 A1 | 12/2010 | Brister et al. |
| 2010/0325868 A1 | 12/2010 | Wang et al. |
| 2010/0326842 A1 | 12/2010 | Mazza et al. |
| 2010/0331642 A1* | 12/2010 | Bruce ................ A61B 5/6846 |
| | | 606/129 |
| 2010/0331644 A1 | 12/2010 | Neale et al. |
| 2010/0331647 A1 | 12/2010 | Shah et al. |
| 2010/0331648 A1 | 12/2010 | Kamath et al. |
| 2010/0331651 A1 | 12/2010 | Groll |
| 2010/0331653 A1 | 12/2010 | Stafford |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0004276 A1 | 1/2011 | Blair et al. |
| 2011/0009727 A1 | 1/2011 | Mensinger et al. |
| 2011/0015509 A1 | 1/2011 | Peyser |
| 2011/0016691 A1 | 1/2011 | Alden et al. |
| 2011/0021889 A1 | 1/2011 | Hoss et al. |
| 2011/0022411 A1 | 1/2011 | Hjelm et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0040163 A1 | 2/2011 | Telson et al. |
| 2011/0040256 A1 | 2/2011 | Bobroff et al. |
| 2011/0040263 A1 | 2/2011 | Hordum et al. |
| 2011/0046456 A1 | 2/2011 | Hordum et al. |
| 2011/0046467 A1 | 2/2011 | Simpson et al. |
| 2011/0046977 A1 | 2/2011 | Goodnow et al. |
| 2011/0054275 A1 | 3/2011 | Stafford |
| 2011/0054282 A1 | 3/2011 | Nekoomaram et al. |
| 2011/0060196 A1 | 3/2011 | Stafford |
| 2011/0060530 A1 | 3/2011 | Fennell |
| 2011/0070633 A1 | 3/2011 | Matsumoto et al. |
| 2011/0073475 A1 | 3/2011 | Kastanos et al. |
| 2011/0077469 A1 | 3/2011 | Blocker et al. |
| 2011/0077490 A1 | 3/2011 | Simpson et al. |

(56) References Cited

U.S. PATENT DOCUMENTS

| | | |
|---|---|---|
| 2011/0077494 A1 | 3/2011 | Doniger et al. |
| 2011/0077659 A1 | 3/2011 | Mandecki et al. |
| 2011/0081726 A1 | 4/2011 | Berman et al. |
| 2011/0082484 A1* | 4/2011 | Saravia ................. A61M 5/158 |
| | | 606/167 |
| 2011/0087196 A1 | 4/2011 | Hunn et al. |
| 2011/0097090 A1 | 4/2011 | Cao |
| 2011/0106126 A1 | 5/2011 | Love et al. |
| 2011/0112696 A1 | 5/2011 | Yodfat et al. |
| 2011/0118579 A1 | 5/2011 | Goode, Jr. et al. |
| 2011/0118580 A1 | 5/2011 | Goode, Jr. et al. |
| 2011/0123971 A1 | 5/2011 | Berkowitz et al. |
| 2011/0124992 A1 | 5/2011 | Brauker et al. |
| 2011/0124997 A1 | 5/2011 | Goode, Jr. et al. |
| 2011/0125040 A1 | 5/2011 | Crawford et al. |
| 2011/0125410 A1 | 5/2011 | Goode, Jr. et al. |
| 2011/0130970 A1 | 6/2011 | Goode, Jr. et al. |
| 2011/0130971 A1 | 6/2011 | Goode, Jr. et al. |
| 2011/0130998 A1 | 6/2011 | Goode, Jr. et al. |
| 2011/0137257 A1 | 6/2011 | Gyrn et al. |
| 2011/0137571 A1 | 6/2011 | Power et al. |
| 2011/0144465 A1 | 6/2011 | Shults et al. |
| 2011/0148905 A1 | 6/2011 | Simmons et al. |
| 2011/0152637 A1 | 6/2011 | Kateraas et al. |
| 2011/0172510 A1 | 7/2011 | Chickering, III et al. |
| 2011/0178378 A1 | 7/2011 | Brister et al. |
| 2011/0178461 A1 | 7/2011 | Chong et al. |
| 2011/0184258 A1 | 7/2011 | Stafford |
| 2011/0184482 A1 | 7/2011 | Eberman et al. |
| 2011/0184752 A1 | 7/2011 | Ray et al. |
| 2011/0190603 A1* | 8/2011 | Stafford ........... A61B 5/150358 |
| | | 600/309 |
| 2011/0190614 A1 | 8/2011 | Brister et al. |
| 2011/0191044 A1 | 8/2011 | Stafford |
| 2011/0193704 A1 | 8/2011 | Harper et al. |
| 2011/0201910 A1 | 8/2011 | Rasdal et al. |
| 2011/0201911 A1 | 8/2011 | Johnson et al. |
| 2011/0208027 A1 | 8/2011 | Wagner et al. |
| 2011/0213225 A1 | 9/2011 | Bernstein et al. |
| 2011/0218414 A1 | 9/2011 | Kamath et al. |
| 2011/0218490 A1 | 9/2011 | Ocvirk et al. |
| 2011/0230741 A1 | 9/2011 | Liang et al. |
| 2011/0231107 A1 | 9/2011 | Brauker et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0253533 A1 | 10/2011 | Shults et al. |
| 2011/0257495 A1 | 10/2011 | Hoss et al. |
| 2011/0257521 A1 | 10/2011 | Fraden |
| 2011/0257895 A1 | 10/2011 | Brauker et al. |
| 2011/0263958 A1 | 10/2011 | Brauker et al. |
| 2011/0263959 A1 | 10/2011 | Young et al. |
| 2011/0264378 A1 | 10/2011 | Breton et al. |
| 2011/0270062 A1 | 11/2011 | Goode, Jr. et al. |
| 2011/0270158 A1 | 11/2011 | Brauker et al. |
| 2011/0275919 A1 | 11/2011 | Petisce et al. |
| 2011/0282327 A1 | 11/2011 | Kellogg et al. |
| 2011/0287528 A1 | 11/2011 | Fern et al. |
| 2011/0288574 A1 | 11/2011 | Curry et al. |
| 2011/0289497 A1 | 11/2011 | Kiaie et al. |
| 2011/0290645 A1 | 12/2011 | Brister et al. |
| 2011/0313543 A1 | 12/2011 | Brauker et al. |
| 2011/0319729 A1 | 12/2011 | Donnay et al. |
| 2011/0319733 A1 | 12/2011 | Stafford |
| 2011/0319738 A1 | 12/2011 | Woodruff et al. |
| 2011/0319739 A1 | 12/2011 | Kamath et al. |
| 2011/0320130 A1 | 12/2011 | Valdes et al. |
| 2012/0010642 A1 | 1/2012 | Lee et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0088995 A1 | 4/2012 | Fennell et al. |
| 2012/0095406 A1 | 4/2012 | Gyrn et al. |
| 2012/0108934 A1 | 5/2012 | Valdes et al. |
| 2012/0108983 A1 | 5/2012 | Banet et al. |
| 2012/0116322 A1 | 5/2012 | Brink et al. |
| 2012/0123385 A1 | 5/2012 | Edwards et al. |
| 2012/0143135 A1 | 6/2012 | Cole et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0179113 A1 | 7/2012 | Yokota et al. |
| 2012/0184909 A1 | 7/2012 | Gyrn et al. |
| 2012/0190943 A1 | 7/2012 | Donnay et al. |
| 2012/0190989 A1 | 7/2012 | Kaiser et al. |
| 2012/0197098 A1 | 8/2012 | Donnay et al. |
| 2012/0197222 A1 | 8/2012 | Donnay et al. |
| 2012/0245447 A1 | 9/2012 | Karan et al. |
| 2012/0265042 A1 | 10/2012 | Neinast et al. |
| 2012/0296327 A1 | 11/2012 | Hutchins et al. |
| 2012/0303043 A1 | 11/2012 | Donnay et al. |
| 2013/0035575 A1 | 2/2013 | Mayou et al. |
| 2013/0047981 A1 | 2/2013 | Bacon |
| 2013/0109940 A1 | 5/2013 | Yang et al. |
| 2013/0111248 A1 | 5/2013 | Ghesquiere et al. |
| 2013/0150691 A1 | 6/2013 | Pace et al. |
| 2013/0184547 A1 | 7/2013 | Taub et al. |
| 2013/0199312 A1 | 8/2013 | Wilmer et al. |
| 2013/0225959 A1 | 8/2013 | Bugler |
| 2013/0235166 A1 | 9/2013 | Jones et al. |
| 2013/0253289 A1 | 9/2013 | Hadvary et al. |
| 2013/0267811 A1 | 10/2013 | Pryor et al. |
| 2013/0317323 A1 | 11/2013 | Fujiwara et al. |
| 2014/0031655 A1 | 1/2014 | Stafford |
| 2014/0121480 A1 | 5/2014 | Budiman et al. |
| 2014/0148667 A1 | 5/2014 | Boock et al. |
| 2014/0171771 A1 | 6/2014 | Feldman et al. |
| 2014/0188053 A1 | 7/2014 | Lundquist |
| 2014/0228760 A1 | 8/2014 | Ethelfeld |
| 2014/0275907 A1 | 9/2014 | Feldman et al. |
| 2015/0005601 A1 | 1/2015 | Hoss et al. |
| 2015/0018643 A1 | 1/2015 | Cole et al. |
| 2015/0025338 A1 | 1/2015 | Lee et al. |
| 2015/0073238 A1 | 3/2015 | Matsumoto et al. |
| 2015/0105644 A1 | 4/2015 | Yang et al. |
| 2015/0141776 A1 | 5/2015 | Hadvary et al. |
| 2015/0164545 A1 | 6/2015 | Gyrn |
| 2015/0173661 A1 | 6/2015 | Myles |
| 2015/0241407 A1 | 8/2015 | Ou et al. |
| 2015/0326072 A1 | 11/2015 | Petras et al. |
| 2016/0058342 A1 | 3/2016 | Maiz-Aguinaga et al. |
| 2016/0058470 A1 | 3/2016 | Peterson et al. |
| 2016/0058474 A1 | 3/2016 | Peterson et al. |
| 2016/0128615 A1 | 5/2016 | Curry et al. |
| 2016/0157759 A1 | 6/2016 | Yang |
| 2016/0256106 A1 | 9/2016 | Krasnow et al. |
| 2016/0331283 A1 | 11/2016 | Rao et al. |
| 2016/0331284 A1 | 11/2016 | Pace |
| 2016/0338733 A1 | 11/2016 | Shah et al. |
| 2016/0338734 A1 | 11/2016 | Shah et al. |
| 2016/0354555 A1 | 12/2016 | Gibson et al. |
| 2017/0112531 A1 | 4/2017 | Schoonmaker et al. |
| 2017/0112533 A1 | 4/2017 | Schoonmaker et al. |
| 2017/0112534 A1 | 4/2017 | Schoonmaker et al. |
| 2017/0127985 A1 | 5/2017 | Thompson et al. |
| 2017/0128011 A1 | 5/2017 | Frey et al. |
| 2017/0165451 A1 | 6/2017 | Frey et al. |
| 2017/0188908 A1 | 7/2017 | Hoss et al. |
| 2017/0188910 A1 | 7/2017 | Halac et al. |
| 2017/0188912 A1 | 7/2017 | Halac et al. |
| 2017/0216536 A1 | 8/2017 | Scott |
| 2017/0265791 A1 | 9/2017 | Pace et al. |
| 2017/0290533 A1 | 10/2017 | Antonio et al. |
| 2017/0290534 A1 | 10/2017 | Antonio et al. |
| 2017/0290535 A1 | 10/2017 | Rao et al. |
| 2017/0290546 A1 | 10/2017 | Antonio et al. |
| 2017/0319137 A1 | 11/2017 | Tsubouchi et al. |
| 2017/0367630 A1 | 12/2017 | Arita et al. |
| 2017/0368268 A1 | 12/2017 | Chopra |
| 2018/0116572 A1 | 5/2018 | Simpson et al. |
| 2018/0125464 A1 | 5/2018 | Kolb et al. |
| 2018/0235520 A1 | 8/2018 | Rao et al. |
| 2018/0360493 A1 | 12/2018 | Baker et al. |

(56) References Cited

U.S. PATENT DOCUMENTS

| | | | |
|---|---|---|---|
| 2018/0368771 | A1 | 12/2018 | Gray et al. |
| 2019/0133501 | A1 | 5/2019 | Rao et al. |
| 2019/0133638 | A1 | 5/2019 | Il et al. |
| 2019/0298240 | A1 | 10/2019 | Lee et al. |
| 2020/0077928 | A1 | 3/2020 | Brister et al. |
| 2020/0100712 | A1 | 4/2020 | Stafford |
| 2020/0113494 | A1 | 4/2020 | Akiyama |
| 2020/0178899 | A1 | 6/2020 | Chae et al. |
| 2020/0196919 | A1 | 6/2020 | Rao et al. |
| 2020/0397356 | A1 | 12/2020 | Yee et al. |
| 2021/0030969 | A1 | 2/2021 | Huang et al. |
| 2021/0113124 | A1 | 4/2021 | Yee et al. |
| 2021/0161437 | A1 | 6/2021 | Thomas et al. |
| 2021/0177315 | A1 | 6/2021 | Thomas et al. |
| 2021/0204841 | A1 | 7/2021 | Thomas et al. |
| 2021/0204843 | A1 | 7/2021 | Mazza et al. |
| 2021/0378592 | A1 | 12/2021 | Rodriguez et al. |
| 2022/0007973 | A1 | 1/2022 | Rao et al. |
| 2022/0079475 | A1 | 3/2022 | Cole et al. |
| 2022/0125480 | A1 | 4/2022 | Rao et al. |
| 2022/0273240 | A1 | 9/2022 | Hopcroft |
| 2023/0108476 | A1 | 4/2023 | Rao |
| 2024/0293615 | A1 | 9/2024 | Lanigan |

FOREIGN PATENT DOCUMENTS

| | | |
|---|---|---|
| CA | 2468577 | 6/2003 |
| CA | 2495648 | 2/2004 |
| CA | 2143172 | 7/2005 |
| CA | 2498682 | 9/2005 |
| CA | 2555749 | 9/2005 |
| CA | 2632709 | 6/2007 |
| CA | 2396613 | 3/2008 |
| CA | 2678336 | 5/2008 |
| CA | 2615575 | 6/2008 |
| CA | 2626349 | 9/2008 |
| CA | 2701374 | 4/2009 |
| CA | 2413148 | 8/2010 |
| CA | 2728831 | 7/2011 |
| CA | 2766693 | 9/2011 |
| CA | 2617965 | 10/2011 |
| CA | 2766685 | 12/2011 |
| CA | 3050721 | 7/2018 |
| CN | 1202872 | 5/2005 |
| CN | 101163440 | 4/2008 |
| CN | 101268932 | 9/2008 |
| CN | 101296650 | 10/2008 |
| CN | 201370857 | 12/2009 |
| DE | 44 01 400 | 7/1995 |
| DE | 201 10 059 | 8/2002 |
| DE | 101 17 285 | 11/2002 |
| DE | 10 2008 053 216 | 5/2010 |
| EP | 0 010 375 | 4/1980 |
| EP | 0 026 995 | 4/1981 |
| EP | 0 048 090 | 3/1982 |
| EP | 0 078 636 | 5/1983 |
| EP | 0 096 288 | 12/1983 |
| EP | 0 098 592 | 1/1984 |
| EP | 0 125 139 | 11/1984 |
| EP | 0 127 958 | 12/1984 |
| EP | 0 136 362 | 4/1985 |
| EP | 0 170 375 | 2/1986 |
| EP | 0 177 743 | 4/1986 |
| EP | 0 080 304 | 5/1986 |
| EP | 0 184 909 | 6/1986 |
| EP | 0 206 218 | 12/1986 |
| EP | 0 230 472 | 8/1987 |
| EP | 0 241 309 | 10/1987 |
| EP | 0 245 073 | 11/1987 |
| EP | 0 255 291 | 2/1988 |
| EP | 0 278 647 | 8/1988 |
| EP | 0 319 277 | 6/1989 |
| EP | 0 320 109 | 6/1989 |
| EP | 0 353 328 | 2/1990 |
| EP | 0 359 831 | 3/1990 |
| EP | 0 368 209 | 5/1990 |
| EP | 0 390 390 | 10/1990 |
| EP | 0 396 788 | 11/1990 |
| EP | 0 400 918 | 12/1990 |
| EP | 0 453 283 | 10/1991 |
| EP | 0 470 290 | 2/1992 |
| EP | 0 567 725 | 11/1993 |
| EP | 0 286 118 | 1/1995 |
| EP | 0 680 727 | 11/1995 |
| EP | 0 724 859 | 8/1996 |
| EP | 0 805 574 | 11/1997 |
| EP | 1 897 488 | 12/1999 |
| EP | 0 973 289 | 1/2000 |
| EP | 0 678 308 | 5/2000 |
| EP | 1 048 264 | 11/2000 |
| EP | 1 177 802 | 2/2002 |
| EP | 0 729 366 | 7/2002 |
| EP | 1 292 218 | 3/2003 |
| EP | 1 077 634 | 7/2003 |
| EP | 1 092 390 | 7/2004 |
| EP | 1 568 309 | 8/2005 |
| EP | 1 630 898 | 3/2006 |
| EP | 1 666 091 | 6/2006 |
| EP | 1 669 020 | 6/2006 |
| EP | 1 703 697 | 9/2006 |
| EP | 1 704 889 | 9/2006 |
| EP | 1 704 893 | 9/2006 |
| EP | 1 729 128 | 12/2006 |
| EP | 0 987 982 | 1/2007 |
| EP | 1 956 371 | 8/2008 |
| EP | 1 972 270 | 9/2008 |
| EP | 2 031 534 | 3/2009 |
| EP | 2 060 284 | 5/2009 |
| EP | 1 897 487 | 11/2009 |
| EP | 1 897 492 | 11/2009 |
| EP | 2 113 864 | 11/2009 |
| EP | 1 681 992 | 4/2010 |
| EP | 2 201 969 | 6/2010 |
| EP | 1 448 489 | 8/2010 |
| EP | 1 971 396 | 8/2010 |
| EP | 1 725 163 | 12/2010 |
| EP | 2 260 757 | 12/2010 |
| EP | 1 413 245 | 6/2011 |
| EP | 2 327 362 | 6/2011 |
| EP | 2 327 984 | 6/2011 |
| EP | 2 335 587 | 6/2011 |
| EP | 2 153 382 | 2/2012 |
| EP | 2 284 773 | 2/2012 |
| EP | 1 789 116 | 5/2013 |
| EP | 3 251 597 | 11/2019 |
| EP | 3 632 314 | 4/2020 |
| EP | 3 632 315 | 4/2020 |
| EP | 3 851 045 | 7/2021 |
| EP | 3 730 044 | 12/2021 |
| EP | 3 730 045 | 3/2022 |
| EP | 3 766 408 | 4/2022 |
| EP | 3 928 688 | 6/2022 |
| EP | 4 111 949 | 7/2023 |
| EP | 3 300 658 B1 | 1/2024 |
| EP | 4 344 633 | 4/2024 |
| EP | 4 203 819 | 7/2024 |
| GB | 1 394 171 | 5/1975 |
| GB | 1 599 241 | 9/1981 |
| GB | 2 073 891 | 10/1981 |
| GB | 2 067 764 | 1/1984 |
| GB | 2 154 003 | 8/1985 |
| GB | 2 204 408 | 11/1988 |
| GB | 2 254 436 | 10/1992 |
| GB | 2 409 951 | 7/2005 |
| JP | 54-041191 | 4/1979 |
| JP | 55-010581 | 1/1980 |
| JP | 55-010583 | 1/1980 |
| JP | 55-010584 | 1/1980 |
| JP | 55-012406 | 1/1980 |
| JP | 56-163447 | 12/1981 |
| JP | 57-070448 | 4/1982 |
| JP | 60-173457 | 9/1985 |
| JP | 60-173458 | 9/1985 |
| JP | 60-173459 | 9/1985 |

(56)  References Cited

FOREIGN PATENT DOCUMENTS

| | | |
|---|---|---|
| JP | 62-085855 | 4/1987 |
| JP | 62-114747 | 5/1987 |
| JP | 63-058149 | 3/1988 |
| JP | 63-128252 | 5/1988 |
| JP | 63-139246 | 6/1988 |
| JP | 63-294799 | 12/1988 |
| JP | 63-317757 | 12/1988 |
| JP | 63-317758 | 12/1988 |
| JP | 01-114746 | 5/1989 |
| JP | 01-114747 | 5/1989 |
| JP | 01-124060 | 5/1989 |
| JP | 01-134244 | 5/1989 |
| JP | 01-156658 | 6/1989 |
| JP | 02-062958 | 3/1990 |
| JP | 02-120655 | 5/1990 |
| JP | 02-287145 | 11/1990 |
| JP | 02-310457 | 12/1990 |
| JP | 03-020752 | 1/1991 |
| JP | 03-026956 | 2/1991 |
| JP | 03-028752 | 2/1991 |
| JP | 03-500940 | 2/1991 |
| JP | 03-194458 | 8/1991 |
| JP | 03-202764 | 9/1991 |
| JP | 05-072171 | 3/1993 |
| JP | 05-196595 | 8/1993 |
| JP | 06-190050 | 7/1994 |
| JP | 07-055757 | 3/1995 |
| JP | 07-072585 | 3/1995 |
| JP | 07-182462 | 7/1995 |
| JP | 07-311196 | 11/1995 |
| JP | 08-285814 | 11/1996 |
| JP | 08-285815 | 11/1996 |
| JP | 09-021778 | 1/1997 |
| JP | 09-101280 | 4/1997 |
| JP | 09-285459 | 4/1997 |
| JP | 10-170471 | 6/1998 |
| JP | 10-305016 | 11/1998 |
| JP | 11-506629 | 6/1999 |
| JP | 11-225359 | 8/1999 |
| JP | 2003-144417 | 5/2003 |
| JP | 2004-033438 | 2/2004 |
| JP | 2004-214014 | 7/2004 |
| JP | 2004-520103 | 7/2004 |
| JP | 2004-520898 | 7/2004 |
| JP | 2004-358016 | 12/2004 |
| JP | 2006-021031 | 1/2006 |
| JP | 2006-280464 | 10/2006 |
| JP | 2006-527036 | 11/2006 |
| JP | 2007-510499 | 4/2007 |
| JP | 2007-152037 | 6/2007 |
| JP | 2008-506468 | 3/2008 |
| KR | 10-2017-0068964 | 6/2017 |
| SU | 1281988 | 1/1987 |
| WO | WO 89/05119 | 6/1989 |
| WO | WO 89/08713 | 9/1989 |
| WO | WO 90/05300 | 5/1990 |
| WO | WO 90/05910 | 5/1990 |
| WO | WO 91/01680 | 2/1991 |
| WO | WO 91/04704 | 4/1991 |
| WO | WO 91/15993 | 10/1991 |
| WO | WO 92/13271 | 8/1992 |
| WO | WO 94/02062 | 9/1994 |
| WO | WO 95/28878 | 2/1995 |
| WO | WO 96/25089 | 8/1996 |
| WO | WO 96/35370 | 11/1996 |
| WO | WO 96/39977 | 12/1996 |
| WO | WO 97/02847 | 1/1997 |
| WO | WO 97/19344 | 5/1997 |
| WO | WO 97/21457 | 6/1997 |
| WO | WO 97/33513 | 9/1997 |
| WO | WO 97/42882 | 11/1997 |
| WO | WO 97/42883 | 11/1997 |
| WO | WO 97/42886 | 11/1997 |
| WO | WO 97/42888 | 11/1997 |
| WO | WO 97/43962 | 11/1997 |
| WO | WO 98/04902 | 2/1998 |
| WO | WO 98/35053 | 8/1998 |
| WO | WO 98/56293 | 12/1998 |
| WO | WO 99/27849 | 6/1999 |
| WO | WO 99/28736 | 6/1999 |
| WO | WO 99/33504 | 7/1999 |
| WO | WO 99/56613 | 11/1999 |
| WO | WO 00/40159 | 7/2000 |
| WO | WO 00/49940 | 8/2000 |
| WO | WO 00/59370 | 10/2000 |
| WO | WO 00/60350 | 10/2000 |
| WO | WO 00/74753 | 12/2000 |
| WO | WO 00/78992 | 12/2000 |
| WO | WO 01/17875 | 3/2001 |
| WO | WO 01/52727 | 7/2001 |
| WO | WO 01/52935 | 7/2001 |
| WO | WO 01/54753 | 8/2001 |
| WO | WO 01/58348 | 8/2001 |
| WO | WO 02/15778 | 2/2002 |
| WO | WO 02/16905 | 2/2002 |
| WO | WO 02/50534 | 6/2002 |
| WO | WO 02/058537 | 8/2002 |
| WO | WO 02/100457 | 12/2002 |
| WO | WO 03/026728 | 4/2003 |
| WO | WO 03/028784 | 4/2003 |
| WO | WO 03/056319 | 7/2003 |
| WO | WO 03/057027 | 7/2003 |
| WO | WO 03/072164 | 9/2003 |
| WO | WO 03/073936 | 9/2003 |
| WO | WO 03/076893 | 9/2003 |
| WO | WO 03/082091 | 10/2003 |
| WO | WO 03/085372 | 10/2003 |
| WO | WO 2004/006982 | 1/2004 |
| WO | WO 2004/015539 | 2/2004 |
| WO | WO 2004/028337 | 4/2004 |
| WO | WO 2004/030726 | 4/2004 |
| WO | WO 2004/034024 | 4/2004 |
| WO | WO 2004/047445 | 6/2004 |
| WO | WO 2004/049237 | 6/2004 |
| WO | WO 2004/054445 | 7/2004 |
| WO | WO 2004/060436 | 7/2004 |
| WO | WO 2004/061420 | 7/2004 |
| WO | WO 2004/090503 | 10/2004 |
| WO | WO 2004/098405 | 11/2004 |
| WO | WO 2004/098682 | 11/2004 |
| WO | WO 2004/098683 | 11/2004 |
| WO | WO 2004/098684 | 11/2004 |
| WO | WO 2004/098685 | 11/2004 |
| WO | WO 2004/107971 | 12/2004 |
| WO | WO 2004/112602 | 12/2004 |
| WO | WO 2005/011779 | 2/2005 |
| WO | WO 2005/018450 | 3/2005 |
| WO | WO 2005/037184 | 4/2005 |
| WO | WO 2005/041766 | 5/2005 |
| WO | WO 2005/044116 | 5/2005 |
| WO | WO 2005/045744 | 5/2005 |
| WO | WO 2005/046780 | 5/2005 |
| WO | WO 2005/051170 | 6/2005 |
| WO | WO 2005/057175 | 6/2005 |
| WO | WO 2005/065538 | 7/2005 |
| WO | WO 2005/084534 | 9/2005 |
| WO | WO 2005/089103 | 9/2005 |
| WO | WO 2005/092177 | 10/2005 |
| WO | WO 2005/121785 | 12/2005 |
| WO | WO 2005/123186 | 12/2005 |
| WO | WO 2006/001024 | 1/2006 |
| WO | WO 2006/015922 | 2/2006 |
| WO | WO 2006/017358 | 2/2006 |
| WO | WO 2006/020212 | 2/2006 |
| WO | WO 2006/024671 | 3/2006 |
| WO | WO 2006/026741 | 3/2006 |
| WO | WO 2006/032653 | 3/2006 |
| WO | WO 2006/036145 | 4/2006 |
| WO | WO 2006/040083 | 4/2006 |
| WO | WO 2006/042811 | 4/2006 |
| WO | WO 2006/061354 | 6/2006 |
| WO | WO 2006/064397 | 6/2006 |
| WO | WO 2006/072035 | 7/2006 |
| WO | WO 2006/079114 | 7/2006 |

(56) References Cited

FOREIGN PATENT DOCUMENTS

| WO | WO 2006/086423 | 8/2006 |
| WO | WO 2006/094513 | 9/2006 |
| WO | WO 2006/108809 | 10/2006 |
| WO | WO 2006/110742 | 10/2006 |
| WO | WO 2006/114297 | 11/2006 |
| WO | WO 2006/118947 | 11/2006 |
| WO | WO 2006/121921 | 11/2006 |
| WO | WO 2006/124099 | 11/2006 |
| WO | WO 2007/002189 | 1/2007 |
| WO | WO 2007/007459 | 1/2007 |
| WO | WO 2007/016399 | 2/2007 |
| WO | WO 2007/019289 | 2/2007 |
| WO | WO 2007/027788 | 3/2007 |
| WO | WO 2007/041069 | 4/2007 |
| WO | WO 2007/041070 | 4/2007 |
| WO | WO 2007/041248 | 4/2007 |
| WO | WO 2007/053832 | 5/2007 |
| WO | WO 2007/056638 | 5/2007 |
| WO | WO 2007/065285 | 6/2007 |
| WO | WO 2007/089738 | 8/2007 |
| WO | WO 2007/092618 | 8/2007 |
| WO | WO 2007/097754 | 8/2007 |
| WO | WO 2007/101223 | 9/2007 |
| WO | WO 2007/120363 | 10/2007 |
| WO | WO 2007/126444 | 11/2007 |
| WO | WO 2007/140783 | 12/2007 |
| WO | WO 2007/143225 | 12/2007 |
| WO | WO 2007/149319 | 12/2007 |
| WO | WO 2008/001366 | 1/2008 |
| WO | WO 2008/014792 | 2/2008 |
| WO | WO 2008/021913 | 2/2008 |
| WO | WO 2008/031106 | 3/2008 |
| WO | WO 2008/031110 | 3/2008 |
| WO | WO 2008/039944 | 4/2008 |
| WO | WO 2008/042760 | 4/2008 |
| WO | WO 2008/048452 | 4/2008 |
| WO | WO 2008/051920 | 5/2008 |
| WO | WO 2008/051924 | 5/2008 |
| WO | WO 2008/052374 | 5/2008 |
| WO | WO 2008/061552 | 5/2008 |
| WO | WO 2008/062099 | 5/2008 |
| WO | WO 2008/065646 | 6/2008 |
| WO | WO 2008/073813 | 6/2008 |
| WO | WO 2008/086541 | 7/2008 |
| WO | WO 2008/103620 | 8/2008 |
| WO | WO 2008/114223 | 9/2008 |
| WO | WO 2008/115409 | 9/2008 |
| WO | WO 2008/128210 | 10/2008 |
| WO | WO 2008/129532 | 10/2008 |
| WO | WO 2008/130896 | 10/2008 |
| WO | WO 2008/130897 | 10/2008 |
| WO | WO 2008/130898 | 10/2008 |
| WO | WO 2008/133702 | 11/2008 |
| WO | WO 2008/138006 | 11/2008 |
| WO | WO 2008/143943 | 11/2008 |
| WO | WO 2008/144445 | 11/2008 |
| WO | WO 2008/147921 | 12/2008 |
| WO | WO 2008/150917 | 12/2008 |
| WO | WO 2008/153693 | 12/2008 |
| WO | WO 2008/155377 | 12/2008 |
| WO | WO 2008/157821 | 12/2008 |
| WO | WO 2009/007287 | 1/2009 |
| WO | WO 2009/010396 | 1/2009 |
| WO | WO 2009/016635 | 2/2009 |
| WO | WO 2009/016638 | 2/2009 |
| WO | WO 2009/018058 | 2/2009 |
| WO | WO 2009/035773 | 3/2009 |
| WO | WO 2009/039013 | 3/2009 |
| WO | WO 2009/062674 | 5/2009 |
| WO | WO 2009/062675 | 5/2009 |
| WO | WO 2009/066288 | 5/2009 |
| WO | WO 2009/068661 | 6/2009 |
| WO | WO 2009/086216 | 7/2009 |
| WO | WO 2009/096992 | 8/2009 |
| WO | WO 2009/097594 | 8/2009 |
| WO | WO 2010/062898 | 6/2010 |
| WO | WO 2010/077329 | 7/2010 |
| WO | WO 2010/091005 | 8/2010 |
| WO | WO 2010/099507 | 9/2010 |
| WO | WO 2010/112521 | 10/2010 |
| WO | WO 2010/141922 | 12/2010 |
| WO | WO 2011/000528 | 1/2011 |
| WO | WO 2011/002815 | 1/2011 |
| WO | WO 2011/015659 | 2/2011 |
| WO | WO 2011/022418 | 2/2011 |
| WO | WO 2011/025549 | 3/2011 |
| WO | WO 2011/104616 | 9/2011 |
| WO | WO 2011/119896 | 9/2011 |
| WO | WO 2011/119898 | 9/2011 |
| WO | WO 2012/103429 | 8/2012 |
| WO | WO 2013/090215 | 6/2013 |
| WO | WO 2016/183493 | 11/2016 |
| WO | WO 2017/027749 | 2/2017 |
| WO | WO 2017/116915 | 7/2017 |
| WO | WO 2017/134227 | 8/2017 |
| WO | WO 2018/136898 | 7/2018 |
| WO | WO 2018/166963 | 9/2018 |
| WO | WO 2019/005627 | 1/2019 |
| WO | WO 2019/236850 | 12/2019 |
| WO | WO 2019/236859 | 12/2019 |
| WO | WO 2019/236876 | 12/2019 |
| WO | WO 2022/046416 | 3/2022 |
| WO | WO 2022/060677 | 3/2022 |

OTHER PUBLICATIONS

AU, 2007309066 Examiner's Report, Aug. 16, 2013.
AU, 2008265541 Examiner's Report, Oct. 15, 2012.
AU, 2008265541 Examiner's Report, Nov. 29, 2013.
AU, 2010286917 Examiner's Report, Sep. 8, 2014.
AU, 2011230596 Examiner's Report, Feb. 28, 2014.
AU, 2011269796 Examiner's Report, Apr. 3, 2014.
AU, 2016201703 Examiner's Report, Mar. 22, 2017.
AU, 2017254903 Examiner's Report, Dec. 11, 2018.
AU, 2018200899 Examiner's Report, Dec. 6, 2018.
CA, 2,617,192 Examiner's Report, Oct. 22, 2012.
CA, 2,765,712 Examiner's Report, Apr. 10, 2017.
CA, 2,765,712 Examiner's Report, Mar. 27, 2018.
CA, 2,872,576 Examiner's Report, Feb. 17, 2015.
CA, 2,872,576 Examiner's Report, Feb. 19, 2016.
CA, 2,984,939 Examiner's Report, Nov. 15, 2023.
CA, 3,120,335 Examiner's Report, Mar. 31, 2023.
CA, 3,182,961 Examiner's Report, Mar. 29, 2023.
CA, 3,182,961 Examiner's Report, Dec. 6, 2023.
CN, 200780039416.2 Second Office Action, Apr. 25, 2012.
CN, 200780039416.2 First Office Action, Mar. 30, 2011.
CN, 200780045373.9 Notice of Allowance, May 18, 2011.
CN, 200780045373.9 Office Action, Apr. 14, 2010.
CN, 200880005388.7 Second Office Action, May 16, 2012.
CN, 200880005388.7 First Office Action, Jul. 25, 2011.
CN, 201080027344.1 Office Action, Jun. 5, 2014.
CN, 201080027344.1 Office Action, Feb. 6, 2015.
CN, 201080006480.2 Office Action, May 6, 2013.
CN, 201080006480.2 Office Action, Dec. 11, 2013.
CN, 201080006481.7 Office Action, Dec. 2, 2014.
CN, 201180002616.7 Office Action, Apr. 24, 2014.
CN, 201180002617.1 Office Action, Jul. 3, 2014.
CN, 20160144860.1 Office Action, Mar. 23, 2018.
CN, 20160144860.1 Office Action, Dec. 10, 2018.
CN, 20160144860.1 Office Action, May 23, 2019.
CN, 201980082748.1 First Office Action, Jan. 10, 2023.
CN, 201980082748.1 Second Office Action, Jul. 10, 2023.
CN, 201980082748.1 Final Office Action, Nov. 27, 2023.
EP, 06788869.3 Examination Report, Sep. 25, 2012.
EP, 06788869.3 Extended Search Report, Mar. 18, 2010.
EP, 06804122.7 Decision to Refuse the Application, Feb. 25, 2013.
EP, 06804122.7 Examination Report, Nov. 30, 2011.
EP, 06804122.7 Examination Report, Jan. 25, 2011.
EP, 06813967.4 Extended Search Report, Mar. 4, 2010.
EP, 06815715.5 Extended Search Report, Oct. 30, 2009.

(56) References Cited

OTHER PUBLICATIONS

EP, 06851063.5 Extended Search Report, Sep. 21, 2009.
EP, 07842173.2 Examination Report, Mar. 21, 2013.
EP, 07842173.2 Extended Search Report, Dec. 29, 2010.
EP, 07842180.7 Examination Report, Oct. 23, 2012.
EP, 07842180.7 Examination Report, Dec. 14, 2011.
EP, 07842180.7 Examination Report, Feb. 23, 2011.
EP, 07842180.7 Extended Search Report, Sep. 28, 2009.
EP, 07843396.8 Extended Search Report, Dec. 22, 2010.
EP, 07854298.2 Extended Search Report, Mar. 29, 2010.
EP, 08730066.1 Extended Search Report, Oct. 5, 2012.
EP, 10739015.5 Extended Search Report, May 10, 2013.
EP, 10739031.2 Extended Search Report, May 7, 2013.
EP, 10739031.2 Examination Report, Oct. 28, 2016.
EP, 10739031.2 Notice of Opposition, Dec. 20, 2018.
EP, 10739031.2 Reply to Notice of Opposition, May 21, 2019.
EP, 10739031.2 Reply to Notice of Opposition Reply, Aug. 8, 2019.
EP, 10739031.2 Summons to Attend Oral Proceedings, Sep. 17, 2019.
EP, 10739031.2 Written Submissions, Dec. 3, 2019.
EP, 10739031.2 Response to Written Submissions, Jan. 24, 2020.
EP, 10739031.2 Summons to Attend Oral Proceedings, May 20, 2020.
EP, 10739031.2 Written Submissions, Nov. 20, 2020.
EP, 10739031.2 Response to Written Submissions, Jan. 7, 2021.
EP, 10739031.2 Decision and Grounds for Revoking Patent, Jun. 9, 2021.
EP, 10739031.2 Grounds of Appeal, Oct. 19, 2021.
EP, 10739031.2 Response to Grounds of Appeal, Mar. 1, 2022.
EP, 10739031.2 Response to Response to Grounds of Appeal, Jul. 29, 2022.
EP, 10739031.2 Response to Response to Response to Grounds of Appeal, Jan. 18, 2023.
EP, 10812438.9 Extended Search Report, Dec. 10, 2013.
EP, 11760268.0 Decision of the Oral Proceedings, Sep. 27, 2022.
EP, 11760268.0 Minutes of Oral Proceedings, Aug. 11, 2022.
EP, 11760268.0 Communication from Board of Appeals, Mar. 31, 2022.
EP, 11760268.0 Response to Written Submissions, Jan. 14, 2020.
EP, 11760268.0 Response to Notice of Appeal, Sep. 5, 2019.
EP, 11760268.0 Statement of Grounds of Appeal, Apr. 23, 2019.
EP, 11760268.0 Grounds of Appeal, Apr. 18, 2019.
EP, 11760268.0 Notice of Appeal Abbott Diabetes Care Inc., Feb. 25, 2019.
EP, 11760268.0 Notice of Appeal Dexcom, Feb. 22, 2019.
EP, 11760268.0 Interlocutory Decision, Dec. 13, 2018.
EP, 11760268.0 Response to Summons to Attend Oral Proceedings, Sep. 13, 2018.
EP, 11760268.0 Letter Regarding the Opposition Procedure, Sep. 12, 2018.
EP, 11760268.0 Summons to Attend Oral Proceedings, Mar. 22, 2018.
EP, 11760268.0 Comments on Reply to Notice of Opposition, Dec. 27, 2017.
EP, 11760268.0 Reply to Notice of Opposition, Sep. 4, 2017.
EP, 11760268.0 Notice of Opposition, Mar. 29, 2017.
EP, 11760268.0 Extended Search Report, Apr. 14, 2014.
EP, 13000104.3 Extended Search Report, Mar. 12, 2013.
EP, 13000105.0 Examination Report, Oct. 18, 2016.
EP, 13000105.0 Minutes of the Oral Proceedings, Oct. 18, 2016.
EP, 13000105.0 Notice of Opposition, Jan. 4, 2019.
EP, 14179905.6 Summons to Attend Oral Proceedings, Apr. 10, 2017.
EP, 14179905.6 Notice of Opposition, May 19, 2016.
EP, 14179905.6 Extended Search Report, Dec. 23, 2014.
EP, 15002441.2 Extended Search Report, Dec. 18, 2015.
EP, 15184320.8 Examination Report, Apr. 18, 2017.
EP, 16176370.1 Extended Search Report, Dec. 7, 2016.
EP, 16793637.6 Extended Search Report, Oct. 9, 2018.
EP, 17182379.2 Extended Search Report, Feb. 21, 2018.

EP, 17201183.5 Extended Search Report, May 7, 2019.
EP, 17201183.5 Examination Report, May 7, 2019.
EP, 18192278.2 Extended Search Report, Mar. 13, 2019.
EP, 18208224.8 Extended Search Report, Oct. 11, 2019.
EP, 18741791.0 Examination Report, Dec. 15, 2023.
EP, 18741791.0 Extended Search Report, Sep. 23, 2020.
EP, 19151577.4 Extended Search Report, Aug. 16, 2019.
EP, 19151577.4 Examination Report, May 27, 2022.
EP, 19184881.1 Extended Search Report, Dec. 4, 2019.
EP, 19900891.3 Extended Search Report, Sep. 26, 2022.
EP, 20177703.4 Reply to Reply to Reply to Notice of Opposition ADC, Dec. 18, 2023.
EP, 20177703.4 Reply to Notice of Intervention, Nov. 17, 2023.
EP, 20177703.4 Reply to Reply to Notice of Opposition, Jun. 29, 2023.
EP, 20177703.4 Notice of Intervention, Jun. 23, 2023.
EP, 20177703.4 Reply to Notice of Opposition, Feb. 22, 2023.
EP, 20177703.4 Grounds of Opposition, Sep. 28, 2022.
EP, 20177703.4 Notice of Opposition, Sep. 28, 2022.
EP, 20177703.4 Examination Report, Jun. 25, 2021.
EP, 20177703.4 Extended Search Report, Sep. 25, 2020.
EP, 20177712.5 Response to Written Submissions Dexcomm, Feb. 26, 2024.
EP, 20177712.5 Reply to Reply to Reply to Notice of Opposition ADC, Dec. 18, 2023.
EP, 20177712.5 Reply to Notice of Intervention, Nov. 17, 2023.
EP, 20177712.5 Reply to Reply to Notice of Opposition Dexcom, Sep. 27, 2023.
EP, 20177712.5 Reply to Reply to Notice of Opposition Gulde & Partner Patent, Aug. 30, 2023.
EP, 20177712.5 Notice of Intervention, Jun. 23, 2023.
EP, 20177712.5 Reply to Notice of Opposition, May 23, 2023.
EP, 20177712.5 Grounds of Opposition Gulde & Partner Patent, Dec. 22, 2022.
EP, 20177712.5 Grounds of Opposition Dexcom, Dec. 22, 2022.
EP, 20177712.5 Notice of Opposition Gulde & Partner Patent, Dec. 22, 2022.
EP, 20177712.5 Notice of Opposition Dexcom, Dec. 22, 2022.
EP, 20177712.5 Extended Search Report, Sep. 30, 2020.
EP, 20195922.8 Response to Summons to Attend Oral Proceedings, Feb. 15, 2024.
EP, 20195922.8 Written Submissions Dexcom, Dec. 12, 2023.
EP, 20195922.8 Written Submissions ADC, Oct. 23, 2023.
EP, 20195922.8 Summons to Attend Oral Proceedings, Sep. 21, 2023.
EP, 20195922.8 Reply to Notice of Intervention, Aug. 29, 2023.
EP, 20195922.8 Reply to Reply to Notice of Opposition, Aug. 21, 2023.
EP, 20195922.8 Reply to Notice of Opposition, Jun. 20, 2023.
EP, 20195922.8 Notice of Intervention, Jun. 13, 2023.
EP, 20195922.8 Grounds of Opposition Dexcom, Jan. 26, 2023.
EP, 20195922.8 Notice of Opposition Dexcom, Jan. 26, 2023.
EP, 20195922.8 Extended Search Report, Dec. 16, 2020.
EP, 21152231.3 Extended Search Report, May 11, 2021.
EP, 21192910.4 Extended Search Report, Jan. 31, 2022.
EP, 21211041.5 Extended Search Report, Mar. 3, 2022.
EP, 22168031.7 Extended Search Report, Aug. 17, 2022.
EP, 22169853.3 Extended Search Report, Sep. 2, 2022.
EP, 23166498.8 Extended Search Report, Nov. 17, 2023.
EP, 23190032.5 Extended Search Report, Nov. 17, 2023.
IL, 198329 Office Action, Mar. 5, 2012.
JP, 2009-534798 Office Action, Sep. 25, 2012.
JP, 2009-534799 Final Office Action, Feb. 19, 2013.
JP, 2009-534799 Office Action, Sep. 27, 2011.
JP, 2012-526736 Office Action, Apr. 15, 2014.
JP, 2012-526736 Office Action, Dec. 16, 2014.
JP, 2013-501503 Office Action, Mar. 3, 2015.
JP, 2015-159805 Office Action, Aug. 9, 2016.
JP, 2016-44196 Office Action, Apr. 11, 2017.
JP, 2021-531135 Office Action, Aug. 9, 2023.
JP, 2021-531135 Office Action, Feb. 22, 2023.
MX, MX/a/2009/004322 Office Action, Mar. 11, 2013.
MX, MX/a/2009/004322 Office Action, Sep. 19, 2012.

(56)    References Cited

OTHER PUBLICATIONS

MX, MX/a/2009/004398 Office Action, Sep. 24, 2012.
MY, PI2021004760 Examination Report, Mar. 30, 2022.
MY, PI2021005830 Examination Report, Sep. 30, 2022.
MY, PI2021005830 Examination Report, Aug. 29, 2022.
MY, PI2022007295 Examination Report, Jul. 11, 2023.
MY, PI2023005466 Examination Report, Dec. 28, 2023.
NL, 2009963 Search Report, Aug. 12, 2023.
RU, 2009135048 Office Action, Dec. 20, 2011.
RU, 2009119430 Office Action, Jun. 5, 2011.
US, Third Declaration of Gary Fletcher, Ph.D., IPR No. 2024-00520, Jan. 31, 2024.
US, Petition For Inter Partes Review Of U.S. Pat. No. 11,266,335, IPR No. 2024-00520, Jan. 31, 2024.
US, Petition For Inter Partes Review Of U.S. Pat. No. 11,202,591, IPR No. 2023-01409, Oct. 11, 2023.
US, Petitioner's Explanation of Material Differences Between Petitions, IPR No. 2023-01397, Oct. 6, 2023.
US, Declaration of Gary D. Fletcher, Ph.D, IPR No. 2023-01396 and IPR No. 2023-01397, Oct. 6, 2023.
US, Petition For Inter Partes Review Of U.S. Pat. No. 11,266,335, IPR No. 2023-01397, Oct. 6, 2023.
US, Petitioner's Explanation of Material Differences Between Petitions, IPR No. 2023-01396, Oct. 6, 2023.
US, Petition For Inter Partes Review Of U.S. Pat. No. 11,266,335, IPR No. 2023-01396, Oct. 6, 2023.
US, Notice of Final Written Decision re Inter Partes Review of the '649 Patent, IPR No. 2022-00605, Jul. 13, 2023.
US, Final Written Decision, IPR No. 2022-00605, Jul. 10, 2023.
US, Record of Oral Hearing, IPR No. 2022-00605, Apr. 26, 2023.
US, Supplemental Declaration of Gary D. Fletcher, Ph.D, IPR No. 2022-00605, Jan. 11, 2023.
US, Petitioner's Reply to Patent Owner's Response to Petition, IPR No. 2022-00605, Jan. 11, 2023.
US, Second Declaration by Dr. Michael Cima in Support of Patent Owner's Response, IPR No. 2022-00605, Oct. 19, 2022.
US, Patent Owner's Response, IPR No. 2022-00605, Oct. 19, 2022.
US, Institution Decision, IPR No. 2022-00605, Jul. 27, 2022.
US, Patent Owner's Preliminary Sur-Reply, IPR No. 2022-00605, Jun. 28, 2022.
US, Petitioner's Preliminary Reply to Patent Owner's Preliminary Response, IPR No. 2022-00605, Jun. 21, 2022.
US, Patent Owner's Preliminary Response, IPR No. 2022-00605, May 24, 2022.
US, Petition for Inter Partes Review of U.S. Pat. No. 10,945,649, IPR No. 2022-00605, Feb. 15, 2022.
US, Institution Decision, IPR No. 2022-00637, Jul. 27, 2022.
US, Patent Owner's Preliminary Sur-Reply, IPR No. 2022-00637, Jun. 28, 2022.
US, Petitioner's Preliminary Reply to Patent Owner's Preliminary Response, IPR No. 2022-00637, Jun. 21, 2022.
US, Patent Owner's Preliminary Response, IPR No. 2022-00637, Jun. 9, 2022.
US, Petition for Inter Partes Review of U.S. Pat. No. 11,013,440, IPR No. 2022-00637, Feb. 8, 2022.
US, Reexamination U.S. Appl. No. 90/019,329 Order Granting Request for Reexamination of U.S. Pat. No. 11,013,440, Jan. 23, 2024.
US, Request for Ex Parte Reexamination Under 35.U.S.C. §§ 302-307 and 37 C.F.R. § 1.510 of U.S. Pat. No. 11,013,440, Dec. 11, 2023.
US, Reexamination U.S. Appl. No. 90/019,331 Order Granting Request for Reexamination of U.S. Pat. No. 11,000,216, Jan. 23, 2024.
US, Request for Ex Parte Reexamination Under 35.U.S.C. §§ 302-307 and 37 C.F.R. § 1.510 of U.S. Pat. No. 11,000,216, Dec. 11, 2023.
US, Reexamination U.S. Appl. No. 90/019,307 Order Granting Request for Reexamination of U.S. Pat. No. 10,973,443, Dec. 22, 2023.
US, Request for Ex Parte Reexamination Under 35.U.S.C. §§ 302-307 and 37 C.F.R. § 1.510 of U.S. Pat. No. 10,973,443, Nov. 27, 2023.
US, Request for Ex Parte Reexamination Under 35.U.S.C. §§ 302-307 and 37 C.F.R. § 1.510 of U.S. Pat. No. 10,959,654, Dec. 11, 2023.
US, Reexamination U.S. Appl. No. 95/002,162 Request to Review Order Denying Request for Reexamination, Dec. 13, 2012.
US, Reexamination U.S. Appl. No. 95/002,162 Order Denying Request for Reexamination, Nov. 13, 2012.
US, Request for Reexamination U.S. Appl. No. 95/002,162 of U.S. Pat. No. 8,175,673, Sep. 7, 2012.
US, Reexamination U.S. Appl. No. 95/002,113 Request to Review Order Denying Request for Reexamination, Dec. 13, 2012.
US, Reexamination U.S. Appl. No. 95/002,113 Order Denying Request for Reexamination, Nov. 13, 2012.
US, Request for Reexamination U.S. Appl. No. 95/002,113 of U.S. Pat. No. 6,990,366, Aug. 30, 2012.
US, Reexamination U.S. Appl. No. 90/011,730 Notice of Intent to Issue Ex Parte Reexamination Certificate, Apr. 5, 2012.
US, Reexamination U.S. Appl. No. 90/011,730 Office Action, Jan. 11, 2012.
US, Reexamination U.S. Appl. No. 90/011,730 Order Granting Request for Reexamination, Aug. 24, 2011.
US, Request for Reexamination U.S. Appl. No. 90/011,730 of U.S. Pat. No. 6,990,366, Jun. 3, 2011.
US, Reexamination U.S. Appl. No. 90/010,791 Ex Parte Reexamination Certificate, May 17, 2011.
US, Reexamination U.S. Appl. No. 90/010,791 Office Action, Dec. 17, 2010.
US, Reexamination U.S. Appl. No. 90/010,791 Office Action, May 28, 2010.
US, Reexamination U.S. Appl. No. 90/010,791 Order Granting Request for Reexamination, Feb. 22, 2010.
US, Request for Reexamination U.S. Appl. No. 90/010,791 of U.S. Pat. No. 6,990,366, Dec. 22, 2009.
US, Reexamination U.S. Appl. No. 90/009,328 Notice of Intent to Issue Ex Parte Reexamination Certificate, Nov. 20, 2009.
US, Reexamination U.S. Appl. No. 90/009,328 Office Action, Sep. 30, 2009.
US, Reexamination U.S. Appl. No. 90/009,328 Office Action, Aug. 4, 2009.
US, Reexamination U.S. Appl. No. 90/009,328 Order Granting Request for Reexamination, Dec. 9, 2008.
US, Request for Reexamination U.S. Appl. No. 90/009,328 of U.S. Pat. No. 6,990,366, Nov. 10, 2008.
US, Reexamination U.S. Appl. No. 90/009,104 Notice of Intent to Issue Ex Parte Reexamination Certificatem Nov. 20, 2009.
US, Reexamination U.S. Appl. No. 90/009,104 Office Action, Sep. 30, 2009.
US, Reexamination U.S. Appl. No. 90/009,104 Office Action, Aug. 4, 2009.
US, Reexamination U.S. Appl. No. 90/009,104 Office Action, Oct. 16, 2008.
US, Reexamination U.S. Appl. No. 90/009,104 Order Granting Request for Reexamination, Jun. 5, 2008.
US, Request for Reexamination U.S. Appl. No. 90/009,104 of U.S. Pat. No. 6,990,366, Apr. 8, 2008.
US, Reexamination U.S. Appl. No. 90/008,457 Notice of Intent to Issue Ex Parte Reexamination Certificate, Mar. 13, 2008.
US, Reexamination U.S. Appl. No. 90/008,457 Order Granting Request for Reexamination, Feb. 23, 2007.
US, Request for Reexamination U.S. Appl. No. 90/008,457 of U.S. Pat. No. 6,990,366, Jan. 23, 2007.
US, Request for Reexamination U.S. Appl. No. 90/008,172 of U.S. Pat. No. 6,990,366, Aug. 16, 2006.
US, Reexamination U.S. Appl. No. 90/007,910 Patent Board Decision, May 17, 2013.
US, Reexamination U.S. Appl. No. 90/007,910 Decision on Appeal, Jan. 18, 2011.
US, Reexamination U.S. Appl. No. 90/007,910 Advisory Action, Jul. 30, 2009.

(56) References Cited

OTHER PUBLICATIONS

US, Reexamination U.S. Appl. No. 90/007,910 Advisory Action, Feb. 6, 2009.

US, Reexamination U.S. Appl. No. 90/007,910 Examiner's Answer to Appeal Brief, Nov. 19, 2009.

US, Reexamination U.S. Appl. No. 90/007,910 Office Action, Oct. 2, 2008.

US, Reexamination U.S. Appl. No. 90/007,910 Office Action, Feb. 13, 2008.

US, Reexamination U.S. Appl. No. 90/007,910 Order Granting Request for Reexamination, Mar. 27, 2006.

US, Request for Reexamination U.S. Appl. No. 90/007,910 of U.S. Pat. No. 6,175,752, Feb. 1, 2006.

US, Reexamination U.S. Appl. No. 90/009,270 Order Denying Request for Reexamination, Dec. 1, 2008.

US, Request for Reexamination U.S. Appl. No. 90/009,270 of U.S. Pat. No. 6,175,752, Sep. 8, 2008.

US, Reexamination U.S. Appl. No. 90/009,497 Notice of Intent to Issue Reexamination Certificate, Aug. 23, 2010.

US, Reexamination U.S. Appl. No. 90/009,497 Order Granting Request, Jul. 30, 2009.

US, Request for Reexamination U.S. Appl. No. 90/009,497 of U.S. Pat. No. 6,175,752, Jun. 17, 2009.

WO, PCT/US2006/029541 ISR and Written Opinion, Apr. 24, 2007.

WO, PCT/US2006/033885 ISR and Written Opinion, Aug. 3, 2007.

WO, PCT/US2006/037312 ISR and Written Opinion, Apr. 17, 2007.

WO, PCT/US2006/037928 ISR and Written Opinion, Jul. 11, 2008.

WO, PCT/US2006/062690 ISR and Written Opinion, Jan. 2, 2008.

WO, PCT/US2007/078065 ISR and Written Opinion, Apr. 11, 2008.

WO, PCT/US2007/078073 ISR and Written Opinion, Apr. 11, 2008.

WO, PCT/US2007/079774 ISR and Written Opinion, Apr. 1, 2008.

WO, PCT/US2007/082114 ISR and Written Opinion, May 9, 2008.

WO, PCT/US2007/082121 ISR and Written Opinion, May 9, 2008.

WO, PCT/US2008/054186 ISR and Written Opinion, Aug. 8, 2008.

WO, PCT/US2008/065154 ISR and Written Opinion, Sep. 3, 2008.

WO, PCT/US2010/002401 ISR and Written Opinion, Nov. 12, 2010.

WO, PCT/US2010/022860 ISR and Written Opinion, Mar. 23, 2010.

WO, PCT/US2010/022928 ISR and Written Opinion, Mar. 21, 2010.

WO, PCT/US2010/047065 ISR and Written Opinion, Dec. 21, 2010.

WO, PCT/US2010/047381 ISR and Written Opinion, Oct. 15, 2010.

WO, PCT/US2010/047414 ISR and Written Opinion, Dec. 27, 2010.

WO, PCT/US2010/047415 ISR and Written Opinion, Oct. 25, 2010.

WO, PCT/US2010/050772 ISR and Written Opinion, Dec. 3, 2010.

WO, PCT/US2010/050888 ISR and Written Opinion, Nov. 29, 2010.

WO, PCT/US2010/051861 ISR and Written Opinion, Nov. 30, 2010.

WO, PCT/US2011/029881 ISR and Written Opinion, May 20, 2011.

WO, PCT/US2011/029883 ISR and Written Opinion, Jun. 2, 2011.

WO, PCT/US2011/029884 ISR and Written Opinion, Jun. 1, 2011.

WO, PCT/US2012/062551 ISR and Written Opinion, Jan. 2, 2013.

WO, PCT/US2012/068839 ISR and Written Opinion, Feb. 22, 2013.

WO, PCT/US2013/052397 ISR and Written Opinion, Dec. 2, 2013.

WO, PCT/US2016/032485 ISR and Written Opinion, Sep. 12, 2016.

WO, PCT/US2018/014745 ISR and Written Opinion, Jun. 4, 2018.

WO, PCT/US2019/035843 ISR and Written Opinion, Sep. 18, 2019.

WO, PCT/US2021/040541 ISR and Written Opinion, Dec. 20, 2021.

WO, PCT/US2021/045576 ISR and Written Opinion, Jan. 27, 2022.

WO, PCT/US2021/048086 ISR and Written Opinion, Feb. 28, 2022.

WO, PCT/US2021/050672 ISR and Written Opinion, Jan. 5, 2022.

WO, PCT/US2022/037291 ISR and Written Opinion, Nov. 22, 2022.

WO, PCT/US2022/037291 Invitation to Pay Additional Fees, Sep. 29, 2022.

WO, PCT/US2023/010054 ISR and Written Opinion, May 15, 2023.

WO, PCT/US2023/010054 Invitation to Pay Additional Fees, Mar. 24, 2023.

"Abbott Receives CE Mark for Freestyle® Libre, A Revolutionary Glucose Monitoring System for People With Diabetes", 2014, 7 pages.

Abruna, H. D., et al., "Rectifying Interfaces Using Two-Layer Films of Electrochemically Polymerized Vinylpyridine and Vinylbipyridine Complexes of Ruthenium and Iron on Electrodes", Journal of the American Chemical Society, 1981, vol. 103, No. 1, pp. 1-5.

ACCU-CHEK Compact Plus Owner's Booklet, 2008, pp. 1-100.

ACCU-CHEK Softclix Plus Lancet Device retrieved from https://web.archive.org/web/20061018055737/http://www.accu-check.com/us/rewrite/content/en_US/2.1.7.1:10/article/ACCM_general_article_3303.htm, 2006, pp. 1-2.

Affidavit of Richard Paragas signed on May 18, 2016, pp. 1-4.

Affidavit of Paul Neale signed on May 18, 2016, pp. 1-2.

Ahson, S., et al., "RFID Handbook: Applications, Technology, Security, and Privacy", 2008, Chapter 4, Far-Field Tag Antenna Design Methodology, and Chapter 13, RFID Tags for Metallic Object Identification, pp. 71 and 253-254.

Albery, W.J., et al., "Amperometric Enzyme Electrodes Part II: Conducting Salts as Electrode Materials for the Oxidation of Glucose Oxidase", Journal of ElectroAnalytical Chemistry, 1985, vol. 194, pp. 223-235.

Albery, W.J., et al., "Amperometric Enzyme Electrodes", Philosophical Transactions of the Royal Society of London, 1987, vol. 316, pp. 107-119.

Alcock, S J, et al., "Continuous analyte monitoring to aid clinical practice," IEEE Engineering in Medicine & BioloXY Magazine, 1994, vol. 13. pp. 319-325.

"Alcove", Webster's New College Dictionary, 2001, p. 26.

Ambade, V. N., et al., "Methods for Estimation of Blood Glucose: A Comparative Evaluation", Medical Journal Armed Forces India, 1998, vol. 54, No. 2, pp. 131-133.

Anderson, A. J., "Foundations of Computer Technology", 1994, pp. 55-57.

Anderson, L. B., et al., "Thin-Layer Electrochemistry: Steady-State Methods of Studying Rate Processes", Journal of ElectroAnalytical Chemistry, 1965, vol. 10, pp. 295-305.

Application Note AN048, Antenna Part No. FR05-S1-N-0-102, Compact Reach Xtend™, Bluetooth®, 802.11b/g WLAN Chip Antenna, 2008, pp. 1-13.

Application Note AVR2023—AT86RF231 PCB reference design for antenna diversity, Atmel Corporation, 2008, pp. 1-15.

Application Note nRF9E5 RF and antenna layout, Nordic Semiconductor, 2006, pp. 1-13.

Armour, J. C., et al., "Application of Chronic Intravascular Blood Glucose Sensor in Dogs," Diabetes, 1990, vol. 39, pp. 1519-1526.

ASTM International, Designation D2240-05, 2010, pp. 1-13.

Aussedat, B., et al., "A User-Friendly Method for Calibrating a Subcutaneous Glucose Sensor-Based Hypoglycemic Alarm", Biosensors & Bioelectronics, 1997, vol. 12, No. 11, pp. 1061-1071.

Bartlett, P. N., et al., "Covalent Binding of Electron Relays to Glucose Oxidase", Journal of the Chemical Society, Chemical Communications, 1987, pp. 1603-1604.

Bartlett, P. N., et al., "Modification of Glucose Oxidase by Tetrathiafulvalene", Journal of the Chemical Society, Chemical Communications, 1990, pp. 1135-1136.

Benkič, K., et al., "Using RSSI value for distance estimation in Wireless sensor networks based on ZigBee", 15th International Conference on Systems, Signals and Image Processing, Bratislava, Slovakia, 2008, pp. 1-4.

Bennion, N., et al., "Alternate Site Glucose Testing: A Crossover Design", Diabetes Technology & Therapeutics, 2002, vol. 4, No. 1, pp. 25-33.

Bindra, D.S., et al., "Pulsed Amperometric Detection of Glucose in Biological Fluids at a Surface-Modified Gold Electrode", American Chemical Society, 1989, vol. 61, No. 22, pp. 2566-2570.

Bindra, D.S., et al., "Design and in Vitro Studies of a Needle-Type Glucose Sensor for Subcutaneous Monitoring," Anal. Chem., 1991, vol. 63, No. 17, pp. 1692-1696.

(56)                    References Cited

OTHER PUBLICATIONS

Biosensors: Fundamentals and Applications, Turner et al., Eds., 1987, pp. 1-786.

Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, 2002, vol. 4624, pp. 1-10.

"Bluetooth Antenna Design", National Semiconductor Application Note, 2005, pp. 1-16.

Bluetooth Core Specification 4.0, Jun. 30, 2010, Master Table of Contents & Compliance Requirements, pp. 1-89.

Bobbioni-Harsch, E et al., "Lifespan of subcutaneous glucose sensors and their performances during dynamic glycaemia changes in rats," J. Biomed. Eng., 1993, vol. 15, pp. 457-463.

Boise, M., "Dexcom CEO Kevin Sayer Explains G6", 2018, retrieved from https://beyondtype1.org/dexcom-ceo-kevin-sayer-explains-g6/, 9 pages.

Bonnett, A. H., et al., "Squirrel-Cage Rotor Options for AC Induction Motors", IEEE Transactions on Industry Applications, 2001, vol. 37, No. 4, pp. 1197-1209.

Brandt, J., et al., "Covalent Attachment of Proteins to Polysaccharide Carriers by Means of Benzoquinone", Biochimica et Biophysica Acta, 1975, vol. 386, pp. 196-202.

Breton, M. D., et al., "Optimum Subcutaneous Glucose Sampling and Fourier Analysis of Continuous Glucose Monitors", Journal of Diabetes Science and Technology, 2008, vol. 2, No. 3, pp. 495-500.

Brooks, S. L., et al., "Development of an On-Line Glucose Sensor for Fermentation Monitoring", Biosensors, 1987/88, vol. 3, pp. 45-56.

Brownlee, M., et al., "A Glucose-Controlled Insulin-Delivery System: Semisynthetic Insulin Bound to Lectin", Science, 1979, vol. 206, pp. 1190-1191.

Bühling, K. J., et al., "Optimal timing for postprandial glucose measurement in pregnant women with diabetes and a non-diabetic pregnant population evaluated by the Continuous Glucose Monitoring System (CGMS®)", Journal of Perinatal Medicine, 2005, vol. 33, No. 2, pp. 125-131.

Callaway, Jr., E. H., "Wireless Sensor Networks: Architectures and Protocols", 2004, Chapter 8, Antennas and the Definition of RF Performance, pp. 201-202.

Cass, A.E.G et al., "Ferrocene-Mediated Enzyme Electrode for Amperometric Determination of Glucose," Anal. Chem., 1984, vol. 56, No. 4, pp. 667-671.

Cass, A.E.G et al., "Ferricinium Ion as an Electron Acceptor for Oxido-Reductases", Journal of ElectroAnalytical Chemistry, 1985, vol. 190, pp. 117-127.

Castner, J. F., et al., "Mass Transport and Reaction Kinetic Parameters Determined Electrochemically for Immobilized Glucose Oxidase", Biochemistry, 1984, vol. 23, No. 10, pp. 2203-2210.

Certified Copy of U.S. Appl. No. 60/424,099, filed Nov. 5, 2002.

Certified True Copy of Preliminary Amendment filed on Apr. 20, 2018 for U.S. Pat. No. 10,827,954, 7 pages.

Certified True Copy of Excerpts of the File History of U.S. Pat. No. 10,973,443, 22 pages.

CGMs Changing Diabetes Management: Kevin Sayer, DIC Interview Transcript, 2019, retrieved from https://www.diabetesincontrol.com/cgms-changing-diabetes-management-kevin-sayer-dic-interview-transcript/, 10 pages.

Cheyne, E.H., et al., "Performance of a Continuous Glucose Monitoring System During Controlled Hypoglycaemia in Healthy Volunteers", Diabetes Technology & Therapeutics, 2002, vol. 4, No. 5, pp. 607-613.

Choleau, C., et al., "Calibration of a Subcutaneous Amperometric Glucose Sensor Implanted for 7 Days in Diabetic Patients Part 2. Superiority of the One-Point Calibration Method", Biosensor & Bioelectronics, 2002, vol. 17, No. 8, pp. 647-654.

Choleau, C., et al., "Calibration of a Subcutaneous Amperometric Glucose Sensor Part 1. Effect of Measurement Uncertainties on the Determination of Sensor Sensitivity and Background Current", Biosensor & Bioelectronics, 2002, vol. 17, No. 8, pp. 641-646.

Claremont, D. J., et al., "Biosensors for Continuous In Vivo Glucose Monitoring", Proceedings of the Annual International Conference of the IEEE Engineering in Medicine and Biology Society, 1988, vol. 10, pp. 1-2.

Clark Jr., L. C., et al., "Electrode Systems for Continuous Monitoring in Cardiovascular Surgery", Annals New York Academy of Sciences, 1962, pp. 29-45.

Clark Jr., L. C., et al., "Differential Anodic Enzyme Polarography for the Measurement of Glucose", Oxygen Transport to Tissue: Instrumentation, Methods, and Physiology, 1973, pp. 127-133.

Clark Jr., L. C., et al., "Long-term Stability of Electroenzymatic Glucose Sensors Implanted in Mice", American Society of Artificial Internal Organs Transactions, 1988, vol. XXXIV, pp. 259-265.

Clarke, W. L., et al., "Evaluating Clinical Accuracy of Systems for Self-Monitoring of Blood Glucose", Diabetes Care, 1987, vol. 10, No. 5, pp. 622-628.

Clarke, W., et al., "Statistical Tools to Analyze Continuous Glucose Monitor Data", Diabetes Technology & Therapeutics, 2009, vol. 11, Suppl. 1, pp. S-45-S-54.

Cleo™ 90 Infusion Set, 510(k) Summary of Safety and Effectiveness, Aug. 10, 2004, pp. 1-618.

Cleo® 90 Infusion Set Training Guide, 2011, 1 page.

Compact Plus Blood Glucose Meter retrieved from https://web.archive.org/web/20090316065810/http://www.accu-check.com/us/rewrite/content/en_US/2.1.9:0/article/ACCM_general_article_5136.htm, 2009, pp. 1-3.

Complaint Abbott Diabetes Care Inc. v. Dexcom, Inc. U.S. District Court Delaware C.A. No. 05-590 filed Aug. 11, 2005.

Complaint, Amended, Abbott Diabetes Care Inc. v. Dexcom, Inc. U.S. District Court Delaware C.A. No. 05-590 filed Jun. 27, 2006.

Complaint Abbott Diabetes Care Inc. v. Dexcom, Inc. U.S. District Court Delaware C.A. No. 06-514 filed Aug. 17, 2006.

Cox, M., "An Overview of Continuous Glucose Monitoring Systems", Journal of Pediatric Health Care, 2009, vol. 23, No. 5, pp. 344-347.

Csöregi, E., et al., "Design and Optimization of a Selective Subcutaneously Implantable Glucose Electrode Based on 'Wired' Glucose Oxidase", Analytical Chemistry, 1995, vol. 67, No. 7, pp. 1240-1244.

Csöregi, E., et al., "Design, Characterization, and One-Point in Vivo Calibration of a Subcutaneously Implanted Glucose Electrode", Analytical Chemistry, 1994, vol. 66 No. 19, pp. 3131-3138.

Csöregi, E., et al., "On-Line Glucose Monitoring by Using Microdialysis Sampling and Amperometric Detection Based on 'Wired' Glucose Oxidase in Carbon Paste", Mikrochimica Acta, 1995, vol. 121, pp. 31-40.

Cullen, M.T., et al., "The Changing Presentations of Diabetic Ketoacidosis During Pregnancy", Amer. J. Perinatol, 1996, vol. 13, No. 7, pp. 449-451 (abstract only).

In Vivo Glucose Sensing, Cunningham et al., Eds., 2010, Chemical Analysis, vol. 174, pp. 1-466.

Darley, J., "Is your user experience as good as your technology?", 2019, retrieved from https://www.massdevice.com/is-your-user-experience-as-good-as-your-technology/, pp. 1-16.

Davis, G., "Electromechanical Techniques for the Development of Amperometric Biosensors", Biosensors, 1985, vol. 1, pp. 161-178.

De Block, C., et al., "Minimally-Invasive and Non-Invasive Continuous Glucose Monitoring Systems: Indications, Advantages, Limitations and Clinical Aspects", Current Diabetes Reviews, 2008, vol. 4, No. 3, pp. 159-168.

"Deciding When to Submit a 510(k) for a Change to an Existing Device, Guidance for Industry and Food and Drug Administration Staff", 2017, pp. 1-77.

"Deciding When to Submit a 510(k) for a Software Change to an Existing Device, Guidance for Industry and Food and Drug Administration Staff", 2017, pp. 1-31.

IPR2022-00605 (Ex. 2001) Declaration of Michael Cima, Ph.D dated May 24, 2022, pp. 1-70.

IPR2022-00637 (Ex. 2001) Declaration of Michael Cima, Ph.D dated Jun. 9, 2022, pp. 1-79.

IPR2022-00605 (Ex. 1003) Declaration of Gary D. Fletcher, Ph.D dated Feb. 15, 2022, pp. 1-122.

(56)         References Cited

OTHER PUBLICATIONS

IPR2022-00605 (Ex. 1003) Corrected Declaration of Gary D. Fletcher, Ph.D dated Feb. 18, 2022, pp. 1-124.
IPR2022-00637 (Ex. 1035) Second Declaration of Gary D. Fletcher, Ph.D dated Feb. 28, 2022, pp. 1-136.
Decuir, J., "Bluetooth 4.0: Low Energy", IEEE SCV Consultants' Network of Silicon Valley, 2012, pp. 1-68.
Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", The Journal of Physical Chemistry, 1987, vol. 91, No. 6, pp. 1285-1289.
Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", Journal of the American Chemical Society, 1988, vol. 110, No. 8, pp. 2615-2620.
Degani, Y., et al., "Electrical Communication Between Redox Centers of Glucose Oxidase and Electrodes via Electrostatically and Covalently Bound Redox Polymers", Journal of the American Chemical Society, 1989, vol. 111, pp. 2357-2358.
Dehez, B., et al., "Development of a Spherical Induction Motor With Two Degrees of Freedom", IEEE Transactions on Magnetics, 2006, vol. 42, No. 8, pp. 2077-2089.
Delve Talks: Jake Leach, Dexcom, retrieved from https://www.delve.com/podcasts/delve-talks-jake-leach-dexcom, 2019, pp. 1-9.
Dementyev, A., et al., "Power Consumption Analysis of Bluetooth Low Energy, ZigBee and ANT Sensor Nodes in a Cyclic Sleep Scenario", IEEE International Wireless Symposium (IWS), 2013, Beijing, China, pp. 1-4.
Denisevich, P., et al., "Unidirectional Current Flow and Charge State Trapping at Redox Polymer Interfaces on Bilayer Electrodes: Principles, Experimental Demonstration, and Theory", Journal of the American Chemical Society, 1981, vol. 103, pp. 4727-4737.
"Dexcom CEO tells investors not to fear new competition from Abbott's Freestyle Libre", 2017, retrieved from https://www.mobihealthnews.com/content/dexcom-ceo-tells-investors-not-to-fear-new-competition-abbotts-freestyle-libre, pp. 1-3.
Dexcom CEO—Prime Position in Our Market—Mad Money—CNBC.mp4, Transcript 2023 by Sonix, 2 pages.
DexCom (DXCM) 2017 Q4 Earnings Call Transcript, 2017, retrieved from https://docoh.com/transcript/1093557/2017Q4/DXCM, 11 pages.
DexCom (DXCM) Q1 2018 Results—Earnings Call Transcript, 2018, retrieved from https://seekingalpha.com/article/4168949-dexcom-dxcm-q1-2018-results-earnings-call-transcript, 4 pages.
Dexcom, Inc. NasdaqGS:DXCM Company Conference Presentation, 2019, 10 pages.
Dexcom, Inc. NasdaqGS:DXCM Company Conference Presentation, 2020, 9 pages.
Dexcom, Inc. NasdaqGS:DXCM Company Conference Presentation, 2021, 16 pages.
Dexcom G5 Mobile System User Guide, 2020, pp. 1-410.
Dexcom G6 Continuous Glucose Monitoring System User Guide, 2019, pp. 1-27.
Dexcom G6 Start Here Set up Guide, 2019, pp. 1-8.
Dexcom G6 Using Your G6 Guide, Mar. 2020, pp. 1-7.
Dexcom G6, Winner Health & Wellness Award, Core77 Design Awards, 2019, retrieved from https://designawards.core77.com/health-wellness/85111/Dexcom-G6, pp. 1-8.
Dexcom G7 Inserting Sensor Instructions for Use, 2021, pp. 1-2.
Dexcom G7, Start Here, Operational Manual, 2022, pp. 1-9 (English Abstract).
Dexcom G7, User Guide, 2022, p. 1-179 (English Abstract).
Dexcom Seven® Plus Continuous Glucose Monitoring System User's Guide, 2011, pp. 1-144.
DexCom™ STS™ Continuous Glucose Monitoring System User's Guide, 2006, pp. 1-57.
DexCom™ STS™ Continuous Glucose Monitoring System Summary of Safety and Effectiveness Data, 2006, 20 pages.
DexCom™ STS™ Sensor Instructions for Use, 2006, pp. 1-6.

Dexcom STS-7 Continuous Glucose Monitoring System FDA Premarket Approval (PMA), 2007, pp. 1-7.
Dexcom STS®-7 Continuous Glucose Monitoring System Summary of Safety and Effectiveness Data, 2007, 14 pages.
Dexcom STS®-7 Continuous Glucose Monitoring System User's Guide, 2007, pp. 1-74.
Dicks, J.M., et al., "Ferrocene Modified Polypyrrole with Immobilised Glucose Oxidase and its Application in Amperometric Glucose Microbiosensors", Annales de Biologie Clinique, 1989, vol. 47, pp. 607-619.
Diem, P., et al., "Clinical Performance of a Continuous Viscometric Affinity Sensor for Glucose", Diabetes Technology & Therapeutics, 2004, vol. 6, pp. 790-799.
Diglas, J., et al., "Reduced pain perception with Pen Mate™, an automatic needle insertion device for use with an insulin pen", Practical Diabetes International, 1999, vol. 16, No. 2, pp. 39-41.
"Does Dexcom Really Have a Future If It Can't Match Abbott's Scale", 2019, retrieved from https://www.sprucepointcap.com/reports/dxcm_research_thesis_3-21-2019.pdf, p. 46.
ECMA International Standard ECMA-340, Near Field Communication Interface and Protocol (NFCIP-1), 2nd Edition, 2004, pp. 1-65.
El-Khatib, F. H, et al., "Adaptive Closed-Loop Control Provides Blood-Glucose Regulation Using Subcutaneous Insulin and Glucagon Infusion in Diabetic Swine", Journal of Diabetes Science and Technology, 2007, vol. 1, No. 2, pp. 181-192.
Ellis, C. D., et al., "Selectivity and Directed Charge Transfer through an Electroactive Metallopolymer Film", Journal of the American Chemical Society, 1981, vol. 103, No. 25, pp. 7480-7483.
Email from John Shaw of Shaw & Keller dated May 16, 2023, 2 pages.
Email chain from Sophie Hood, oldest email dated Jan. 24, 2023, 5 pages.
Engstrom, R. C., "Electrochemical Pretreatment of Glassy Carbon Electrodes", Analytical Chemistry, 1982, vol. 54, No. 13, pp. 2310-2314.
Engstrom, R. C., et al., "Characterization of Electrochemically Pretreated Glassy Carbon Electrodes", Analytical Chemistry, 1984, vol. 56, No. 2, pp. 136-141.
European Standard, ISO 11607-1, Packaging for terminally sterilized medical devices—Part 1: Requirements for materials, sterile barrier systems and packaging systems, 2006, 32 pages.
European Standard, ISO 13485, Medical devices—Quality management systems—Requirement for regulatory purposes, 2003, 69 pages.
European Standard, ISO 15197, In vitro diagnostic test systems—Requirements for blood glucose monitoring systems for self-testing in managing diabetes mellitus, 2003, 43 pages.
Explore the Monroe Street Market Community, retrieved from https://www.monroestreetmarket.com/floor-plans/apartment/B-231 on May 10, 2023, 2 pages.
Facchinetti, A., et al., "A New Index to Optimally Design and Compare Continuous Glucose Monitoring Glucose Prediction Algorithms", Diabetes Technology & Therapeutics, 2011, vol. 13, No. 2, pp. 111-119.
"FDA authorizes first fully interoperable continuous glucose monitoring system, streamlines review pathway for similar devices", FDA News Release, 2018, retrieved from https://www.fda.gov/news-events/press-announcements/fda-authorizes-first-fully-interoperable-continuous-glucose-monitoring-system-streamlines-review, 3 pages.
Feldman, B., et al., "Electron Transfer Kinetics at Redox Polymer/Solution Interfaces Using Microelectrodes and Twin Electrode Thin Layer Cells", Journal of ElectroAnalytical Chemistry, 1985, vol. 194, pp. 63-81.
Feldman, B., et al., "A Continuous Glucose Sensor Based on Wired Enzyme™ Technology—Results from a 3-Day Trial in Patients with Type 1 Diabetes", Diabetes Technology & Therapeutics, 2003, vol. 5, No. 5, pp. 769-779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.
File History of U.S. Pat. No. 10,292,632.

US 12,605,185 B2

Page 26

(56) References Cited

OTHER PUBLICATIONS

File History of U.S. Pat. No. 10,945,649.
File History of U.S. Pat. No. 11,013,440.
U.S. Appl. No. 60/587,787.
U.S. Appl. No. 10/633,367.
U.S. Appl. No. 12/250,760.
Fischer, H., et al., "Intramolecular Electron Transfer Medicated by 4,4'-Bypyridine and Related Bridging Groups", Journal of the American Chemical Society, 1976, vol. 98, No. 18, pp. 5512-5517.
Food and Drug Administration, HHS, 2009, Code of Federal Regulation § 820.30, Subpart C-Design Controls, pp. 147-148.
Foulds, N. C., et al., "Enzyme Entrapment in Electrically Conducting Polymers: Immobilisation of Glucose Oxidase in Polypyrrole and its Application in Amperometric Glucose Sensors", Journal of the Chemical Society, Faraday Transactions 1, 1986, vol. 82, pp. 1259-1264.
Foulds, N. C., et al., "Immobilization of Glucose Oxidase in Ferrocene-Modified Pyrrole Polymers", Analytical Chemistry, 1988, vol. 60, No. 22, pp. 2473-2478.
Freedman, D., et al., Statistics: Second Edition, 1991, Chapter 5, p. 74.
Freestyle Libre Pro Flash Glucose Monitoring System Summary of Safety and Effectiveness Data, 2016, 31 pages.
FreeStyle Lite Blood Glucose Monitoring System Owner's Booklet, 2006, 15 pages.
FreeStyle Navigator Continuous Glucose Monitoring System FDA Premarket Approval (PMA), 2008, pp. 1-7.
Freestyle Navigator Continuous Glucose Monitor FDA Premarket Approval (PMA), May 2022, pp. 1-6.
Freestyle Navigator Summary of Safety and Effectiveness Data, 2008, pp. 1-27.
Freestyle Navigator User's Guide, 2008, pp. 1-195.
Frenzel, L. E., "Printed-Circuit-Board Antennas", retrieved from https://www.electronicdesign.com/technologies/boards/article/21751417/printedcircuitboard-antennasprint/3266, Electronic Design, 2005, pp. 1-4.
Frew, J. E., et al., "Electron-Transfer Biosensors", Philosophical Transactions of the Royal Society of London, 1987, vol. 316, pp. 95-106.
Fujipoly Silver ZEBRA® Connector Data Sheet FSDS 01-34, Version 5, 2006, pp. 1-7.
Garg, S., et al., "Improvement in Glycemic Excursions with a Transcutaneous, Real-Time Continuous Glucose Sensor", Diabetes Care, 2006, vol. 29, No. 1, pp. 44-50.
Garibotto, J., et al., "An Innovative Application of Shape Memory Alloy Technology Yields a Novel Therapeutic Approach to Diabetes Management", Insulet Corporation, 2006, p. A41.
Gilligan, B. J., et al., "Evaluation of a Subcutaneous Glucose Sensor out to 3 Months in a Dog Model", Diabetes Care, 1994, vol. 17, No. 8, pp. 882-887.
Gonzales, W. V., et al., "The Progress of Glucose Monitoring—A Review of Invasive to Minimally and Non-Invasive Techniques, Devices and Sensors", Sensors, 2019, vol. 19, No. 800, pp. 1-45.
Gonzalez, O. L., et al., "Low-Cost Wireless Sensors—Designer Reference Manual", Freescale Semiconductor, 2007, pp. 1-146.
Gorton, L., et al., "Selective Detection in Flow Analysis Based on the Combination of Immobilized Enzymes and Chemically Modified Electrodes", Analytica Chimica Acta, 1991, vol. 250, pp. 203-248.
Gregg, B. A., et al., "Cross-Linked Redox Gels Containing Glucose Oxidase for Amperometric Biosensor Applications," Analytical Chemistry, 1990, vol. 62, No. 3, pp. 258-263.
Gregg, B. A., et al., "Redox Polymer Films Containing Enzymes. 1. A Redox-Conducting Epoxy Cement: Synthesis, Characterization, and Electrocatalytic Oxidation of Hydroquinone", Journal of Physical Chemistry, 1991, vol. 95, No. 15, pp. 5970-5975.
Gregg, T. H., "How Continuous Glucose Monitoring is Transforming Diabetes Treatment", Qualcomm Life Connect, 2013, pp. 1-33.
Guardian® RT Continuous Glucose Monitoring System REF MMT-7900 User Guide, 2005, pp. 1-128.

Guerci, B., et al., "Clinical Performance of CGMS in Type 1 Diabetic Patients Treated by Continuous Subcutaneous Insulin Infusion Using Insulin Analogs", Diabetes Care, 2003, vol. 26, No. 3, pp. 582-589.
Guerra, S., et al., "A Dynamic Risk Measure from Continuous Glucose Monitoring Data", Diabetes Technology & Therapeutics, 2011, vol. 13, No. 8, pp. 843-852.
Güler, N. F., et al., "Theory and Applications of Biotelemetry", Journal of Medical Systems, 2002, vol. 26, No. 2, pp. 159-178.
Gunasingham, et al., "Electrochemically Modulated Optrode for Glucose", Biosensors & Bioelectronics, 1992, vol. 7, pp. 353-359.
Hale, P. D., et al., "A New Class of Amperometric Biosensor Incorporating a Polymeric Electron-Transfer Mediator", Journal of the American Chemical Society, 1989, vol. 111, No. 9, pp. 3482-3484.
Hao, Y., "Wireless body sensor networks for health-monitoring applications", Physiol. Meas., 2008, vol. 29, R27-R56.
Harrison, D. J. et al., "Characterization of Perfluorosulfonic Acid Polymer Coated Enzyme Electrodes and a Miniaturized Integrated Potentiostat for Glucose Analysis in Whole Blood," Anal. Chem., 1988, vol. 60, No. 19, pp. 2002-2007.
Hawkridge, F. M., et al., "Indirect Coulometric Titration of Biological Electron Transport Components", Analytical Chemistry, 1973, vol. 45, No. 7, pp. 1021-1027.
Heftman, G., "Chip Antenna Reduces Cell-Phone Dimensions", Microwaves & RF, 1999, p. 182.
Heise, T., et al., "Hypoglycemia Warning Signal and Glucose Sensors: Requirements and Concepts", Diabetes Technology & Therapeutics, 2003, vol. 5, No. 4, pp. 563-571.
Heller, A., "Electrical Connection of Enzyme Redox Centers to Electrodes," J. Phys. Chem., 1992, vol. 96, No. 9, pp. 3579-3587.
Heller, A., "Electrical Wiring of Redox Enzymes," Acc. Chem. Res., 1990, vol. 23, No. 5, pp. 129-134.
Heller, A., et al., "Amperometric Biosensors Based on Three-Dimensional Hydrogel-Forming Epoxy Networks", Sensors and Actuators B, 1993, vol. 13-14, pp. 180-183.
Heller, A., "Implanted Electrochemical Glucose Sensors for the Management of Diabetes", Annnu. Rev. Biomed. Eng., 1999, vol. 1, pp. 153-175.
Hemmerich, K. J., et al., "Sterilization Methods Stand the Test of Time", 2004, retrieved from https://www.mddionline.com/sterilization/sterilization-methods-stand-test-time, pp. 1-8.
Hirsch, I. B., "Realistic Expectations and Practical Use of Continuous Glucose Monitoring for the Endocrinologist", The Journal of Clinical Endocrinology & Metabolism, 2009, vol. 94, No. 7, pp. 2232-2238.
Hirsch, I. B., "Introduction: History of Glucose Monitoring", Clinical Compendia, 2018, vol. 2018, No. 1, 1 page.
Hoel, P. G., Elementary Statistics: Fourth Edition, 1976, Chapter 5, pp. 113-114.
Hoss, U., et al., "Continuous glucose monitoring in the tissue: Do we really need to calibrate in-vivo?", Feb. 28, 2009, pp. 1-21.
Hoss, U., et al., "Continuous Glucose Monitoring in Subcutaneous Tissue Using Factory-Calibrated Sensors: A Pilot Study", Diabetes Technology & Therapeutics, 2010, vol. 12, No. 8, pp. 591-597.
Hoss, U., et al., "Feasibility of Factory Calibration for Subcutaneous Glucose Sensors in Subjects With Diabetes", Journal of Diabetes Science and Technology, 2014, vol. 8, No. 1, pp. 89-94.
"Housing", "recess", "release", and "retain", Merriam-Webster's Collegiate Dictionary, Tenth Edition, 1999, pp. 563, 975, 987, and 999.
"Housing" and "recess", The New Penguin English Dictionary, 2000, pp. 678 and 1167.
Howe, D., "Comparing the Dexcom G6 to the G5", 2018, retrieved from https://beyondtype1.org/comparing-the-dexcom-g6-to-the-g5/, pp. 1-10.
Huang, Y., et al., "Antennas from Theory to Practice", 2008, Chapter 8, Antenna Diversity, pp. 322-325.
Hughes, M. D., "The Business of Self-Monitoring of Blood Glucose: A Market Profile", Journal of Diabetes Science and Technology, 2009, vol. 3, No. 5, pp. 1219-1223.

(56) References Cited

OTHER PUBLICATIONS

Ianniello, R. M., et al., "Immobilized Enzyme Chemically Modified Electrode as an Amperometric Sensor", Analytical Chemistry, 1981, vol. 53, No. 13, pp. 2090-2095.
Ianniello, R. M., et al., "Differential Pulse Voltammetric Study of Direct Electron Transfer in Glucose Oxidase Chemically Modified Graphite Electrodes", Analytical Chemistry, 1982, vol. 54, No. 7, pp. 1098-1101.
IEEE 100 The Authoritative Dictionary of IEEE Standards Terms, Seventh Edition, 2000, 3 pages.
Ikeda, T., et al., "Kinetics of Outer-Sphere Electron Transfers Between Metal Complexes in Solutions and Polymeric Films on Modified Electrodes", Journal of the American Chemical Society, 1981, vol. 103, No. 25, pp. 7422-7425.
Ikeda, T., et al., "Glucose Oxidase-Immobilized Benzoquinone-Carbon Paste Electrode as a Glucose Sensor", Agricultural and Biological Chemistry, 1985, vol. 49, No. 2, pp. 541-543.
Ikeda, T., et al., "Artificial Pancreas—Investigation of the Stability of Glucose Sensors Using a Telemetry System" (English language translation of abstract), Jpn. J. Artif. Organs, 1990, vol. 19, No. 2, pp. 889-892.
International Standard, ISO 14971, Medical devices—Application of risk management to medical devices, 2007, 90 pages.
"An Interview with Kevin Sayer, President and CEO of Dexcom, About The New G6", 2021, 5 pages.
"In Vitro Diagnostic Products for Human Use", Federal Register, 1974, vol. 39, No. 126, pp. 24136-24147.
Isermann, R., "Supervision, Fault-Detection and Fault-Diagnosis Methods—An Introduction", Control Engineering Practice, 1997, vol. 5, No. 5, pp. 639-652.
Isermann, R., et al., "Trends in the Application of Model-Based Fault Detection and Diagnosis of Technical Processes", Control Engineering Practice, 1997, vol. 5, No. 5, pp. 709-719.
Jain, A.K., et al., "Wound Rotor Induction Generator With Sensorless Control and Integrated Active Filter for Feeding Nonlinear Loads in a Stand-Alone Grid", IEEE Transactions on Industrial Electronics, 2008, vol. 55, No. 1, pp. 218-228.
James, Jr., et al., "Handbook of Microstrip Antennas", 1969, pp. 1038-1047.
Johnson, J. M., et al., "Potential-Dependent Enzymatic Activity in an Enzyme Thin-Layer Cell", Analytical Chemistry, 1982, vol. 54, No. 8, pp. 1377-1383.
Johnson, K. W., "Reproducible Electrodeposition of Biomolecules for the Fabrication of Miniature Electroenzymatic Biosensors", Sensors and Actuators B, 1991, vol. 5, pp. 85-89.
Johnson, K. W., et al., "In vivo evaluation of an electroenzymatic glucose sensor implanted in subcutaneous tissue," Biosensors and Bioelectronics, 1992, vol. 7, pp. 709-714.
Johnson, P. C., "Peripheral Circulation", John Wiley & Sons, 1978, p. 198.
Jonsson, G., et al., "An Amperometric Glucose Sensor Made by Modification of a Graphite Electrode Surface With Immobilized Glucose Oxidase and Adsorbed Mediator", Biosensors, 1985, vol. 1, pp. 355-368.
Josowicz, M., et al., "Electrochemical Pretreatment of Thin Film Platinum Electrodes", Journal of the Electrochemical Society, 1988, vol. 135, No. 1, pp. 112-115.
Jovanovic, L., "The Role of Continuous Glucose Monitoring in Gestational Diabetes Mellitus", Diabetes Technology & Therapeutics, 2000, vol. 2, Supplement 1, pp. S-67-S-71.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", Diabetes Care, 2001, vol. 24, No. 7, pp. 1303-1304.
Kal, S., "Basic Electronics—Devices, Circuits and IT Fundamentals", 2006, Chapter 13, Microcomputers and Microprocessors, p. 412.

Kaplan, S. M., "Wiley Electrical and Electronics Engineering Dictionary", IEEE Press, 2004, pp. 141, 142, 548, 549.
Katakis, I., et al., "L-α-Glycerophosphate and $_L$-Lactate Electrodes Based on the Electrochemical 'Wiring' of Oxidases", Analytical Chemistry, 1992, vol. 64, No. 9, pp. 1008-1013.
Katakis, I., et al., "Electrostatic Control of the Electron Transfer Enabling Binding of Recombinant Glucose Oxidase and Redox Polyelectrolytes", Journal of the American Chemical Society, 1994, vol. 116, No. 8, pp. 3617-3618.
Kenausis, G., et al., "'Wiring' of Glucose Oxidase and Lactate Oxidase Within a Hydrogel Made with Poly(vinyl pyridine) complexed with [Os(4,4'-dimethoxy-2,2'-bipyridine) $_2$Cl] $^{+/2+}$", Journal of the Chemical Society, Faraday Transactions, 1996, vol. 92, No. 20, pp. 4131-4136.
Klonoff, D. C., "A Review of Continuous Glucose Monitoring Technology", Diabetes Technology & Therapeutics, 2005, vol. 7, No. 5, pp. 770-775.
Klueh, U., et al., "Inflammation and Glucose Sensors: Use of Dexamethasone to Extend Glucose Sensor Function and Life Span in Vivo", Journal of Diabetes Science and Technology, 2007, vol. 1, No. 4, pp. 496-504.
Klueh, U., et al., "Blood-Induced Interference of Glucose Sensor Function in Vitro: Implications for in Vivo Sensor Function", Journal of Diabetes Science and Technology, 2007, vol. 1, No. 6, pp. 842-849.
Kondepati, V., et al., "Recent Progress in Analytical Instrumentation for Glycemic Control in Diabetic and Critically Ill Patients", Analytical Bioanalytical Chemistry, 2007, vol. 388, pp. 545-563.
Koudelka, M., et al., "In-Vivo Behaviour of Hypodermically Implanted Microfabricated Glucose Sensors", Biosensors & Bioelectronics, 1991, vol. 6, pp. 31-36.
Kovatchev, B. P., et al., "Evaluating the Accuracy of Continuous Glucose-Monitoring Sensors", Diabetes Care, 2004, vol. 27, No. 8, pp. 1922-1928.
Kulys, J., et al., "Mediatorless Peroxidase Electrode and Preparation of Bienzyme Sensors", Bioelectrochemistry and Bioenergetics, 1990, vol. 24, pp. 305-311.
Lager, W., et al., "Implantable Electrocatalytic Glucose Sensor", Hormone Metabolic Research, 1994, vol. 26, pp. 526-530.
León, L. P., et al., "Continuous-Flow Analysis for Glucose in Serum, with Use of Hexokinase and Glucose-6-Phosphate Dehydrogenase Co-Immobilized in Tubular Form", Clinical Chemistry, 1980, vol. 26, No. 1, pp. 123-129.
Lindner, E., et al., "Flexible (Kapton-Based) Microsensor Arrays of High Stability for Cardiovascular Applications", Journal of the Chemical Society, Faraday Transactions, 1993, vol. 89, No. 2, pp. 361-367.
Lo, B., et al., "Key Technical Challenges and Current Implementations of Body Sensor Networks", Body Sensor Networks, 2005, pp. 1-5.
Lodwig, V., et al., "Continuous Glucose Monitoring with Glucose Sensors: Calibration and Assessment Criteria", Diabetes Technology & Therapeutics, 2003, vol. 5, No. 4, pp. 573-587.
Lortz, J., et al., "What is Bluetooth? We Explain The Newest Short-Range Connectivity Technology", Smart Computing Learning Series, Wireless Computing, 2002, vol. 8, Issue 5, pp. 72-74.
Loy, M., et al., "ISM-Band and Short Range Device Antennas", Texas Instruments Application Report, 2005, pp. 1-38.
Maidan, R. et al., "Elimination of Electroaxidizable Interferant-Produced Currents in Amperometric Biosensors," Analytical Chemistry, 1992, vol. 64, No. 23, pp. 2889-2896.
Malin, S. F., et al., "Noninvasive Prediction of Glucose by Near-Infrared Diffuse Reflectance Spectroscopy", Clinical Chemistry, 1999, vol. 45, No. 9, pp. 1651-1658.
Mastrototaro, J.J., et al., "An Electroenzymatic Glucose Sensor Fabricated on a Flexible Substrate," Sensors and Biosensors B Chemical, 1991, B5, pp. 139-144.
Mauras, N., et al., "Lack of Accuracy of Continuous Sensors in Healthy, Nondiabetic Children: Results of the Diabetes Research in Children Network (DirecNet) Accuracy Study", Journal of Pediatrics, 2004, pp. 770-775.

(56)             References Cited

OTHER PUBLICATIONS

Mcgarraugh, G., et al., "Glucose Measurements Using Blood Extracted from the Forearm and the Finger", TheraSense, Inc., 2001, 16 Pages.

Mcgarraugh, G., et al., "Physiological Influences on Off-Finger Glucose Testing", Diabetes Technology & Therapeutics, 2001, vol. 3, No. 3, pp. 367-376.

Mckean, B., et al., "A Telemetry-Instrumentation System for Chronically Implanted Glucose and Oxygen Sensors," IEEE Transactions on Biomedical Engineering, 1988, vol. 35, No. 7, pp. 526-532.

Mcneil, C. J., et al., "Thermostable Reduced Nicotinamide Adenine Dinucleotide Oxidase: Application to Amperometric Enzyme Assay", Analytical Chemistry, 1989, vol. 61, No. 1, pp. 25-29.

Medtronic Guardian® REAL-Time Continuous Glucose Monitoring System User Guide, 2006, pp. 1-181.

Medtronic Guardian® REAL-Time Continuous Glucose Monitoring System User Guide, 2006, pp. 1-184.

Medtronic MiniMed Guardian RT FDA Premarket Approval (PMA), 2005, pp. 1-6.

Medtronic MiniMed Guardian RT Summary of Safety and Effectiveness Data, 2005, 13 pages.

Medtronic MiniMed Paradigm® REAL-TIME 522 and 722 Insulin Pumps User Guide, 2008, pp. 1-262.

Medtronic MiniMed Sen-Serter® User Guide, 2006, pp. 1-96.

IPR2022-00605 (Ex. 1027) The Merriam-Webster Dictionary, Merriam Webster, Incorporated (2005), pp. 66, 403, and 415.

Microchip Technology Inc., MRF24J40MA Data Sheet, 2008, pp. 1-30.

IPR2022-00605 (Ex. 2008) MiniMed® Glucose Sensor, REF MMT-7002, Instructions for Use, May 1999, pp. 1-4.

Minimed Technologies, "Tape Tips and Other Infusion Site Information", 1995.

Minimed Quick-set™ retrieved from https://web.archive.org/web/20010412224824/http://www.minimed.com/patientfam/pf_ipt_pumpinfusion_quickset.shtml, Apr. 12, 2001, pp. 1-2.

Minimed Sof-set Micro QR® Sof-set Ultimate QR® retrieved from https://web.archive.org/web/20010412225617/http://www.minimed.com/patientfam/pf_ipt_pumpinfusion_sofset.shtml, Apr. 12, 2001, pp. 1-2.

Miyawaki, O., et al., "Electrochemical and Glucose Oxidase Coenzyme Activity of Flavin Adenine Dinucleotide Covalently Attached to Glassy Carbon at the Adenine Amino Group", Biochimica et Biophysica Acta, 1985, vol. 838, pp. 60-68.

Moatti-Sirat, D., et al., "Evaluating In Vitro and In Vivo the Interference of Ascorbate and Acetaminophen on Glucose Detection by a Needle-Type Glucose Sensor", Biosensors & Bioelectronics, 1992, vol. 7, pp. 345-352.

Moatti-Sirat, D., et al., "Reduction of Acetaminophen Interference in Glucose Sensors by a Composite Nafion Membrane: Demonstration in Rats and Man", Diabetologia, 1994, vol. 37, pp. 610-616.

Moatti-Sirat, D., et al., "Towards Continuous Glucose Monitoring: In Vivo Evaluation of a Miniaturized Glucose Sensor Implanted for Several Days in Rat Subcutaneous Tissue," Diabetolocia, 1992, vol. 35, No. 3 (1 page—Abstract only).

IPR2022-00605 (Ex. 2003) "Monitoring Your Blood Sugar", retrieved from https://www.cdc.gov/diabetes/managing/managing-blood-sugar/bloodglucosemonitoring.html, 2021, pp. 1-3.

Moore, B., "The Potential Use of Radio Frequency Identification Devices for Active Monitoring of Blood Glucose Levels", Journal of Diabetes Science and Technology, 2009, vol. 3, No. 1, pp. 180-183.

Morak, J., et al., "Design and Evaluation of a Telemonitoring Concept Based on NFC-Enabled Mobile Phones and Sensor Devices", IEEE Transactions on Information Technology in Biomedicine, 2012, vol. 16, No. 1, pp. 17-23.

Morbiducci, U., et al., "Improved Usability of the Minimal Model of Insulin Sensitivity Based on an Automated Approach and Genetic algorithms for Parameter Estimation", Clinical Science, vol. 112, 2007, pp. 257-263.

Mougiakakou, S. G., et al., "A Real Time Simulation Model of Glucose-Insulin Metabolism for Type 1 Diabetes Patients", Proceedings of the 2005 IEEE, 2005, pp. 298-301.

Movassaghi, S., et al., "Wireless Technologies for Body Area Networks: Characteristics and Challenges", 2012 International Symposium on Communications and Information Technologies (ISCIT), 2012, Gold Coast, QLD, Australia, pp. 42-47.

"Murata Puts Antenna on a Chip", Passives, 1999, vol. 44, 1 page.

Nagy, G., et al., "A New Type of Enzyme Electrode: The Ascorbic Acid Eliminator Electrode", Life Sciences, 1982, vol. 31, No. 23, pp. 2611-2616.

Nakamura, S., et al., "Effect of Periodate Oxidation on the Structure and Properties of Glucose Oxidase", Biochimica et Biophysica Acta., 1976, vol. 445, pp. 294-308.

Narasimham, K., et al., "p-Benzoquinone Activation of Metal Oxide Electrodes for Attachment of Enzymes", Enzyme and Microbial Technology, 1985, vol. 7, pp. 283-286.

Occupational Safety and Health Admin., Labor, 2003, 29 CFR § 1910.1030 Bloodborne pathogens, pp. 260-273.

Ohara, T. J., et al., "Glucose Electrodes Based on Cross-Linked [Os(bpy)$_2$Cl]$^{+/2+}$ Complexed Poly(1-vinylimadazole) Films," Analytical Chemistry, 1993, vol. 65, No. 23, pp. 3512-3516.

Ohara, T. J., et al., "'Wired' Enzyme Electrodes for Amperometric Determination of Glucose or Lactate in the Presence of Interfering Substances", Analytical Chemistry, 1994, vol. 66, No. 15, pp. 2451-2457.

Ohara, T. J., "Osmium Bipyridyl Redox Polymers Used in Enzyme Electrodes", Platinum Metals Review, 1995, vol. 39, No. 2, pp. 54-62.

Olievier, C. N., et al., "In Vivo Measurement of Carbon Dioxide Tension with a Miniature Electrodes", Pflugers Archiv: European Journal of Physiology, 1978, vol. 373, pp. 269-272.

Omnipod image, Exhibit 182 of ADC Reply Brief SJ, Daubert, Sep. 22, 2022, 2 pages.

OmniPod Insulet UST400 User Manual, 2011, pp. 1-190.

OneTouch® Ultra™ Blood Glucose Monitoring System Owner's Booklet, 2000, 23 pages.

OneTouch Ultra2 Blood Glucose Monitoring System Owner's Booklet, 2005, 34 pages.

Opinion of the Court, Supreme Court of the United States, No. 04-1350, *KSR International co.,* Petitioner v. *Teleflex Inc et al.,* Apr. 30, 2007.

Order, Federal Communications Commission, 2006, pp. 1-8.

Osmonics, Poretics® Polycarbonate Membrane; Product Leaflet; Engineering Purity, 2002, pp. 1-2.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", Journal of ElectroAnalytical Chemistry, 1989, vol. 260, pp. 487-494.

Palleschi, G., et al., "A Study of Interferences in Glucose Measurements in Blood by Hydrogen Peroxide Based Glucose Probes", Analytical Biochemistry, 1986, vol. 159, pp. 114-121.

Pankratov, I., et al., "Sol-Gel Derived Renewable-Surface Biosensors", Journal of ElectroAnalytical Chemistry, 1995, vol. 393, pp. 35-41.

Panteleon, A. E., et al., "The Role of the Independent Variable to Glucose Sensor Calibration", Diabetes Technology & Therapeutics, 2003, vol. 5, No. 3, pp. 401-410.

Parker, S. P., ed., McGraw-Hill Dictionary of Mechanical and Design Engineering, 1984 (excerpted), pp. 1-4.

Parker, R., et al., "Robust H∞ Glucose Control in Diabetes Using a Physiological Model", AIChE Journal, 2000, vol. 46, No. 12, 2000, pp. 2537-2549.

Passey, R. B., et al., "Evaluation and Comparison of 10 Glucose Methods and the Reference Method Recommendation in the Proposed Product Class Standard (1974)", Clinical Chemistry, 1977, vol. 23, No. 1, pp. 131-139.

Pathak, C., et al., "Rapid Photopolymerization of Immunoprotective Gels in Contact with Cells and Tissue", Journal of the American Chemical Society, 1992, vol. 114, No. 21, pp. 8311-8312.

(56) References Cited

OTHER PUBLICATIONS

Patton, S. R., et al., "Continuous Glucose Monitoring Versus Self-monitoring of Blood Glucose in Children with Type 1 Diabetes—Are there Pros and Cons for Both?", US Endocrinol., 2012, vol. 8, No. 1, pp. 27-29.

Pickup, J., "Developing Glucose Sensors for In Vivo Use", Tibtech, 1993, vol. 11, pp. 285-291.

Pickup, J., et al., "Implantable Glucose Sensors: Choosing the Appropriate Sensing Strategy", Biosensors, 1987/88, vol. 3, pp. 335-346.

Pickup, J. C., et al., "In Vivo Molecular Sensing In Diabetes Mellitus: An Implantable Glucose Sensor With Direct Electron Transfer," Diabetologia, 1989, vol. 32, No. 3, pp. 213-217.

Pickup, J., et al., "Potentially-Implantable, Amperometric Glucose Sensors with Mediated Electron Transfer: Improving the Operating Stability", Biosensors, 1989, vol. 4, pp. 109-119.

Pishko, M. V., et al., "Amperometric Glucose Microelectrodes Prepared Through Immobilization of Glucose Oxidase in Redox Hydrogels," Anal. Chem., 1991, vol. 63, No. 20, pp. 2268-2272.

Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", Diabetologia, 1993, vol. 36, pp. 658-663.

Poitout, V., et al., "Calibration in Dogs of a Subcutaneous Miniaturized Glucose Sensor Using a Glucose Meter for Blood Glucose Determination", Biosensors & Bioelectronics, 1992, vol. 7, pp. 587-592.

Poitout, V., et al., "In Vitro and in Vivo Evaluation in Dogs of a Miniaturized Glucose Sensor," ASAIO Transactions, 1991, vol. 37, No. 3 (1 page—Abstract only).

Pollak, A., et al., "Enzyme Immobilization by Condensation Copolymerization into Cross-Linked Polyacrylamide Gels", Journal of the American Chemical Society, 1980, vol. 102, No. 20, pp. 6324-6336.

Program, 2nd International Conference on Advanced Technologies & Treatments for Diabetes, Athens, Greece, 2009, 3 pages.

Quinn, C. P., et al., "Kinetics of Glucose Delivery to Subcutaneous Tissue in Rats Measured with 0.3-mm Amperometric Microsensors", The American Physiological Society, 1995, E155-E161.

Ratner, B. D., "Reducing Capsular Thickness and Enhancing Angeiogenesis Around Implant Drug Release Systems", Journal of Controlled Release, 2002, vol. 78, pp. 211-218.

Reach, G., et al., "Can Continuous Glucose Monitoring Be Used for the Treatment of Diabetes?", Analytical Chemistry, 1992, vol. 64, No. 6, pp. 381-386.

Rebrin, K., et al., "Automated Feedback Control of Subcutaneous Glucose Concentration in Diabetic Dogs," Diabetologia, 1989, vol. 32, No. 8, pp. 573-576.

"Recess", Cambridge Dictionary of American English, 2000, pp. 710-711.

Repas, R., "Sensor Sense: RFID for smart position sensing", retrieved from https://www/machinedesign/com/automation-iiot/article/21818777/sensor-sense-rfid-for-smart-position-sensing, 2010, pp. 1-2.

"Retract", The Chambers Dictionary, 1998, p. 1410.

"Retract", The New Oxford American Dictionary, 2001, p. 1455.

"Retract", Webster's Third New International Dictionary, 1993, pp. 1939-1940.

Rodriguez, N., et al., "Flexible Communication and Control Protocol for Injectable Neuromuscular Interfaces", IEEE Transactions on Biomedical Circuits and Systems, 2007, vol. 1, No. 1, pp. 19-27.

Roe, J. N., et al., "Bloodless Glucose Measurements", Critical Review in Therapeutic Drug Carrier Systems, vol. 15, Issue 3, 1998, pp. 199-241.

IPR2022-00605 (Ex. 1024) "Rotor," Dictionary of Mechanical Engineering, Fourth Ed., G.H.F. Nayler, Society of Automotive Engineers, Inc., 1996, p. 328.

IPR2022-00605 (Ex. 1025) "Rotor," Random House Kernerman Webster's College Dictionary, K Dictionaries Ltd. (2010), available at https://www.thefreedictionary.com/rotor.

IPR2022-00605 (Ex. 1026) "Rotate," Random House Kernerman Webster's College Dictionary, K Dictionaries Ltd. (2010), available at https://www.thefreedictionary.com/rotate.

Sakakida, M., et al., "Ferrocene-mediated needle-type glucose sensor covered with newly designed biocompatible membrane," Sensors and Actuators B, 1993, vols. 13-14, pp. 319-322.

Sakakida, M., et al., "Development of ferrocene-mediated needle-type glucose sensor as a measure of true subcutaneous tissue glucose concentrations", Artif Organs Today, 1992, vol. 2, No. 2, pp. 145-458.

Salditt, P., "Trends in Medical Device Design and Manufacturing", SMTA News and Journal of Surface Mount Technology, 2004, vol. 17, pp. 19-24.

Salehi, C., et al., "A Telemetry-Instrumentation System for Long-Term Implantable Glucose and Oxygen Sensors", Analytical Letters, 1996, vol. 29, No. 13, pp. 2289-2308.

Samuels, G. J., et al., "An Electrode-Supported Oxidation Catalyst Based on Ruthenium (IV). pH "Encapsulation" in a Polymer Film", Journal of the American Chemical Society, 1981, vol. 103, No. 2, pp. 307-312.

Sandham, W., et al., "Blood Glucose Prediction for Diabetes Therapy Using a Recurrent Artificial Neural Network", 9th European Signal Processing Conference, 1998, Rhodes, Greece, pp. 1-4.

Sasso, S. V., et al., "Electropolymerized 1,2-Diaminobenzene as a Means to Prevent Interferences and Fouling and to Stabilize Immobilized Enzyme in Electrochemical Biosensors", Analytical Chemistry, 1990, vol. 62, No. 11, pp. 1111-1117.

IPR2022-00605 (Ex. 1013) Scheduling Order in *Abbott Diabetes Care Inc., et al.* v. *Dexcom, Inc.,* 1:21-cv-00977 (D. Del.), dated Dec. 2, 2021.

Scheller, F., et al., "Enzyme Electrodes and Their Application", Philosophical Transactions of the Royal Society of London B, 1987, vol. 316, pp. 85-94.

Schmehl, R. H., et al., "The Effect of Redox Site Concentration on the Rate of Mediated Oxidation of Solution Substrates by a Redox Copolymer Film", Journal of ElectroAnalytical Chemistry, 1983, vol. 152, pp. 97-109.

Schmidt, F. J., et al., "Calibration of a Wearable Glucose Sensor", The International Journal of Artificial Organs, 1992, vol. 15, No. 1, pp. 55-61.

Schmidtke, D. W., et al., "Accuracy of the One-Point In Vivo Calibration of "Wired" Glucose Oxidase Electrodes Implanted in Jugular Veins of Rats in Periods of Rapid Rise and Decline of the Glucose Concentration", Analytical Chemistry, 1998, vol. 70, No. 10, pp. 2149-2155.

Schmidtke, D. W., et al., "Measurement and Modeling of the Transient Difference Between Blood and Subcutaneous Glucose Concentrations in the Rat After Injection of Insulin", Proceedings of the National Academy of Sciences, 1998, vol. 95, pp. 294-299.

Schoepke, E., "Chip Antenna Layout Considerations for 802.11 Applications", Johanson Technology, 2006, retrieved from https://www.johansontechnology.com/chip-antenna-layout-considerations-for-802-11-applications, pp. 1-7.

Sharawi, M. S., "Use of low-cost patch antennas in modern wireless technology", IEEE Potentials, 2006, pp. 35-38 and 47.

Shaw, G. W., et al., "In Vitro Testing of a Simply Constructed, Highly Stable Glucose Sensor Suitable for Implantation in Diabetic Patients", Biosensors & Bioelectronics, 1991, vol. 6, pp. 401-406.

Shenoi, B. A., ed., Introduction to Digital Signal Processing and Filter Design, 2006, "Introduction", Chapter 1, pp. 1-30.

Shichiri, M., et al., "Glycaemic Control in Pancreatectomized Dogs with a Wearable Artificial Endocrine Pancreas," Diabetologia, 1983, vol. 24, No. 3, pp. 179-18.

Shichiri, M., et al., "Membrane Design for Extending the Long-Life of an Implantable Glucose Sensor", Diabetes Nutrition and Metabolism, 1989, vol. 2, pp. 309-313.

Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.

Shichiri, M., et al., "Telemetry Glucose Monitoring Device with Needle-type Glucose Sensor: A Useful Tool for Blood Glucose Monitoring in Diabetic Individuals," Diabetes Care, 1986, vol. 9, No. 3, pp. 298-301.

(56)                References Cited

OTHER PUBLICATIONS

Shichiri, M., et al., "In Vivo Characteristics of Needle-Type Glucose Sensor—Measurement of Subcutaneous Glucose Concentrations in Human Volunteers," Horm Metab Res Suppl. 1988, vol. 20, pp. 17-20.

Shichiri, M., et al., "Wearable Artificial Endocrine Pancreas With Needle-Type Glucose Sensor," The Lancet, 1982, vol. 2, No. 8308, pp. 1129-1131.

Shults, M., "A Telemetry-Instrumentation System for Monitoring Multiple Subcutaneously Implanted Glucose Sensors," IEEE Transactions on Biomedical Engineering, 1994, vol. 41, No. 10, pp. 937-942.

Sittampalam, G., et al., "Surface-Modified Electrochemical Detector for Liquid Chromatography", Analytical Chemistry, 1983, vol. 55, No. 9, pp. 1608-1610.

Smith, S. S., ed., The Scientist and Engineer's Guide to Digital Signal Processing, Second Edition, 1997-1999, "Digital Signal Processors", Chapter 28, pp. 503-534.

Soegijoko, S., et al., "External Artificial Pancreas: A New Control Unit Using Microprocessor", Hormone and Metabolic Research Supplement Series, 1982, vol. 12, pp. 165-169.

Sparacino, G., et al., "Glucose Concentration Can Be Predicted Ahead in Time from Continuous Glucose Monitoring Sensor Time-Series", IEEE Transactions on Biomedical Engineering, 2007, vol. 54, No. 5, pp. 931-937.

Sprules, S. D., et al., "Evaluation of a New Disposable Screen-Printed Sensor Strip for the Measurement of NADH and Its Modification to Produce a Lactate Biosensor Employing Microliter Volumes", Electroanalysis, 1996, vol. 8, No. 6, pp. 539-543.

Sternberg, F., et al., "Calibration Problems of Subcutaneous Glucosensors when Applied "In-Situ" in Man", Hormone and Metabolic Research, 1994, vol. 26, pp. 523-526.

Sternberg, R., et al., "Covalent Enzyme Coupling on Cellulose Acetate Membranes for Glucose Sensor Development", Analytical Chemistry, 1988, vol. 60, No. 24, pp. 2781-2786.

Sternberg, R., et al., "Study and Development of Multilayer Needle-type Enzyme-based Glucose Microsensors," Biosensors, 1988, vol. 4, pp. 27-40.

"Submission and Review of Sterility Information in Premarket Notification (510(k)) Submissions for Devices Labeled as Sterile, Guidance for Industry and Food and Drug Administration Staff", 2016, pp. 1-11.

Suekane, M., et al., "Immobilization of Glucose Isomerase", Zettschrift fur Allgemeine Mikrobiologie, 1982, vol. 22, No. 8, pp. 565-576.

Tajima, S., et al., "Simultaneous Determination of Glucose and 1,5-Anydroglucitol", Chemical Abstracts, 1989, vol. 111, No. 25, p. 394.

Tarasevich, M. R., "Bioelectrocatalysis", Comprehensive Treatise of Electrochemistry, 1985, vol. 10, pp. 231-295.

Tatsuma, T., et al., "Enzyme Monolayer- and Bilayer-Modified Tin Oxide Electrodes for the Determination of Hydrogen Peroxide and Glucose", Analytical Chemistry, 1989, vol. 61, No. 21, pp. 2352-2355.

Taylor, C., et al., ""Wiring" of Glucose Oxidase Within a Hydrogel Made with Polyvinyl Imidazole Complexed with [(Os-4,4'-dimethoxy-2,2'-bipyridine)Cl]$^{+/2+}$", Journal of ElectroAnalytical Chemistry, 1995, vol. 396, pp. 511-515.

Tegnestedt, C., et al., "Levels and sources of sound in the intensive care unit—an observational study of three room types", Acta Anaesthiesiologica Scandinavica, 2013, pp. 1-10.

Thompson, M., et al., "In Vivo Probes: Problems and Perspectives", Clinical Biochemistry, 1986, vol. 19, pp. 255-261.

Tierney, M. J., et al., "Effect of Acetaminophen on the Accuracy of Glucose Measurements Obtained with the GlucoWatch Biographer", Diabetes Technology & Therapeutics, 2000, vol. 2, No. 2, pp. 199-207.

Townsend, K., et al., "Getting Started with Bluetooth Low Energy—Chapter 1", 2014, pp. 1-26.

Trojanowicz, M., et al., "Enzyme Entrapped Polypyrrole Modified Electrode for Flow-Injection Determination of Glucose", Biosensors & Bioelectronics, 1990, vol. 5, pp. 149-156.

Tsalikian, E., et al., "Accuracy of the GlucoWatch G2® Biographer and the Continuous Glucose Monintoring System During Hypoglycemia: Experience of the Diabetes Research in Children Network", Diabetes Care, 2004, vol. 27, No. 3, pp. 722-726.

Tung, S., "Layers of Security for Active RFID Tags", RFID Handbook: Applications, Technology, Security, and Privacy, Edited by Ehson, et al., Chapter 33, 2008, pp. 1-28.

Turner, A.P.F., et al., "Diabetes Mellitus: Biosensors for Research and Management", Biosensors, 1985, vol. 1, pp. 85-115.

Turner, R.F.B., et al., "A Biocompatible Enzyme Electrode for Continuous in vivo Glucose Monitoring in Whole Blood", Sensors and Actuators B, 1990, vol. 1, pp. 561-564.

Tuzhi, P., et al., "Constant Potential Pretreatment of Carbon Fiber Electrodes for in Vivo Electrochemistry", Analytical Letters, 1991, vol. 24, No. 6, pp. 935-945.

Umana, M., "Protein-Modified Electrochemically Active Biomaterial Surface", U.S. Army Research Office, Analytical and Chemical Sciences Research Triangle Institute, 1988, pp. 1-9.

United States Court of Appeals for the Federal Circuit, No. 06-1402, Leapfrog Enterprises, Inc. v. Fisher-Price, Inc. and Mattel, Inc., May 9, 2007.

Updike, S. J., et al., "Principles of Long-term Fully Implanted Sensors with Emphasis on Radiotelemetric Monitoring of Blood Glucose from inside a Subcutaneous Foreign Body Capsule (FBC)", Biosensors in the Body: Continuous In vivo Monitoring, Chapter 4, 1997, pp. 117-137.

Updike, S. J., et al., "A Subcutaneous Glucose Sensor With Improved Longevity, Dynamic Range, and Stability of Calibration", Diabetes Care, 2000, vol. 23, pp. 208-214.

Urban, G., et al., "Miniaturized Thin-Film Biosensors Using Covalently Immobilized Glucose Oxidase", Biosensors & Bioelectronics, 1991, vol. 6, pp. 555-562.

Velho, G., et al., "In Vitro and In Vivo Stability of Electrode Potentials in Needle-Type Glucose Sensors", Diabetes, 1989, vol. 38, No. 2, pp. 164-171.

Velho, G. et al., "Strategies for Calibrating a Subcutaneous Glucose Sensor," Biomed. Biochim. Acta, 1989, 48 (11112), pp. 957-964.

Von Woedtke, T., et al., "In Situ Calibration of Implanted Electrochemical Glucose Sensors", Biomedica Biochimica Acta, 1989, vol. 48, pp. 943-952.

Vreeke, M. S., et al., "Hydrogen Peroxide Electrodes Based on Electrical Connection of Redox Centers of Various Peroxidases to Electrodes through a Three-Dimensional Electron- Relaying Polymer Network", Diagnostic Biosensors Polymers, Chapter 15, 1993, pp. 180-193.

Vreeke, M., et al., "Hydrogen Peroxide and B-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", Analytical Chemistry, 1992, vol. 64, No. 24, pp. 3084-3090.

Wang, D. L., et al., "Miniaturized Flexible Amperometric Lactate Probe", Analytical Chemistry, 1993, vol. 65, No. 8, pp. 1069-1073.

Wang, J., et al., "Activation of Glassy Carbon Electrodes by Alternating Current Electrochemical Treatment", Analytica Chimica Acta, 1985, vol. 167, pp. 325-334.

Wang, J., et al., "Amperometric Biosensing of Organic Peroxides with Peroxidase-Modified Electrodes", Analytica Chimica Acta, 1991, vol. 254, pp. 81-88.

Wang, J., et al., "Screen-Printable Sol-Gel Enzyme-Containing Carbon Inks", Analytical Chemistry, 1996, vol. 68, No. 15, pp. 2705-2708.

Wang, J., et al., "Sol-Gel-Derived Metal-Dispersed Carbon Composite Amperometric Biosensors", Electroanalysis, 1997, vol. 9, No. 1, pp. 52-55.

Wang, X.H., et al., "Bluetooth: Opening a blue sky for healthcare", Mobile Information Systems, 2006, vol. 2, pp. 151-167.

Ward, W. K., et al., "Rise in Background Current Over Time in a Subcutaneous Glucose Sensor in the Rabbit: Relevance to Calibration and Accuracy", Biosensors & Bioelectronics, 2000, vol. 15, pp. 53-61.

(56) References Cited

OTHER PUBLICATIONS

Waterhouse, R., "Printed Antennas for Wireless Communications," 2007, pp. 116-129 and 284-289.

Watkin, J., "An Introduction to Flash Glucose Monitoring", 2013, 14 pages.

Williams, D. L., et al., "Electrochemical-Enzymatic Analysis of Blood Glucose and Lactate", Analytical Chemistry, 1970, vol. 42, No. 1, pp. 118-121.

Wilson, G. S., et al., "Progress Toward the Development of an Implantable Sensor for Glucose," Clinical Chemistry, 1992, vol. 38, No. 9, pp. 1613-1617.

Wong, KL, "Planar Antennas for Wireless Communications," 2003, Chapter 1, Introduction and Overview, pp. 4-17, 38-45, and 218-221.

Yabuki, S., et al., "Electro-Conductive Enzyme Membrane", Journal of the Chemical Society, Chemical Communications, 1989, pp. 945-946.

Yang, L., et al., "Determination of Oxidase Enzyme Substrates Using Cross-Flow Thin-Layer Amperometry", Electroanalysis, 1996, vol. 8, No. 8-9, pp. 716-721.

Yao, S. J., et al., "The Interference of Ascorbate and Urea in Low-Potential Electrochemical Glucose Sensing", Proceedings of the Twelfth Annual International Conference of the IEEE Engineering in Medicine and Biology Society, 1990, vol. 12, Part 2, pp. 487-489.

Yao, T., "A Chemically-Modified Enzyme Membrane Electrode as an Amperometric Glucose Sensor", Analytica Chimica Acta, 1983, vol. 148, pp. 27-33.

Ye, L. et al., "High Current Density "Wired" Quinoprotein Glucose Dehydrogenase Electroade," Anal. Chem., 1993, vol. 65, No. 3, pp. 238-241.

Yildiz, A., et al., "Evaluation of an Improved Thin-Layer Electrode", Analytical Chemistry, 1968, vol. 40, No. 7, pp. 1018-1024.

Zamzow, K., et al., "New Wearable Continuous Blood Glucose Monitor (BGM) and Artificial Pancreas (AP)", Diabetes, 1990, vol. 39, p. 5A-20.

Z-Carbon Connector, retrieved from http://www.zaxisconnector.com/SS_zc.shtml, 2004, 2 pages.

Zhang, Y., et al., "Application of Cell Culture Toxicity Tests to the Development of Implantable Biosensors", Biosensors & Bioelectronics, 1991, vol. 6, pp. 653-661.

Zhang, Y., et al., "Elimination of the Acetaminophen Interference in an Implantable Glucose Sensor", Analytical Chemistry, 1994, vol. 66, No. 7, pp. 1183-1188.

Zhu, J., et al., "Fabrication and Characterization of Glucose Sensors Based on a Microarray $H_2O_2$ electrode", Biosensors & Bioelectronics, 1994, vol. 9, pp. 295-300.

Zisser, H. C., "The OmniPod Insulin Management System: the Latest Innovation in Insulin Pump Therapy", Diabetes Ther, 2010, vol. 1, No. 1, pp. 10-24.

Z-Silver Connector, retrieved from http://www.zaxisconnector.com/SS_zs.shtml, 2004, 2 pages.

DE, Statement of Defense (Counterclaim), Case No. 21 O 6562/23, Sep. 1, 2023.

DE, Infringement Action of EP 3 766 408 B1, Feb. 20, 2023.

GB, Claim No. HP-2023-000012 and Claim No. HP-2023-000016 Order for Directions—Trial D, Jul. 24, 2023.

GB, Claim No. HP-2023-000012 Reply and Defence to Counterclaim, Jul. 5, 2023.

GB, Claim No. HP-2023-000012 Application Notice, Jun. 19, 2023.

GB, Claim No. HP-2023-000012 Defence and Counterclaim, Jun. 14, 2023.

GB, Particulars of Claim, May 15, 2023.

GB, Claimant's Initial List of Disclosure Documents, May 15, 2023.

GB, Grounds of Invalidity, May 15, 2023.

GB, Claim No. HP-2021-000025 Annex 4 to Abbott's Closing Submissions, Jul. 18, 2023.

GB, Claim No. HP-2021-000025 Annex 3 to Abbott's Closing Submissions, Jul. 18, 2023.

GB, Claim No. HP-2021-000025 Annex 2 to Abbott's Closing Submissions, Jul. 18, 2023.

GB, Claim No. HP-2021-000025 Annex 1 to Abbott's Closing Submissions, Jul. 19, 2023.

GB, Claim No. HP-2021-000025 Abbott's Closing Submissions Trial C, Jul. 18, 2023.

GB, Claim No. HP-2021-000025 Annex CA2 of Dexcom's Closing Skeleton Argument Trial C, Jul. 18, 2023.

GB, Claim No. HP-2021-000025 of Dexcom's Closing Skeleton Argument Trial C, Jul. 18, 2023.

GB, Claim No. HP-2021-000025 Abbott's Supplementary Skeleton Argument Trial C, Jul. 7, 2023.

GB, Claim No. HP-2021-000025 Annex 2 to Abbott's Opening Skeleton Argument—Commercial devices and their key features, Jul. 5, 2023.

GB, Claim No. HP-2021-000025 Annex 1 to Abbott's Opening Skeleton Argument—Claim Integers, Jul. 5, 2023.

GB, Claim No. HP-2021-000025 Abbott's Opening Skeleton Argument Trial C, Jul. 5, 2023.

GB, Claim No. HP-2021-000025 Annex 3 of Dexcom's Opening Skeleton Argument—Trial C, Jul. 5, 2023.

GB, Claim No. HP-2021-000025 Annex 2 of Dexcom's Opening Skeleton Argument—Trial C, Jul. 5, 2023.

GB, Claim No. HP-2021-000025 Annex 1 of Dexcom's Opening Skeleton Argument—Trial C, Jul. 5, 2023.

GB, Claim No. HP-2021-000025 of Dexcom's Opening Skeleton Argument—Trial C, Jul. 5, 2023.

GB, Claim No. HP-2021-000025 and Claim No. HP-2021- 000026 Fifth Expert Report of Andrew Varde, Jun. 23, 2023.

GB, Claim No. HP-2021-000025 PTR Order, Jun. 20, 2023.

GB, Claim No. HP-2021-000025 Second Expert Report of Douglas Jennings, Jun. 9, 2023.

GB, Claim No. HP-2021-000025 and Claim No. HP-2021-000026 Fourth Expert Report of Andrew Varde, Jun. 9, 2023.

GB, Claim No. HP-2021-000025 Third Expert Report of Dr. Michael Schoemaker, Jun. 2, 2023.

GB, Claim No. HP-2021-000025 Claim Integer (Exhibit DJ-9), May 12, 2023.

GB, Claim No. HP-2021-000025 Trial B—Joint CGK Statement (Exhibit DJ-2), May 12, 2023.

GB, Claim No. HP-2021-000025 First Expert Report of Douglas Jennings, May 12, 2023.

GB, Claim No. HP-2021-000025 and Claim No. HP-2021-000026 Third Expert Report of Andrew Varde, May 11, 2023.

GB, Claim No. HP-2021-000025 and Claim No. HP-2021-000026 Third Letter (Exhibit PG-12), May 10, 2023.

GB, Claim No. HP-2021-000025 and Claim No. HP-2021-000026 Third Expert Report of Pantelis Georgiou, May 10, 2023.

GB, Claim No. HP-2021-000025 Re-Re-Amended Reply and Defence to Counterclaim, Apr. 28, 2023.

GB, Claim No. HP-2021-000025 Defendants' Response to the Claimant's Reply to Issues of Fact Raised in Defendants' Grounds of Opposition—EP918, Apr. 25, 2023.

GB, Claim No. HP-2021-000025 Re-Re-Re-Re-Amended Grounds of Invalidity, Apr. 24, 2023.

GB, Claim No. HP-2021-000025 Claimants' Notice to Admit Facts, Apr. 6, 2023.

GB, Claim No. HP-2021-000025 Re-Amended Reply and Defence to Counterclaim, Mar. 28, 2023.

GB, Claim No. HP-2021-000025 Reply to Issues of Fact Raised in Defendants' Grounds of Opposition—EP918, Mar. 17, 2023.

GB, Claim No. HP-2021-000025 Consent Order, Mar. 14, 2023.

GB, Claim No. HP-2021-000025 Re-Re-Re-Amended Grounds of Invalidity, Mar. 14, 2023.

GB, Claim No. HP-2021-000025 Consent Order, Mar. 10, 2023.

GB, Claim No. HP-2021-000025 Defendants' Amended Grounds of Opposition to the Claimant' Application Under Section 75(1) of the Patents Act 1977, EP918, Feb. 28, 2023.

GB, Claim No. HP-2021-000025 Sealed Order, Jan. 12, 2023.

GB, Claim No. HP-2021-000025 Statement of Grounds of Amendment of EP (UK) 2,549,918, Dec. 23, 2022.

GB, Claim No. HP-2021-000025 Application Notice, Dec. 23, 2022.

(56) References Cited

OTHER PUBLICATIONS

GB, Claim No. HP-2021-000025 Amended Reply and Defence to Counterclaim, Apr. 19, 2022.
GB, Claim No. HP-2021-000025 Amended Defence and Counterclaim, Mar. 28, 2022.
GB, Claim No. HP-2021-000025 Amended Grounds of Invalidity, Mar. 28, 2022.
GB, Claim No. HP-2021-000025 Defendants' Amended Response to Claimants' Notice to Admit Facts—Trial C Patents, Mar. 9, 2022.
GB, Claim No. HP-2021-000026 Sealed Order, Jan. 12, 2023.
GB, Claim No. HP-2021-000026 Statement of Grounds of Amendment of EP (UK) 2,549,918, Dec. 23, 2022.
GB, Claim No. HP-2021-000026 Defendants' Amended Response to Claimants' Notice to Admit Facts—Trial C Patents, Mar. 9, 2022.
US, Scheduling Order, Case No. 23-239-KAJ, Sep. 19, 2023.
US, Dexcom, Inc.'s Answer, Affirmative Defenses, and Counterclaims, Case No. 23-CV-239-UNA (D. Delaware), May 12, 2023.
US, Complaint, Case 23-CV-239-UNA (D. Delaware), Mar. 3, 2023.
US, Joint Letter to the Honorable Kent A. Jordan Regarding Additional Issues Related to the Upcoming Trial, Case No. 21-CV-977-KAJ (D. Delaware)—Public Version, Oct. 6, 2023.
US, Amended [Proposed] Final Pretrial Order, Case No. 21-CV-977-KAJ (D. Delaware), Sep. 20, 2023.
US, Exhibit 3P to the Proposed Pretrial Order Abbott's Statement of Issues of Law Which Remain to be Litigated, Case No. 21-CV-977-KAJ (D. Delaware), Sep. 20, 2023.
US, Exhibit 3D to the Proposed Pretrial Order Dexcom's Statement of Issues of Law Which Remain to be Litigated, Case No. 21-CV-977-KAJ (D. Delaware), Sep. 20, 2023.
US, Exhibit 2P to the Proposed Pretrial Order Abbott's Statement of Issues of Fact Which Remain to be Litigated, Case No. 21-CV-977-KAJ (D. Delaware), Sep. 20, 2023.
US, Exhibit 2D to Proposed Pretrial Order Dexcom's Statement of Contested Facts, Case No. 21-CV-977-KAJ (D. Delaware), Sep. 20, 2023.
US, Exhibit 1 to the Proposed Pretrial Order Parties' Joint Statement of Uncontroverted Facts, Case No. 21-CV-977-KAJ (D. Delaware), Sep. 20, 2023.
US, Memorandum Opinion, Case No. 21-CV-977-KAJ (D. Delaware)—Public Version, Aug. 15, 2023.
US, Order, Case No. 21-CV-977-KAJ (D. Delaware), Aug. 15, 2023.
US, Appendix of Attachments and Exhibits for Plaintiffs' Opening Letter Brief in Support of Plaintiffs' Motion to Strike Defendant's New Claim Constructions, Case No. 21-CV-977-KAJ (D. Delaware)—Public Version, Aug. 10, 2023.
US, Opening Letter Brief in Support of Plaintiffs' Motion to Strike Defendant's New Claim Constructions, Case No. 21-CV-977-KAJ (D. Delaware)—Public Version, Aug. 10, 2023.
US, Dexcom's Letter Brief in Opposition to Abbott's Motion to Strike, Case No. 21-CV-977-KAJ (D. Delaware)—Public Version, Aug. 9, 2023.
US, Plaintiffs' Motion to Strike Defendant's New Claim Constructions, Case No. 21-CV-977-KAJ (D. Delaware), Aug. 3, 2023.
US, Plaintiffs' Letter Response to the Court's Questions Regarding the IPR Final Written Decision Relating to U.S. Pat. No. 10,945,649, Case No. 21-CV-977-KAJ (D. Delaware)—Public Version, Jul. 26, 2023.
US, Letter to Hon. Kent Jordan re Impact of Final Written Decision, Case No. 21-CV-977-KAJ (D. Delaware), Jul. 19, 2023.
US, *Abbott* v *Dexcom*—Trial C–Construction Schedule, Case No. 21-CV-977-KAJ (D. Delaware), Jul. 18, 2023.
US, Notice of Final Written Decision Re Inter Partes Review of the '649 Patent, Case No. 21-CV-977-KAJ (D. Delaware), Jul. 13, 2023.
US, Transcript of Motion Hearing, Case No. 21-CV-977-KAJ (D. Delaware), Jun. 30, 2023.

US, Defendant Dexcom, Inc.'s Reply Brief in Support of its Motion to Strike Abbott's Late-Disclosed Supplemental Declarations, Case No. 21-CV-977-KAJ (D. Delaware)—Public Version, Jun. 26, 2023.
US, Appendix of Exhibits in Support of Dexcom, Inc.'s Opposition to Plaintiffs' Motion for Summary Judgement and Daubert Challenges—vol. 2, Case No. 21-CV-977-KAJ (D. Delaware)—Public Version, Jun. 23, 2023.
US, Appendix of Exhibits in Support of Dexcom, Inc.'s Opposition to Plaintiffs' Motion for Summary Judgement and Daubert Challenges—vol. 1, Case No. 21-CV-977-KAJ (D. Delaware)—Public Version, Jun. 23, 2023.
US, Defendant Dexcom, Inc.'s Appendix to Brief in Support of its Reply to Abbott Diabetes Care Inc. and Abbott Diabetes Care Limited's Opposition to Dexcom Inc.'s Motions for Summary Judgement, Case No. 21-CV-977-Kaj (D. Delaware)–Public Version, Jun. 23, 2023.
US, Appendix of Exhibits and Attachments for Plaintiffs' Responsive Letter Brief In Opposition to Dexcom's Motion to Strike Expert Declarations (D.I. 408), Case No. 21-CV-977-KAJ (D. Delaware)—Public Version, Jun. 23, 2023.
US, Plaintiffs' Responsive Letter Brief in Opposition to Defendant's Motion to Strike Expert Declarations, Case No. 21-CV-977-KAJ (D. Delaware)—Public Version, Jun. 23, 2023.
US, Defendant Dexcom, Inc.'s Appendix to Brief in Support of its Reply to Abbott Diabetes Care Inc. and Abbott Diabetes Care Limited's Opposition to Dexcom Inc.'s Motions to Exclude Expert Reports and Testimony, Case No. 21-CV-977-KAJ (D. Delaware)—Public Version, Jun. 16, 2023.
US, Defendant Dexcom, Inc.'s Reply in Support of its Motions to Exclude Expert Reports and Testimony, Case No. 21-CV-977-KAJ (D. Delaware)—Public Version, Jun. 16, 2023.
US, Defendant Dexcom, Inc.'s Opening Brief in Support of its Motion to Strike Abbott's Late-Disclosed Supplemental Declarations, Case No. 21-CV-977-KAJ (D. Delaware)—Public Version, Jun. 16, 2023.
US, Dexcom, Inc.'s Motion to Strike Plaintiffs' Untimely Expert Opinions, Case No. 21-CV-977-KAJ (D. Delaware), Jun. 16, 2023.
US, Appendix of Exhibits (vol. 3 of 3, Exhibits 151-171) for Plaintiffs' Answering Briefs In Opposition to Dexcom's Motions for Summary Judgement (D.I. 331) and to Exclude Expert Reports and Testimony (D.I. 337), Case No. 21-CV-977-KAJ (D. Delaware)—Public Version, Jun. 7, 2023.
US, Appendix of Exhibits (vol. 2 of 3, Exhibits 138-150) for Plaintiffs' Answering Briefs In Opposition to Dexcom's Motions for Summary Judgement (D.I. 331) and to Exclude Expert Reports and Testimony (D.I. 337), Case No. 21-CV-977-KAJ (D. Delaware)—Public Version, Jun. 7, 2023.
US, Appendix of Exhibits (vol. 1 of 3, Exhibits 98-137) for Plaintiffs' Answering Briefs In Opposition to Dexcom's Motions for Summary Judgement (D.I. 331) and to Exclude Expert Reports and Testimony (D.I. 337), Case No. 21-CV-977-KAJ (D. Delaware)—Public Version, Jun. 7, 2023.
US, Plaintiffs' Answering Briefs In Opposition to Dexcom's Motions to Exclude Expert Reports and Testimony, Case No. 21-CV-977-KAJ (D. Delaware)—Public Version, Jun. 7, 2023.
US, Supplemental Declaration of Karl R. Leinsing, MSME, PE, Regarding Validity, Case No. 21-CV-977-KAJ (D. Delaware)—Public Version, Jun. 7, 2023.
US, Declaration of John L. Smith, PH.D., on Validity, in Support of Plaintiffs' Answering Brief in Opposition to Dexcom's Motions for Summary Judgement and Plaintiffs' Answering Brief in Opposition to Dexcom's Motions to Exclude Expert Reports and Testimony, Case No. 21-CV-977-KAJ (D. Delaware)—Public Version, Jun. 7, 2023.
US, Declaration of John L. Smith, PH.D., Regarding Infringement, in Support of Plaintiffs' Answering Brief in Opposition to Dexcom's Motions for Summary Judgement and Plaintiffs' Answering Brief in Opposition to Dexcom's Motions to Exclude Expert Reports and Testimony, Case No. 21-CV-977-KAJ (D. Delaware)—Public Version, Jun. 7, 2023.

(56)                    References Cited

OTHER PUBLICATIONS

US, Declaration of Dr. John E. Anderson in Opposition to Defendant Dexcom, Inc.'s Motions to Exclude Expert Reports and Testimony, Case No. 21-CV-977-KAJ (D. Delaware)—Public Version, Jun. 7, 2023.

US, Declaration of Dr. Eden M. Miller in Opposition to Defendant Dexcom, Inc.'s Motions to Exclude Expert Reports and Testimony, Case No. 21-CV-977-KAJ (D. Delaware)—Public Version, Jun. 7, 2023.

US, Declaration of Catherine M. Lawton in Opposition to Defendant Dexcom, Inc.'s Motions to Exclude Expert Reports and Testimony, Case No. 21-CV-977-KAJ (D. Delaware)—Public Version, Jun. 7, 2023.

US, Declaration of Eric B. Hanson in Support of Dexcom's Opposition to Plaintiffs' Motion for Summary Judgement and Daubert Challenges, Case No. 21-CV-977-KAJ (D. Delaware), Jun. 6, 2023.

US, Defendant Dexcom, Inc.'s Opening Brief in Support of Its Motions to Exclude Expert Reports and Testimony, Case No. 21-CV-977-KAJ (D. Delaware)—Public Version, May 19, 2023.

US, Declaration of Karl R. Leinsing, MSME, PE, in Support of Abbott's Motion for Summary Judgement, Case No. 21-CV-977-KAJ (D. Delaware)—Public Version, May 19, 2023.

US, Video-Recorded Deposition of Neil Sheehan, Ph.D, Case No. 21-CV-977-KAJ (D. Delaware), May 4, 2023.

US, Video Deposition of Karl R. Leinsing, MSME, PE, vol. I, Case No. 21-CV-977-KAJ (D. Delaware), May 3, 2023.

US, Videotaped Deposition of John Mastrototaro, Ph.D, Case No. 21-CV-977-KAJ (D. Delaware), Apr. 26, 2023.

US, Video-Recorded Deposition of John Smith, Ph.D, Case No. 21-CV-977-KAJ (D. Delaware), Apr. 21, 2023.

US, Dexcom, Inc.'s Amended Answer to Second Amended Complaint, Case 21-CV-977-KAJ (D. Delaware)—Public Version, Mar. 17, 2023.

US, Expert Report of John L. Smith, Ph.D., on Infringement of the Asserted Claims of U.S. Pat. No. 10,827,954, Case No. 21-CV-977-KAJ (D. Delaware), Mar. 14, 2023.

US, Oral Argument Hearing Before Hon. Kent A. Jordan, U.S. Circuit Court Judge, Case No. 21-CV-977-KAJ (D. Delaware), Mar. 9, 2023.

US, Defendant Dexcom, Inc.'s Supplemental Responses to Plaintiffs Abbott Diabetes Care Inc's. and Abbott Diabetes Care Limited's Notice of Rule 30(b)(6) Deposition, Case No. 21-CV-977-KAJ (D. Delaware), Feb. 8, 2023.

US, Exhibit 216-1F from DexCom, Inc.'s Final Invalidity Contentions, Case No. 21-CV-977-KAJ (D. Delaware), Feb. 9, 2023.

US, Exhibit 216-2F from DexCom, Inc.'s Final Invalidity Contentions, Case No. 21-CV-977-KAJ (D. Delaware), Feb. 9, 2023.

US, Exhibit 216-3F from DexCom, Inc.'s Final Invalidity Contentions, Case No. 21-CV-977-KAJ (D. Delaware), Feb. 9, 2023.

US, Exhibit 216-4F from DexCom, Inc.'s Final Invalidity Contentions, Case No. 21-CV-977-KAJ (D. Delaware), Feb. 9, 2023.

US, Exhibit 216-5F from DexCom, Inc.'s Final Invalidity Contentions, Case No. 21-CV-977-KAJ (D. Delaware), Feb. 9, 2023.

US, Exhibit 216-6F from DexCom, Inc.'s Final Invalidity Contentions, Case No. 21-CV-977-KAJ (D. Delaware), Feb. 9, 2023.

US, Exhibit 216-7F from DexCom, Inc.'s Final Invalidity Contentions, Case No. 21-CV-977-KAJ (D. Delaware), Feb. 9, 2023.

US, Exhibit 216-8F from DexCom, Inc.'s Final Invalidity Contentions, Case No. 21-CV-977-KAJ (D. Delaware), Feb. 9, 2023.

US, Exhibit 216-10F from DexCom, Inc.'s Final Invalidity Contentions, Case No. 21-CV-977-KAJ (D. Delaware), Feb. 9, 2023.

US, Exhibit 216-11F from DexCom, Inc.'s Final Invalidity Contentions, Case No. 21-CV-977-KAJ (D. Delaware), Feb. 9, 2023.

US, Exhibit 216-12F from DexCom, Inc.'s Final Invalidity Contentions, Case No. 21-CV-977-KAJ (D. Delaware), Feb. 9, 2023.

US, Exhibit 216-13F from DexCom, Inc.'s Final Invalidity Contentions, Case No. 21-CV-977-KAJ (D. Delaware), Feb. 9, 2023.

US, Exhibit 341-1F from DexCom, Inc.'s Final Invalidity Contentions, Case No. 21-CV-977-KAJ (D. Delaware), Feb. 9, 2023.

US, Exhibit 341-2F from DexCom, Inc.'s Final Invalidity Contentions, Case No. 21-CV-977-KAJ (D. Delaware), Feb. 9, 2023.

US, Exhibit 341-3F from DexCom, Inc.'s Final Invalidity Contentions, Case No. 21-CV-977-KAJ (D. Delaware), Feb. 9, 2023.

US, Exhibit 341-4F from DexCom, Inc.'s Final Invalidity Contentions, Case No. 21-CV-977-KAJ (D. Delaware), Feb. 9, 2023.

US, Exhibit 341-5F from DexCom, Inc.'s Final Invalidity Contentions, Case No. 21-CV-977-KAJ (D. Delaware), Feb. 9, 2023.

US, Exhibit 341-6F from DexCom, Inc.'s Final Invalidity Contentions, Case No. 21-CV-977-KAJ (D. Delaware), Feb. 9, 2023.

US, Exhibit 341-7F from DexCom, Inc.'s Final Invalidity Contentions, Case No. 21-CV-977-KAJ (D. Delaware), Feb. 9, 2023.

US, Exhibit 341-8F from DexCom, Inc.'s Final Invalidity Contentions, Case No. 21-CV-977-KAJ (D. Delaware), Feb. 9, 2023.

US, Exhibit 341-10F from DexCom, Inc.'s Final Invalidity Contentions, Case No. 21-CV-977-KAJ (D. Delaware), Feb. 9, 2023.

US, Exhibit 341-11F from DexCom, Inc.'s Final Invalidity Contentions, Case No. 21-CV-977-KAJ (D. Delaware), Feb. 9, 2023.

US, Exhibit 341-12F from DexCom, Inc.'s Final Invalidity Contentions, Case No. 21-CV-977-KAJ (D. Delaware), Feb. 9, 2023.

US, Exhibit 341-13F from DexCom, Inc.'s Final Invalidity Contentions, Case No. 21-CV-977-KAJ (D. Delaware), Feb. 9, 2023.

US, Exhibit 440-1F from DexCom, Inc.'s Final Invalidity Contentions, Case No. 21-CV-977-KAJ (D. Delaware), Feb. 9, 2023.

US, Exhibit 440-2F from DexCom, Inc.'s Final Invalidity Contentions, Case No. 21-CV-977-KAJ (D. Delaware), Feb. 9, 2023.

US, Exhibit 440-3F from DexCom, Inc.'s Final Invalidity Contentions, Case No. 21-CV-977-KAJ (D. Delaware), Feb. 9, 2023.

US, Exhibit 440-4F from DexCom, Inc.'s Final Invalidity Contentions, Case No. 21-CV-977-KAJ (D. Delaware), Feb. 9, 2023.

US, Exhibit 440-5F from DexCom, Inc.'s Final Invalidity Contentions, Case No. 21-CV-977-KAJ (D. Delaware), Feb. 9, 2023.

US, Exhibit 440-6F from DexCom, Inc.'s Final Invalidity Contentions, Case No. 21-CV-977-KAJ (D. Delaware), Feb. 9, 2023.

US, Exhibit 440-8F from DexCom, Inc.'s Final Invalidity Contentions, Case No. 21-CV-977-KAJ (D. Delaware), Feb. 9, 2023.

US, Exhibit 440-9F from DexCom, Inc.'s Final Invalidity Contentions, Case No. 21-CV-977-KAJ (D. Delaware), Feb. 9, 2023.

US, Exhibit 440-10F from DexCom, Inc.'s Final Invalidity Contentions, Case No. 21-CV-977-KAJ (D. Delaware), Feb. 9, 2023.

US, Exhibit 440-11F from DexCom, Inc.'s Final Invalidity Contentions, Case No. 21-CV-977-KAJ (D. Delaware), Feb. 9, 2023.

US, Exhibit 440-12F from DexCom, Inc.'s Final Invalidity Contentions, Case No. 21-CV-977-KAJ (D. Delaware), Feb. 9, 2023.

US, Exhibit 440-13F from DexCom, Inc.'s Final Invalidity Contentions, Case No. 21-CV-977-KAJ (D. Delaware), Feb. 9, 2023.

US, Exhibit 649-1F from DexCom, Inc.'s Final Invalidity Contentions, Case No. 21-CV-977-KAJ (D. Delaware), Feb. 9, 2023.

US, Exhibit 649-2F from DexCom, Inc.'s Final Invalidity Contentions, Case No. 21-CV-977-KAJ (D. Delaware), Feb. 9, 2023.

US, Exhibit 649-3F from DexCom, Inc.'s Final Invalidity Contentions, Case No. 21-CV-977-KAJ (D. Delaware), Feb. 9, 2023.

US, Exhibit 649-4F from DexCom, Inc.'s Final Invalidity Contentions, Case No. 21-CV-977-KAJ (D. Delaware), Feb. 9, 2023.

US, Exhibit 649-5F from DexCom, Inc.'s Final Invalidity Contentions, Case No. 21-CV-977-KAJ (D. Delaware), Feb. 9, 2023.

US, Exhibit 649-6F from DexCom, Inc.'s Final Invalidity Contentions, Case No. 21-CV-977-KAJ (D. Delaware), Feb. 9, 2023.

US, Exhibit 649-7F from DexCom, Inc.'s Final Invalidity Contentions, Case No. 21-CV-977-KAJ (D. Delaware), Feb. 9, 2023.

US, Exhibit 649-9F from DexCom, Inc.'s Final Invalidity Contentions, Case No. 21-CV-977-KAJ (D. Delaware), Feb. 9, 2023.

US, Exhibit 649-10F from DexCom, Inc.'s Final Invalidity Contentions, Case No. 21-CV-977-KAJ (D. Delaware), Feb. 9, 2023.

US, Exhibit 649-11F from DexCom, Inc.'s Final Invalidity Contentions, Case No. 21-CV-977-KAJ (D. Delaware), Feb. 9, 2023.

US, Exhibit 649-12F from DexCom, Inc.'s Final Invalidity Contentions, Case No. 21-CV-977-KAJ (D. Delaware), Feb. 9, 2023.

US, Exhibit 649-13F from DexCom, Inc.'s Final Invalidity Contentions, Case No. 21-CV-977-KAJ (D. Delaware), Feb. 9, 2023.

US, Exhibit 654-1F from DexCom, Inc.'s Final Invalidity Contentions, Case No. 21-CV-977-KAJ (D. Delaware), Feb. 9, 2023.

(56)        References Cited

OTHER PUBLICATIONS

US, Exhibit 654-2F from DexCom, Inc.'s Final Invalidity Contentions, Case No. 21-CV-977-KAJ (D. Delaware), Feb. 9, 2023.
US, Exhibit 654-3F from DexCom, Inc.'s Final Invalidity Contentions, Case No. 21-CV-977-KAJ (D. Delaware), Feb. 9, 2023.
US, Exhibit 654-4F from DexCom, Inc.'s Final Invalidity Contentions, Case No. 21-CV-977-KAJ (D. Delaware), Feb. 9, 2023.
US, Exhibit 654-5F from DexCom, Inc.'s Final Invalidity Contentions, Case No. 21-CV-977-KAJ (D. Delaware), Feb. 9, 2023.
US, Exhibit 654-6F from DexCom, Inc.'s Final Invalidity Contentions, Case No. 21-CV-977-KAJ (D. Delaware), Feb. 9, 2023.
US, Exhibit 654-7F from DexCom, Inc.'s Final Invalidity Contentions, Case No. 21-CV-977-KAJ (D. Delaware), Feb. 9, 2023.
US, Exhibit 654-8F from DexCom, Inc.'s Final Invalidity Contentions, Case No. 21-CV-977-KAJ (D. Delaware), Feb. 9, 2023.
US, Exhibit 654-10F from DexCom, Inc.'s Final Invalidity Contentions, Case No. 21-CV-977-KAJ (D. Delaware), Feb. 9, 2023.
US, Exhibit 654-11F from DexCom, Inc.'s Final Invalidity Contentions, Case No. 21-CV-977-KAJ (D. Delaware), Feb. 9, 2023.
US, Exhibit 654-12F from DexCom, Inc.'s Final Invalidity Contentions, Case No. 21-CV-977-KAJ (D. Delaware), Feb. 9, 2023.
US, Exhibit 654-13F from DexCom, Inc.'s Final Invalidity Contentions, Case No. 21-CV-977-KAJ (D. Delaware), Feb. 9, 2023.
US, Telephone Conference Before Kent A. Jordan, U.S. Circuit Court Judge, Case No. 21-CV-977-KAJ (D. Delaware), Jan. 3, 2023.
US, Letter to the Honorable Kent A. Jordan Regarding Discovery Disputes, Case No. 21-CV-977-KAJ (D. Delaware), Dec. 28, 2022.
US, Defendant Dexcom, Inc.'s Supplemental Objections and Responses to Plaintiffs' Second Set of Interrogatories, Nos. 11, 14, 15, 21-25, Corrected, Case No. 21-CV-977-KAJ (D. Delaware)—Public Version, Dec. 20, 2022.
US, Defendant Dexcom, Inc.'s Supplemental Objections and Responses to Plaintiffs' Second Set of Interrogatories, Nos. 11, 14, 15, 21-25, Case No. 21-CV-977-KAJ (D. Delaware)—Public Version, Dec. 6, 2022.
US, Defendant Dexcom, Inc.'s Objections and Responses to Plaintiffs' Second Set of Interrogatories, Case No. 21-CV-977-KAJ (D. Delaware)—Public Version, Oct. 11, 2022.
US, Defendant Dexcom, Inc.'s Second Supplemental Preliminary Invalidity Contentions, Case 21-CV-977-KAJ (D. Delaware), Oct. 4, 2022.
US, Defendant's Comments on Plaintiffs' Technology Tutorial, Case 21-CV-977-KAJ (D. Delaware), Sep. 16, 2022.
US, Plaintiffs' Response to Defendant's Third Set of Interrogatories (Nos. 12-15), Case 21-CV-977-KAJ (D. Delaware), Sep. 14, 2022.
US, Plaintiffs' Comments on Defendant's Technology Tutorial, Case 21-CV-977-KAJ (D. Delaware), Sep. 9, 2022.
US, Plaintiffs' Second Supplemental Response to Defendant's First Set of Interrogatories, Nos. 1-10, Interrogatory No. 5, Case 21-CV-977-KAJ (D. Delaware), Sep. 8, 2022.
US, Plaintiffs' First Updated Identification of Asserted Claims, Case 21-CV-977-KAJ (D. Delaware), Sep. 7, 2022.
US, Second Declaration of Dr. Jeffrey Vaitekunas, PH.D, Case 21-CV-977-KAJ (D. Delaware), Aug. 31, 2022.
US, Defendant's Sur-Reply Claim Construction Brief, Case 21-CV-977-KAJ (D. Delaware), Aug. 31, 2022.
US, Defendant Dexcom, Inc.'s Notice of Deposition to Plaintiff Abbott Diabetes Care Limited, Case No. 21-CV-977-KAJ (D. Delaware), Aug. 19, 2022.
US, Defendant Dexcom, Inc.'s Notice of Deposition to Plaintiff Abbott Diabetes Care Inc., Case No. 21-CV-977-KAJ (D. Delaware), Aug. 19, 2022.
US, Second Declaration of Karl R. Leinsing, MSME, PE, Case 21-CV-977-KAJ (D. Delaware), Aug. 17, 2022.
US, Plaintiffs' Reply Brief Regarding Claim Construction, Case 21-CV-977-KAJ (D. Delaware), Aug. 17, 2022.
US, Plaintiffs' Response to Defendant's Second Set of Interrogatories, No. 11, Case 21-CV-977-KAJ (D. Delaware), Aug. 8, 2022.
US, Declaration of Dr. Jeffrey Vaitekunas, PH.D, re Claim Construction for U.S. Pat. Nos. 10,881,341; 10,959,654; 11,000,216; 10,973,443; 10,945,649; 11,013,440; 10,945,647, Case 21-CV-977-KAJ (D. Delaware), Aug. 3, 2022.
US, Defendant's Answering Claim Construction Brief, Case 21-CV-977-KAJ (D. Delaware), Aug. 3, 2022.
US, Declaration of Karl R. Leinsing, Msme, Pe, Case 21-CV-977-KAJ (D. Delaware), Jul. 13, 2022.
US, Plaintiffs' Opening Claim Construction Brief, Case 21-CV-977-KAJ (D. Delaware), Jul. 13, 2022.
US, Dexcom, Inc.'s Answer to Second Amended Complaint, Case 21-CV-977-KAJ (D. Delaware), Jun. 30, 2022.
US, Joint Claim Construction Chart, Case 21-CV-977-KAJ (D. Delaware), Jun. 22, 2022.
US, Plaintiffs' Proposed Claim Constructions, Case 21-CV-977-KAJ, May 27, 2022.
US, Plaintiffs' Second Amended Complaint, Case 21-CV-977-KAJ (D. Delaware), May 20, 2022.
US, Plaintiffs' Identification of Claim Terms For Construction, Case 21-CV-977-KAJ (D. Delaware), May 13, 2022.
US, Exhibit 216-1 from DexCom, Inc.'s Preliminary Invalidity Contentions, Case No. 21-CV-977-KAJ (D. Delaware), May 6, 2022.
US, Exhibit 216-2 from DexCom, Inc.'s Preliminary Invalidity Contentions, Case No. 21-CV-977-KAJ (D. Delaware), May 6, 2022.
US, Exhibit 216-2S from DexCom, Inc.'s Supplemental Preliminary Invalidity Contentions, Case No. 21-CV-977-KAJ (D. Delaware), May 6, 2022.
US, Exhibit 216-3 from DexCom, Inc.'s Preliminary Invalidity Contentions, Case No. 21-CV-977-KAJ (D. Delaware), May 6, 2022.
US, Exhibit 216-3S from DexCom, Inc.'s Supplemental Preliminary Invalidity Contentions, Case No. 21-CV-977-KAJ (D. Delaware), May 6, 2022.
US, Exhibit 216-4 from DexCom, Inc.'s Preliminary Invalidity Contentions, Case No. 21-CV-977-KAJ (D. Delaware), May 6, 2022.
US, Exhibit 216-4S from DexCom, Inc.'s Supplemental Preliminary Invalidity Contentions, Case No. 21-CV-977-KAJ (D. Delaware), May 6, 2022.
US, Exhibit 216-5 from DexCom, Inc.'s Preliminary Invalidity Contentions, Case No. 21-CV-977-KAJ (D. Delaware), May 6, 2022.
US, Exhibit 216-5S from DexCom, Inc.'s Supplemental Preliminary Invalidity Contentions, Case No. 21-CV-977-KAJ (D. Delaware), May 6, 2022.
US, Exhibit 216-6 from DexCom, Inc.'s Preliminary Invalidity Contentions, Case No. 21-CV-977-KAJ (D. Delaware), May 6, 2022.
US, Exhibit 216-6S from DexCom, Inc.'s Supplemental Preliminary Invalidity Contentions, Case No. 21-CV-977-KAJ (D. Delaware), May 6, 2022.
US, Exhibit 216-7 from DexCom, Inc.'s Preliminary Invalidity Contentions, Case No. 21-CV-977-KAJ (D. Delaware), May 6, 2022.
US, Exhibit 216-7S from DexCom, Inc.'s Supplemental Preliminary Invalidity Contentions, Case No. 21-CV-977-KAJ (D. Delaware), May 6, 2022.
US, Exhibit 216-8 from DexCom, Inc.'s Preliminary Invalidity Contentions, Case No. 21-CV-977-KAJ (D. Delaware), May 6, 2022.
US, Exhibit 216-9 from DexCom, Inc.'s Preliminary Invalidity Contentions, Case No. 21-CV-977-KAJ (D. Delaware), May 6, 2022.
US, Exhibit 216-9S from DexCom, Inc.'s Supplemental Preliminary Invalidity Contentions, Case No. 21-CV-977-KAJ (D. Delaware), May 6, 2022.
US, Exhibit 216-10 from DexCom, Inc.'s Preliminary Invalidity Contentions, Case No. 21-CV-977-KAJ (D. Delaware), May 6, 2022.
US, Exhibit 216-10S from DexCom, Inc.'s Supplemental Preliminary Invalidity Contentions, Case No. 21-CV-977-KAJ (D. Delaware), May 6, 2022.

(56) References Cited

OTHER PUBLICATIONS

US, Exhibit 216-11 from DexCom, Inc.'s Preliminary Invalidity Contentions, Case No. 21-CV-977-KAJ (D. Delaware), May 6, 2022.

US, Exhibit 216-11S from DexCom, Inc.'s Supplemental Preliminary Invalidity Contentions, Case No. 21-CV-977-KAJ (D. Delaware), May 6, 2022.

US, Exhibit 216-12 from DexCom, Inc.'s Preliminary Invalidity Contentions, Case No. 21-CV-977-KAJ (D. Delaware), May 6, 2022.

US, Exhibit 216-12S from DexCom, Inc.'s Supplemental Preliminary Invalidity Contentions, Case No. 21-CV-977-KAJ (D. Delaware), May 6, 2022.

US, Exhibit 216-13 from DexCom, Inc.'s Preliminary Invalidity Contentions, Case No. 21-CV-977-KAJ (D. Delaware), May 6, 2022.

US, Exhibit 341-1 from DexCom, Inc.'s Preliminary Invalidity Contentions, Case No. 21-CV-977-KAJ (D. Delaware), May 6, 2022.

US, Exhibit 341-2 from DexCom, Inc.'s Preliminary Invalidity Contentions, Case No. 21-CV-977-KAJ (D. Delaware), May 6, 2022.

US, Exhibit 341-2S from DexCom, Inc.'s Supplemental Preliminary Invalidity Contentions, Case No. 21-CV-977-KAJ (D. Delaware), May 6, 2022.

US, Exhibit 341-3 from DexCom, Inc.'s Preliminary Invalidity Contentions, Case No. 21-CV-977-KAJ (D. Delaware), May 6, 2022.

US, Exhibit 341-3S from DexCom, Inc.'s Supplemental Preliminary Invalidity Contentions, Case No. 21-CV-977-KAJ (D. Delaware), May 6, 2022.

US, Exhibit 341-4 from DexCom, Inc.'s Preliminary Invalidity Contentions, Case No. 21-CV-977-KAJ (D. Delaware), May 6, 2022.

US, Exhibit 341-4S from DexCom, Inc.'s Supplemental Preliminary Invalidity Contentions, Case No. 21-CV-977-KAJ (D. Delaware), May 6, 2022.

US, Exhibit 341-5 from DexCom, Inc.'s Preliminary Invalidity Contentions, Case No. 21-CV-977-KAJ (D. Delaware), May 6, 2022.

US, Exhibit 341-5S from DexCom, Inc.'s Supplemental Preliminary Invalidity Contentions, Case No. 21-CV-977-KAJ (D. Delaware), May 6, 2022.

US, Exhibit 341-6 from DexCom, Inc.'s Preliminary Invalidity Contentions, Case No. 21-CV-977-KAJ (D. Delaware), May 6, 2022.

US, Exhibit 341-6S from DexCom, Inc.'s Supplemental Preliminary Invalidity Contentions, Case No. 21-CV-977-KAJ (D. Delaware), May 6, 2022.

US, Exhibit 341-7 from DexCom, Inc.'s Preliminary Invalidity Contentions, Case No. 21-CV-977-KAJ (D. Delaware), May 6, 2022.

US, Exhibit 341-7S from DexCom, Inc.'s Supplemental Preliminary Invalidity Contentions, Case No. 21-CV-977-KAJ (D. Delaware), May 6, 2022.

US, Exhibit 341-8 from DexCom, Inc.'s Preliminary Invalidity Contentions, Case No. 21-CV-977-KAJ (D. Delaware), May 6, 2022.

US, Exhibit 341-9 from DexCom, Inc.'s Preliminary Invalidity Contentions, Case No. 21-CV-977-KAJ (D. Delaware), May 6, 2022.

US, Exhibit 341-9S from DexCom, Inc.'s Supplemental Preliminary Invalidity Contentions, Case No. 21-CV-977-KAJ (D. Delaware), May 6, 2022.

US, Exhibit 341-10 from DexCom, Inc.'s Preliminary Invalidity Contentions, Case No. 21-CV-977-KAJ (D. Delaware), May 6, 2022.

US, Exhibit 341-10S from DexCom, Inc.'s Supplemental Preliminary Invalidity Contentions, Case No. 21-CV-977-KAJ (D. Delaware), May 6, 2022.

US, Exhibit 341-11 from DexCom, Inc.'s Preliminary Invalidity Contentions, Case No. 21-CV-977-KAJ (D. Delaware), May 6, 2022.

US, Exhibit 341-11S from DexCom, Inc.'s Supplemental Preliminary Invalidity Contentions, Case No. 21-CV-977-KAJ (D. Delaware), May 6, 2022.

US, Exhibit 341-12 from DexCom, Inc.'s Preliminary Invalidity Contentions, Case No. 21-CV-977-KAJ (D. Delaware), May 6, 2022.

US, Exhibit 341-12S from DexCom, Inc.'s Supplemental Preliminary Invalidity Contentions, Case No. 21-CV-977-KAJ (D. Delaware), May 6, 2022.

US, Exhibit 341-13 from DexCom, Inc.'s Preliminary Invalidity Contentions, Case No. 21-CV-977-KAJ (D. Delaware), May 6, 2022.

US, Exhibit 440-1 from DexCom, Inc.'s Preliminary Invalidity Contentions, Case No. 21-CV-977-KAJ (D. Delaware), May 6, 2022.

US, Exhibit 440-1S from DexCom, Inc.'s Supplemental Preliminary Invalidity Contentions, Case No. 21-CV-977-KAJ (D. Delaware), May 6, 2022.

US, Exhibit 440-2 from DexCom, Inc.'s Preliminary Invalidity Contentions, Case No. 21-CV-977-KAJ (D. Delaware), May 6, 2022.

US, Exhibit 440-2S from DexCom, Inc.'s Supplemental Preliminary Invalidity Contentions, Case No. 21-CV-977-KAJ (D. Delaware), May 6, 2022.

US, Exhibit 440-3 from DexCom, Inc.'s Preliminary Invalidity Contentions, Case No. 21-CV-977-KAJ (D. Delaware), May 6, 2022.

US, Exhibit 440-4 from DexCom, Inc.'s Preliminary Invalidity Contentions, Case No. 21-CV-977-KAJ (D. Delaware), May 6, 2022.

US, Exhibit 440-4S from DexCom, Inc.'s Supplemental Preliminary Invalidity Contentions, Case No. 21-CV-977-KAJ (D. Delaware), May 6, 2022.

US, Exhibit 440-5 from DexCom, Inc.'s Preliminary Invalidity Contentions, Case No. 21-CV-977-KAJ (D. Delaware), May 6, 2022.

US, Exhibit 440-5S from DexCom, Inc.'s Supplemental Preliminary Invalidity Contentions, Case No. 21-CV-977-KAJ (D. Delaware), May 6, 2022.

US, Exhibit 440-6 from DexCom, Inc.'s Preliminary Invalidity Contentions, Case No. 21-CV-977-KAJ (D. Delaware), May 6, 2022.

US, Exhibit 440-7 from DexCom, Inc.'s Preliminary Invalidity Contentions, Case No. 21-CV-977-KAJ (D. Delaware), May 6, 2022.

US, Exhibit 440-7S from DexCom, Inc.'s Supplemental Preliminary Invalidity Contentions, Case No. 21-CV-977-KAJ (D. Delaware), May 6, 2022.

US, Exhibit 440-8 from DexCom, Inc.'s Preliminary Invalidity Contentions, Case No. 21-CV-977-KAJ (D. Delaware), May 6, 2022.

US, Exhibit 440-8S from DexCom, Inc.'s Supplemental Preliminary Invalidity Contentions, Case No. 21-CV-977-KAJ (D. Delaware), May 6, 2022.

US, Exhibit 440-9 from DexCom, Inc.'s Preliminary Invalidity Contentions, Case No. 21-CV-977-KAJ (D. Delaware), May 6, 2022.

US, Exhibit 440-10 from DexCom, Inc.'s Preliminary Invalidity Contentions, Case No. 21-CV-977-KAJ (D. Delaware), May 6, 2022.

US, Exhibit 440-11 from DexCom, Inc.'s Preliminary Invalidity Contentions, Case No. 21-CV-977-KAJ (D. Delaware), May 6, 2022.

US, Exhibit 440-12 from DexCom, Inc.'s Preliminary Invalidity Contentions, Case No. 21-CV-977-KAJ (D. Delaware), May 6, 2022.

US, Exhibit 440-12S from DexCom, Inc.'s Supplemental Preliminary Invalidity Contentions, Case No. 21-CV-977-KAJ (D. Delaware), May 6, 2022.

(56) References Cited

OTHER PUBLICATIONS

US, Exhibit 440-13 from DexCom, Inc.'s Preliminary Invalidity Contentions, Case No. 21-CV-977-KAJ (D. Delaware), May 6, 2022.

US, Exhibit 440-13S from DexCom, Inc.'s Supplemental Preliminary Invalidity Contentions, Case No. 21-CV-977-KAJ (D. Delaware), May 6, 2022.

US, Exhibit 649-1 from DexCom, Inc.'s Preliminary Invalidity Contentions, Case No. 21-CV-977-KAJ (D. Delaware), May 6, 2022.

US, Exhibit 649-1S from DexCom, Inc.'s Supplemental Preliminary Invalidity Contentions, Case No. 21-CV-977-KAJ (D. Delaware), May 6, 2022.

US, Exhibit 649-2 from DexCom, Inc.'s Preliminary Invalidity Contentions, Case No. 21-CV-977-KAJ (D. Delaware), May 6, 2022.

US, Exhibit 649-2S from DexCom, Inc.'s Supplemental Preliminary Invalidity Contentions, Case No. 21-CV-977-KAJ (D. Delaware), May 6, 2022.

US, Exhibit 649-3 from DexCom, Inc.'s Preliminary Invalidity Contentions, Case No. 21-CV-977-KAJ (D. Delaware), May 6, 2022.

US, Exhibit 649-3S from DexCom, Inc.'s Supplemental Preliminary Invalidity Contentions, Case No. 21-CV-977-KAJ (D. Delaware), May 6, 2022.

US, Exhibit 649-4 from DexCom, Inc.'s Preliminary Invalidity Contentions, Case No. 21-CV-977-KAJ (D. Delaware), May 6, 2022.

US, Exhibit 649-4S from DexCom, Inc.'s Supplemental Preliminary Invalidity Contentions, Case No. 21-CV-977-KAJ (D. Delaware), May 6, 2022.

US, Exhibit 649-5 from DexCom, Inc.'s Preliminary Invalidity Contentions, Case No. 21-CV-977-KAJ (D. Delaware), May 6, 2022.

US, Exhibit 649-5S from DexCom, Inc.'s Supplemental Preliminary Invalidity Contentions, Case No. 21-CV-977-KAJ (D. Delaware), May 6, 2022.

US, Exhibit 649-6 from DexCom, Inc.'s Preliminary Invalidity Contentions, Case No. 21-CV-977-KAJ (D. Delaware), May 6, 2022.

US, Exhibit 649-6S from DexCom, Inc.'s Supplemental Preliminary Invalidity Contentions, Case No. 21-CV-977-KAJ (D. Delaware), May 6, 2022.

US, Exhibit 649-7 from DexCom, Inc.'s Preliminary Invalidity Contentions, Case No. 21-CV-977-KAJ (D. Delaware), May 6, 2022.

US, Exhibit 649-8 from DexCom, Inc.'s Preliminary Invalidity Contentions, Case No. 21-CV-977-KAJ (D. Delaware), May 6, 2022.

US, Exhibit 649-8S from DexCom, Inc.'s Supplemental Preliminary Invalidity Contentions, Case No. 21-CV-977-KAJ (D. Delaware), May 6, 2022.

US, Exhibit 649-9 from DexCom, Inc.'s Preliminary Invalidity Contentions, Case No. 21-CV-977-KAJ (D. Delaware), May 6, 2022.

US, Exhibit 649-9S from DexCom, Inc.'s Supplemental Preliminary Invalidity Contentions, Case No. 21-CV-977-KAJ (D. Delaware), May 6, 2022.

US, Exhibit 649-10 from DexCom, Inc.'s Preliminary Invalidity Contentions, Case No. 21-CV-977-KAJ (D. Delaware), May 6, 2022.

US, Exhibit 649-11 from DexCom, Inc.'s Preliminary Invalidity Contentions, Case No. 21-CV-977-KAJ (D. Delaware), May 6, 2022.

US, Exhibit 649-12 from DexCom, Inc.'s Preliminary Invalidity Contentions, Case No. 21-CV-977-KAJ (D. Delaware), May 6, 2022.

US, Exhibit 649-13 from DexCom, Inc.'s Preliminary Invalidity Contentions, Case No. 21-CV-977-KAJ (D. Delaware), May 6, 2022.

US, Exhibit 649-13S from DexCom, Inc.'s Supplemental Preliminary Invalidity Contentions, Case No. 21-CV-977-KAJ (D. Delaware), May 6, 2022.

US, Exhibit 654-1 from DexCom, Inc.'s Preliminary Invalidity Contentions, Case No. 21-CV-977-KAJ (D. Delaware), May 6, 2022.

US, Exhibit 654-2 from DexCom, Inc.'s Preliminary Invalidity Contentions, Case No. 21-CV-977-KAJ (D. Delaware), May 6, 2022.

US, Exhibit 654-2S from DexCom, Inc.'s Supplemental Preliminary Invalidity Contentions, Case No. 21-CV-977-KAJ (D. Delaware), May 6, 2022.

US, Exhibit 654-3 from DexCom, Inc.'s Preliminary Invalidity Contentions, Case No. 21-CV-977-KAJ (D. Delaware), May 6, 2022.

US, Exhibit 654-3S from DexCom, Inc.'s Supplemental Preliminary Invalidity Contentions, Case No. 21-CV-977-KAJ (D. Delaware), May 6, 2022.

US, Exhibit 654-4 from DexCom, Inc.'s Preliminary Invalidity Contentions, Case No. 21-CV-977-KAJ (D. Delaware), May 6, 2022.

US, Exhibit 654-4S from DexCom, Inc.'s Supplemental Preliminary Invalidity Contentions, Case No. 21-CV-977-KAJ (D. Delaware), May 6, 2022.

US, Exhibit 654-5 from DexCom, Inc.'s Preliminary Invalidity Contentions, Case No. 21-CV-977-KAJ (D. Delaware), May 6, 2022.

US, Exhibit 654-5S from DexCom, Inc.'s Supplemental Preliminary Invalidity Contentions, Case No. 21-CV-977-KAJ (D. Delaware), May 6, 2022.

US, Exhibit 654-6 from DexCom, Inc.'s Preliminary Invalidity Contentions, Case No. 21-CV-977-KAJ (D. Delaware), May 6, 2022.

US, Exhibit 654-6S from DexCom, Inc.'s Supplemental Preliminary Invalidity Contentions, Case No. 21-CV-977-KAJ (D. Delaware), May 6, 2022.

US, Exhibit 654-7 from DexCom, Inc.'s Preliminary Invalidity Contentions, Case No. 21-CV-977-KAJ (D. Delaware), May 6, 2022.

US, Exhibit 654-7S from DexCom, Inc.'s Supplemental Preliminary Invalidity Contentions, Case No. 21-CV-977-KAJ (D. Delaware), May 6, 2022.

US, Exhibit 654-8 from DexCom, Inc.'s Preliminary Invalidity Contentions, Case No. 21-CV-977-KAJ (D. Delaware), May 6, 2022.

US, Exhibit 654-9 from DexCom, Inc.'s Preliminary Invalidity Contentions, Case No. 21-CV-977-KAJ (D. Delaware), May 6, 2022.

US, Exhibit 654-9S from DexCom, Inc.'s Supplemental Preliminary Invalidity Contentions, Case No. 21-CV-977-KAJ (D. Delaware), May 6, 2022.

US, Exhibit 654-10 from DexCom, Inc.'s Preliminary Invalidity Contentions, Case No. 21-CV-977-KAJ (D. Delaware), May 6, 2022.

US, Exhibit 654-10S from DexCom, Inc.'s Supplemental Preliminary Invalidity Contentions, Case No. 21-CV-977-KAJ (D. Delaware), May 6, 2022.

US, Exhibit 654-11 from DexCom, Inc.'s Preliminary Invalidity Contentions, Case No. 21-CV-977-KAJ (D. Delaware), May 6, 2022.

US, Exhibit 654-11S from DexCom, Inc.'s Supplemental Preliminary Invalidity Contentions, Case No. 21-CV-977-KAJ (D. Delaware), May 6, 2022.

US, Exhibit 654-12 from DexCom, Inc.'s Preliminary Invalidity Contentions, Case No. 21-CV-977-KAJ (D. Delaware), May 6, 2022.

US, Exhibit 654-12S from DexCom, Inc.'s Supplemental Preliminary Invalidity Contentions, Case No. 21-CV-977-KAJ (D. Delaware), May 6, 2022.

US, Exhibit 654-13 from DexCom, Inc.'s Preliminary Invalidity Contentions, Case No. 21-CV-977-KAJ (D. Delaware), May 6, 2022.

(56) References Cited

OTHER PUBLICATIONS

US, Defendant Dexcom, Inc.'s First Supplemental Preliminary Invalidity Contentions, Case 21-CV-977-KAJ, May 6, 2022.
US, Defendant Dexcom, Inc.'s Preliminary Invalidity Contentions, Case 21-CV-977-KAJ, May 6, 2022.
US, Defendant Dexcom, Inc.'s Corrected First Supplemental Response to Plaintiffs' Interrogatories 3 and 4, Case 21-CV-977-KAJ, Mar. 31, 2022.
US, Dexcom, Inc.'s Answer to First Amended Complaint and Affirmative Defenses to Plaintiffs' First Amended Complaint, Case 21-CV-977-KAJ, Feb. 22, 2022.
US, Transcript of Oral Arguments, Case 21-CV-977-KAJ, Feb. 11, 2022.
US, Order Denying Dexcom, Inc.'s Motion to Dismiss, Case 21-CV-977-KAJ, Feb. 8, 2022.
US, Defendant Dexcom, Inc.'s Response to Plaintiff's First Set of Interrogatories, Case 21-CV-977-KAJ, Dec. 10, 2021.
US, Defendant Dexcom, Inc.'s Reply Brief in Support of its Motion to Dismiss Pursuant to Federal Rule of Civil Procedure 12(b)(6), Case 21-CV-977-KAJ, Nov. 22, 2021.
US, Plaintiff's Answering Brief in Opposition to Defendant Motion to Dismiss Under Rule 12(b)(6), Case 21-CV-977-KAJ, Nov. 15, 2021.
US, Defendant Dexcom, Inc.'s Appendix to Opening Brief in Support of its Motion to Dismiss Pursuant to Federal Rule of Civil Procedure 12(b)(6), Case 21-CV-977-KAJ, Nov. 1, 2021.
US, Defendant Dexcom, Inc.'s Opening Brief in Support of its Motion to Dismiss Pursuant to Federal Rule of Civil Procedure 12(b)(6), Case 21-CV-977-KAJ, Nov. 1, 2021.
US, Defendant Dexcom, Inc.'s Motion to Dismiss Under Rule 12(b)(6), Case 21-CV-977-KAJ, Nov. 1, 2021.
US, First Amended Complaint filed by Abbott Diabetes Care Inc. and Abbott Diabetes Care Limited against Dexcom, Inc., Case 21-CV-977-KAJ, Oct. 4, 2021.
US, Complaint filed by Abbott Diabetes Care Inc. and Abbott Diabetes Care Limited against Dexcom, Inc., Case 21-CV-977-KAJ, Jul. 1, 2021.
US, Plaintiff Dexcom, Inc.'s Amended Preliminary Disclosure of Asserted Claims and Infringement Contentions to Abbott Diabetes Care Inc. and Abbott Diabetes Care Sales Corp., Case 21-CV-690-ADA ((D. Texas), Jan. 5, 2022.
US, Joint Claim Construction Brief, Case 20-1679-RGA-JLH (D. Delaware), Feb. 11, 2022.
US, Findings of Fact and Conclusions of Law Regrading Subject Matter Eligibility of U.S. Pat. No. 6,975,308 Under 35 U.S.C. § 101, Case 20-CV-101-ADA (D. Texas), Dec. 7, 2021.
CA, 2,984,939 Examiner's Report, Aug. 7, 2024.
CA, 3,050,721 Examiner's Report, Nov. 8, 2024.
CA, 3,120,335 Examiner's Report, May 27, 2024.
CN, 200880005149.1 Notice of Allowance, Jun. 21, 2013.
CN, 200880005149.1 Fourth Office Action, Dec. 3, 2012.
CN, 200880005149.1 Third Office Action, Feb. 16, 2012.
CN, 200880005149.1 Second Office Action, Aug. 17, 2011.
CN, 200880005149.1 First Office Action, Jul. 29, 2010.
DE, Complaint in Litigation of EP 3300658, Mar. 20, 2024.
EP, 10739031.2 Summons to Attend Oral Proceedings, Oct. 26, 2023.
EP, 10739031.2 Communication from Board of Appeals, Feb. 21, 2024.
EP, 10739031.2 Minutes of Oral Proceedings, May 10, 2024.
EP, 10739031.2 Decision of Oral Proceedings, Jun. 11, 2024.
EP, 17182379.2 Grounds of Opposition, Jul. 12, 2024.
EP, 17182379.2 Notice of Opposition, Jul. 12, 2024.
EP, 17182379.2 Reply to Examination Report, Apr. 9, 2021.
EP, 17182379.2 Reply to Search Report, Oct. 3, 2018.
EP, 19151577.4 Examination Report, Oct. 7, 2024.
EP, 20177703.4 Summons to Attend Oral Proceedings, Apr. 29, 2024.
EP, 20177712.5 Summons to Attend Oral Proceedings, Oct. 1, 2024.

EP, 20177712.5 Response to Summons to Attend Oral Proceedings, Aug. 30, 2024.
EP, 20177712.5 Summons to Attend Oral Proceedings, Jul. 2, 2024.
EP, 20177712.5 Response to Written Submissions Dexcom, Feb. 26, 2024.
EP, 20177712.5 Written Submissions ADC, Jan. 26, 2024.
EP, 20195922.8 Grounds of Appeal, Sep. 6, 2024.
EP, 20195922.8 Notice of Appeal, Jul. 4, 2024.
EP, 20195922.8 Written Submissions Dexcom, May 9, 2024.
EP, 20195922.8 Decision Revoking the European Patent, May 8, 2024.
EP, 20195922.8 Minutes of the Oral Proceedings, May 8, 2024.
EP, 20195922.8 Written Submissions Dexcom, Mar. 15, 2024.
EP, 21211041.5 Response to Summons to Attend Oral Proceedings Dexcom, Nov. 12, 2024.
EP, 21211041.5 Response to Summons to Attend Oral Proceedings, Nov. 12, 2024.
EP, 21211041.5 Summons to Attend Oral Proceedings, Sep. 23, 2024.
EP, 21211041.5 Reply to Notice of Opposition, Jul. 17, 2024.
EP, 21211041.5 Grounds of Opposition Dexcom, Mar. 28, 2024.
EP, 21211041.5 Notice of Opposition Dexcom, Mar. 28, 2024.
EP, 23166498.8 Examination Report, Sep. 2, 2024.
EP, 24152079.0 Extended Search Report, Sep. 4, 2024.
EP, 24152079.0 Partial Search Report, Jun. 14, 2024.
EP, 24183336.7 Extended Search Report, Oct. 11, 2024.
EP, 24187206.8 Extended Search Report, Oct. 9, 2024.
GB, Claim No. HP-2021-000025 Approved Judgement, Oct. 18, 2023.
MX, MX/a/2021/007294 Office Action, Aug. 20, 2024.
RU, 2009134334 Office Action, Feb. 7, 2012.
UP, First Expert Opinion of Dr Michael Schoemaker in Litigation of EP 3977921, Jun. 11, 2024.
US, Notice of Filing Date Accorded to Petition and Time for Filing Patent Owner Preliminary Response, IPR No. 2024-00860, May 23, 2024.
US, Declaration of Dr. Cameron Riviere, Ph.D., IPR No. 2024-00860, May 9, 2024.
US, Petition for Inter Partes Review of U.S. Pat. No. 11,510,625, IPR No. 2024-00860, May 9, 2024.
US, Decision Denying Institution of Inter Partes Review, IPR No. 2024-00520, Aug. 8, 2024.
US, Patent Owner's Authorized Sur-Reply to Petitioner's Reply to Patent Owner's Preliminary Response, IPR No. 2024-00520, Jun. 11, 2024.
US, Petitioner's Authorized Reply to Patent Owner's Preliminary Response, IPR No. 2024-00520, May 31, 2024.
US, Patent Owner's Preliminary Response, IPR No. 2024-00520, May 8, 2024
US, Patent Owner's Exhibit List, IPR No. 2024-00520, Mar. 25, 2024.
US, Telephonic Hearing, IPR No. 2024-00520, Mar. 13, 2024.
US, Petitioner's Explanation of Material Differences Between the Petition in IPR2024-00520 and Previously Filed Petitions in IPR2023-01396 and IPR2023-01397, IPR No. 2024-00520, Jan. 31, 2024.
US, Declaration of Karl R. Leinsing, MSME, PE, IPR No. 2023-01409, Jul. 19, 2024.
US, Patent Owner's Response, IPR No. 2023-01409, Jul. 19, 2024.
US, Deposition of Gary Fletcher, Ph.D., IPR No. 2023-01409, Jun. 26, 2024.
US, Order, IPR No. 2023-01409, May 30, 2024.
US, Notice of Stipulation, IPR No. 2023-01409, May 29, 2024.
US, Patent Owner's Objections to Petitioner's Exhibits to the Petition, IPR No. 2023-01409, Apr. 29, 2024.
US, Patent Owner's Request for Rehearing by the Director, IPR 2023-01409, Apr. 29, 2024.
US, Email of Peter McAndrews, IPR 2023-01409, Apr. 29, 2024.
US, Decision Granting Institution of Inter Partes Review, IPR No. 2023-01409, Apr. 15, 2024.
US, Scheduling Order, IPR 2023-01409, Apr. 15, 2024.
US, Order Conduct of the Proceeding 37 C.F.R. § 42.5, IPR No. 2023-01409, Feb. 6, 2024.

(56) References Cited

OTHER PUBLICATIONS

US, Petitioner's Updated Exhibit List, IPR No. 2023-01409, Feb. 5, 2024.
US, Telephonic Conference Call, IPR No. 2023-01409, Feb. 2, 2024.
US, Patent Owner's Updated Mandatory Notices, IPR No. 2023-01409, Feb. 2, 2024.
US, Email of Andrew M. Mason, IPR 2023-01409, Jan. 30, 2024.
US, Patent Owner's Preliminary Response, IPR No. 2023-01409, Jan. 18, 2024.
US, Notice of Filing Date Accorded to Petition and Time for Filing Patent Owner Preliminary Response, IPR No. 2023-01409, Oct. 18, 2023.
US, Decision Denying Institution of Inter Partes Review, IPR No. 2023-01397, Apr. 16, 2024.
US, Patent Owner's Updated Exhibit List, IPR No. 2023-01397, Mar. 25, 2024.
US, Telephonic Hearing, IPR No. 2023-01397, Mar. 13, 2024.
US, Petitioner's Updated Mandatory Notices Pursuant to 37 C.F.R. § 42.8(a)(3), IPR No. 2023-01397, Feb. 19, 2024.
US, Patent Owner's Updated Mandatory Notices, IPR No. 2023-01397, Feb. 2, 2024.
US, Patent Owner's Preliminary Response, IPR No. 2023-01397, Jan. 18, 2024.
US, Patent Owner's Response to Petitioner's Explanation of Material Differences Between Petitions, IPR Nos. 2023-01396 and 2023-01397, Jan. 18, 2024.
US, Petitioner's Request for Rehearing of Decision Denying Institution, IPR No. 2023-01396, May 16, 2024.
US, Decision Denying Institution of Inter Partes Review, IPR No. 2023-01396, Apr. 16, 2024.
US, Patent Owner's Updated Exhibit List, IPR No. 2023-01396, Mar. 25, 2024.
US, Telephonic Hearing, IPR No. 2023-01396, Mar. 13, 2024.
US, Petitioner's Updated Mandatory Notices Pursuant to 37 C.F.R. § 42.8(a)(3), IPR No. 2023-01396, Feb. 19, 2024.
US, Patent Owner's Preliminary Response, IPR No. 2023-01396, Jan. 18, 2024.
US, Notice of Filing Date Accorded to Petition and Time for Filing Patent Owner Preliminary Response, IPR No. 2023-01396, Oct. 18, 2023.
US, Reexamination U.S. Appl. No. 90/019,329 Ex Parte Reexamination Certificate, Oct. 30, 2024.
US, Reexamination U.S. Appl. No. 90/019,329 Notice of Intent to Issue Ex Parte Reexamination Certificate, Oct. 8, 2024.
US, Reexamination U.S. Appl. No. 90/019,329 Decision on Petition Under 37 C.F.R. § 1.59, Sep. 16, 2024.
US, Reexamination U.S. Appl. No. 90/019,329 Statutory disclaimer per Manual of Patent Examining Procedure (MPEP) 1490, Sep. 3, 2024.
US, Reexamination U.S. Appl. No. 90/019,329 Petition Under 37 C.F.R. § 1.182 to Seal Document Versions Filed via IDS and Substitute Redacted Document Versions Therfor, Aug. 1, 2024.
US, Reexamination No. 90/019,329 Petition Under 37 CFR § 1.59 to Expunge Application Papers, Aug. 1, 2024.
US, Reexamination No. 90/019,329 Ex Parte Reexamination Interview Summary, Jul. 25, 2024.
US, Reexamination U.S. Appl. No. 90/019,329 Decision on Petition Under 37 C.F.R. § 1.59, Jul. 22, 2024.
US, Reexamination No. 90/019,329 Decision Sua Sponte Vacating Notice of Intent to Issue Ex Parte Reexamination Certificate, Jul. 3, 2024.
US, Reexamination No. 90/019,329 Petition Under 37 CFR § 1.59 to Expunge Application Papers, Jun. 12, 2024.
US, Reexamination U.S. Appl. No. 90/019,329 Notification of Concurrent Proceedings, May 15, 2024.
US, Petition Under 37 CFR § 1.181 and/or § 1.182 to Terminate Reexamination No. 90/019,329, Apr. 26, 2024.
US, Reexamination U.S. Appl. No. 90/019,329 Declaration of Gary D. Fletcher, Ph.D., Dec. 11, 2023.

US, Reexamination U.S. Appl. No. 90/019,331 Ex Parte Reexamination Certificate, Nov. 14, 2024.
US, Reexamination U.S. Appl. No. 90/019,331 Notice of Intent to Issue Ex Parte Reexamination Certificate, Oct. 15, 2024.
US, Reexamination U.S. Appl. No. 90/019,331 Decision on Petition Under 37 C.F.R. § 1.59, Sep. 16, 2024.
US, Reexamination U.S. Appl. No. 90/019,331 Decision Granting Petition, Aug. 26, 2024.
US, Reexamination U.S. Appl. No. 90/019,331 Petition Under 37 C.F.R. § 1.182 to Seal Document Versions Filed via IDS and Substitute Redacted Document Versions Therfor, Aug. 1, 2024.
US, Reexamination No. 90/019,331 Petition Under 37 CFR § 1.59 to Expunge Application Papers, Aug. 1, 2024.
US, Reexamination U.S. Appl. No. 90/019,331 Petition to Withdraw From Issue and Reopen the Proceeding, Jul. 26, 2024.
US, Reexamination U.S. Appl. No. 90/019,331 Decision on Petition Under 37 C.F.R. § 1.59, Jul. 16, 2024.
US, Reexamination U.S. Appl. No. 90/019,331 Notice of Intent to Issue Ex Parte Reexamination Certificate, Jul. 10, 2024.
US, Reexamination No. 90/019,331 Petition Under 37 CFR § 1.59 to Expunge Application Papers, Jun. 12, 2024.
US, Reexamination U.S. Appl. No. 90/019,331 Notification of Concurrent Proceedings, May 15, 2024.
US, Reexamination No. 90/019,307 Petition Under 37 CFR § 1.181 to Terminate, Aug. 15, 2024.
US, Reexamination No. 90/019,307 Decision on Petitions, Aug. 7, 2024.
US, Reexamination No. 90/019,307 Petition Under 37 CFR § 1.59 to Expunge Application Papers, Aug. 1, 2024.
US, Reexamination No. 90/019,307 Petition Under 37 CFR § 1.59 to Expunge Application Papers, Jun. 12, 2024.
US, Reexamination U.S. Appl. No. 90/019,307 Notification of Concurrent Proceedings, May 15, 2024.
US, Reexamination No. 90/019,307 Petition Under 37 CFR §§ 1.182 and/or § 1.183 to Allow Filing and Consideration of Response to Patent Owner's Extraordinary Petition to Suspend, Mar. 19, 2024.
US, Reexamination No. 90/019,307 Petition Under 37 CFR § 1.181 and/or § 1.183 to Suspend, Mar. 1, 2024.
US, Ex Parte Reexamination Certificate of U.S. Pat. No. 10,959,654, Nov. 5, 2024.
US, Reexamination U.S. Appl. No. 90/019,330 Notice of Intent to Issue Ex Parte Reexamination Certificate, Oct. 7, 2024.
US, Reexamination U.S. Appl. No. 90/019,330 Decision on Petition Under 37 C.F.R. § 1.59, Sep. 16, 2024.
US, Reexamination U.S. Appl. No. 90/019,330 Decision Granting Petition and Vacating a Reexamination Certificate, Aug. 26, 2024.
US, Ex Parte Reexamination Certificate of U.S. Pat. No. 10,959,654, Aug. 5, 2024.
US, Reexamination U.S. Appl. No. 90/019,330 Petition Under 37 C.F.R. § 1.182 to Seal Document Versions Filed via IDS and Substitute Redacted Document Versions Therfor, Aug. 1, 2024.
US, Reexamination No. 90/019,330 Petition Under 37 CFR § 1.59 to Expunge Application Papers, Aug. 1, 2024.
US, Reexamination U.S. Appl. No. 90/019,330 Petition to Withdraw From Issue and Reopen the Proceeding, Jul. 26, 2024.
US, Reexamination U.S. Appl. No. 90/019,330 Decision on Petition Under 37 C.F.R. § 1.59, Jul. 16, 2024.
US, Reexamination U.S. Appl. No. 90/019,330 Notice of Intent to Issue Ex Parte Reexamination Certificate of U.S. Pat. No. 10,959,654, Jul. 1, 2024.
US, Reexamination No. 90/019,330 Petition Under 37 CFR § 1.59 to Expunge Application Papers, Jun. 12, 2024.
US, Reexamination U.S. Appl. No. 90/019,330 Notification of Concurrent Proceedings, May 15, 2024.
US, Reexamination U.S. Appl. No. 90/019,330 Order Granting Request for Reexamination of U.S. Pat. No. 10,959,654, Jan. 23, 2024.
US, Reexamination U.S. Appl. No. 90/019,330 Declaration of John Mastrototaro, Ph.D., Dec. 11, 2023.
WO, PCT/US2008/054165 ISR and Written Opinion, Jun. 5, 2008.
WO, PCT/US2008/067791 ISR and Written Opinion, Sep. 30, 2008.
WO, PCT/US24/11756 ISR and Written Opinion, Jun. 28, 2024.

(56) References Cited

OTHER PUBLICATIONS

WO, PCT/US24/11756 Invitation to Pay Additional Fees, May 7, 2024.
WO, PCT/US24/16127 ISR and Written Opinion, Sep. 11, 2024.
WO, PCT/US24/16127 Invitation to Pay Additional Fees, Jun. 4, 2024.
WO, PCT/US24/18665 ISR and Written Opinion, Jun. 21, 2024.
"27 Winners Announced at the 19th Annual Medical Design Excellence Awards (MDEA) Award Ceremony", UBM Americas, 2017, 4 pages.
"55 Chosen as Winners in Annual BIG Innovation Awards", 2018, retrieved from https://www.bintelligence.com/posts/55-chosen-as-winners-in-annual-big-innovation-awards, 2 pages.
2017 Good Design Award, retrieved from https://www.g-mark.org/gallery/winners/9dda01a3-803d-11ed-af7e-0242ac130002, 9 pages.
"2019 Top 10 Innovations", The Scientist, retrieved from https://www.the-scientist.com/2019-top-10-innovations-66738, 7 pages.
Abbott 2023 Annual Report, retrieved from https://www.abbottinvestor.com/static-files/6cb09c09-2422-40e0-a24b-6545ffcf5267, pp. 1-82.
Abbott Clinical Trials Competitor and Ecosystem Players, 2020, 28 pages.
"Abbott's Freestyle Libre® Is Named Best Medical Technology in Last 50 Years By The Galien Foundation", 2022, PRNewswire, 1 page.
"Abbott's Freestyle® Libre 2 ICGM Cleared in U.S. for Adults and Children With Diabetes, Achieving Highest Level of Accuracy and Performance Standards", retrieved from https://abbott.mediaroom.com/2020-06-15-Abbotts-FreeStyle-R-Libre-2-iCGM-Cleared-in-U-S-for-Adults-and-Children-with-Diabetes-Achieving-Highest-Level-of-Accuracy-and-Performance-tandards#:~:text=FDA%20clears%20Abbott's%20FreeStyle%20Libre,high%20or%20low%20without%20scanning, on Jul. 7, 2024, 3 pages.
"Abbott's Freestyle Libre® 3 Receives U.S. FDA Clearance—Features World's Smallest, Thinnest and Most Accurate 14-Day Glucose Sensor", 2022, PRNewswire, 3 pages.
"Abbott's Freestyle Libre Flash Glucose Monitoring System Wins the IMSTA Most Innovative Product Multi-National Award 2017", retrieved from https://www.ie.abbott/media-center/news/abbotts-freestyle-libre-flash-glucose-monitoring-system-wins-the-imsta-award-2017.html, 2 pages.
"Abbott's Freestyle® Libre 14 Day Flash Glucose Monitoring System Now Approved in U.S.", 2018, PRNewswire, 2 pages.
About the Edison Awards retrieved from https://edisonawards.com/about/, 2024, 3 pages.
ACCU-CHEK® Softclix Lancet Device retrieved from file:///C:/Users/afredericks/Downloads/softclix-user-manual.pdf, 2007, 2 pages.
Using your ACCU-CHEK® Multiclix Lancet Device, 2005, retrieved from https://www.northcoastmed.com/wp-content/uploads/2023/03/multiclix_userguide.pdf, 2 pages.
Ahn, D., "Abbott's Euro approved wearable glucose monitor is different than anything on the market", 2014, retrieved from https://www.imedicalapps.com/2014/09/abbotts-wearable-glucose-monitor/, 6 pages.
American National Standard, ANSI/AAMI HE75:2009, Human factors engineering—Design of medical devices, 2010, 465 pages.
Automated Retractable VanishPoint Syringe 510(k) Safety and Effectiveness Summary, 1998, 5 pages.
"BinaxNOW, FreeStyle Libre 2 win BIG innovation honors", 2021, retrieved from https://www.abbott.com/corpnewsroom/strategy-and-strength/binaxnow-freestyle-libre-win-big-innovation-honors.html, 6 pages.
"Bluetooth rival unveiled by Nokia", 2006, retrieved from news.bbc.co.uk/1/hi/technology/5403564.stm, 2 pages.
Blum, A., "Freestyle Libre Glucose Monitoring System", Clinical Pharmacology Update, 2018, vol. 36, No. 2, pp. 203-204.
Breton, M., et al., "Fully Integrated Artificial Pancreas in Type 1 Diabetes: Modular Closed-Loop Glucose Control Maintains Near Normoglycemia", Diabetes, 2012, vol. 61, No. 9, pp. 2230-2237.
Cather, D. E., "Cgm Frustrations Survey", 2020, 36 pages.
Certified Copy of U.S. Appl. No. 61/149,639, filed Feb. 3, 2009.

CES 2022 Innovation Award Honorees, retrieved from https://www.ces.tech/innovation-awards/honorees/2022/best-of/f/freestyle-libre-3-system.aspx, 1 page.
2019 Chicago Innovation Award Winner Abbott Laboratories, retrieved from https://chicagoinnovation.com/winners/abbott-laboratories/, 4 pages.
Continuous Glucose Monitoring Systems Product Reference Guide, Diabetes Health, 2006-2007, pp. 50-51.
Das, S. D., et al., "Review—Electrochemistry and Other Emerging Technologies for Continuous Glucose Monitoring Devices", ECS Sensors Plus, 2022, 19 pages.
Design Concepts Project Status Update, Glucose Sensor Applicator Dexcom (project #2554), 2014, 5 pages.
Dexcom G5 Mobile System User Guide, 2015, pp. 1-260.
Dexcom G5 Quick Start Guide, 2020, pp. 1-31.
Dexcom G6 Continuous Glucose Monitoring System User Guide, 2022, 346 pages.
Dexcom G6 Start Here Set up Guide, 2022, pp. 18 pages.
Dexcom G6 Continuous Glucose Monitoring (CGM) System Section 510(k) Approval, 2022, 7 pages.
"The Dexcom G7. The most accurate CGM system.[1]" retrieved from https://www.dexcom.com/g7-cgm-system on Jun. 27, 2024, 20 pages.
Dexcom G7 Continuous Glucose Monitoring (CGM) System Section 510(k) Approval, 2022, 10 pages.
Dexcom G7 User Guide, 2024, p. i-186.
Edison Awards Announces 2016 Gold, Silver, and Bronze Awards Winners, Edison Awards, 9 pages.
Edison Best New Product Awards™ 2021 Winners retrieved from https://edisonawards.com/2021-winners/, 19 pages.
Edison Best New Product Awards™ 2022 Winners retrieved from https://edisonawards.com/2022-winners/, 52 pages.
Email from Christopher M Dougherty dated Dec. 17, 2019, 68 pages.
Englert, K., et al., "Skin and Adhesive Issues With Continuous Glucose Monitors: A Sticky Situation", Journal of Diabetes Science and Technology, 2014, vol. 8, No. 4, pp. 745-751.
U.S. Appl. No. 61/317,243.
U.S. Appl. No. 61/345,562.
U.S. Appl. No. 61/361,374.
U.S. Appl. No. 61/411,262.
U.S. Appl. No. 61/569,287.
U.S. Appl. No. 62/524,247.
Freckmann, G., et al., "Performance Evaluation of Three Continuous Glucose Monitoring Systems: Comparison of Six Sensors per Subject in Parallel", Journal of Diabetes Science and Technology, 2013, vol. 7, No. 4, pp. 842-853.
Freestyle Libre Brochure, 2016, 10 pages.
Freestyle Libre Fact Sheet, 2016, retrieved from www.FreeStyleLibre.de, 2 pages.
Freestyle Libre FAQ, 2024, retrieved from https://www.freestyle.abbott/uk-en/support/faq/question-answer.html?q=UKFaqquestion-55#, 2 pages.
"FreeStyle Libre Honored by Prix Galien", 2019, 4 pages.
FreeStyle Libre In-Service Guide, 2021, 28 pages.
FreeStyle Libre 2 Get Started Guide, 2023, pp. 1-28.
FreeStyle Libre 2 HCP Pulse Report, 2021, 13 pages.
"FreeStyle Libre 2—Zucker messen ohne stechen per Sensor und App", German Innovation Awards Gold Winner, 2020, retrieved from https://www.german-innovation-award.de/preistraeger/preis/gewinner/freestyle-libre-2-zucker-messen-ohne-stechen-per-sensor-und-app/#:~:text=Beschreibung%20Die%20kontinuierliche%20Glukosemessung%20mit,um%20die%20Glukosewerte%20kontinuierlich%20aufzuzeichnen, 1 page.
FreeStyle Libre 3 Get Started Guide, 2023, pp. 1-20.
FreeStyle Libre 3 User's Manual, 2022-2023, pp. iv-241.
The Galien Foundation is proud to announce the laureates of the best-of-the-best from the half century 1970-2020, The 2022 Galien Golden Jubilee Winners, retrieved from https://www.galienfoundation.org/galien-golden-jubilee, 3 pages.
Gough, D. A., et al., "Development of the Implantable Glucose Sensor: What Are the Prospects and Why Is It Taking So Long?", Diabetes, 1995, vol. 44, pp. 1005-1009.

(56) References Cited

OTHER PUBLICATIONS

Harris, J. M., et al., "Common Causes of Glucose Oxidase Instability in In Vivo Biosensing: A Brief Review", Journal of Diabetes Science and Technology. 2013, vol. 7, No. 4, pp. 1030-1038.
Hermanides, J., et al., "Current Application of Continuous Glucose Monitoring in the Treatment of Diabetes", Diabetes Care, 2011, vol. 34, Suppl. 2, pp. S197-S201.
Hovorka, R., "Continuous glucose monitoring and closed-loop systems", Diabetic Medicine, 2005, vol. 23, pp. 1-12.
Insert Molding, 1996, retrieved from https://www.mddionline.com/equipment/insert-molding, 4 pages.
International Diabetes Device 2022 Blue Book, Seagrove Partners, 142 pages.
International Standard, IEC 62366, Medical devices—Application of usability engineering to medical devices, 2007, 214 pages.
Joseph, J. I., et al., "Glucose Sensing in the Subcutaneous Tissue: Attempting to Correlate the Immune Response with Continuous Glucose Monitoring Accuracy", Diabetes Technology & Therapeutics, 2018, vol. 20, No. 5, pp. 321-324.
Kaye, R., et al., "Medical Device Use-Safety: Incorporating Human Factors Engineering into Risk Management", 2000, retrieved from https://www.qualysinnova.com/download/files/MD-Use-Safety.pdf, pp. 1-33.
Lomas, P., "Dexcom G7 Release: The Most Exciting New Features", 2024, retrieved from https://notjustapatch.com/dexcom-g7-features/, 13 pages.
Lovett, L., "What's next for Dexcom? CEO, CTO talk G6 for inpatient use, expanding CGMs for patients without diabetes", 2020, retrieved from https://www.mobihealthnews.com/news/whats-next-dexcom-ceo-cto-talk-g6-inpatient-use-expanding-cgms-patients-without-diabetes, 6 pages.
Medtronic MiniMed Enlite Serter User Guide, 2014, 26 pages.
Medtronic MiniMed iPro2 User Guide, 2010, pp. 1-99.
Medtronic MiniMed One-press Serter User Guide, 2015, 26 pages.
Medtronic MiniMed Paradigm® 512 and 712 Insulin Pumps User Guide, 2005, pp. 1-136.
Meltsner, M A, et al., "Observations on rotating needle insertions using a brachytherapy robot", Phys. Med. Biol., 2007, vol. 52, pp. 6027-6037.
Microlet® 2 Lancing Device, 2008, retrieved from https://image.tigermedical.com/Manuals/BAY6606-20141216010820833.pdf, 1 page.
Nichols, S. P., et al., "Biocompatible Materials for Continuous Glucose Monitoring Devices", Chem Rev., 2013, vol. 113, No. 4, pp. 2528-2549.
Ólafsdóttir, A. F., et al., "A Clinical Trial of the Accuracy and Treatment Experience of the Flash Glucose Monitor FreeStyle Libre in Adults with Type 1 Diabetes", Diabetes Technology & Therapeutics, 2017, vol. 19, No. 3, pp. 164-172.
"Periphery", Cambridge Dictionary of American English, 2000, p. 631.
"Product Review: Abbott FreeStyle Libre Flash Glucose Monitor", DiabetesMine Team, 2021, retrieved from https://www.healthline.com/diabetesmine/abbott-freestyle-libre-review#bottom-line, 6 pages.
"Real-World Data Show Abbott's Freestyle Libre® Systems And GLP-1 Medicines Work Better Together For People With Type 2 Diabetes", 2024, PRNewswire, 2 pages.
Rice, M. J., et al., "Continuous Measurement of Glucose: Facts and Challenges", Anesthesiology, 2012, vol. 116, No. 1, pp. 199-204.
Rigo, R. S., et al., "Cutaneous Reactions to Continuous Glucose Monitoring and Continuous Subcutaneous Insulin Infusion Devices in Type 1 Diabetes Mellitus", Journal of Diabetes Science and Technology, 2021, vol. 15, No. 4, pp. 786-791.
Rocchitta, G., et al., "Enzyme Biosensors for Biomedical Applications: Strategies for Safeguarding Analytical Performances in Biological Fields", Sensors, 2016. Vol. 16, No. 6, 21 pages.
Sclater, N., et al., eds., Mechanisms and Mechanical Devices Sourcebook, Fourth Edition, 2007, Chapter 12—Shaft Couplings and Connections, pp. 290-307.
"Transcutaneous", Webster's Third New International Dictionary, 2002, pp. 2426.

Tsumura, R., et al., "Histological Evaluation of Tissue Damage Caused by Rotational Needle Insertion", Proceedings of the Annual International Conference of the IEEE Engineering in Medicine and Biology Society, 2016, pp. 5120-5123.
Van Den Boom, L., et al., "Changes in the utilization of blood glucose test strips among patients using intermittent-scanning continuous glucose monitoring in Germany", Diabetes, Obesity and Metabolism, 2020, vol. 22, pp. 922-928.
Xu, J., et al., "Anti-Biofouling Strategies for Long-Term Continuous Use of Implantable Sensors", Chemosensors, 2020, vol. 20 No. 3, 29 pages.
GB, Claim No. HP-2023-000012 and Claim No. HP-2023-000016 Second Expert Report of Colin Anthony Chong, Oct. 1, 2024.
GB, Claim No. HP-2023-000012 Second Expert Report of Eugene Randal Prais, Oct. 1, 2024.
GB, Claim No. HP-2023-000012 and Claim No. HP-2023-000016 Exhibit CC-8 to the First Expert Report of Colin Anthony Chong, Aug. 13, 2024.
GB, Claim No. HP-2023-000012 and Claim No. HP-2023-000016 First Expert Report of Colin Anthony Chong, Aug. 13, 2024.
GB, Claim No. HP-2023-000012 Exhibit ERP-20 to the Expert Report of Eugene Randal Prais, Aug. 13, 2024.
GB, Claim No. HP-2023-000012 Exhibit ERP-18 to the Expert Report of Eugene Randal Prais, Aug. 13, 2024.
GB, Claim No. HP-2023-000012 Expert Report of Eugene Randal Prais, Aug. 13, 2024.
GB, Claim No. HP-2023-000012 Amended Grounds of Invalidity, Mar. 15, 2024.
GB, Claim No. HP-2023-000012 Order, Mar. 7, 2024.
GB, Claim No. HP-2023-000012 Dexcom's Statement of Case on Validity, Feb. 8, 2024.
US, Abbott's Initial Claim Charts, Case No. 23-239-KAJ, Dec. 20, 2023.
US, Reference PTX-0619 of Dexcom's Reply in Support of Its Renewed Motion for Judgment as a Matter of Law and Motion for a New Trial, Case No. 21-CV-977-KAJ, Jul. 12, 2024.
US, Dexcom's Reply in Support of Its Renewed Motion for Judgment as a Matter of Law and Motion for a New Trial, Case No. 21-CV-977-KAJ, Jul. 12, 2024.
US, Plaintiffs' Reply Brief in Support of Their Motion for Judgment as a Matter of Law Under Federal Rule of Civil Procedure 50 and for a New Trial Under Federal Rule of Civil Procedure 59, Case No. 21-CV-977-KAJ (D. Delaware), Jul. 12, 2024.
US, Reference DX4961 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
US, Reference DX4756 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
US, Reference DX4720 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
US, Reference DX1550 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
US, Reference DX0179 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
US, Reference DDX-8 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
US, Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
US, Plaintiffs' Opening Brief in Support of Their Motion for Judgment as a Matter of Law Under Federal Rule of Civil Procedure

(56) References Cited

OTHER PUBLICATIONS 50 and for a New Trial Under Federal Rule of Civil Procedure 59, Case No. 21-CV-977-KAJ (D. Delaware), May 24, 2024.

US, Defendant Dexcom, Inc.'s Opening Brief in Support of Its Renewed Motion for Judgment as a Matter of Law and Motion for New Trial, Case No. 21-CV-977-KAJ (D. Delaware), May 24, 2024.

US, Reference Exhibit B of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024..

US, Reference Exhibit A of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.

US, Reference DDX-4 of Defendant Dexcom, Inc.'s Appendix to Motion for Judgment as a Matter of Law or, Alternatively, for a New Trial, Case No. 21-CV-977-KAJ (D. Delaware)–Public Version, May 24, 2024.

US, Reference DX4726 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.

US, Reference DX4721 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.

US, Reference DX4719 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.

US, Reference DX0381 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.

US, Reference DX0189 of Defendant Dexcom, Inc.'s Appendix to Motion for Judgment as a Matter of Law or, Alternatively, for a New Trial, Case No. 21-CV-977-KAJ (D. Delaware)–Public Version, May 24, 2024.

US, Reference DX0183 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.

US, Reference DX0012 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.

US, Reference PDX07 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.

US, Reference PTX-3026 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.

US, Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.

US, Joint Status Report, Case No. 21-CV-977-KAJ (D. Delaware), May 7, 2024.

US, Plaintiffs' Renewed Motion for Judgment as a Matter of Law, Case No. 21-CV-977-KAJ (D. Delaware), Apr. 19, 2024.

US, Dexcom, Inc's Renewed Motion for Judgment as a Matter of Law and Motion for New Trial, Case No. 21-CV-977-KAJ (D. Delaware), Apr. 19, 2024.

US, Joint Status Report, Case No. 21-CV-977-KAJ (D. Delaware), Apr. 5, 2024.

US, [Joint Proposed] Final Jury Instructions, Case No. 21-CV-977-KAJ (D. Delaware), Mar. 17, 2024.

US, [Joint Proposed] Final Jury Instructions, Case No. 21-CV-977-KAJ (D. Delaware), Mar. 7, 2024.

US, [Proposed] Final Pretrial Order, vol. 2, Case No. 21-CV-977-KAJ (D. Delaware), Mar. 7, 2024.

US, Exhibit 7P to the Proposed Pretrial Order Abbott's Brief Summary of Opinion Testimony, Case No. 21-CV-977-KAJ (D. Delaware), Mar. 7, 2024.

US, Exhibit 7D to the Proposed Pretrial Order Dexcom's Brief Summary of Opinion Testimony, Case No. 21-CV-977-KAJ (D. Delaware), Mar. 7, 2024.

US, Exhibit 6D to the Proposed Pretrial Order Dexcom's Deposition Designations, Case No. 21-CV-977-KAJ (D. Delaware), Mar. 7, 2024.

US, Exhibit 5P to the Proposed Pretrial Order Abbott's List of Trial Exhibits, Case No. 21-CV-977-KAJ (D. Delaware), Mar. 7, 2024.

US, Exhibit 5D to the Proposed Pretrial Order Dexcom's List of Trial Exhibits, Case No. 21-CV-977-KAJ (D. Delaware), Mar. 7, 2024.

US, Exhibit 3P to the Proposed Pretrial Order Abbott's Statement of Issues of Law Which Remain to be Litigated, Case No. 21-CV-977-KAJ (D. Delaware), Mar. 7, 2024.

US, Exhibit 3D to the Proposed Pretrial Order Dexcom's Statement of Issues of Law Which Remain to be Litigated, Case No. 21-CV-977-KAJ (D. Delaware), Mar. 7, 2024.

US, Exhibit 2P to the Proposed Pretrial Order Abbott's Statement of Issues of Fact Which Remain to be Litigated, Case No. 21-CV-977-KAJ (D. Delaware), Mar. 7, 2024.

US, Exhibit 2D to Proposed Pretrial Order Dexcom's Statement of Contested Facts, Case No. 21-CV-977-KAJ (D. Delaware), Mar. 7, 2024.

US, Exhibit 1 to the Proposed Pretrial Order Parties' Joint Statement of Uncontroverted Facts, Case No. 21-CV-977-KAJ (D. Delaware), Mar. 7, 2024.

US, [Proposed] Final Pretrial Order, Case No. 21-CV-977-KAJ (D. Delaware), Mar. 7, 2024.

US, Joint Stipulation and [Proposed] Order Regarding Dismissal of Certain Asserted Patent Claims, Case No. 21-CV-977-KAJ (D. Delaware), Mar. 1, 2024.

US, Defendant Dexcom, Inc.'s Notice Pursuant to 35 U.S.C. § 282, Case No. 21-CV-977-KAJ (D. Delaware), Feb. 9, 2024.

US, Letter to the Honorable Kent A. Jordan Regarding Pretrial Order, Case No. 21-CV-977-KAJ (D. Delaware), Feb. 2, 2024.

US, [Joint Proposed] Final Jury Instructions, Case No. 21-CV-977-KAJ (D. Delaware), Jan. 31, 2024.

US, Dexcom's Motions In Limine, Abbott Exhibit 11, Case No. 21-CV-977-KAJ (D. Delaware), Jan. 12, 2024.

US, Dexcom's Motions In Limine, Abbott Exhibit 9, Case No. 21-CV-977-KAJ (D. Delaware), Jan. 12, 2024.

US, Dexcom's Motions In Limine, Abbott Exhibit 8, Case No. 21-CV-977-KAJ (D. Delaware), Jan. 12, 2024.

US, Dexcom's Motions In Limine, Abbott Exhibit 3, Case No. 21-CV-977-KAJ (D. Delaware), Jan. 12, 2024.

US, Abbott's Motions In Limine, Dexcom Exhibit B, Case No. 21-CV-977-KAJ (D. Delaware), Jan. 12, 2024.

US, [Proposed] Final Pretrial Order, vol. 3, Case No. 21-CV-977-KAJ (D. Delaware)—Public Version, Jan. 12, 2024.

US, [Proposed] Final Pretrial Order, vol. 2, Case No. 21-CV-977-KAJ (D. Delaware)—Public Version, Jan. 12, 2024.

US, Exhibit 7P to the Proposed Pretrial Order Abbott's Brief Summary of Opinion Testimony, Case No. 21-CV-977-KAJ (D. Delaware), Jan. 4, 2024.

US, Exhibit 7D to the Proposed Pretrial Order Dexcom's Brief Summary of Opinion Testimony, Case No. 21-CV-977-KAJ (D. Delaware), Jan. 4, 2024.

US, Exhibit 6P to the Proposed Pretrial Order Abbott's Deposition Designations, Case No. 21-CV-977-KAJ (D. Delaware), Jan. 4, 2024.

US, Exhibit 6D to the Proposed Pretrial Order Dexcom's Deposition Designations, Case No. 21-CV-977-KAJ (D. Delaware), Jan. 4, 2024.

US, Exhibit 5P to the Proposed Pretrial Order Abbott's List of Trial Exhibits, Case No. 21-CV-977-KAJ (D. Delaware), Jan. 4, 2024.

US, Exhibit 5D to the Proposed Pretrial Order Dexcom's List of Trial Exhibits, Case No. 21-CV-977-KAJ (D. Delaware), Jan. 4, 2024.

(56)                    References Cited

OTHER PUBLICATIONS

US, Exhibit 4 to the Proposed Pretrial Order Joint List of Trial Exhibits, Case No. 21-CV-977-KAJ (D. Delaware), Jan. 4, 2024.
US, Exhibit 3P to the Proposed Pretrial Order Abbott's Statement of Issues of Law Which Remain to be Litigated, Case No. 21-CV-977-KAJ (D. Delaware), Jan. 4, 2024.
US, Exhibit 3D to the Proposed Pretrial Order Dexcom's Statement of Issues of Law Which Remain to be Litigated, Case No. 21-CV-977-KAJ (D. Delaware), Jan. 4, 2024.
US, Exhibit 2P to the Proposed Pretrial Order Abbott's Statement of Issues of Fact Which Remain to be Litigated, Case No. 21-CV-977-KAJ (D. Delaware), Jan. 4, 2024.
US, Exhibit 2D to Proposed Pretrial Order Dexcom's Statement of Contested Facts, Case No. 21-CV-977-KAJ (D. Delaware), Jan. 4, 2024.
US, Exhibit 1 to the Proposed Pretrial Order Parties' Joint Statement of Uncontroverted Facts, Case No. 21-CV- 977-KAJ (D. Delaware), Jan. 4, 2024.
US, [Proposed] Final Pretrial Order, Case No. 21-CV-977-KAJ (D. Delaware), Jan. 4, 2024.
US, Supplemental Declaration of Karl R. Leinsing, MSME, PE, Regarding Validity, Case No. 21-CV-977-KAJ (D. Delaware)—Public Version, Jun. 23, 2023.
US, Plaintiffs' Opening Brief in Support of Its Motions for Summary Judgement and Daubert Challenges, Case No. 21-CV-977-KAJ (D. Delaware)—Public Version, May 19, 2023.
US, Order, Case No. 21-CV-977-KAJ (D. Delaware), Mar. 22, 2023.
US, Memorandum Opinion, Case No. 21-CV-977-KAJ (D. Delaware), Mar. 22, 2023.
US, Plaintiffs' Second Set of Interrogatories (Nos. 10-33) to Defendant, Case 21-CV-977-KAJ (D. Delaware), Sep. 8, 2022.
AU, 2019404908 Examiner's Report, Feb. 17, 2025.
CA, 3,228,738 Examiner's Report, May 8, 2025.
CN, 202211091194.1 Notification of Filing Divisional Application, Mar. 27, 2025.
EP, 17182379.2 Written Submissions, Aug. 6, 2025.
EP, 17182379.2 Summons to Attend Oral Proceedings, Jul. 4, 2025.
EP, 17182379.2 Reply to Reply to Opposition, May 16, 2025.
EP, 17182379.2 Reply to Opposition, Feb. 27, 2025.
EP, 19900891.3 Examination Report, May 8, 2025.
EP, 20177703.4 Response to Withdrawals, Jan. 7, 2025.
EP, 20177703.4 Withdrawal of Intervention, Dec. 27, 2024.
EP, 20177703.4 Withdrawal of Opposition, Dec. 27, 2024.
EP, 20177703.4 Written Submissions Dexcom, Nov. 22, 2024.
EP, 20195922.8 Withdrawal of Intervention, Dec. 27, 2024.
EP, 20195922.8 Withdrawal of Opposition, Dec. 27, 2024.
EP, 21211041.5 Grounds of Appeal, Apr. 23, 2025.
EP, 21211041.5 Withdrawal of Opposition, Dec. 27, 2024.
EP, 21211041.5 Notice of Appeal, Dec. 17, 2024.
EP, 21211041.5 Minutes of Oral Proceedings, Dec. 13, 2024.
EP, 23190032.5 Examination Report, May 19, 2025.
EP, 24152079.0 Examination Report, Dec. 2, 2024.
EP, 24194029.5 Extended Search Report, Nov. 18, 2024.
EP, 24201435.5 Extended Search Report, Jan. 27, 2025.
EP, 24218309.3 Extended Search Report, Jul. 9, 2025.
EP, 24220160.6 Extended Search Report, Jun. 17, 2025.
GB, Claim No. HP-2023-000012 and Claim No. HP-2023-000016 Dexcom's Written Closing for Trial D, Redacted, Nov. 27, 2024.
GB, Claim No. HP-2023-000012 and Claim No. HP-2023-000016 Abbott's Closing Skeleton Argument—Trial D, Redacted, Nov. 27, 2024.
GB, Claim No. HP-2023-000012 and Claim No. HP-2023-000016 Annex 1 to Dexcom's Opening Skeleton Argument for Trial D, Nov. 13, 2024.
GB, Claim No. HP-2023-000012 and Claim No. HP-2023-000016 Annex 2 to Dexcom's Opening Skeleton Argument for Trial D, Nov. 13, 2024.
GB, Claim No. HP-2023-000012 and Claim No. HP-2023-000016 Annex 3 to Dexcom's Opening Skeleton Argument for Trial D, Nov. 13, 2024.
GB, Claim No. HP-2023-000012 and Claim No. HP-2023-000016 Dexcom's Opening Skeleton Argument for Trial D, Redacted, Nov. 13, 2024.
GB, Claim No. HP-2023-000012 and Claim No. HP-2023-000016 Abbott's Opening Skeleton Argument Trial D: commencing Nov. 18, 2024, Redacted, Nov. 13, 2024.
GB, Claim No. HP-2023-000012 and Claim No. HP-2023-000016 Trial D—Joint CGK Statement, Nov. 11, 2024.
JP, 2023-516522 Office Action, Mar. 5, 2025.
JP, 2023-514023 Office Action, Apr. 16, 2025.
JP, 2023-514024 Office Action, Apr. 30, 2025.
JP, 2024-31538 Office Action, Oct. 16, 2024.
MX, MX/a/2021/007294 Second Office Action, Feb. 19, 2025.
MY, PI2021003022 Examination Report, Mar. 5, 2025.
MY, PI2022002786 Examination Report, Jan. 8, 2025.
UP, Second Expert Opinion of Dr Michael Schoemaker in Litigation of EP 3977921, Nov. 8, 2024.
US, Decision Denying Institution of Inter Partes Review, IPR No. 2024-00860, Nov. 20, 2024.
US, Patent Owner's Response to Petitioner's Explanation of Parallel Petitions Challenging U.S. Pat. No. 11,510,325, IPR No. 2024-00860, Aug. 23, 2024.
US, Patent Owner Preliminary Response Pursuant to 37 C.F.R. § 42.107, IPR No. 2024-00860, Aug. 23, 2024.
US, Declaration of Julia Castellano, IPR No. 2024-00860, Aug. 21, 2024.
US, Declaration of Scott E. Davis, IPR No. 2024-00860, Jun. 5, 2024.
US, Petitioner's Explanation Of Parallel Petitions Challenging U.S. Pat. No. 11,510,325, IPR No. 2024-00860, May 9, 2024.
US, Termination Due to Settlement After Institution of Trial, IPR No. 2023-01409, Jan. 7, 2025.
US, Joint Motion to Treat Settlement Agreement as Business Confidential Information. IPR No. 2023-01409, Jan. 3, 2025.
US, Joint Motion to Terminate Proceeding Under 35 U.S.C. § 317(a), IPR No. 2023-01409, Jan. 3, 2025.
US, Order Setting Oral Argument, IPR No. 2023-01409, Dec. 11, 2024.
US, Patent Owner's Sur-Reply, IPR No. 2023-01409, Dec. 10, 2024.
US, Deposition of Gary D. Fletcher, Ph.D., IPR No. 2023-01409, Dec. 4, 2024.
US, Patent Owner's Request for Oral Argument, IPR No. 2023-01409, Dec. 3, 2024.
US, Petitioner's Request for Oral Argument, IPR No. 2023-01409, Dec. 3, 2024.
US, Patent Owner's Objections to Petitioner's Exhibits Submitted With Its Reply, IPR No. 2023-01409With Its Reply, IPR No. 2023-01409, Nov. 1, 2024.
US, Petitioner's Updated Exhibit List, IPR No. 2023-01409, Oct. 25, 2024.
US, Second Declaration of Gary Fletcher, Ph.D., IPR No. 2023-01409, Oct. 25, 2024.
US, Petitioner's Reply to Patent Owner's Response, IPR No. 2023-01409, Oct. 25, 2024.
US, Deposition of Karl R. Leinsing, MSME, PE, IPR No. 2023-01409, Oct. 17, 2024.
US, Conference Call Before The Patent Trial And Appeal Board Before Judge Cynthia Hardman, IPR No. 2023-01409, Oct. 17, 2024.
US, Notice of Joint Stipulation to Modify Schedule, IPR No. 2023-01409, Sep. 26, 2024.
US, Decision Denying Patent Owner's Request on Rehearing of Decision Denying Institution, IPR No. 2023-01396, Aug. 9, 2024.
US, Reexamination No. 90/019,307 Final Office Action, Jul. 8, 2025.
US, Reexamination No. 90/019,307 Office Action, Mar. 18, 2025.
US, Reexamination No. 90/019,307 Decision on Petition, Feb. 13, 2025.
US, Reexamination U.S. Appl. No. 90/019,329 Decision on Petition Under 37 C.F.R. § 1.181, Mar. 18, 2025.
US, Dexcom's Notice of Appeal, Case No. 21-CV-977-KAJ, Nov. 26, 2024.

(56)        References Cited

OTHER PUBLICATIONS

US, Order, Case No. 21-CV-977-KAJ, Nov. 21, 2024.
US, Order, Case No. 21-CV-977-KAJ, Nov. 13, 2024.
US, Memorandum Opinion, Case No. 21-CV-977-KAJ, Nov. 13, 2024.
WO, PCT/US25/13698 ISR and Written Opinion, Jun. 5, 2025.
WO, PCT/US25/13698 Invitation to Pay Additional Fees, Apr. 15, 2025.
WO, PCT/US25/27260 Invitation to Pay Additional Fees, Jul. 24, 2025.
Abbott Patent Marking Diabetes, 2024, retrieved from https://www.abbott.com/patents/diabetes-patents.html, 6 pages.
"The Advantages of the Cleo® 90 Infusion Set Are Clear", 2019, retrieved from https://web.archive.org/web/20220816002119/https://smiths-medical.com/-/media/M/Smiths-medical_com//Files/Import-Files/Product-Literature/IN193873GB-092019_LR.pdf, 2 pages.
Burge, M. R., et al., "Continuous Glucose Monitoring: The Future of Diabetes Management", Diabetes Spectrum, 2008, vol. 21, No. 2, pp. 112-119.
Clancy, N. T., et al., "A new device for assessing changes in skin viscoelasticity using indentation and optical measurement", Skin Research and Technology, 2010, vol. 16, pp. 210-228.
Cleo® 90 Infusion Set 510(k) Premarket Notification, 2004, 1 page.
Dexcom STS Continuous Monitors FDA Premarket Approval (PMA), 2006, 2 pages.
Freestyle Navigator Answers to Frequently Asked Questions, 2007, retrieved from https://web.archive.org/web/20080917183534/http://www.freestylenavigator.com/ab_nav/url/c ontent/en_US/3 0.10.10:1 O/general_content/General_ContenL0000004.htm, 2 pages.
"The Future is Bright for Veteran-centric Rehabilitation Research Publications", Journal of Rehabilitation Research & Development (JRRD), 2013, retrieved from https://www.rehab.research.va.gov/jrrd/index.html, 2 pages.
Mazze, R. S., et al., "Evaluating the Accuracy, Reliability, and Clinical Applicability of Continuous Glucose Monitoring (CGM): Is CGM Ready for Real Time?", Diabetes Technology & Therapeutics, 2009, vol. 11, No. 1., pp. 11-18.
Medtronic MiniMed Guardian® REAL-Time Components, 2007, retrieved from https://web.archive.org/20071013095335/http:/www.medtronicdiabetes.com/products/guardian/components.html, 2 pages.
Medtronic MiniMed Guardian® REAL-Time Features, 2007, retrieved from https://web.archive.org/20071025084715/http:/www.medtronicdiabetes.com/products/guardian/features.html, 2 pages.
Piper, H. G., et al., "Real-Time Continuous Glucose Monitoring in Pediatric Patients During and After Cardiac Surgery", Pediatrics, 2006, vol. 118, No. 3, pp. 1176-1184.
Rabiee, A., et al., "Numerical and Clinical Accuracy of a Continuous Glucose Monitoring System during Intravenous Insulin Therapy in the Surgical and Burn Intensive Care Units", Journal of Diabetes Science and Technology, 2009, vol. 3, No. 4, pp. 951-959.
Sacks, A. H., et al., "Skin blood flow changes and tissue deformations produced by cylindrical indentors", Journal of Rehabilitation Research and Development, 1985, vol. 22, No. 3, pp. 1-6.
Schneider, M., et al., "Evaluating the use of the Cleo® 90 infusion set for patients on a palliative care unit", International Journal of Palliative Nursing, 2009, vol. 15,. No. 8, pp. 372-376.
CN, 202180063087.5 First Office Action, Aug. 14, 2025.
EP, 17182379.2 Decision Revoking the European Patent, Nov. 24, 2025.
EP, 17182379.2 Minutes of the Oral Proceedings, Nov. 24, 2025.
EP, 18741791.0 Examination Report, Sep. 12, 2025.
EP, 19151577.4 Examination Report, Sep. 3, 2025.
EP, 20177712.5 Decision Revoking the European Patent, Nov. 28, 2025.
EP, 20177712.5 Minutes of the Oral Proceedings, Nov. 28, 2025.
EP, 20177712.5 Written Submissions Guide, Aug. 21, 2025.
EP, 20177712.5 Response to Summons to Attend Oral Proceedings, Aug. 21, 2025.
EP, 21192910.4 Notice of Intervention, Nov. 14, 2025.
EP, 21192910.4 Notice of Opposition Stolmar, Sep. 10, 2025.
EP, 21192910.4 Notice of Opposition Strawman, Sep. 10, 2025.
EP, 21211041.5 Summons to Attend Oral Proceedings, Dec. 15, 2025.
EP, 21772864.1 Examination Report, Dec. 9, 2025.
EP, 23166498.8 Examination Report, Dec. 10, 2025.
EP, 23190032.5 Examination Report, Dec. 10, 2025.
EP, 24194029.5 Examination Report, Aug. 26, 2025.
EP, 24201435.5 Examination Report, Oct. 26, 2025.
JP, 2023-514023 Final Office Action, Aug. 20, 2025.
JP, 2023-532327 Office Action, Jul. 23, 2025.
JP, 2025-026588 Office Action, Aug. 27, 2025.
MX, MX/a/2021/007294 Third Office Action, Sep. 10, 2025.
WO, PCT/US25/27260 ISR and Written Opinion, Sep. 16, 2025.

* cited by examiner

100

124

1100B

1100B

1200

1228

1234

1262

1202

1264

1208

1212

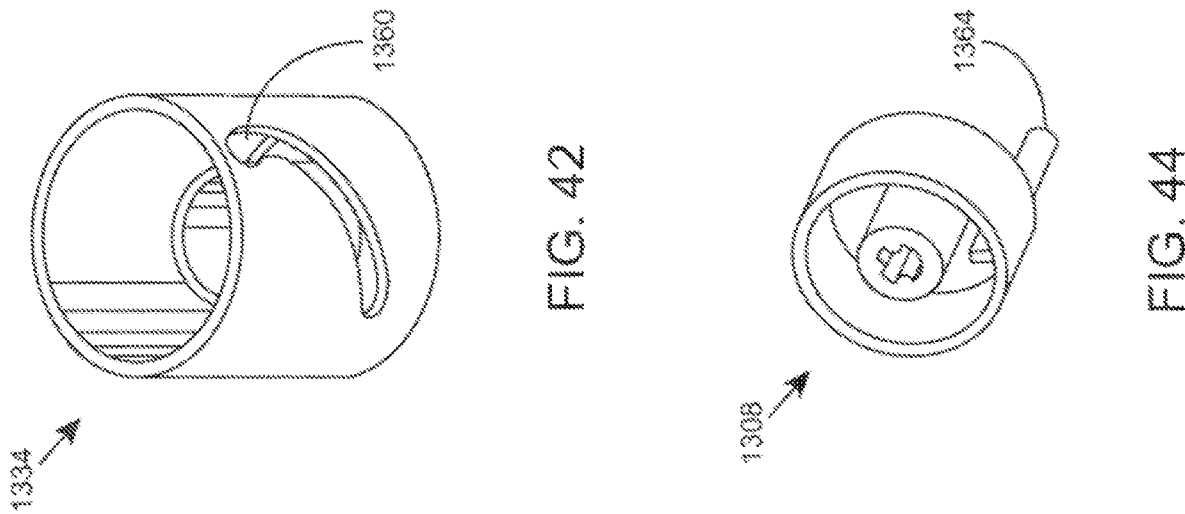
FIG. 41
FIG. 42
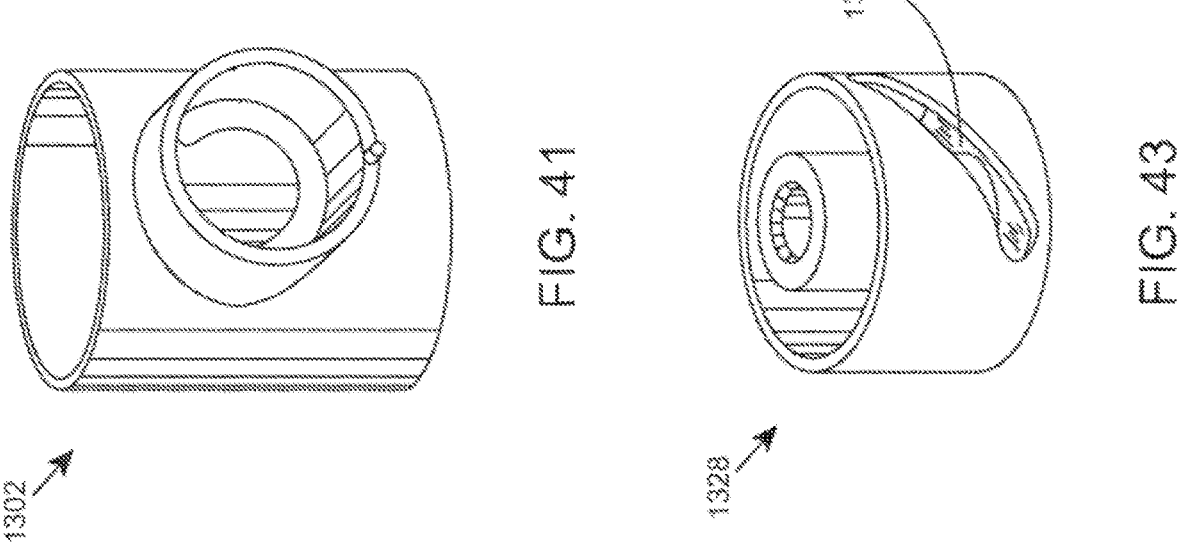
FIG. 43
FIG. 44

1400

1500

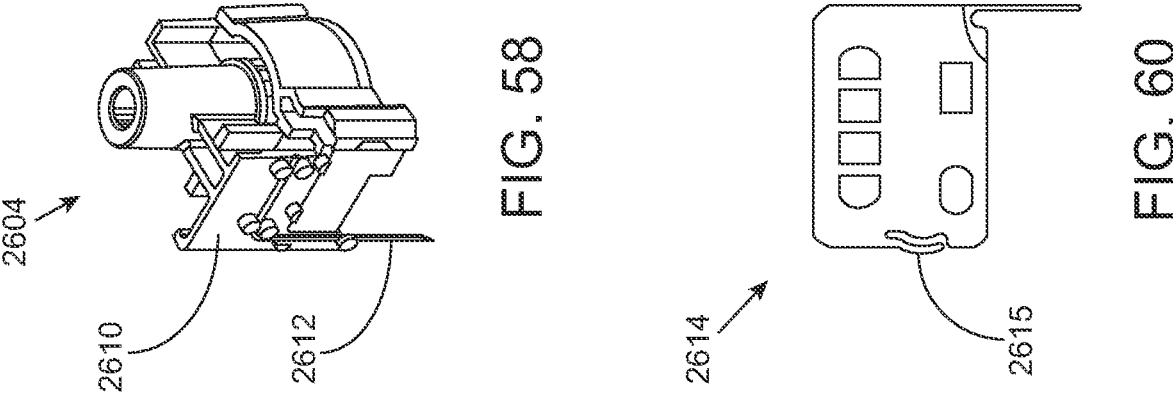
FIG. 58
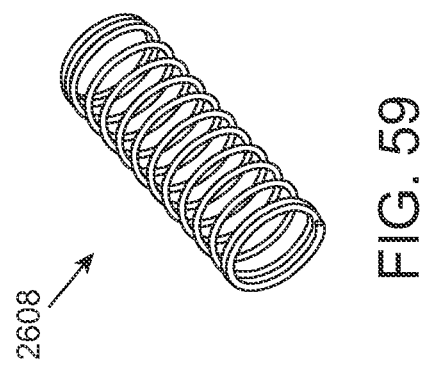
FIG. 60
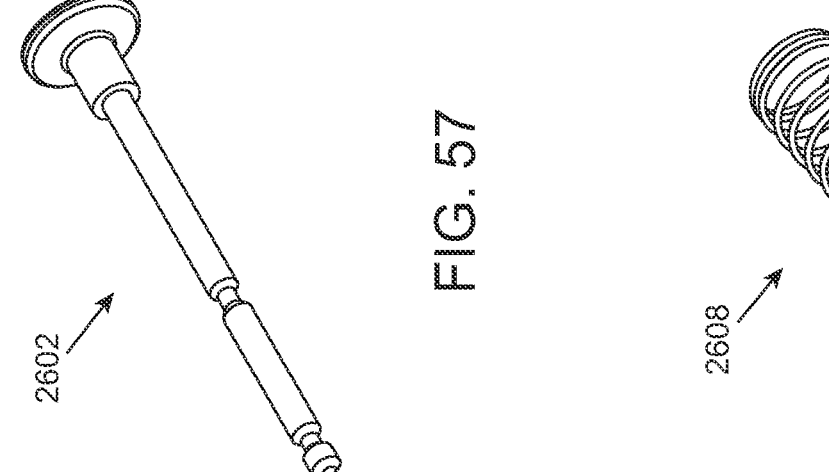
FIG. 57
FIG. 59

2622

2618

2616

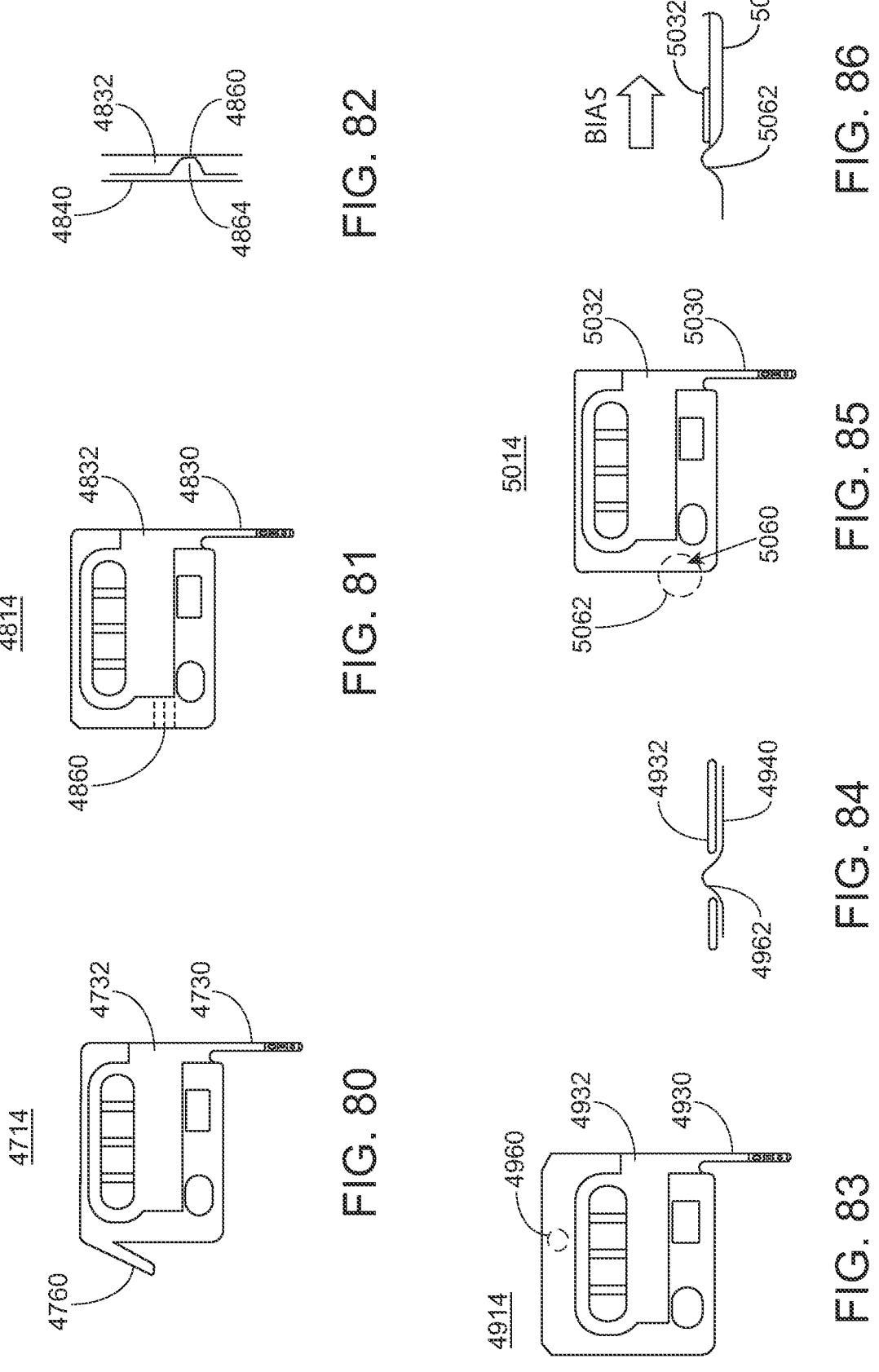

6450

6440

6452

6448

6448

6450

6440

6448

6448

6440

6448

6472

6448

6440

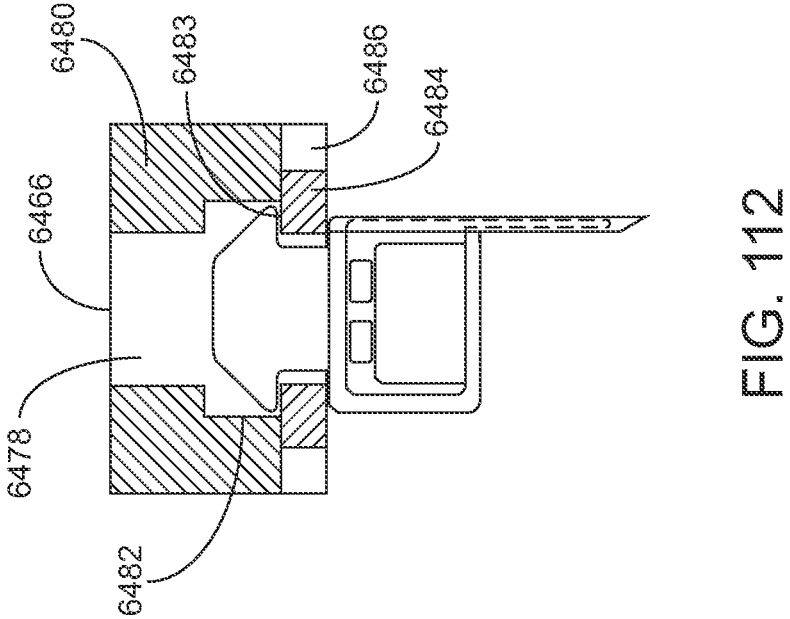
FIG. 112
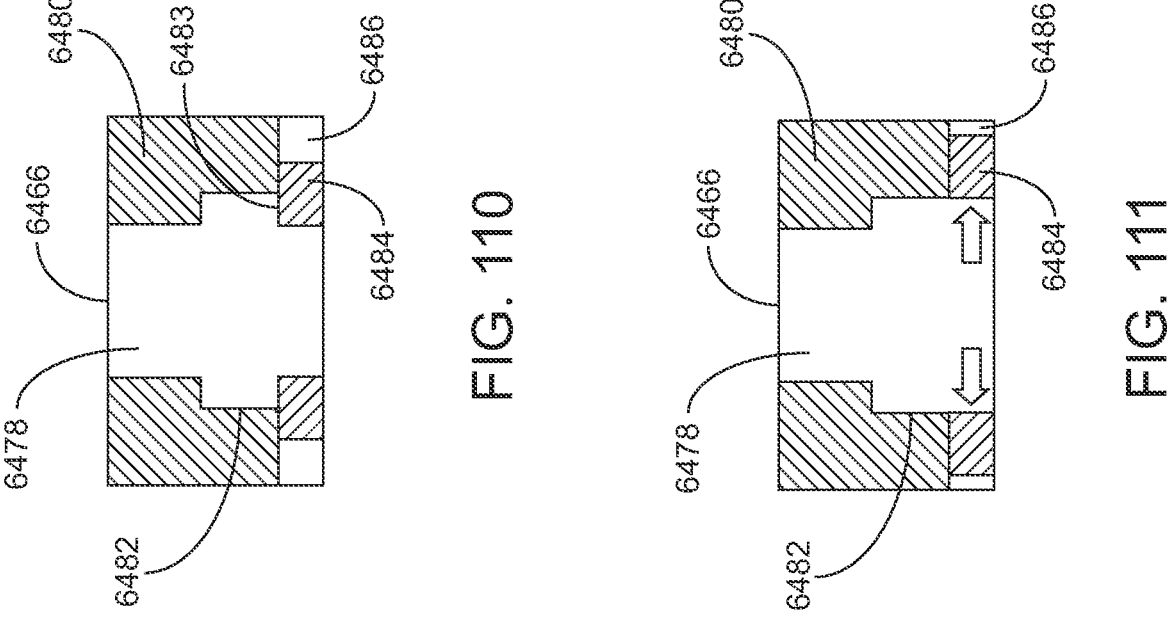
FIG. 110
FIG. 111

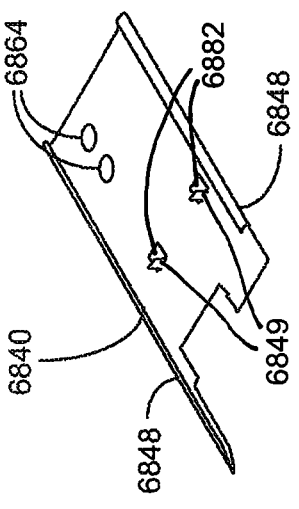
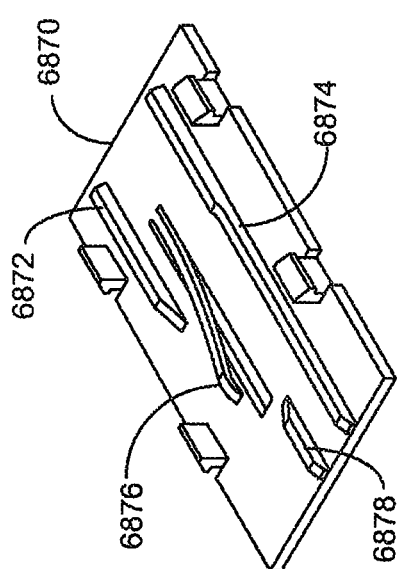
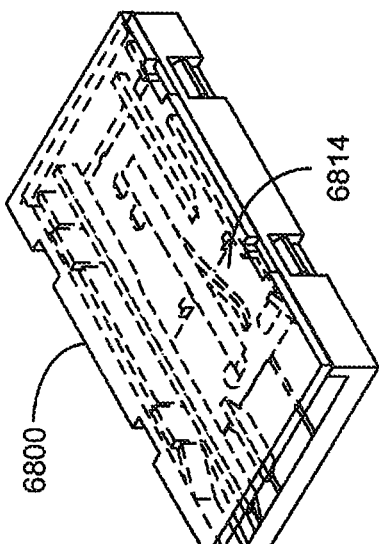
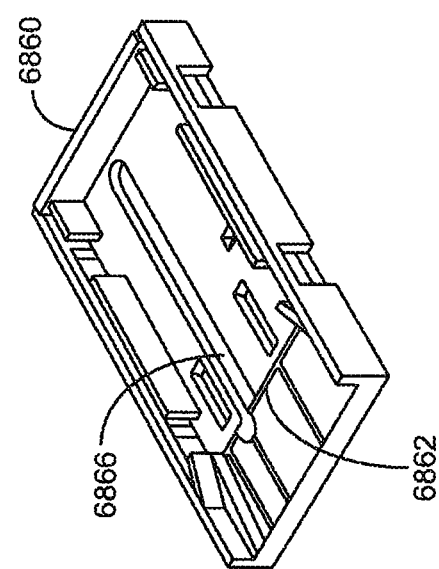
FIG. 122

SECTION A-A

SECTION B-B

SECTION C-C

SECTION D-D

SECTION A-A

SECTION B-B

SECTION C-C

MEDICAL DEVICE INSERTERS AND PROCESSES OF INSERTING AND USING MEDICAL DEVICES

RELATED APPLICATIONS

The present application is a continuation of U.S. patent application Ser. No. 18/114,775, filed Feb. 27, 2023, which is a continuation of U.S. patent application Ser. No. 16/387, 023, filed Apr. 17, 2019, now abandoned, which is a continuation of U.S. patent application Ser. No. 14/884,622, filed Oct. 15, 2015, now U.S. Pat. No. 10,292,632, which is a continuation of U.S. patent application Ser. No. 13/071, 497, filed Mar. 24, 2011, now U.S. Pat. No. 9,186,098, which claims the benefit of U.S. Provisional Application Nos. 61/317,243, filed Mar. 24, 2010; 61/345,562, filed May 17, 2010; 61/361,374, filed Jul. 2, 2010; and 61/411,262, filed Nov. 8, 2010, all of which are incorporated herein by reference in their entireties and for all purposes.

INCORPORATION BY REFERENCE

Patents, applications and/or publications described herein, including the following patents, applications and/or publications are incorporated herein by reference for all purposes: U.S. Pat. Nos. 4,545,382; 4,711,245; 5,262,035; 5,262,305; 5,264,104; 5,320,715; 5,356,786; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,041,468; 7,167,818; and 7,299,082; 7,381,184; 7,740,581; 7,811,231 U.S. Published Application Nos. 2005/0182306; 2006/ 0091006; 2007/0056858, now U.S. Pat. No. 8,298,389; 2007/0068807, now U.S. Pat. No. 7,846,311; 2007/ 0095661; 2007/0108048, now U.S. Pat. No. 7,918,975; 2007/0149873; 2007/0149875, now U.S. Pat. No. 8,515, 518; 2007/0199818, now U.S. Pat. No. 7,811,430; 2007/ 0227911, now U.S. Pat. No. 7,887,682; 2007/0233013; 2008/0058625, now U.S. Pat. No. 7,920,907; 2008/ 0064937; 2008/0066305, now U.S. Pat. No. 7,895,740; 2008/0071157; 2008/0071158; 2008/0081977, now U.S. Pat. No. 7,618,369; 2008/0102441, now U.S. Pat. No. 7,822, 557; 2008/0148873, now U.S. Pat. No. 7,802,467; 2008/ 0161666; 2008/0179187; 2008/0267823; 2008/0319295, now U.S. Pat. No. 8,597,188; 2008/0319296, now U.S. Pat. No. 8,617,069; 2009/0018425, now U.S. Pat. No. 8,160,670; 2009/0247857, now U.S. Pat. No. 8,346,335; 2009/0257911, now U.S. Pat. No. 8,252,229, 2009/0281406; 2009/ 0294277; 2009/0054748, now U.S. Pat. No. 7,885,698; 2009/0054749; 2010/0030052; 2010/0065441, now U.S. Pat. No. 8,636,884; 2010/0081905; 2010/0081909, now U.S. Pat. No. 8,219,173; 2010/0213057; 2010/0325868, now U.S. Pat. No. 7,866,026; 2010/0326842; 2010/ 0326843, now U.S. Pat. No. 8,437,827; 2010/0331643; 2011/0046466; U.S. patent application Ser. Nos. 12/624, 767; 12/625,185, now U.S. Pat. No. 8,354,013; Ser. Nos. 12/625,208; 12/625,524, now U.S. Pat. No. 8,390,455; Ser. No. 12/625,525, now U.S. Pat. No. 8,358,210; Ser. No. 12/625,528, now U.S. Pat. No. 8,115,635; Ser. Nos. 12/628, 177; 12/628,198; 12/628,201; 12/628,203; 12/628,210;

12/698,124; 12/698,129; 12/699,653; 12/699,844; 12/714, 439; 12/730,193; 12/794,721, now U.S. Pat. No. 8,595,607; Ser. Nos. 12/807,278; 12/842,013; 12/870,818; 12/871,901, now U.S. Pat. No. 8,514,086; Ser. Nos. 12/873,301; 12/873, 302; 13/011,897; and U.S. Provisional Application Nos. 61/238,646; 61/246,825; 61/247,516; 61/249,535; 61/317, 243; 61/325,155; 61/345,562; and 61/359,265.

BACKGROUND OF THE INVENTION

The detection and/or monitoring of glucose levels or other analytes, such as lactate, oxygen, A1C, or the like, in certain individuals is vitally important to their health. For example, the monitoring of glucose is particularly important to individuals with diabetes. Diabetics generally monitor glucose levels to determine if their glucose levels are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including convenience, testing discretion, pain associated with glucose testing, and cost.

Devices have been developed for the automatic monitoring of analyte(s), such as glucose, in bodily fluid such as in the blood stream or in interstitial fluid ("ISF"), or other biological fluid. Some of these analyte measuring devices are configured so that at least a portion of the devices are positioned below a skin surface of a user, e.g., in a blood vessel or in the subcutaneous tissue of a user, so that the monitoring is accomplished in vivo.

With the continued development of analyte monitoring devices and systems, there is a need for such analyte monitoring devices, systems, and methods, as well as for processes for manufacturing analyte monitoring devices and systems that are cost effective, convenient, and with reduced pain, provide discreet monitoring to encourage frequent analyte monitoring to improve glycemic control.

SUMMARY

An apparatus for inserting a medical device through the skin of a subject is provided, which includes a housing defining a longitudinal cavity therein and a interference member extending into the cavity; a biasing member; a driver member coupled to the biasing member for movement from a proximal position to a distal position and further configured for movement between a misaligned configuration in which the driver member is impeded from distal movement by the interference member and an aligned configuration in which the driver member is not impeded from distal movement by the interference member; and an actuator having an alignment surface for moving the driver member from the misaligned configuration to the aligned configuration.

In some embodiments, the actuator is movable from a proximal position to a distal position. In some embodiments, distal movement of the actuator compresses the first biasing member. In some embodiments, the first position of the driver member is at an oblique angle with respect to the longitudinal cavity. In some embodiments, the second position of the driver member includes a configuration substantially aligned with the longitudinal cavity.

An apparatus for inserting a medical device through the skin of a subject is provided, which includes a housing defining a cantilever member; a sharp movable within the housing from a retracted position to a partially exposed position; and an electrochemical sensor releasably coupled to the sharp for movement with the sharp, and for subsequent insertion in the skin of a subject; wherein the cantilever member resiliently contacts at least one of the sharp and the sensor.

In some embodiments, the housing includes a distal opening for release of the electrochemical sensor therefrom. In some embodiments, the housing defines a longitudinal notch for reception of a drive member of an inserter. In some embodiments, the housing contains a desiccant. In some embodiments, the housing defines one or more longitudinal ridges for aligning one of the sharp and the sensor.

These and other features, objects, and advantages of the disclosed subject matter will become apparent to those persons skilled in the art upon reading the detailed description as more fully described below.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIGS. 41-44 are perspective views of components of the inserter of FIG. 37 in accordance with the disclosed subject matter;

FIGS. 57-60 are perspective views of various components of the inserter of FIG. 56;

FIGS. 80-90 are views of analyte sensors in accordance with the disclosed subject matter;

FIGS. 106-112 are views of a sharp and sharp carrier in accordance with the disclosed subject matter;

FIG. 122 is a perspective view with parts separated of an embodiment of a sharp/sensor cartridge in accordance with the disclosed subject matter;

DETAILED DESCRIPTION OF THE EMBODIMENTS

Figure 1:
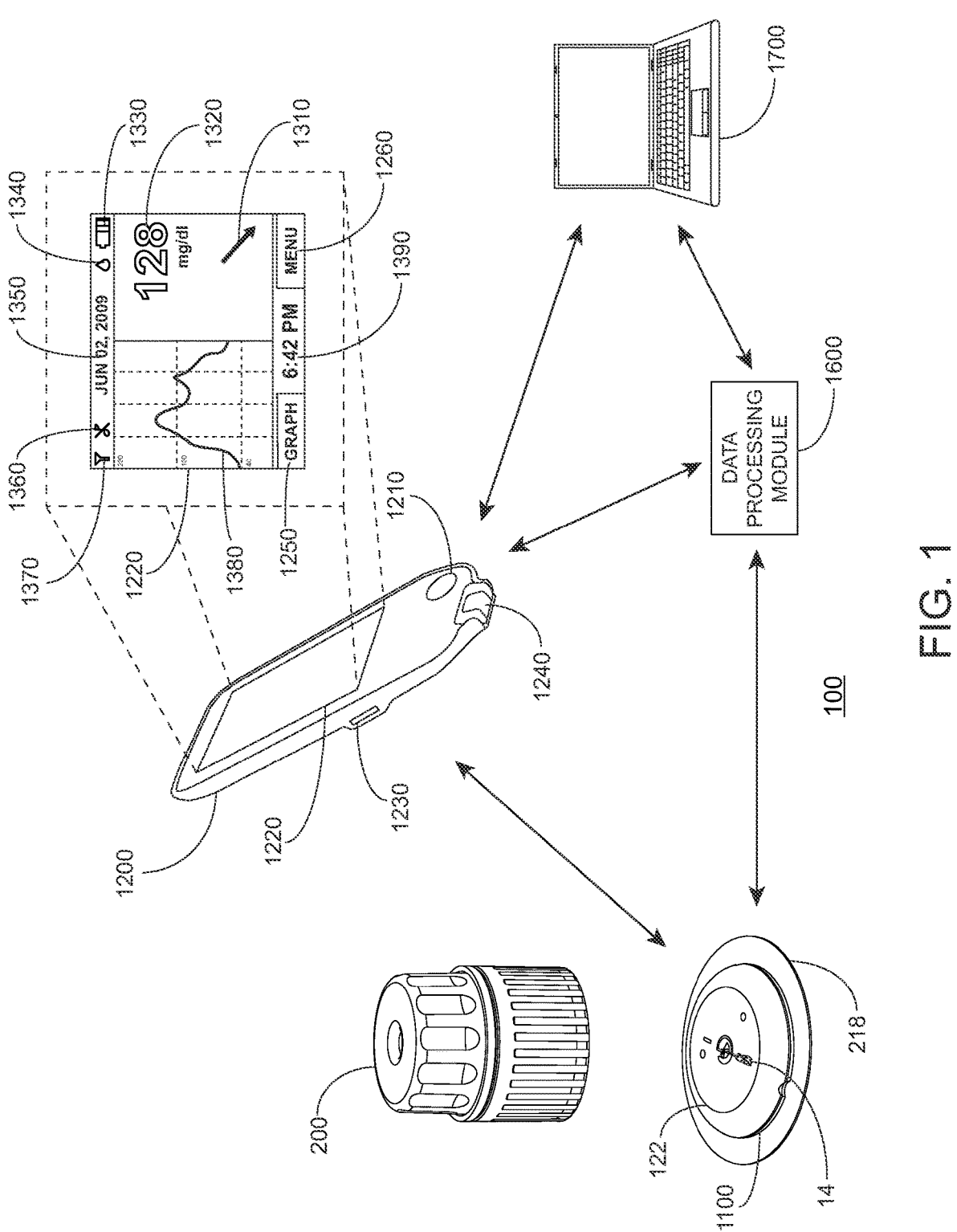
FIG. 1 illustrates an analyte monitoring system for real time analyte (e.g., glucose) measurement, data acquisition and/or processing in certain embodiments.

A detailed description of the disclosure is provided herein. It should be understood, in connection with the following description, that the subject matter is not limited to particular embodiments described, as the particular embodiments of the subject matter may, of course, vary. It is also to be understood that the terminology used herein is for the purpose of describing particular embodiments only, and is not intended to be limiting, since the scope of the disclosed subject matter will be limited only by the appended claims.

Where a range of values is provided, it is understood that each intervening value between the upper and lower limit of that range, and any other stated or intervening value in that stated range, is encompassed within the disclosed subject matter. Every range stated is also intended to specifically disclose each and every "subrange" of the stated range. That is, each and every range smaller than the outside range specified by the outside upper and outside lower limits given for a range, whose upper and lower limits are within the range from said outside lower limit to said outside upper limit (unless the context clearly dictates otherwise), is also to be understood as encompassed within the disclosed subject matter, subject to any specifically excluded range or limit within the stated range. Where a range is stated by specifying one or both of an upper and lower limit, ranges excluding either or both of those stated limits, or including one or both of them, are also encompassed within the disclosed subject matter, regardless of whether or not words such as "from," "to," "through," or "including" are or are not used in describing the range.

Unless defined otherwise, all technical and scientific terms used herein have the same meaning as commonly understood by one of ordinary skill in the art to which this disclosed subject matter belongs. Although any methods and materials similar or equivalent to those described herein can also be used in the practice or testing of the present disclosed subject matter, this disclosure may specifically mention certain exemplary methods and materials.

All publications mentioned in this disclosure are, unless otherwise specified, incorporated by reference herein for all purposes, including without limitation to disclose and describe the methods and/or materials in connection with which the publications are cited.

The publications discussed herein are provided solely for their disclosure prior to the filing date of the present application. Nothing herein is to be construed as an admission that the present disclosed subject matter is not entitled to antedate such publication by virtue of prior invention. Further, the dates of publication provided may be different from the actual publication dates, which may need to be independently confirmed.

As used herein and in the appended claims, the singular forms "a," "an," and "the" include plural referents unless the context clearly dictates otherwise.

Nothing contained in the Abstract or the Summary should be understood as limiting the scope of the disclosure. The Abstract and the Summary are provided for bibliographic and convenience purposes and due to their formats and purposes should not be considered comprehensive.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosed subject matter. Any recited method can be carried out in the order of events recited, or in any other order which is logically possible.

Reference to a singular item includes the possibility that there are plural of the same item present. When two or more items (for example, elements or processes) are referenced by an alternative "or," this indicates that either could be present separately or any combination of them could be present together except where the presence of one necessarily excludes the other or others.

Generally, embodiments of the present disclosure relate to an apparatus for inserting a medical device at least partially into the skin of the patient. Some embodiments relate to in vivo methods and devices for detecting at least one analyte such as glucose in body fluid. Accordingly, embodiments include in vivo analyte sensors configured so that at least a portion of the sensor is positioned in the body of a user (e.g., within the ISF), to obtain information about at least one analyte of the body, e.g., transcutaneously positioned in user's body. In certain embodiments, an in vivo analyte sensor is coupled to an electronics unit that is maintained on the body of the user to process information obtained from the sensor.

In certain embodiments, analyte information is communicated from a first device such as an on body electronics unit to a second device which may include user interface features, including a display, and/or the like. Information may be communicated from the first device to the second device automatically and/or continuously when the analyte information is available, or may not be communicated automatically and/or continuously, but rather stored or logged in a memory of the first device. Accordingly, in many embodiments of the system, analyte information derived by the sensor/on body electronics (for example, on body electronics) is made available in a user-usable or viewable form only when queried by the user such that the timing of data communication is selected by the user. In some embodiments, the display of information is selected by the user, while the timing of data communication is not.

In this manner, analyte information is only provided or evident to a user (provided at a user interface device) in some embodiments when desired by the user even though an in vivo analyte sensor automatically and/or continuously monitors the analyte level in vivo, i.e., the sensor automatically monitors analyte such as glucose on a pre-defined time interval over its usage life. For example, an analyte sensor may be positioned in vivo and coupled to on body electronics for a given sensing period, e.g., about 14 days. In certain embodiments, the sensor-derived analyte information is automatically communicated from the sensor electronics assembly to a remote monitor device or display device for output to a user throughout the 14 day period according to a schedule programmed at the on body electronics (e.g., about every 1 minute or about every 5 minutes or about every 10 minutes, or the like). In certain embodiments, sensor-derived analyte information is only communicated from the sensor electronics assembly to a remote monitor device or display device at user-determined times, e.g., whenever a user decides to check analyte information. At such times, a communications system is activated, and sensor-derived information is then sent from the on body electronics to the remote device or display device.

In still other embodiments, the information may be communicated from the first device to the second device automatically and/or continuously when the analyte information is available, and the second device stores or logs the received information without presenting or outputting the information to the user. In such embodiments, the information is received by the second device from the first device when the information becomes available (e.g., when the sensor detects the analyte level according to a time schedule). However, the received information is initially stored in the second device and only output to a user interface or an output component of the second device (e.g., display) upon detection of a request for the information on the second device.

Accordingly, in certain embodiments an inserter as described herein is used to place a sensor electronics assembly on the body so that at least a portion of the in vivo sensor is in contact with bodily fluid such as ISF. Once the sensor is electrically coupled to the electronics unit, sensor derived analyte information may be communicated from the on body electronics to a display device on-demand by powering on the display device (or it may be continually powered), and executing a software algorithm stored in and accessed from a memory of the display device, to generate one or more request commands, control signal or data packet to send to the on body electronics. The software algorithm executed under, for example, the control of the microprocessor or application specific integrated circuit (ASIC) of the display device may include routines to detect the position of the on body electronics relative to the display device to initiate the transmission of the generated request command, control signal and/or data packet.

Display devices may also include programming stored in memory for execution by one or more microprocessors and/or ASICs to generate and transmit the one or more request command, control signal or data packet to send to the on body electronics in response to a user activation of an input mechanism on the display device such as depressing a button on the display device, triggering a soft button associated with the data communication function, and so on. The input mechanism may be alternatively or additionally provided on or in the on body electronics which may be configured for user activation. In certain embodiments, voice commands or audible signals may be used to prompt or instruct the microprocessor or ASIC to execute the software routine(s) stored in the memory to generate and transmit the one or more request command, control signal or data packet to the on body device. In the embodiments that are voice activated or responsive to voice commands or audible signals, on body electronics and/or display device includes a microphone, a speaker, and processing routines stored in the respective memories of the on body electronics and/or the display device to process the voice commands and/or audible signals. In certain embodiments, positioning the on body electronics and the display device within a predetermined distance (e.g., close proximity) relative to each other initiates one or more software routines stored in the memory of the display device to generate and transmit a request command, control signal or data packet.

Different types and/or forms and/or amounts of information may be sent for each on demand reading, including but not limited to one or more of current analyte level information (i.e., real time or the most recently obtained analyte level information temporally corresponding to the time the reading is initiated), rate of change of an analyte over a predetermined time period, rate of the rate of change of an analyte (acceleration in the rate of change), historical analyte information corresponding to analyte information obtained prior to a given reading and stored in memory of the assembly. Some or all of real time, historical, rate of change, rate of rate of change (such as acceleration or deceleration) information may be sent to a display device for a given reading. In certain embodiments, the type and/or form and/or amount of information sent to a display device may be preprogrammed and/or unchangeable (e.g., preset at manufacturing), or may not be preprogrammed and/or unchangeable so that it may be selectable and/or changeable in the field one or more times (e.g., by activating a switch of the system, etc.). Accordingly, in certain embodiments, for each on demand reading, a display device will output a current (real time) sensor-derived analyte value (e.g., in numerical format), a current rate of analyte change (e.g., in the form of an analyte rate indicator such as an arrow pointing in a direction to indicate the current rate), and analyte trend history data based on sensor readings acquired by and stored in memory of on body electronics (e.g., in the form of a graphical trace). Additionally, the on skin or sensor temperature reading or measurement associated with each on demand reading may be communicated from the on body electronics to the display device. The temperature reading or measurement, however, may not be output or displayed on the display device, but rather, used in conjunction with a software routine executed by the display device to correct or compensate the analyte measurement output to the user on the display device.

As described, embodiments include inserters for in vivo analyte sensors and on body electronics that together provide body wearable sensor electronics assemblies. In certain embodiments, in vivo analyte sensors are fully integrated with on body electronics (fixedly connected during manufacture), while in other embodiments they are separate but connectable post manufacture (e.g., before, during or after sensor insertion into a body). On body electronics may include an in vivo glucose sensor, electronics, battery, and antenna encased (except for the sensor portion that is for in vivo positioning) in a waterproof housing that includes or is attachable to an adhesive pad. In certain embodiments, the housing withstands immersion in about one meter of water for up to at least 30 minutes. In certain embodiments, the housing withstands continuous underwater contact, e.g., for longer than about 30 minutes, and continues to function properly according to its intended use, e.g., without water damage to the housing electronics where the housing is suitable for water submersion.

Embodiments include sensor insertion devices, which also may be referred to herein as sensor delivery units, or the like. Insertion devices may retain on body electronics assemblies completely in an interior compartment, i.e., an insertion device may be "pre-loaded" with on body electronics assemblies during the manufacturing process (e.g., on body electronics may be packaged in a sterile interior compartment of an insertion device). In such embodiments, insertion devices may form sensor assembly packages (including sterile packages) for pre-use or new on body electronics assemblies, and insertion devices configured to apply on body electronics assemblies to recipient bodies.

Embodiments include portable handheld display devices, as separate devices and spaced apart from an on body electronics assembly, that collect information from the assemblies and provide sensor derived analyte readings to users. Such devices may also be referred to as meters, readers, monitors, receivers, human interface devices, companions, or the like. Certain embodiments may include an integrated in vitro analyte meter. In certain embodiments, display devices include one or more wired or wireless communications ports such as USB, serial, parallel, or the like, configured to establish communication between a display device and another unit (e.g., on body electronics, power unit to recharge a battery, a PC, etc.). For example, a display device communication port may enable charging a display device battery with a respective charging cable and/or data exchange between a display device and its compatible informatics software.

Compatible informatics software in certain embodiments include, for example, but not limited to stand alone or network connection enabled data management software program, resident or running on a display device, personal computer, a server terminal, for example, to perform data analysis, charting, data storage, data archiving and data communication as well as data synchronization. Informatics software in certain embodiments may also include software for executing field upgradable functions to upgrade firmware of a display device and/or on body electronics unit to upgrade the resident software on the display device and/or the on body electronics unit, e.g., with versions of firmware that include additional features and/or include software bugs or errors fixed, etc. Embodiments may include a haptic feedback feature such as a vibration motor or the like, configured so that corresponding notifications (e.g., a successful on-demand reading received at a display device), may be delivered in the form of haptic feedback.

Embodiments include programming embedded on a computer readable medium, i.e., computer-based application software (may also be referred to herein as informatics software or programming or the like) that processes analyte information obtained from the system and/or user self-reported data. Application software may be installed on a host computer such as a mobile telephone, PC, an Internet-enabled human interface device such as an Internet-enabled phone, personal digital assistant, or the like, by a display device or an on body electronics unit. Informatics programming may transform data acquired and stored on a display device or on body unit for use by a user.

Embodiments of the subject disclosure are described primarily with respect to glucose monitoring devices and systems, and methods of glucose monitoring, for convenience only and such description is in no way intended to limit the scope of the disclosure. It is to be understood that the analyte monitoring system may be configured to monitor a variety of analytes at the same time or at different times.

As described in detail below, embodiments include devices, systems, kits and/or methods to monitor one or more physiological parameters such as, for example, but not limited to, analyte levels, temperature levels, heart rate, user activity level, over a predetermined monitoring time period. Also provided are methods of manufacturing. Predetermined monitoring time periods may be less than about 1 hour, or may include about 1 hour or more, e.g., about a few hours or more, e.g., about a few days of more, e.g., about 3 or more days, e.g., about 5 days or more, e.g., about 7 days or more, e.g., about 10 days or more, e.g., about 14 days or more, e.g., about several weeks, e.g., about 1 month or more. In certain embodiments, after the expiration of the predetermined monitoring time period, one or more features of the system may be automatically deactivated or disabled at the on body electronics assembly and/or display device.

For example, a predetermined monitoring time period may begin with positioning the sensor in vivo and in contact with a body fluid such as ISF, and/or with the initiation (or powering on to full operational mode) of the on body electronics. Initialization of on body electronics may be implemented with a command generated and transmitted by a display device in response to the activation of a switch and/or by placing the display device within a predetermined distance (e.g., close proximity) to the on body electronics, or by user manual activation of a switch on the on body electronics unit, e.g., depressing a button, or such activation may be caused by the insertion device, e.g., as described in U.S. patent application Ser. No. 12/698,129 filed on Feb. 1, 2010 and U.S. Provisional Application Nos. 61/238,646, 61/246,825, 61/247,516, 61/249,535, 61/317,243, 61/345, 562, and 61/361,374, the disclosures of each of which are incorporated herein by reference for all purposes.

When initialized in response to a received command from a display device, the on body electronics retrieves and executes from its memory software routine to fully power on the components of the on body electronics, effectively placing the on body electronics in full operational mode in response to receiving the activation command from the display device. For example, prior to the receipt of the command from the display device, a portion of the components in the on body electronics may be powered by its internal power supply such as a battery while another portion of the components in the on body electronics may be in powered down or maintained in a low power state including no power state, inactive mode, or all components may be in an inactive, powered down mode. Upon receipt of the command, the remaining portion (or all) of the components of the on body electronics is switched to active, fully operational mode.

Embodiments of on body electronics may include one or more printed circuit boards with electronics including control logic implemented in ASIC, microprocessors, memory, and the like, and transcutaneously positionable analyte sensors forming a single assembly. On body electronics may be configured to provide one or more signals or data packets associated with a monitored analyte level upon detection of a display device of the analyte monitoring system within a predetermined proximity for a period of time (for example, about 2 minutes, e.g., 1 minute or less, e.g., about 30 seconds or less, e.g., about 10 seconds or less, e.g., about 5 seconds or less, e.g., about 2 seconds or less) and/or until a confirmation, such as an audible and/or visual and/or tactile (e.g., vibratory) notification, is output on the display device indicating successful acquisition of the analyte related signal from the on body electronics. A distinguishing notification may also be output for unsuccessful acquisition in certain embodiments.

In certain embodiments, the monitored analyte level may be correlated and/or converted to glucose levels in blood or other fluids such as ISF. Such conversion may be accomplished with the on body electronics, but in many embodiments will be accomplished with display device electronics. In certain embodiments, glucose level is derived from the monitored analyte level in the ISF.

Analyte sensors may be insertable into a vein, artery, or other portion of the body containing analyte. In certain embodiments, analyte sensors may be positioned in contact with ISF to detect the level of analyte, where the detected analyte level may be used to infer the user's glucose level in blood or interstitial tissue.

Embodiments include transcutaneous sensors and also wholly implantable sensors and wholly implantable assemblies in which a single assembly including the analyte sensor and electronics are provided in a sealed housing (e.g., hermetically sealed biocompatible housing) for implantation in a user's body for monitoring one or more physiological parameters.

Embodiments include analyte monitors that are provided in small, lightweight, battery-powered and electronically-controlled systems. Such systems may be configured to detect physical parameters of subjects, such as signals indicative of in vivo analyte levels using an electrochemical sensor, and collect such signals, with or without processing. Any suitable measurement technique may be used to obtain signals from the sensors, e.g., may detect current, may employ potentiometry, etc. Techniques may include, but are not limited to amperometry, coulometry, and voltammetry. In some embodiments, sensing systems may be optical, colorimetric, and the like. In some embodiments, the portion of the system that performs this initial processing may be configured to provide the raw or at least initially processed data to another unit for further collection and/or processing. Such provision of data may be affected, for example, by a wired connection, such as an electrical, or by a wireless connection, such as an IR or RF connection.

In certain systems, the analyte sensor is in communication with on body electronics. The on-body unit may include a housing in which the on body electronics and at least a portion of the sensor are received.

Certain embodiments are modular. The on-body unit may be separately provided as a physically distinct assembly from a monitor unit, e.g., which displays or otherwise indicates analyte levels to a user. The on-body unit may be configured to provide the analyte levels detected by the sensor and/or other information (such as temperature, sensor life, etc.) over a communication link to the monitor unit. The monitor unit, in some embodiments, may include, e.g., a mobile telephone device, an in vitro glucose meter, a personal digital assistant, or other consumer electronics such as MP3 device, camera, radio, personal computer, etc., or other communication-enabled data-processing device.

The display unit may perform a variety of functions such as but not limited to data storage and/or processing and/or analysis and/or communication, etc., on the received analyte data to generate information pertaining to the monitored analyte levels and/or process the other information. The monitor unit may incorporate a display screen, which can be used, for example, to display measured analyte levels, and/or an audio component such as a speaker to audibly provide information to a user, and/or a vibration device to provide tactile feedback to a user. It is also useful for a user of an analyte-monitoring system to be able to see trend indications (including the magnitude and direction of any ongoing trend, e.g., the rate of change of an analyte or other parameter, and the amount of time a subject is above and/or below a threshold, such as a hypoglycemic and/or hyperglycemic threshold, etc.); such data may be displayed either numerically, or by a visual indicator such as an arrow that may vary in visual attributes, like size, shape, color, animation, or direction. The monitor unit may further be adapted to receive information from or about an in vitro analyte test strip, which may be manually or automatically entered into the monitor unit. In some embodiments, a monitor unit may incorporate an in vitro analyte test strip port and related electronics in order to be able to make discrete (e.g., blood glucose) measurements using an in vitro test strip (see, e.g., U.S. Pat. No. 6,175,752, the disclosure of which is incorporated by reference herein for all purposes).

The modularity of these systems may vary where one or more components may be constructed to be single use and one or more may be constructed to be re-useable. In some embodiments, the sensor is designed to be attachable and detachable from the on body electronics (and the on-body unit may be reusable), e.g., so that one or more of the components may be reused one or more times, while in other embodiments, the sensor and on body electronics may be provided as an integrated, undetachable package, which may be designed to be disposable after use, i.e., not re-used.

Embodiments of In Vivo Monitoring Systems

For purpose of illustration, and not limitation, the inserters described herein may be used in connection with an exemplary analyte monitoring system as depicted in FIG. 1. It is understood that the inserters described herein may be used with any medical device on its own or in connection with a system. FIG. 1 shows an exemplary in vivo-based analyte monitoring system 100 in accordance with embodiments of the present disclosure. As shown, in certain embodiments, analyte monitoring system 100 includes on body electronics 1100 electrically coupled to in vivo analyte sensor 14 (a proximal portion of which is shown in FIG. 1), and attached to adhesive layer 218 for attachment on a skin surface on the body of a user. On body electronics 1100 includes on body housing 122 that defines an interior compartment.

Also shown in FIG. 1 is insertion device 200 (or insertion devices 300, 400, 2400, 2500, 2700, 3700 described herein) that, when operated, transcutaneously positions a portion of analyte sensor 14 through a skin surface and in fluid contact with ISF, and positions on body electronics 1100 and adhesive layer 218 on a skin surface, as will be described in greater detail herein. In certain embodiments, on body electronics 1100, analyte sensor 14 and adhesive layer 218 are sealed within the housing of insertion device 200 before use, and in certain embodiments, adhesive layer 218 is also sealed within the housing or the adhesive layer can provide a seal for preserving the sterility of the apparatus. Additional details regarding insertion devices are discussed, e.g., in U.S. patent application Ser. No. 12/698,129 and U.S. Provisional Application Nos. 61/238,646, 61/246,825, 61/247, 516, 61/249,535, and 61/345,562, the disclosures of each of which are incorporated herein by reference for all purposes.

Referring back to the FIG. 1, analyte monitoring system 100 includes display device 1200 which includes a display 1220 to output information to the user, an input component 1210 such as a button, actuator, a touch sensitive switch, a capacitive switch, pressure sensitive switch, jog wheel or the like, to input data or command to display device 1200 or otherwise control the operation of display device 1200. It is noted that some embodiments may include display-less devices or devices without any user interface components. These devices may be functionalized to store data as a data logger and/or provide a conduit to transfer data from on body electronics and/or a display-less device to another device and/or location. Embodiments will be described herein as display devices for exemplary purposes which are in no way intended to limit the embodiments of the present disclosure. It will be apparent that display-less devices may also be used in certain embodiments.

In certain embodiments, on body electronics 1100 may be configured to store some or all of the monitored analyte related data received from analyte sensor 14 in a memory during the monitoring time period, and maintain it in memory until the usage period ends. In such embodiments, stored data is retrieved from on body electronics 1100 at the conclusion of the monitoring time period, for example, after removing analyte sensor 14 from the user by detaching on body electronics 1100 from the skin surface where it was positioned during the monitoring time period. In such data logging configurations, real time monitored analyte level is not communicated to display device 1200 during the monitoring period or otherwise transmitted from on body electronics 1100, but rather, retrieved from on body electronics 1100 after the monitoring time period.

In certain embodiments, input component 1210 of display device 1200 may include a microphone and display device 1200 may include software configured to analyze audio input received from the microphone, such that functions and operation of the display device 1200 may be controlled by voice commands. In certain embodiments, an output component of display device 1200 includes a speaker for outputting information as audible signals. Similar voice responsive components such as a speaker, microphone and software routines to generate, process and store voice driven signals may be provided to on body electronics 1100.

In certain embodiments, display 1220 and input component 1210 may be integrated into a single component, for example a display that can detect the presence and location of a physical contact touch upon the display such as a touch screen user interface. In such embodiments, the user may control the operation of display device 1200 by utilizing a set of pre-programmed motion commands, including, but not limited to, single or double tapping the display, dragging a finger or instrument across the display, motioning multiple fingers or instruments toward one another, motioning multiple fingers or instruments away from one another, etc. In certain embodiments, a display includes a touch screen having areas of pixels with single or dual function capacitive elements that serve as LCD elements and touch sensors.

Display device 1200 also includes data communication port 1230 for wired data communication with external devices such as remote terminal (personal computer) 1700, for example. Example embodiments of the data communication port 1230 include USB port, mini USB port, RS-232 port, Ethernet port, Firewire port, or other similar data communication ports configured to connect to the compatible data cables. Display device 1200 may also include an integrated in vitro glucose meter, including in vitro test strip port 1240 to receive an in vitro glucose test strip for performing in vitro blood glucose measurements.

Referring still to FIG. 1, display 1220 in certain embodiments is configured to display a variety of information— some or all of which may be displayed at the same or different time on display 1220. In certain embodiments the displayed information is user-selectable so that a user can customize the information shown on a given display screen. Display 1220 may include but is not limited to graphical display 1380, for example, providing a graphical output of glucose values over a monitored time period (which may show important markers such as meals, exercise, sleep, heart rate, blood pressure, etc, numerical display 1320, for example, providing monitored glucose values (acquired or received in response to the request for the information), and trend or directional arrow display 1310 that indicates a rate of analyte change and/or a rate of the rate of analyte change, e.g., by moving locations on display 1220.

As further shown in FIG. 1, display 1220 may also include date display 1350 providing for example, date information for the user, time of day information display 1390 providing time of day information to the user, battery level indicator display 1330 which graphically shows the condition of the battery (rechargeable or disposable) of the display device 1200, sensor calibration status icon display 1340 for example, in monitoring systems that require periodic, routine or a predetermined number of user calibration events, notifying the user that the analyte sensor calibration is necessary, audio/vibratory settings icon display 1360 for displaying the status of the audio/vibratory output or alarm state, and wireless connectivity status icon display 1370 that provides indication of wireless communication connection with other devices such as on body electronics, data processing module 1600, and/or remote terminal 1700. As additionally shown in FIG. 1, display 1220 may further include simulated touch screen button 1250, 1260 for accessing menus, changing display graph output configurations or otherwise for controlling the operation of display device 1200.

Referring back to FIG. 1, in certain embodiments, display 1220 of display device 1200 may be additionally, or instead of visual display, configured to output alarms notifications such as alarm and/or alert notifications, glucose values etc, which may be audible, tactile, or any combination thereof. In one aspect, the display device 1200 may include other output components such as a speaker, vibratory output component and the like to provide audible and/or vibratory output indication to the user in addition to the visual output indication provided on display 1220. Further details and other display embodiments can be found in, e.g., U.S. patent application Ser. No. 12/871,901, U.S. Provisional Application Nos. 61/238,672, 61/247,541, 61/297,625, the disclosures of each of which are incorporated herein by reference for all purposes.

After the positioning of on body electronics 1100 on the skin surface and analyte sensor 14 in vivo to establish fluid contact with ISF (or other appropriate body fluid), on body electronics 1100 in certain embodiments is configured to wirelessly communicate analyte related data (such as, for example, data corresponding to monitored analyte level and/or monitored temperature data, and/or stored historical analyte related data) when on body electronics 1100 receives a command or request signal from display device 1200. In certain embodiments, on body electronics 1100 may be configured to at least periodically broadcast real time data associated with monitored analyte level which is received by display device 1200 when display device 1200 is within communication range of the data broadcast from on body electronics 1100, i.e., it does not need a command or request from a display device to send information.

For example, display device 1200 may be configured to transmit one or more commands to on body electronics 1100 to initiate data transfer, and in response, on body electronics 1100 may be configured to wirelessly transmit stored analyte related data collected during the monitoring time period to display device 1200. Display device 1200 may in turn be connected to a remote terminal 1700 such as a personal computer and functions as a data conduit to transfer the stored analyte level information from the on body electronics 1100 to remote terminal 1700. In certain embodiments, the received data from the on body electronics 1100 may be stored (permanently or temporarily) in one or more memory of the display device 1200. In certain other embodiments, display device 1200 is configured as a data conduit to pass the data received from on body electronics 1100 to remote terminal 1700 that is connected to display device 1200.

Referring still to FIG. 1, also shown in analyte monitoring system 100 are data processing module 1600 and remote terminal 1700. Remote terminal 1700 may include a personal computer, a server terminal a laptop computer or other suitable data processing devices including software for data management and analysis and communication with the components in the analyte monitoring system 100. For example, remote terminal 1700 may be connected to a local area network (LAN), a wide area network (WAN), or other data network for uni-directional or bi-directional data communication between remote terminal 1700 and display device 1200 and/or data processing module 1600.

Remote terminal 1700 in certain embodiments may include one or more computer terminals located at a physician's office or a hospital. For example, remote terminal 1700 may be located at a location other than the location of display device 1200. Remote terminal 1700 and display device 1200 could be in different rooms or different buildings. Remote terminal 1700 and display device 1200 could be at least about one mile apart, e.g., at least about 100 miles apart, e.g., at least about 1000 miles apart. For example, remote terminal 1700 could be in the same city as display device 1200, remote terminal 1700 could be in a different city than display device 1200, remote terminal 1700 could be in the same state as display device 1200, remote terminal 1700 could be in a different state than display device 1200, remote terminal 1700 could be in the same country as display device 1200, or remote terminal 1700 could be in a different country than display device 1200, for example.

In certain embodiments, a separate, optional data communication/processing device such as data processing module 1600 may be provided in analyte monitoring system 100. Data processing module 1600 may include components to communicate using one or more wireless communication protocols such as, for example, but not limited to, infrared (IR) protocol, Bluetooth® protocol, Zigbee® protocol, and 802.11 wireless LAN protocol. Additional description of communication protocols including those based on Bluetooth® protocol and/or Zigbee® protocol can be found in U.S. Patent Publication No. 2006/0193375 incorporated herein by reference for all purposes. Data processing module 1600 may further include communication ports, drivers or connectors to establish wired communication with one or more of display device 1200, on body electronics 1100, or remote terminal 1700 including, for example, but not limited to USB connector and/or USB port, Ethernet connector and/or port, FireWire connector and/or port, or RS-232 port and/or connector.

In certain embodiments, data processing module 1600 is programmed to transmit a polling or query signal to on body electronics 1100 at a predetermined time interval (e.g., once every minute, once every five minutes, or the like), and in response, receive the monitored analyte level information from on body electronics 1100. Data processing module 1600 stores in its memory the received analyte level information, and/or relays or retransmits the received information to another device such as display device 1200. More specifically in certain embodiments, data processing module 1600 may be configured as a data relay device to retransmit or pass through the received analyte level data from on body electronics 1100 to display device 1200 or a remote terminal (for example, over a data network such as a cellular or WiFi data network) or both.

In certain embodiments, on body electronics 1100 and data processing module 1600 may be positioned on the skin surface of the user within a predetermined distance of each other (for example, about 1-12 inches, or about 1-10 inches, or about 1-7 inches, or about 1-5 inches) such that periodic communication between on body electronics 1100 and data processing module 1600 is maintained. Alternatively, data processing module 1600 may be worn on a belt or clothing item of the user, such that the desired distance for communication between the on body electronics 1100 and data processing module 1600 for data communication is maintained. In a further aspect, the housing of data processing module 1600 may be configured to couple to or engage with on body electronics 1100 such that the two devices are combined or integrated as a single assembly and positioned on the skin surface. In further embodiments, data processing module 1600 is detachably engaged or connected to on body electronics 1100 providing additional modularity such that data processing module 1600 may be optionally removed or reattached as desired.

Referring again to FIG. 1, in certain embodiments, data processing module 1600 is programmed to transmit a command or signal to on body electronics 1100 at a predetermined time interval such as once every minute, or once every 5 minutes or once every 30 minutes or any other suitable or desired programmable time interval to request analyte related data from on body electronics 1100. When data processing module 1600 receives the requested analyte related data, it stores the received data. In this manner, analyte monitoring system 100 may be configured to receive the continuously monitored analyte related information at the programmed or programmable time interval, which is stored and/or displayed to the user. The stored data in data processing module 1600 may be subsequently provided or transmitted to display device 1200, remote terminal 1700 or the like for subsequent data analysis such as identifying frequency of periods of glycemic level excursions over the monitored time period, or the frequency of the alarm event occurrence during the monitored time period, for example, to improve therapy related decisions. Using this information, the doctor, healthcare provider or the user may adjust or recommend modification to the diet, daily habits and routines such as exercise, and the like.

In another embodiment, data processing module 1600 transmits a command or signal to on body electronics 1100 to receive the analyte related data in response to a user activation of a switch provided on data processing module 1600 or a user initiated command received from display device 1200. In further embodiments, data processing module 1600 is configured to transmit a command or signal to on body electronics 1100 in response to receiving a user initiated command only after a predetermined time interval has elapsed. For example, in certain embodiments, if the user does not initiate communication within a programmed time period, such as, for example about 5 hours from last communication (or 10 hours from the last communication, or 24 hours from the last communication), the data processing module 1600 may be programmed to automatically transmit a request command or signal to on body electronics 1100. Alternatively, data processing module 1600 may be programmed to activate an alarm to notify the user that a predetermined time period of time has elapsed since the last communication between the data processing module 1600 and on body electronics 1100. In this manner, users or healthcare providers may program or configure data processing module 1600 to provide certain compliance with analyte monitoring regimen, so that frequent determination of analyte levels is maintained or performed by the user.

In certain embodiments, when a programmed or programmable alarm condition is detected (for example, a detected glucose level monitored by analyte sensor 14 that is outside a predetermined acceptable range indicating a physiological condition) which requires attention or intervention for medical treatment or analysis (for example, a hypoglycemic condition, a hyperglycemic condition, an impending hyperglycemic condition or an impending hypoglycemic condition), the one or more output indications may be generated by the control logic or processor of the on body electronics 1100 and output to the user on a user interface of on body electronics 1100 so that corrective action may be timely taken. In addition to or alternatively, if display device 1200 is within communication range, the output indications or alarm data may be communicated to display device 1200 whose processor, upon detection of the alarm data reception, controls the display 1220 to output one or more notification.

In certain embodiments, control logic or microprocessors of on body electronics 1100 include software programs to determine future or anticipated analyte levels based on information obtained from analyte sensor 14, e.g., the current analyte level, the rate of change of the analyte level, the acceleration of the analyte level change, and/or analyte trend information determined based on stored monitored analyte data providing a historical trend or direction of analyte level fluctuation as function time during monitored time period. Predictive alarm parameters may be programmed or programmable in display device 1200, or the on body electronics 1100, or both, and output to the user in advance of anticipating the user's analyte level reaching the future level. This provides the user an opportunity to take timely corrective action.

Information, such as variation or fluctuation of the monitored analyte level as a function of time over the monitored time period providing analyte trend information, for example, may be determined by one or more control logic or microprocessors of display device 1200, data processing module 1600, and/or remote terminal 1700, and/or on body electronics 1100. Such information may be displayed as, for example, a graph (such as a line graph) to indicate to the user the current and/or historical and/or and predicted future analyte levels as measured and predicted by the analyte monitoring system 100. Such information may also be displayed as directional arrows (for example, see trend or directional arrow display 1310) or other icon(s), e.g., the position of which on the screen relative to a reference point indicated whether the analyte level is increasing or decreasing as well as the acceleration or deceleration of the increase or decrease in analyte level. This information may be utilized by the user to determine any necessary corrective actions to ensure the analyte level remains within an acceptable and/or clinically safe range. Other visual indicators, including colors, flashing, fading, etc., as well as audio indicators including a change in pitch, volume, or tone of an audio output and/or vibratory or other tactile indicators may also be incorporated into the display of trend data as means of notifying the user of the current level and/or direction and/or rate of change of the monitored analyte level. For example, based on a determined rate of glucose change, programmed clinically significant glucose threshold levels (e.g., hyperglycemic and/or hypoglycemic levels), and current analyte level derived by an in vivo analyte sensor, the system 100 may include an algorithm stored on computer readable medium to determine the time it will take to reach a clinically significant level and will output notification in advance of reaching the clinically significant level, e.g., 30 minutes before a clinically significant level is anticipated, and/or 20 minutes, and/or 10 minutes, and/or 5 minutes, and/or 3 minutes, and/or 1 minute, and so on, with outputs increasing in intensity or the like.

Referring again back to FIG. 1, in certain embodiments, software algorithm(s) for execution by data processing module 1600 may be stored in an external memory device such as an SD card, microSD card, compact flash card, XD card, Memory Stick card, Memory Stick Duo card, or USB memory stick/device including executable programs stored in such devices for execution upon connection to the respective one or more of the on body electronics 1100, remote terminal 1700 or display device 1200. In a further aspect, software algorithms for execution by data processing module 1600 may be provided to a communication device such as a mobile telephone including, for example, WiFi or Internet enabled smart phones or personal digital assistants (PDAs) as a downloadable application for execution by the downloading communication device.

Examples of smart phones include Windows®, Android™, iPhone® operating system, Palm® WebOS™, Blackberry® operating system, or Symbian® operating system based mobile telephones with data network connectivity functionality for data communication over an internet connection and/or a local area network (LAN). PDAs as described above include, for example, portable electronic devices including one or more microprocessors and data communication capability with a user interface (e.g., display/output unit and/or input unit, and configured for performing data processing, data upload/download over the internet, for example. In such embodiments, remote terminal 1700 may be configured to provide the executable application software to the one or more of the communication devices described above when communication between the remote terminal 1700 and the devices are established.

In still further embodiments, executable software applications may be provided over-the-air (OTA) as an OTA download such that wired connection to remote terminal 1700 is not necessary. For example, executable applications may be automatically downloaded as software download to the communication device, and depending upon the configuration of the communication device, installed on the device for use automatically, or based on user confirmation or acknowledgement on the communication device to execute the installation of the application. The OTA download and installation of software may include software applications and/or routines that are updates or upgrades to the existing functions or features of data processing module 1600 and/or display device 1200.

Referring back to remote terminal 1700 of FIG. 1, in certain embodiments, new software and/or software updates such as software patches or fixes, firmware updates or software driver upgrades, among others, for display device 1200 and/or on body electronics 1100 and/or data processing module 1600 may be provided by remote terminal 1700 when communication between the remote terminal 1700 and display device 1200 and/or data processing module 1600 is established. For example, software upgrades, executable programming changes or modification for on body electronics 1100 may be received from remote terminal 1700 by one or more of display device 1200 or data processing module 1600, and thereafter, provided to on body electronics 1100 to update its software or programmable functions. For example, in certain embodiments, software received and installed in on body electronics 1100 may include software bug fixes, modification to the previously stalled software parameters (modification to analyte related data storage time interval, resetting or adjusting time base or information of on body electronics 1100, modification to the transmitted data type, data transmission sequence, or data storage time period, among others). Additional details describing field upgradability of software of portable electronic devices, and data processing are provided in U.S. application Ser. Nos. 12/698,124, 12/794,721, now U.S. Pat. No. 8,595,607, Ser. Nos. 12/699,653, and 12/699,844, and U.S. Provisional Application Nos. 61/359,265, and 61/325,155 the disclosures of which are incorporated by reference herein for all purposes.

The Sensor

The analyte sensor 14 of the analyte measurement system 100 may be used to monitor levels of a wide variety of analytes. Analytes that may be monitored include, for example, acetylcholine, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid-stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. One or more analytes may be monitored by a given sensor. In those embodiments that monitor more than one analyte, the analytes may be monitored at the same or different times, which may use the same on body electronics (e.g., simultaneously) or with different on body electronics.

In one embodiment of the present disclosure, sensor 14 is physically positioned in or on the body of a user whose analyte level is being monitored. Sensor 14 may be configured to continuously sample the analyte level of the user and convert the sampled analyte level, e.g., glucose concentration into a corresponding data signal, e.g., a current or voltage, for input into on body electronics. Alternatively, sensor 14 may be configured to sample analyte levels on demand. The on body electronics may amplify, filter, average, and/or otherwise process signal provided by the sensor.

Figure 2:
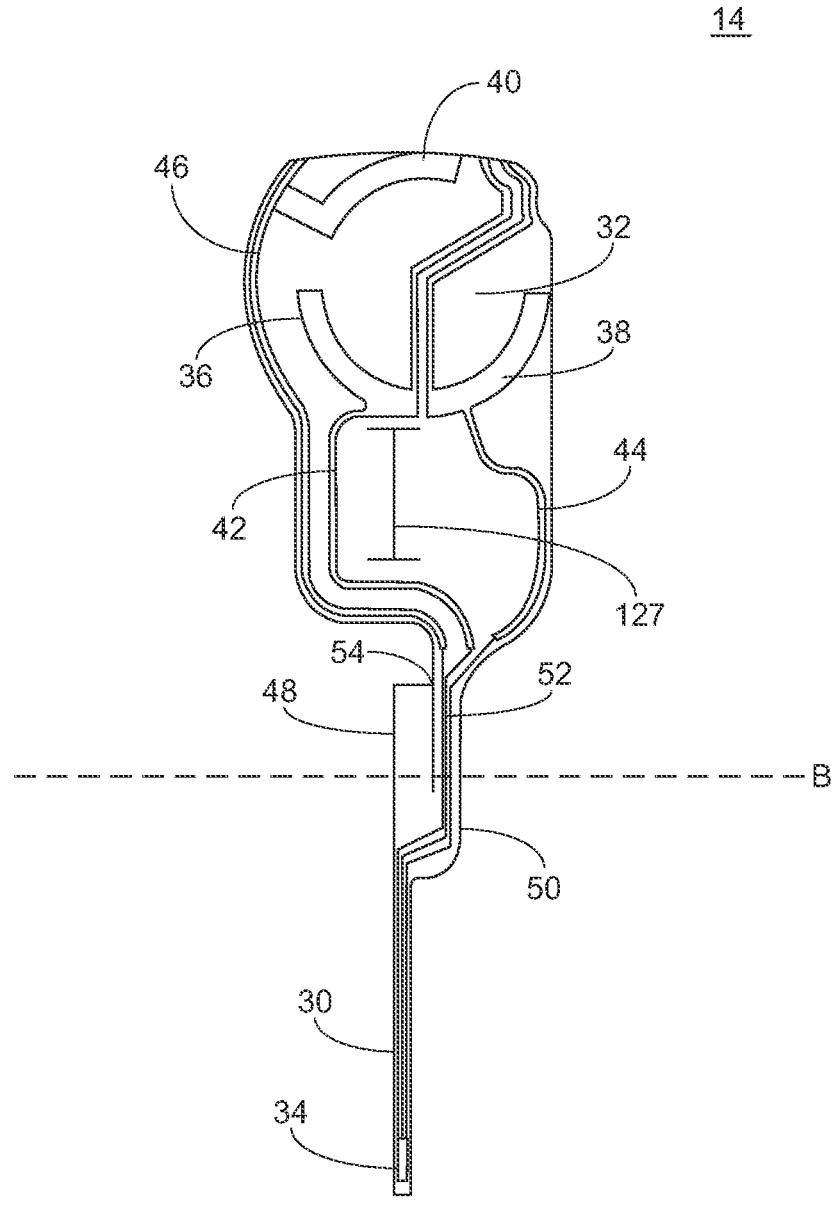
FIGS. 2-3 are views of an electrochemical sensor in accordance with a further embodiment of the disclosed subject matter.

An embodiment of the sensor 14 is illustrated in FIG. 2. It is understood that the inserters described herein can be used with other medical devices. The shape(s) described herein are exemplary only. Other sensor shapes are contemplated. In some embodiments, sensor 14 includes a substrate which is a dielectric, e.g., a polymer or plastic material, such as polyester or polyamide. In this embodiment, the sensor is constructed so that a portion is positionable beneath skin and a portion is above skin. Accordingly, sensor 14 includes an insertion or internal portion 30 and an external or electrical contact portion 32. In some embodiments, the contact portion 32 includes several conductive contacts 36, 38, and 40 (herein shown as three contacts) for connection to other electronics, e.g., at the on body electronics 1100 (See FIG. 1). The contacts provided in this embodiment are for a working electrode, a reference electrode, and a counter electrode. In some embodiments, two or more working electrodes are provided. The operative portions of these electrodes, that is, working electrode, reference electrode, and counter electrode (not individually shown), are provided at the insertion portion, e.g., at the distal end of insertion portion 30, e.g., portion 34. In some embodiments, one or more electrodes may be external to the body, e.g., an external counter electrode. The contact and operative portions of the electrodes are connected by circuit traces 42, 44, and 46 running on the surface of the substrate. In some embodiments, the traces are provided in channels, or may be embedded within the substrate, or may traverse different sides of the substrate. The conductive contacts, conductive traces, and electrodes are fabricated from conductive material, such as platinum, palladium, gold, carbon, or the like. More than one material may be used for a given sensor. Further details of sensors are described, e.g., in U.S. Pat. Nos. 6,175,572 and 6,103,033, which are incorporated by reference herein for all purposes.

Sensor 14 may include a proximal retention portion 48. The insertion portion 30 and the proximal retention portion 48 are sized and configured to be positioned with a sharp for installation into the skin of a subject, as described herein. In use, the sensor 14 may be configured to bend (e.g., along the line B) and therefore be positioned in two substantially perpendicular, intersecting planes. Such bending may occur prior to or during coupling to the on body electronics as described below (See FIG. 17).

Figure 3:
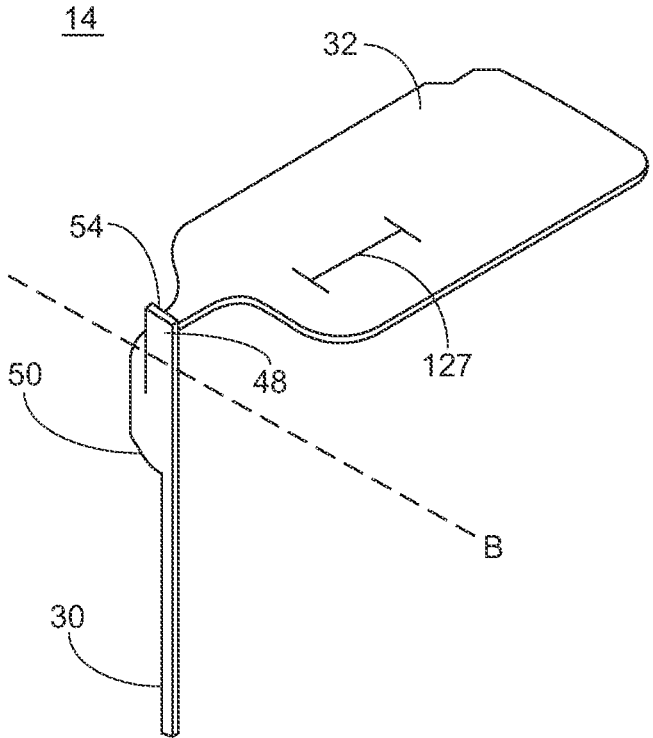

Portions 48 and 52 provide a path for electrical connections, e.g., the conductive traces, between the proximal and distal portions of the sensor. Sensor 14 is further provided with a notch or cut-out 54. Such configuration facilitates the sensor 14 to bend (e.g., along the line indicated by line B) such that retention portion 48 remains upright and therefore be positioned in two substantially perpendicular, intersecting planes, as illustrated in FIG. 3. As will be described below, the sensor tab 50 can be encased in the on body housing 122 to aid in securing and positioning the sensor 14. Proximal retention portion 48 maintains its longitudinal alignment with insertion portion 30 for positioning within an insertion sharp.

Embodiments of analyte sensors have been described herein to operate electrochemically, through an arrangement of electrodes having chemical sensing layers applied thereto, by generating an electrical current proportional to the volume of a redox reaction of the analyte (and indicative of analyte concentration), catalyzed by an analyte-specific oxidizing enzyme. Embodiments exist in which the number of electrodes provided to bring about and detect the level of these reactions is two, three, or a greater number. However, other types of sensors may be employed as described herein.

A portion of sensor 14 may be situated above the surface of the skin, with a distal portion 30 penetrating through the skin and into the subcutaneous space in contact with the user's biofluid, such as ISF. Further details regarding the electrochemistry of sensor 14 is provided in U.S. Pat. Nos. 5,264,104; 5,356,786; 5,262,035; 5,320,725; and 6,990,366, each of which is incorporated by reference herein for all purposes.

In some embodiments, the sensor is implantable into a subject's body for a usage period (e.g., a minute or more, at least one day or more, about one to about 30 days or even longer, about three to about fourteen days, about three to about seven days, or in some embodiments, longer periods of up to several weeks) to contact and monitor an analyte present in a biological fluid. In this regard, the sensor can be disposed in a subject at a variety of sites (e.g., abdomen, upper arm, thigh, etc.), including intramuscularly, transcutaneously, intravascularly, or in a body cavity.

In some embodiments, sensor 14 is employed by insertion and/or implantation into a user's body for some usage period. In such embodiments, the substrate may be formed from a relatively flexible material.

While the embodiments illustrated in FIGS. 2-3 have three electrodes, other embodiments can include a fewer or greater number of electrodes. For example, a two-electrode sensor can be utilized. The sensor 14 may be externally-powered and allow a current to pass which is proportional to the amount of analyte present. Alternatively, the sensor 14 itself may act as a current source in some embodiments. In some two-electrode embodiments, the sensor may be self-biasing and there may be no need for a reference electrode. An exemplary self-powered, two-electrode sensor is described in U.S. patent application Ser. No. 12/393,921, filed Feb. 26, 2009, and entitled "Self-Powered Analyte Sensor," which is hereby incorporated by reference herein for all purposes. The level of current provided by a self-powered sensor may be low, for example, on the order of nanoamperes, in certain embodiments.

Insertion Assembly

Insertion assemblies are provided which are used to install a medical device to the subject. In some embodiments, an insertion assembly includes an inserter and the medical device itself. The inserter can be configured to insert various medical devices into the subject, such as, for example, an analyte sensor, an infusion set, or a cannula. In some embodiments, the inserter can be configured to install a combination of such devices, e.g., a combined sensor/infusion set, etc., at the same or different times or locations. For example, in certain embodiments, a given inserter can be configured to install a first device and a second device at different times. In this regard, the inserter can be reusable. For example, an inserter may be modifiable to be used with more than one medical device, to include more than one type of medical device, e.g., by attaching an adapter and/or detaching a portion of an inserter. The inserter can install the medical device in, under, or through the skin of the subject, or place the medical device on the surface of the skin. The medical device can include features or structures, e.g., barbs, tabs, adhesive, etc., to maintain the device in position with respect to the skin after insertion. The inserter device may also be used as a lancet, e.g., to pierce the skin without inserting or installing a medical device.

In some embodiments, an insertion assembly includes an inserter, a medical device, such as an analyte sensor, and a mount for supporting the medical device at least partially in or on the skin of the subject. In some embodiments, the mount is a support structure, plate and/or member which is attached, adhered, or otherwise secured to the skin of the subject. The mount may be inserted simultaneously with the medical device by the inserter. In other embodiments, the mount is installed after or before installation of the medical device. A mount may be applied by the inserter or separately. The mount may include features or structures (e.g., adhesive, guides, barbs, tabs, etc.) to maintain the sensor in position with respect to the skin after insertion and/or maintain the sensor in relative position with respect to the sensor control unit. In some embodiments, an adhesive pad or strip is used to secure the medical device, e.g., the sensor and/or the sensor control unit, and no mount is used.

In some embodiments, an insertion assembly includes an inserter, an analyte sensor, a mount, and a power supply. The mount and power supply may be inserted simultaneously with the analyte sensor by the inserter. In other embodiments, the mount and battery are installed after or before installation of the analyte sensor. In such case, the mount and/or power supply may be applied by the inserter or separately. The power supply may be used to provide a current or a potential to the sensor and/or to provide power for communication of one or more signals to the monitor unit.

In some embodiments, an insertion assembly includes an inserter, a medical device such as an analyte sensor, a mount, and a sensor control unit. The mount and sensor control unit may be deployed and/or installed simultaneously with the analyte sensor by the inserter. In other embodiments, the mount and sensor control unit are installed after or before installation of the analyte sensor. For example, the mount and the analyte sensor may be installed by the inserter, and the sensor control unit may be subsequently installed. In other embodiments, the mount is installed, followed by insertion of the analyte sensor by the inserter, and further followed by installation of the sensor control unit. In other embodiments, the mount and sensor control unit are installed first, and the analyte sensor is subsequently installed.

In some embodiments, electronics of the sensor control unit provide a voltage or current to the analyte sensor. In some embodiments, the electronics processes signals are provided by the analyte sensor. In further embodiments, the electronics may include communication functionality for providing signal relating to signal provided by the analyte sensor to a further component, such as, e.g., a monitor unit, a computer, or other component. In some embodiments, communications circuitry, such as RFID antenna or other communications circuitry, is provided. The power supply may be used to power some or all of these functions. In some embodiments, power is provided from the monitor unit, e.g., via inductive coupling.

An inserter may include a plurality of different components. For example, an inserter may include one or more components for advancing a sharp towards the skin of the subject. The sensor and sensor control unit and/or mounting structure may be supported by a support structure, such as a carriage. A driver may be provided for advancing the sharp and/or the analyte sensor/support structure. In some embodiments, the actuator is directly or indirectly coupled to the sharp and/or support structure, such that manual force and speed applied by the subject to the actuator is transferred to the sharp and/or support structure. In some embodiments, the applied force drives the sharp and/or support structure between a retracted position and an advanced position. In some embodiments, the sensor and sensor control unit and/or mounting structure is maintained in a retracted position prior to installation by contacting projections extending inwardly from a sheath. In accordance with this embodiment, the sensor and sensor control unit and/or mounting structure are temporarily maintained operatively between the support structure and the projections disposed on the interior wall of the sheath.

An inserter can also include one or more components for retracting the sharp, while allowing the analyte sensor and optional mount and/or electronics to remain on the subject. The components for retracting the sharp can include a retractor. It is understood that the retractor and the actuator may be the same structure or include some common components. In some embodiments, the retractor is directly or indirectly coupled to the sharp such that the manual force applied by the user is transferred from the retractor to the sharp to retract the sharp from the skin. In other embodiments, a drive assembly may be provided to retract the sharp. For example, the drive assembly may include a spring, motor, hydraulic piston, etc., to retract the sharp away from the skin of the subject. The drive assembly may also include a linear drive component.

In some embodiments, the retractor withdraws the sharp upon actuation by the user. In such cases, the user actuates the retractor when it is desired to withdraw the sharp. For example, the retractor may include a release switch. Upon activation of the release switch, the drive assembly, e.g., the spring or other driver, retracts the sharp from the skin. In other embodiments, the retractor and the actuator include common components. After activating the actuator to advance the sharp and the analyte sensor, the user releases the actuator, which allows the drive assembly to withdraw the sharp from the skin.

In some embodiments, the retractor withdraws the sharp without further user interaction after actuation of insertion. For example, the inserter may include features or components which automatically retract the sharp upon advancement of the sharp and support structure by a predetermined amount. Inserter devices, in which no further action by the user is required to initiate withdrawal of the sharp after insertion, are referred to herein as having "automatic" withdrawal of the sharp.

Inserter Devices

Figures 4, 5:
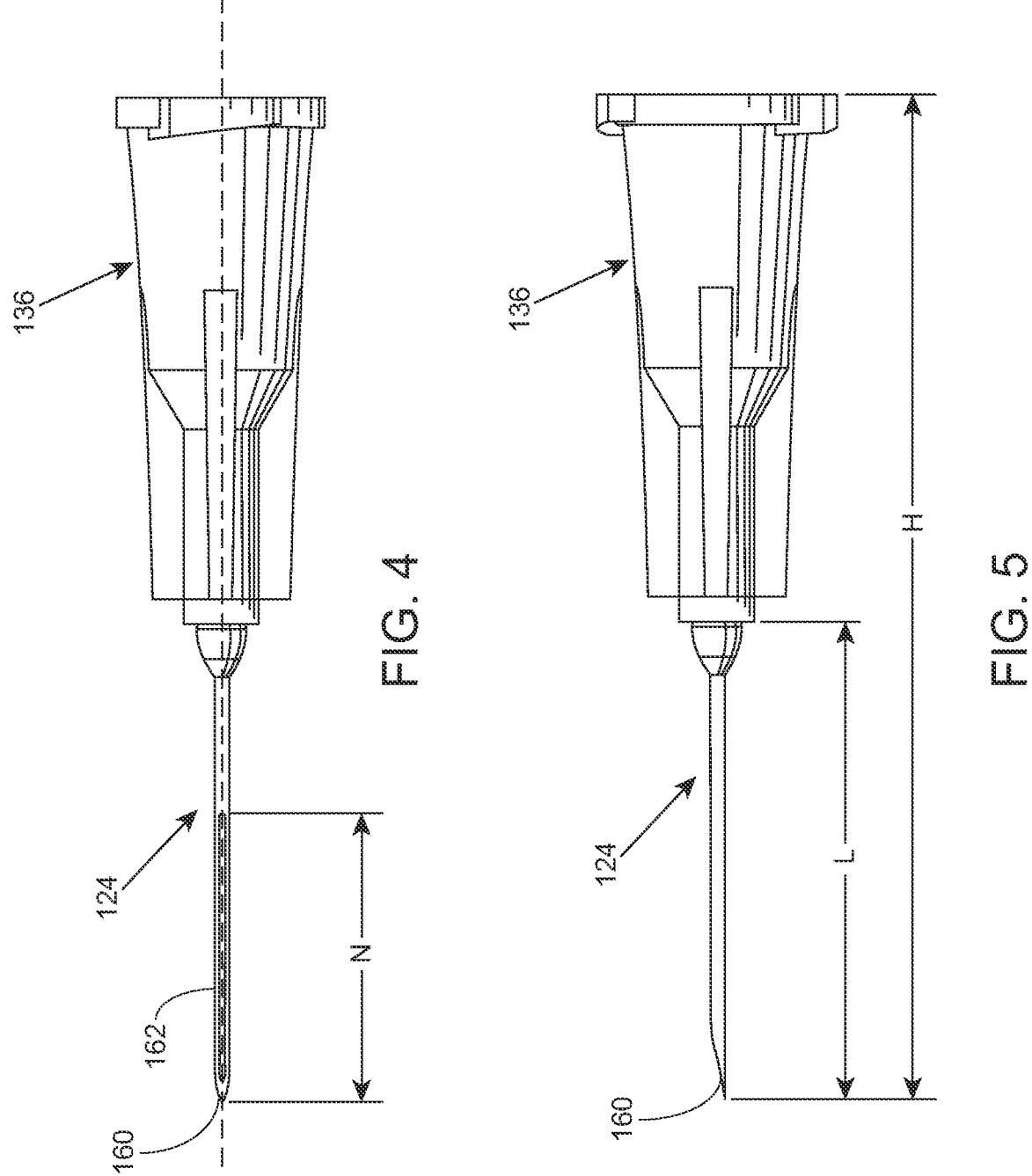
FIGS. 4-5 are schematic views of a needle hub in accordance with one embodiment of the disclosed subject matter.

One embodiment of a needle hub for an inserter is illustrated in FIGS. 4-5. Needle hub 136 supports sharp 124, having a sharpened distal portion 160. In some embodiments, as discussed herein, a longitudinal wall opening or gap 162 is provided in at least a portion of the wall of the sharp 124. The length N of the gap 162 is selected to be commensurate with the length of the insertion portion 30 through to the proximal retention portion 48 of the sensor, and in certain embodiments may be about 3 mm to about 50 mm, e.g., about 5 mm, or about 10 mm, or about 15 mm, or about 20 mm. The length L of the sharp 124 may be about 3 mm to about 50 mm, e.g., 5 mm or more, or about 10 mm, or about 20 mm, or about 30 mm, or about 50 mm, and is selected based upon the length of the insertion portion 30 of a sensor and the desired depth of the insertion portion 30 of the sensor 14. In some embodiments, the distance or spacing between the two edges of the gap is about 0.2 mm to about 0.5 mm e.g., about 0.22 mm, about 0.25 mm, etc.

Figure 7:
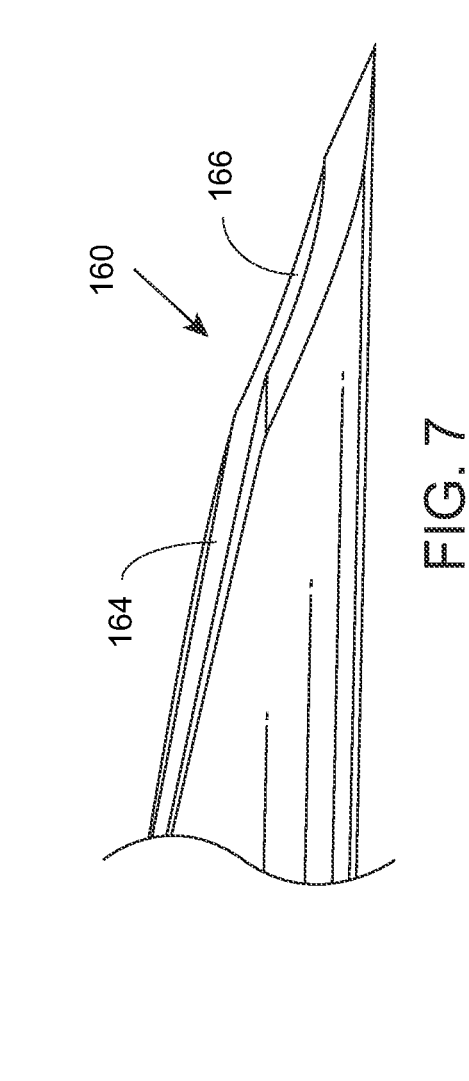
FIG. 7 is a side view of a sharp in accordance with one embodiment of the disclosed subject matter.
Figure 6:
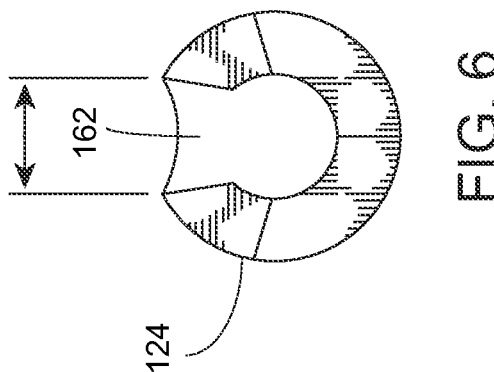
FIG. 6 is a distal end view of a sharp in accordance with one embodiment of the disclosed subject matter.
Figure 8:
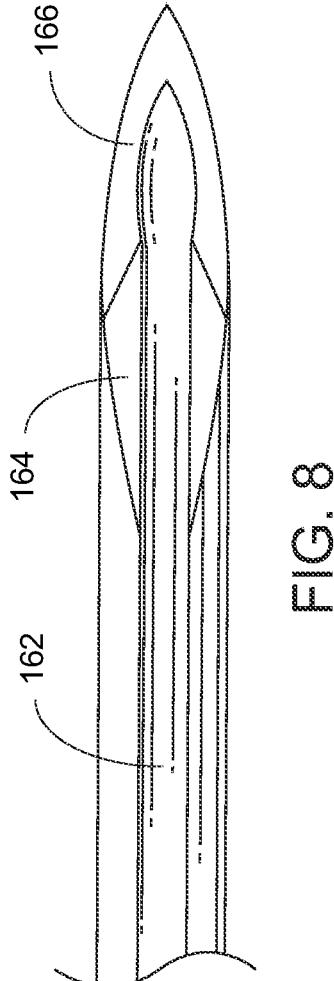
FIG. 8 is a side view of a sharp in accordance with one embodiment of the disclosed subject matter.
Figure 9:
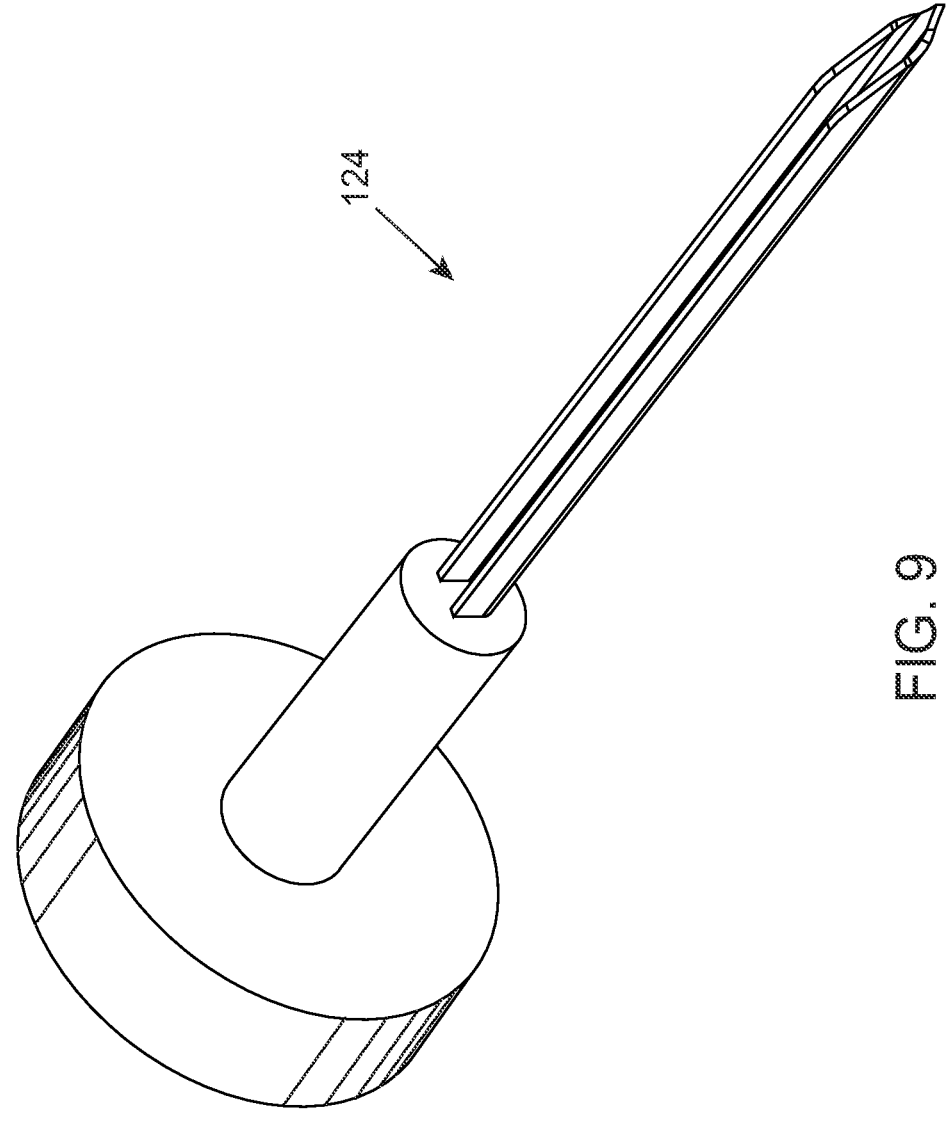
FIG. 9 is a perspective view of a sharp in accordance with one embodiment of the disclosed subject matter.

The distal portion 160 of sharp 124 is illustrated in greater detail in FIGS. 6-8. As illustrated in FIG. 6, sharp 124 has a substantially "C"- or "U"-shaped profile in this embodiment, but may have other configurations, e.g., substantially "V"-shaped. A longitudinal gap 162 is provided in the wall of the sharp 124. FIG. 7 illustrates distal portion 160 as provided with an angled tip. In some embodiments, the angled tip may be provided with a first angled tip portion 164 and a second steep-angled tip portion 166. The exemplary configuration, which includes multiple edges and faces, provides a sharp point to reduce penetration force, trauma, and bleeding for the subject. The distal section of the sensor body has a width sized to fit within the gap 162 of the insertion sharp 124 having a diameter less than about 20 gauge to about 26 gauge, e.g., 21 gauge to about 25 gauge, where in certain embodiments the sharp is 21 gauge or 23 gauge or 25 gauge. Such sharp may be used with a sensor having a width or diameter—at least the portion that is carried by the sharp—of about 0.20 mm to about 0.80 mm, e.g., about 0.25 mm to about 0.60 mm, where, in some embodiments, the width or diameter of at least a portion of a sensor is 0.27 mm or 0.33 mm or 0.58 mm. In some embodiments, sharp 124 is fabricated from a sheet of metal and folded into a substantially "V," "U" or "C" configuration in cross-section. Various technologies can be used to manufacture a folded sheet of metal to form sharp 124. For example, etched-sheet metal technology can be used to form the sharp 124. In this manner, the sharp can be formed having a very sharp edge so that penetration through the skin during insertion is less painful. In other embodiments, a progressive die technology may be utilized to form a complex sheet-metal shape that has a sharp edge as depicted in FIG. 9. In some embodiments, the sharp 124 can be molded with a plastic cap so that the sharp can be handled during the inserter assembly process. Further, the die cut sharp may be molded with plastic to reinforce the "V," "U" or "C" shaped sheet metal configuration. In other embodiments, a laser-cut sharp can be formed. In this manner, the laser can be used to form the wall opening or gap 162 and first-angled tip portion 164 and a second, steep-angled tip portion 166.

Figure 10:
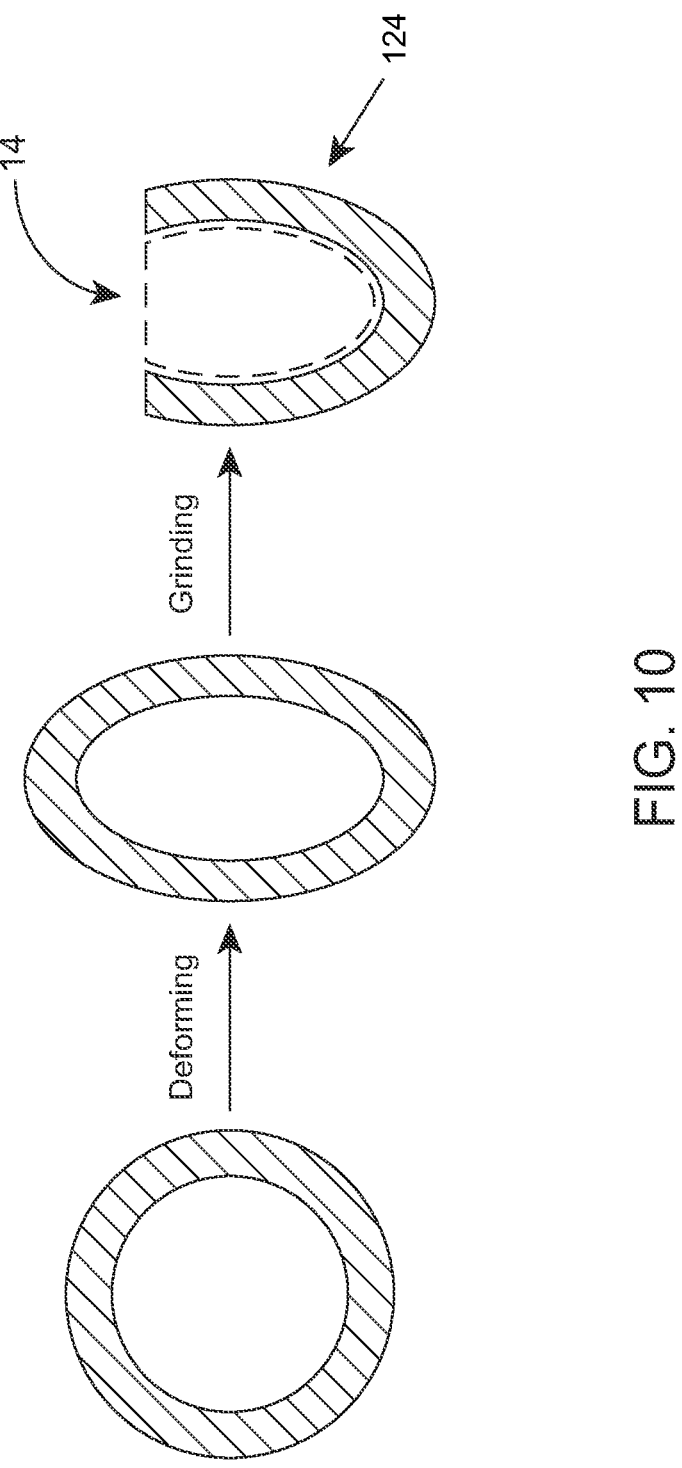
FIG. 10 is a schematic view of an alternate embodiment for forming a sharp to be used in an inserter in accordance with one embodiment of the disclosed subject matter.

In another embodiment, a sharp 124 may be formed from a standard hypodermic needle utilizing the method depicted in FIG. 10. First, the hypodermic needle (having a circular cross-section) is cut to the desired length for sharp 124. Next, the hypodermic needle is compressed so that its cross-section is permanently deformed from a circular shape to an oval shape. The tip of the hypodermic needle is then ground to a bevel to produce a sharp point to reduce the required penetration force, as previously discussed. Finally, the top section of the needle is removed by appropriate techniques (e.g., grinding, electropolishing, etc.). The resulting sharp 124 has a "U"-shaped configuration and provides ample space for the insertion of sensor 14. In some embodiments, the tip-grinding step and the compression step may be carried out in reversed order.

Due to the compression step, a user may initially start with a larger diameter hypodermic needle so that the finished sharp 124 will have similar dimensions to the previously described sharps.

Figure 11:
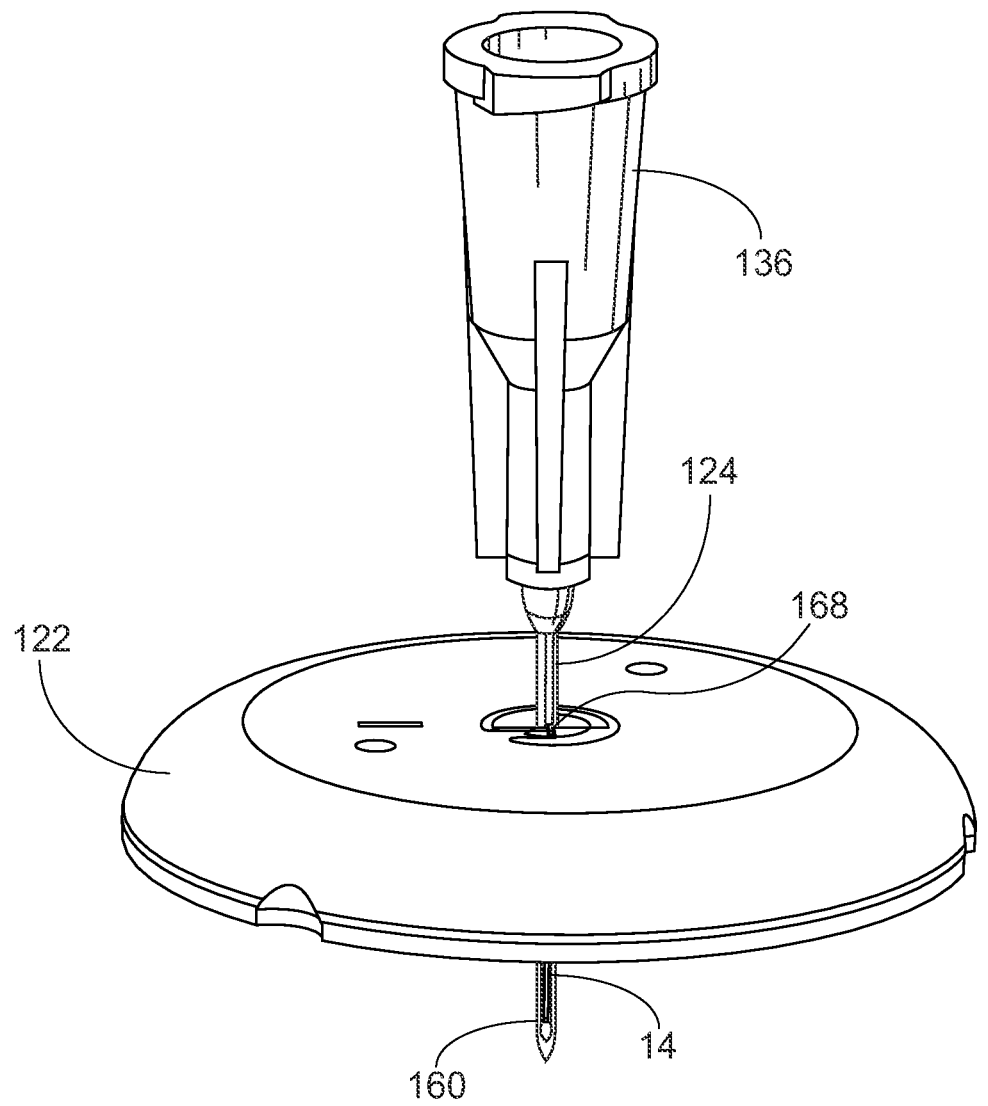
FIG. 11 is a perspective view of an inserter in accordance with one embodiment of the disclosed subject matter.
Figure 12:
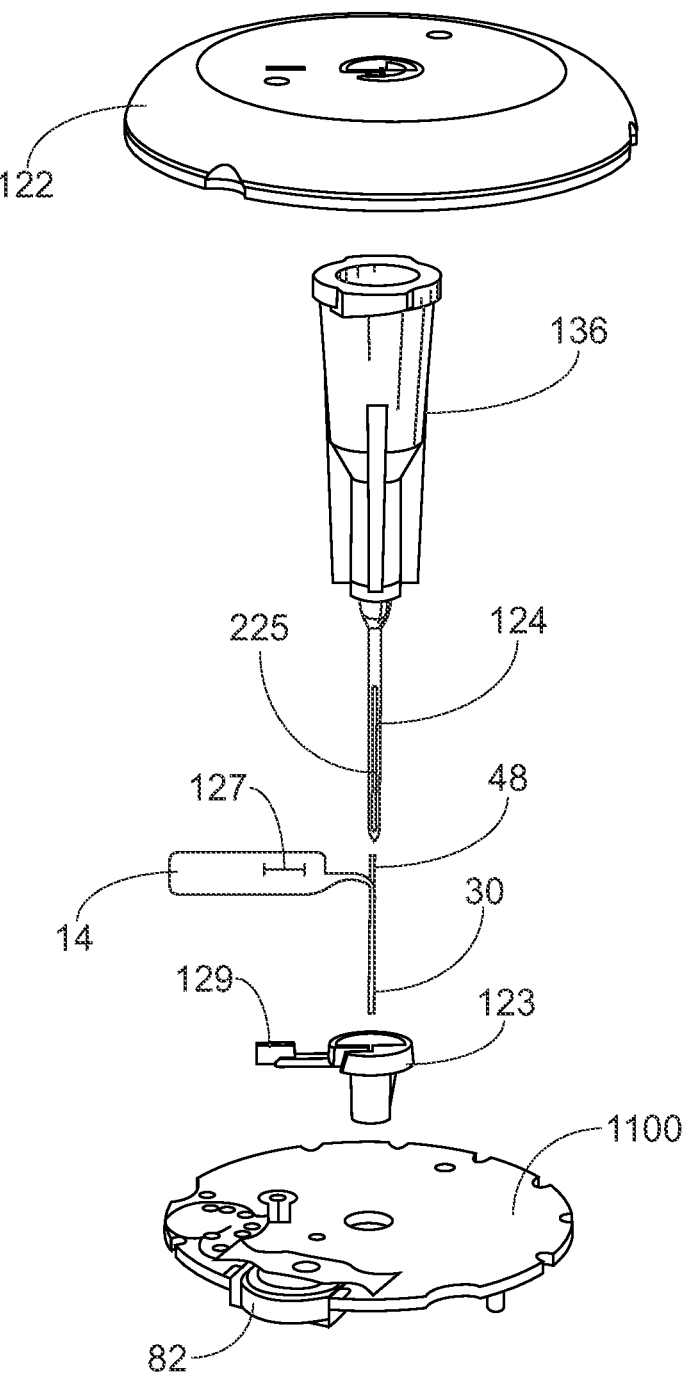
FIG. 12 is a perspective view with parts separated of an inserter in accordance with one embodiment of the disclosed subject matter.

FIGS. 11-12 illustrate the position of on body housing 122 with respect to the needle hub 136 and sharp 124. The on body housing 122 can be configured to hold at least a portion of sensor 14 and sensor control unit. As illustrated in FIG. 11, the sharp 124 extends through an aperture 168 in the on body housing 122. Thus, in some embodiments, the sharp 124 is uncoupled to on body housing 122. The distal portion of sensor 14 is positioned within the sharp 124. As further illustrated in FIG. 12, electronics of the sensor control unit (e.g., a printed circuit board containing electronics components of the on-body unit) and sensor hub 123 are positioned within on body housing 122. Sensor 14 may include a positioning structure, or slit 127, which receives a positioning member, such as tab 129 of sensor hub 123. A power supply 82, such as a battery, e.g., a single use disposable battery, or rechargeable battery, is provided. The power supply 82 is used to provide potential or current to the sensor in some embodiments. In embodiments where a passive communications protocol such as passive RFID is used, no power supply is provided for the communications. Such power is provided by the monitor unit. In some embodiments, where the sensor control unit is used to transmit one or more signals, one or more power supplies may be used to provide power for such communications circuitry. In some embodiments, the active operational life of the battery may exceed the active operational life of the sensor 14.

Figure 13:
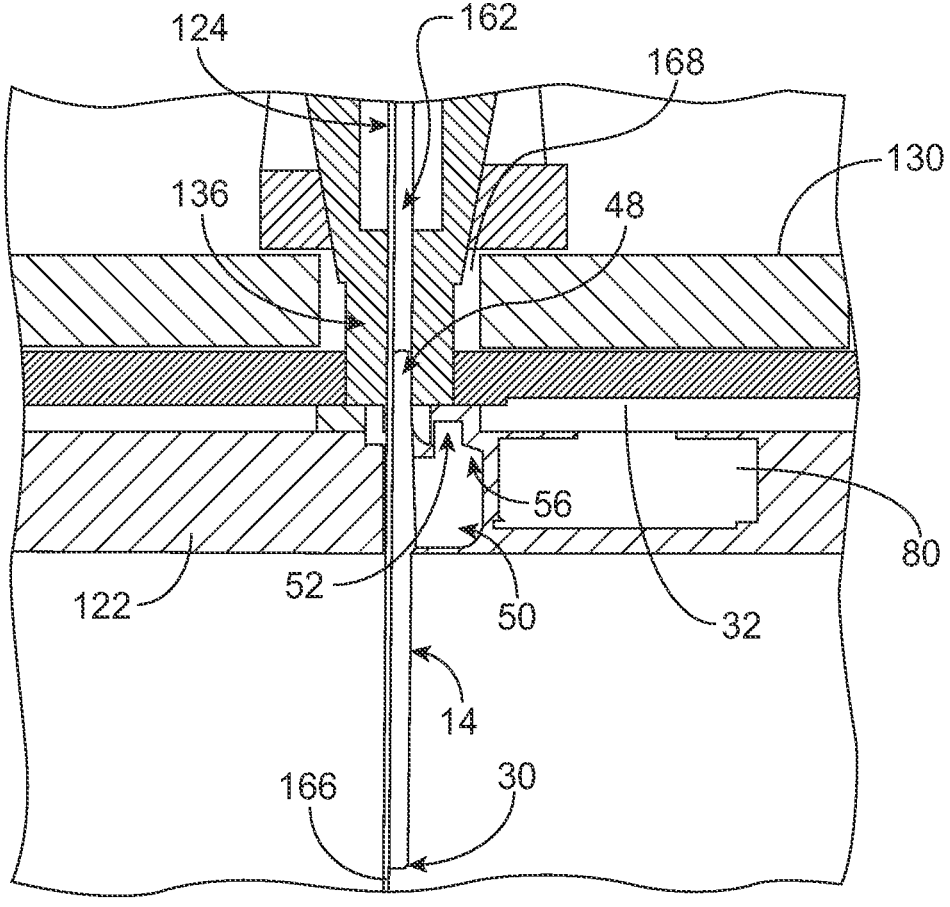
FIG. 13 is an enlarged sectional view with parts separated of an inserter in accordance with one embodiment of the disclosed subject matter.
Figure 52:
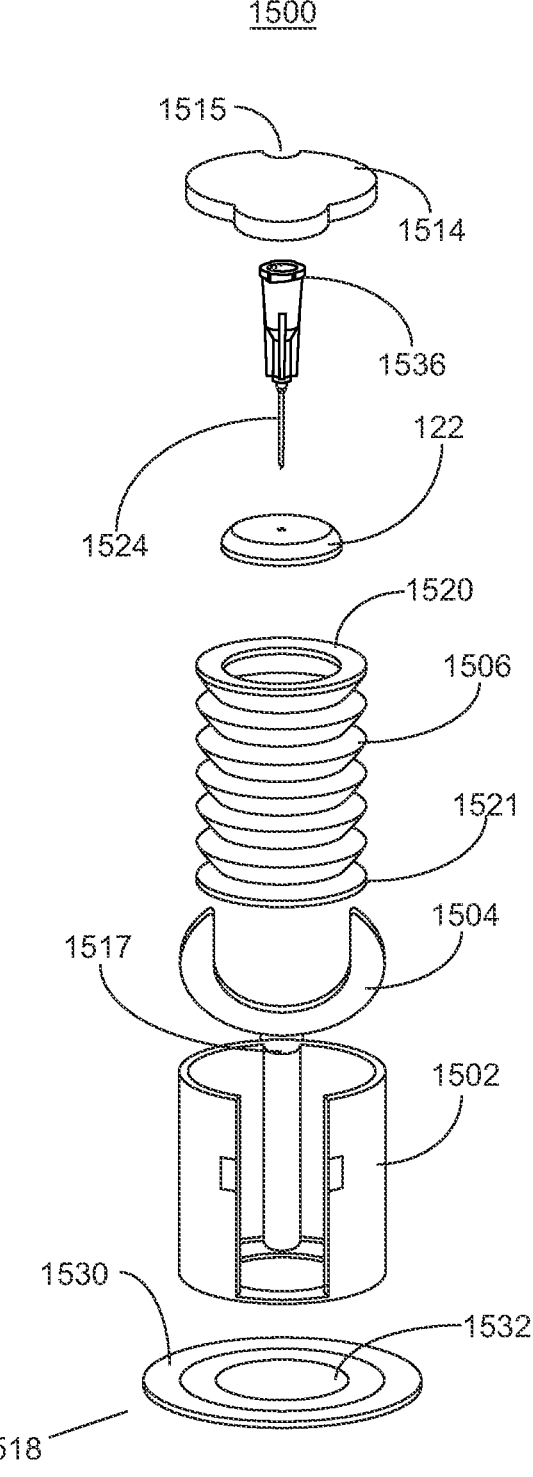
FIG. 52 is an exploded perspective view of another embodiment of the disclosed subject matter.

FIG. 13 illustrates in cross-section the orientation of the on body housing 122 with respect to the sharp 124 of an inserter, such as inserter 1500 (see FIG. 52). As discussed herein, sensor 14 is disposed in a substantially bent configuration in some embodiments, such that a portion of the sensor, e.g., the insertion portion 30 and the proximal retention portion 48, are substantially vertical (e.g., substantially aligned with the longitudinal axis of an inserter and substantially perpendicular to the skin surface) and the contact portion 32 (shown in profile) is oriented in a substantially horizontal configuration, and in electrical contact with the data-processing unit electronics, such as circuit 80. The sensor tab 50 can be encased in the plastic of the on body housing 122 (e.g., "overmolded") and secured in place. The notch 56 provides further stability to the sensor 14, e.g., by allowing the sensor tab 50 to be encased by the material of the on body housing 122, and further provides a means for vertically orienting the sensor 14 during mounting, e.g., by allowing vertical positioning of the notch 56 with respect to a vertical landmark of the on body housing 122.

The sensor 14, mounted with the on body housing 122, can be disposed within a recess of the carriage 130 such as a concave recess in the carriage 130. Alternatively, the sensor 14, mounted with the on body housing 122, can be disposed between the support structure and one or more projections extending from the wall of the sheath. In yet another alternative, the sensor 14, mounted with the on body housing 122, can be held in position by a releasable friction fit coupling to the sharp 124. In this manner, the carriage need not have a recess within which the sensor mounted with the on body housing is disposed. In the initial configuration of the inserter, the sharp 124 extends through a longitudinal aperture 168 formed in a carriage 130. In some embodiments, the aperture 168 is appropriately sized, such that neither the sharp 124 nor needle hub 136 is in contact with the carriage 130. Accordingly, the needle hub 136 (and sharp 124) on the one hand, and the carriage 130 (FIG. 13) and the on body housing 122, on the other hand, move simultaneously, but independently from one another. In other embodiments, a friction fit may be provided between the aperture and the sharp.

The insertion portion 30 and proximal retention portion 48 of the sensor 14 are disposed within a longitudinal bore 162 within the sharp 124 (See, e.g., FIG. 6). The proximal retention portion 48 is disposed within the longitudinal bore of the sharp 124 and provides additional stability to the mounting of the sensor 14 within the sharp 124. The longitudinal wall gap or opening 162 of sharp 124 is aligned with the sensor 14, such that the tab 50 and the contact portion 32 extend laterally outward from the sharp 124.

Figure 14:
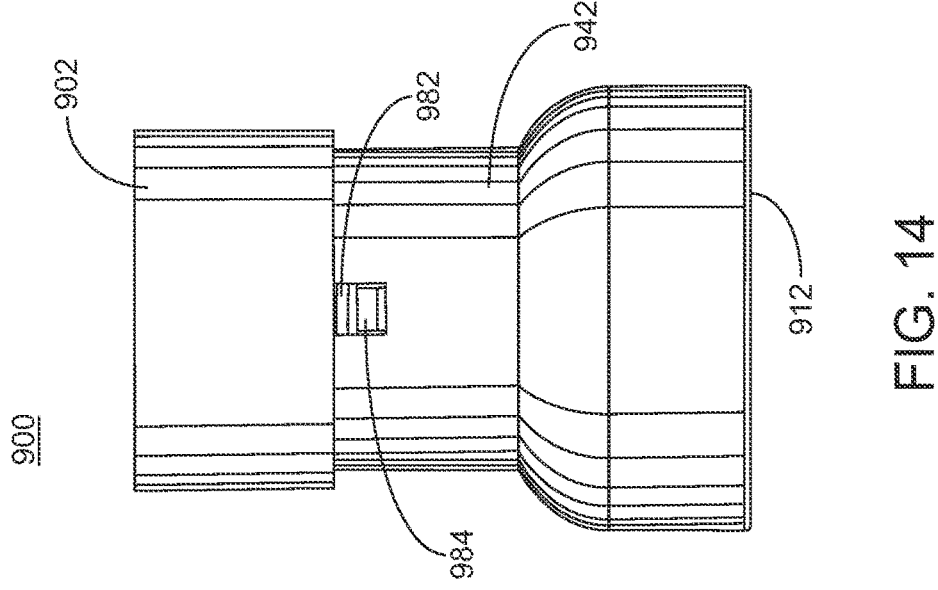
FIG. 14 is a side view of another inserter in accordance with the disclosed subject matter.

An embodiment of an inserter is illustrated in FIGS. 14-17. An inserter 900 includes a handle 902 and may include a removable distal cap or seal (not shown) for maintaining a sterile environment for the medical device and sharp housed therein. As illustrated in FIG. 14, distal cap or seal is removed from handle 902. Inserter 900 includes a base 942 that defines a distal surface 912 for placement on the skin of a subject. Inserter 900 may be utilized to advance a medical device into the skin of the subject. In some embodiments, handle 902 is advanced relative to base 942 in order to advance the sensor into the skin of the patient.

Figure 15:
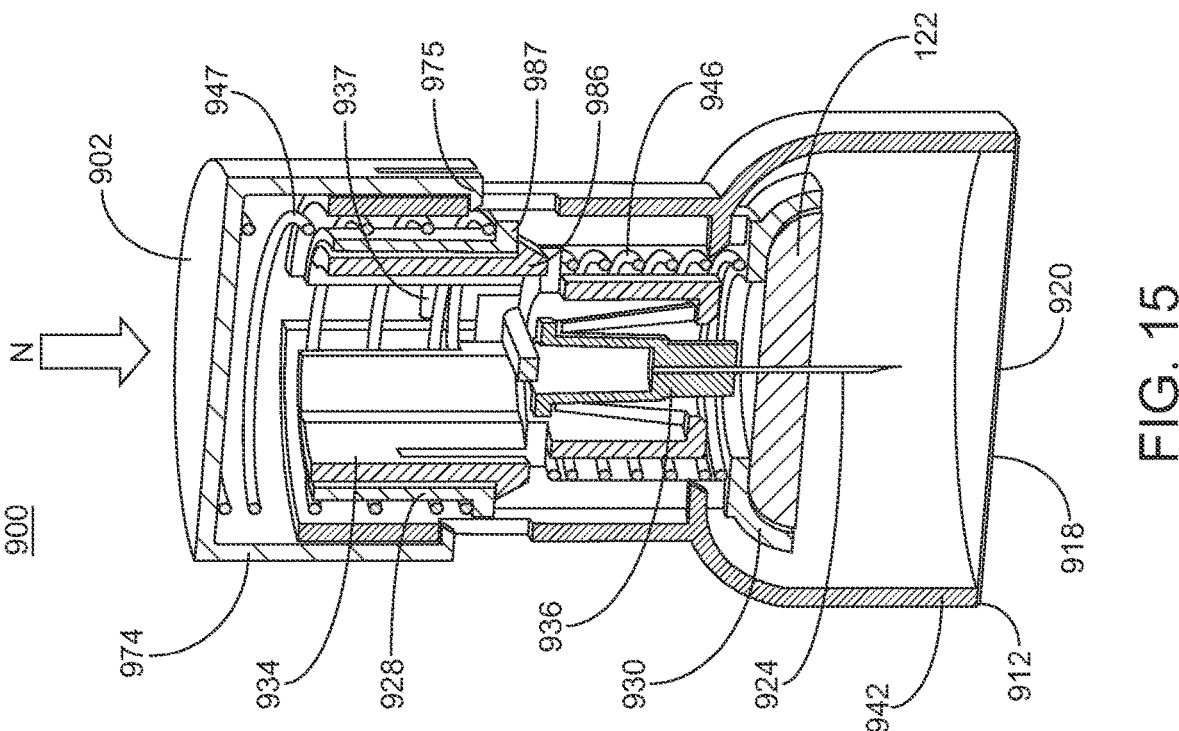
FIGS. 15-17 are sectional, perspective views of the inserter of FIG. 14 in accordance with another embodiment of the disclosed subject matter.

As illustrated in FIG. 15, the inserter 900 includes an initial configuration in which the handle 902 is disposed in a proximal position with respect to the base 942. In such configuration, the sharp 924 is disposed in a configuration spaced apart from the aperture 920 of the adhesive layer 918. Extending distally from the upper surface of handle 902 are side walls 974, which terminate in a shoulder portion 975.

Needle carrier 934 is axially slidable within handle 902 and base 942 in the direction of arrow N. Needle carrier 934 supports needle hub 936, from which sharp 924 extends longitudinally within the inserter 900. In some embodiments, the sharp is supported at an oblique angle, e.g., between 0° and 90° with respect to the skin surface. Initially, needle carrier 934 is coupled to inner rail 928 through inter-engagement of finger 986 of needle carrier 934 with shoulder 987 of inner rail 928.

Figure 16:
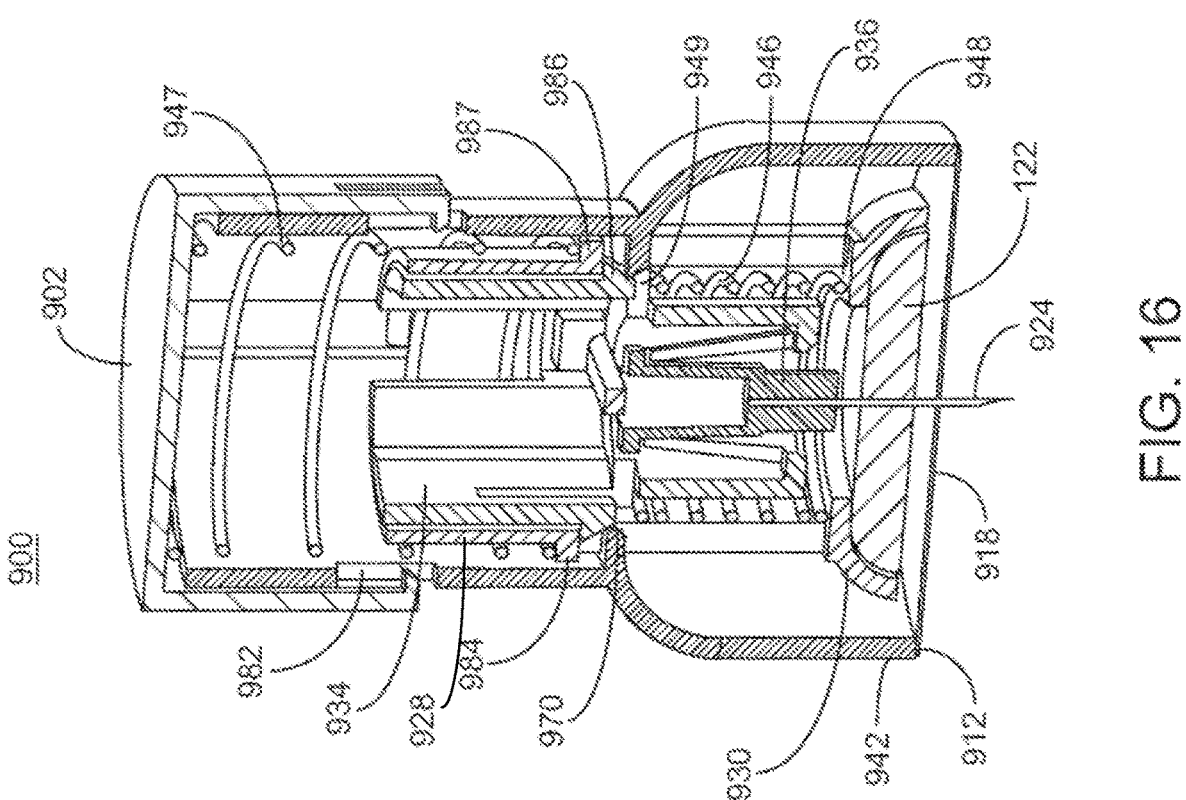

Inserter 900 includes an advancement spring 947. Inner rail 928 includes a spring retention portion 984 for advancement spring 947. The inner surface of handle 902 serves as an upper engagement surface for advancement spring 947. In some embodiments, spring retention portion 984 is fabricated having several projections that extend through an aperture 982 in the wall of base 942. Spring retention portion 984 is resiliently movable. As downward force is applied to handle 902, the ledge 937 of handle 902 contacts spring retention portion 984, driving such projections inward. Such inward motion releases the inner rail 928, and allows advancement spring 947 to advance the inner rail 928 distally, thereby advancing the sharp 924 into the skin of the subject, as illustrated in FIG. 16.

Retraction spring 946 is disposed between spring retention portion 948 of base 942 and shoulder portion 949 of needle carrier 934. Initially, retraction spring 946 is in a compressed state. As carriage 930 reaches a distal position, the distal surface of the on body housing 122 engages the upper surface of adhesive pad 918, thereby becoming adhered to the skin surface S of the subject. At the same time, flanges 970 of base 942 engage fingers 986 disposed on the needle carrier 934. Fingers 986 are pivoted outwards by flanges 970. Such pivoting of fingers causes fingers 986 to become disengaged from shoulder 984 of inner rail 928. Shuttle 934 is thereby disengaged from inner rail 928.

Figure 17:
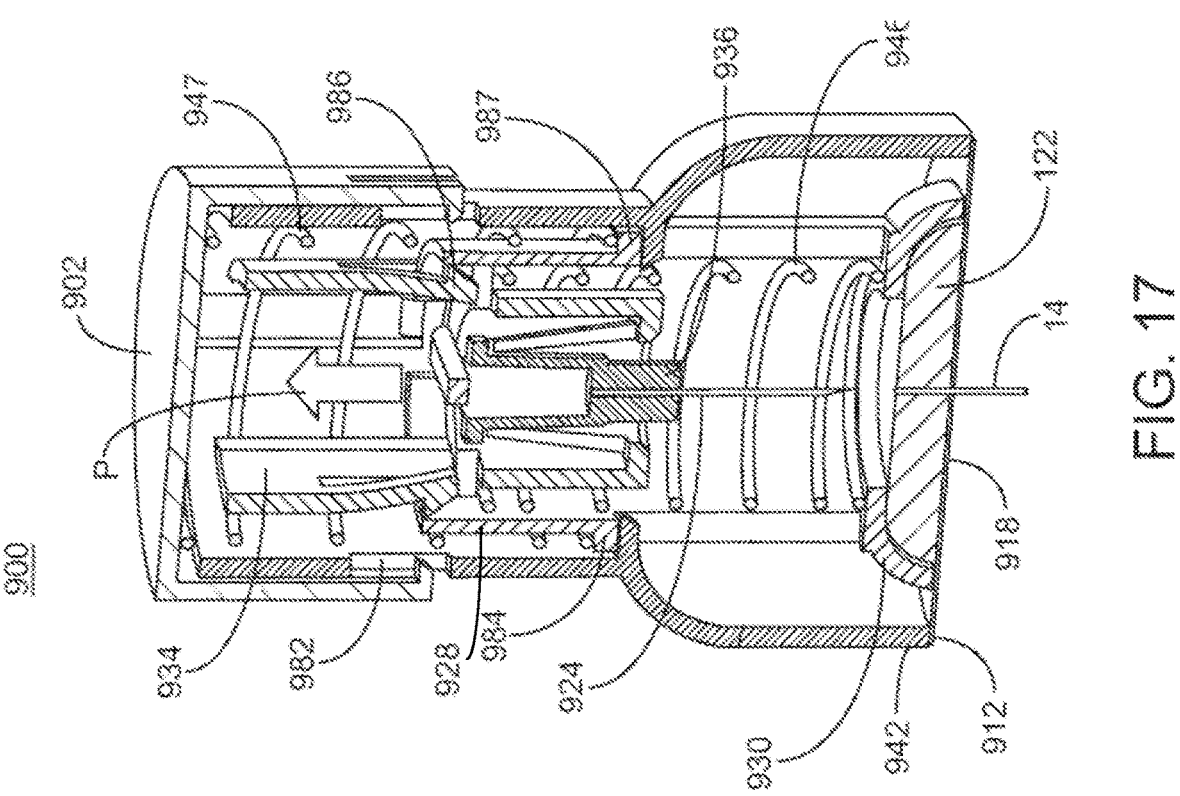

As illustrated in FIG. 17, disengagement of the shuttle 934 from the inner rail 928 permits the spring 946 to expand, thereby advancing the needle carrier 934 to a proximal position, thereby withdrawing the sharp 924 from the skin of the subject, while leaving the sensor 14 in the skin.

A further embodiment of an inserter is illustrated in FIGS. 18-21 and designated inserter 1000. Inserter 1000 is substantially identical to inserter 900 described herein, with the substantial differences noted herein and illustrated in the accompanying figures.

Figure 18:
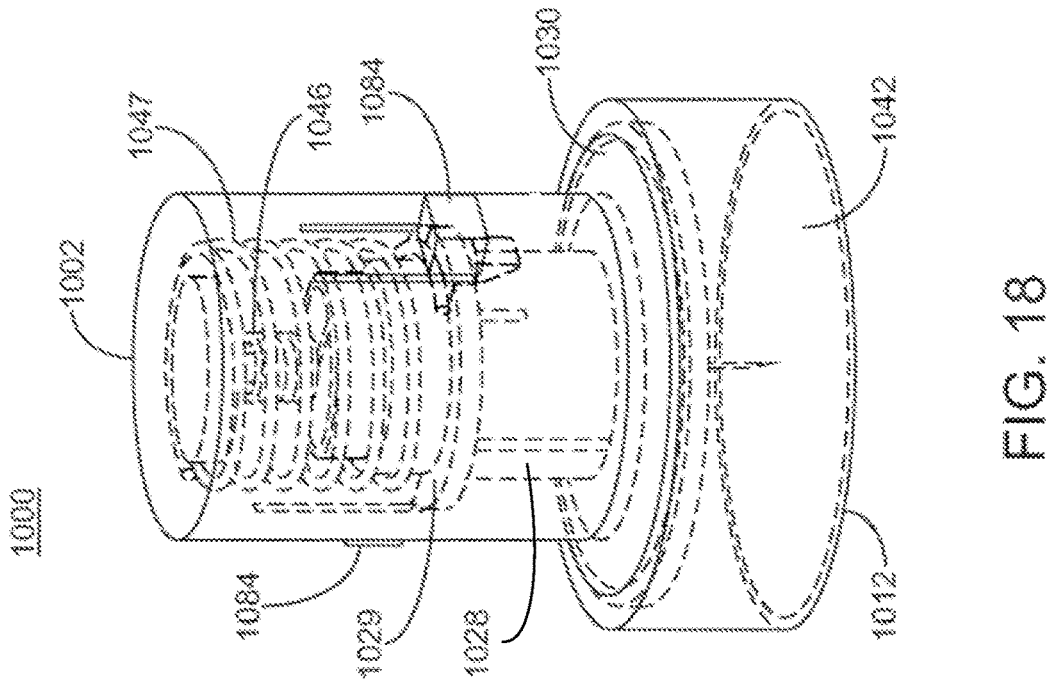
FIG. 18 is a perspective view of another inserter in accordance with the disclosed subject matter.

An inserter 1000 includes a housing 1002, and may include a removable distal cap or seal (not shown) for maintaining a sterile environment for the medical device and sharp housed therein. As illustrated in FIG. 18, distal cap or seal is removed from housing 1002. Inserter 1000 includes a base 1042 which defines a distal surface 1012 for placement on the skin of a subject. Inserter 1000 may be utilized to advance a medical device into the skin of the subject. In some embodiments, side buttons 1084 are depressed relative to base 1042 in order to advance the medical device into the skin of the patient.

Figure 19:
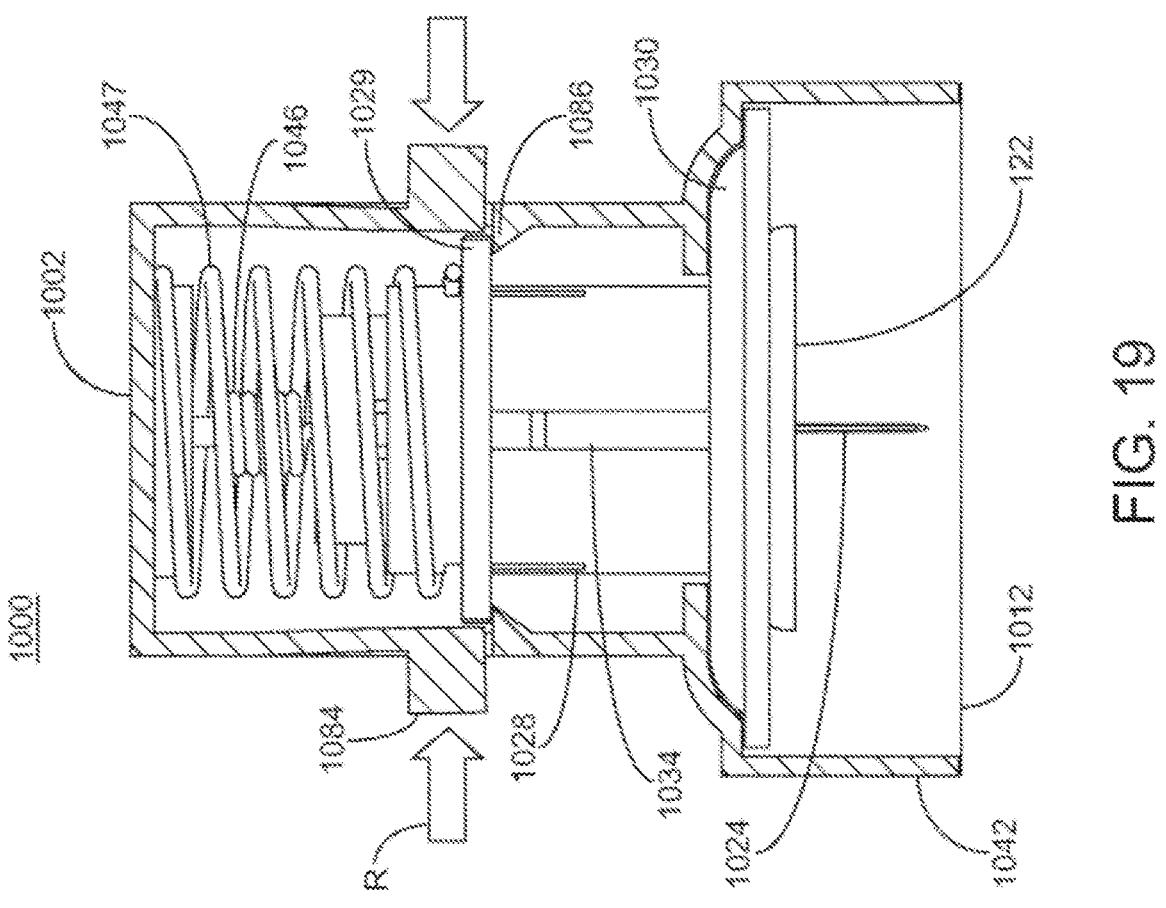
FIGS. 19-21 are side views with transparency of the inserter of FIG. 18 in accordance with another embodiment of the disclosed subject matter.

As illustrated in FIG. 19, the inserter 1000 includes an initial configuration in which the sharp 1024 is disposed in a configuration spaced apart from distal portion 1012 of the base 1042. It is understood that inserter 1000 may incorporate an adhesive layer (not shown) positioned across the distal portion 1012 of base 1042.

Figure 21:
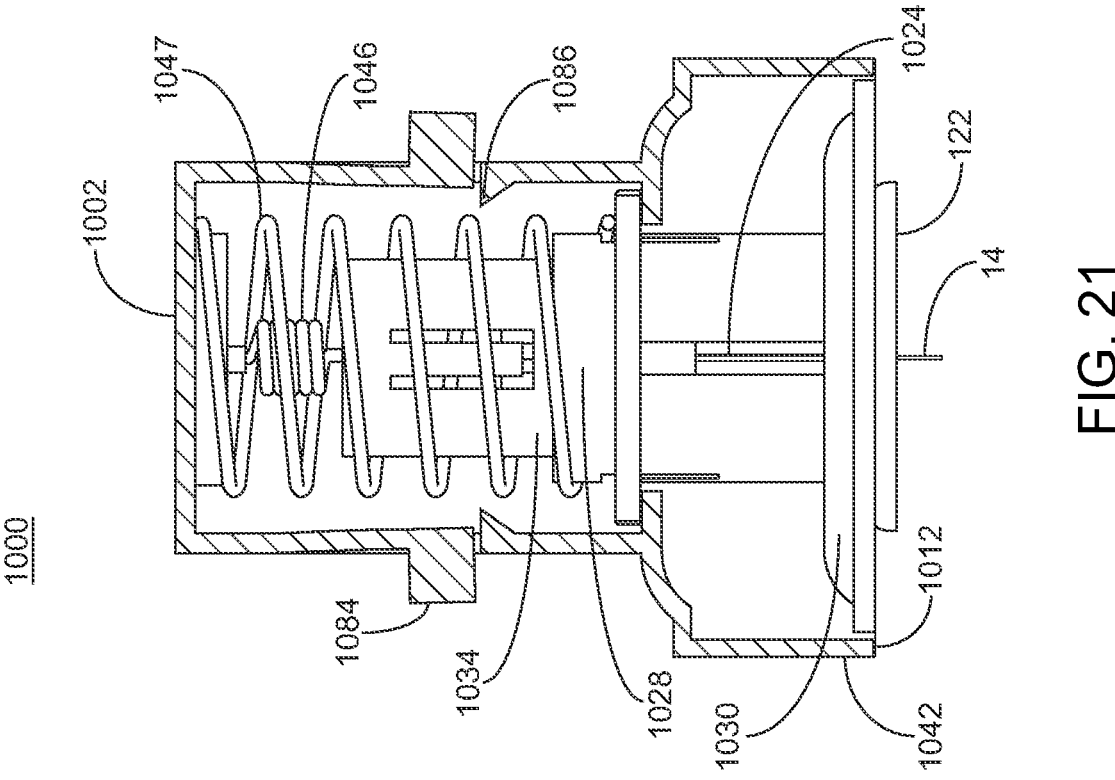
Figure 20:
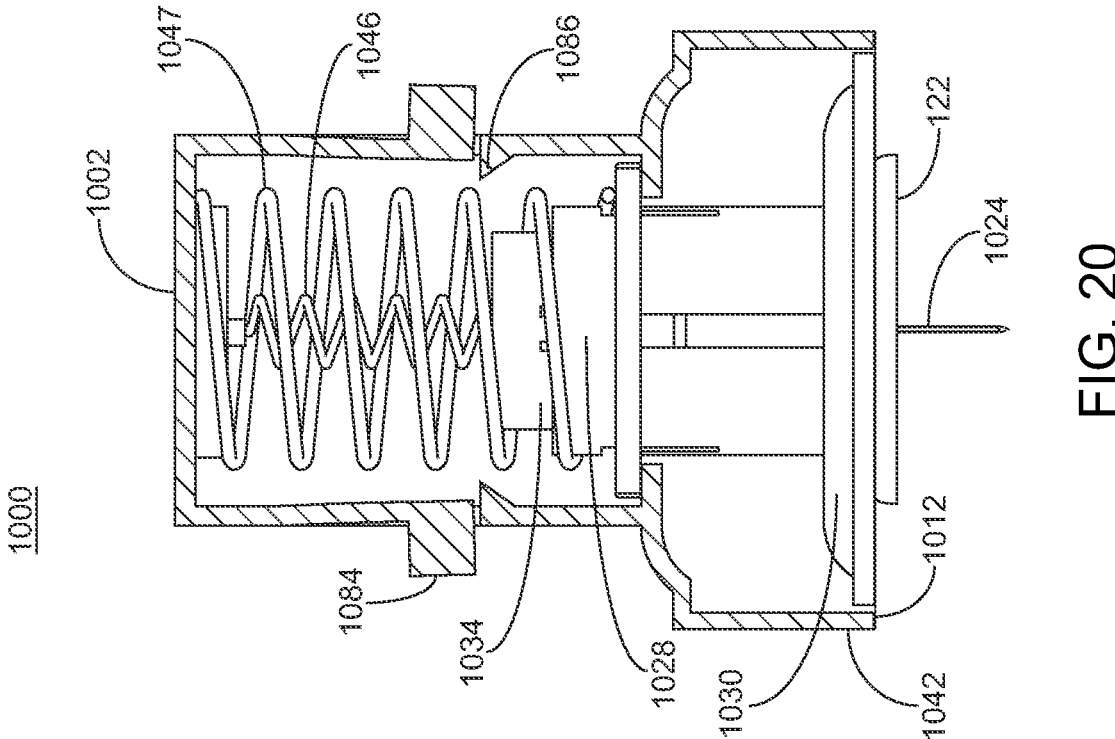

On-body unit inserter 1028 includes carriage 1030 for supporting on body housing 122. On-body unit inserter 1028 also includes flange 1029 which normally rests on shoulder portions 1086 (as illustrated in FIGS. 19-21). When side buttons 1084 are depressed inwardly, latch portions on flange 1029 are deflected from engagement with shoulder portions 1086. As illustrated in FIG. 20, advancement spring 1047 is released from compression, thereby advancing on-body unit inserter 1028 as elsewhere, along with needle carrier 1034 into the skin of the subject.

Retraction spring 1046 is disposed between needle carrier 1034 and housing 1002. Initially, retraction spring 1046 is in a compressed state. As carriage 1030 reaches a distal position, on-body unit inserter 1028 is disengaged from needle carrier 1034. The distal surface of the on body housing 122 engages the skin or the upper surface of adhesive pad (not shown), thereby becoming adhered to the skin surface S of the subject. Latches on needle carrier 1034 attach it to on-body unit inserter 1028. Upon firing the inserter by pressing tabs 1084, the on-body unit inserter 1028 is pushed by spring 1047 towards the skin surface, bringing along needle carrier 1034 and loading extension spring 1046. As on-body unit inserter 1028 reaches the distal position (towards the skin of the subject), protrusions on housing 1002 disengage latches on needle carrier 1034, connecting it to on-body unit inserter 1028. Extension spring 1046 now pulls needle carrier 1034 back into the proximal position.

As illustrated in FIG. 21, disengagement of the needle carrier 1034 from on-body unit inserter 1028 permits the spring 1046 to contract with the bias, thereby advancing the needle carrier 1034 to a proximal position and withdrawing the sharp 1024 from the skin of the subject, while leaving the sensor 14 in the skin.

A further embodiment of an inserter is illustrated in FIGS. 22-25. Inserter 1100B is substantially identical to inserters 900 and 1000 described herein, with the substantial differences noted herein and illustrated in the accompanying figures.

Figure 22:
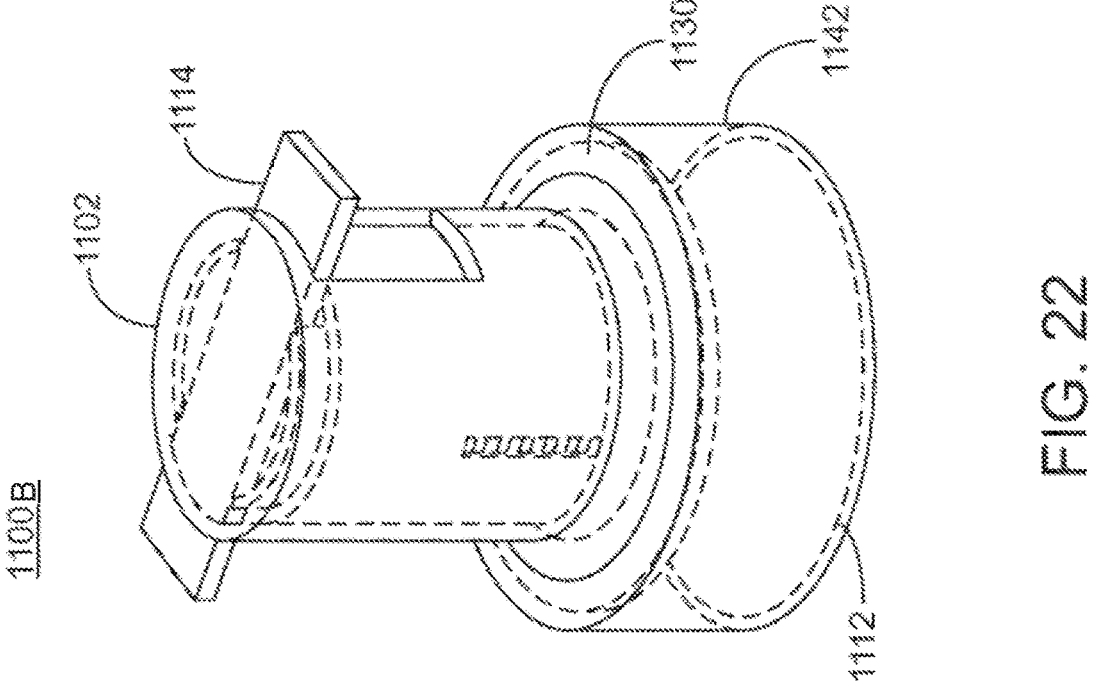
FIG. 22 is a perspective view of another inserter in accordance with the disclosed subject matter.

An inserter 1100B includes a housing 1102 and may include a removable distal cap or seal (not shown) for maintaining a sterile environment for the medical device and/or sharp housed therein. As illustrated in FIG. 22, distal cap or seal is removed from housing 1102. Inserter 1100B includes a base 1142 which defines a distal surface 1112 for placement on the skin of a subject. Inserter 1100B may be utilized to advance a medical device into the skin of the subject. In some embodiments, a manual actuator bar 1114 is depressed relative to base 1142 in order to advance the medical device into the skin of the patient. It is understood that inserter 1100B may incorporate an adhesive layer (not shown) which is positioned across the distal portion 1112 of base 1142.

Figure 23:
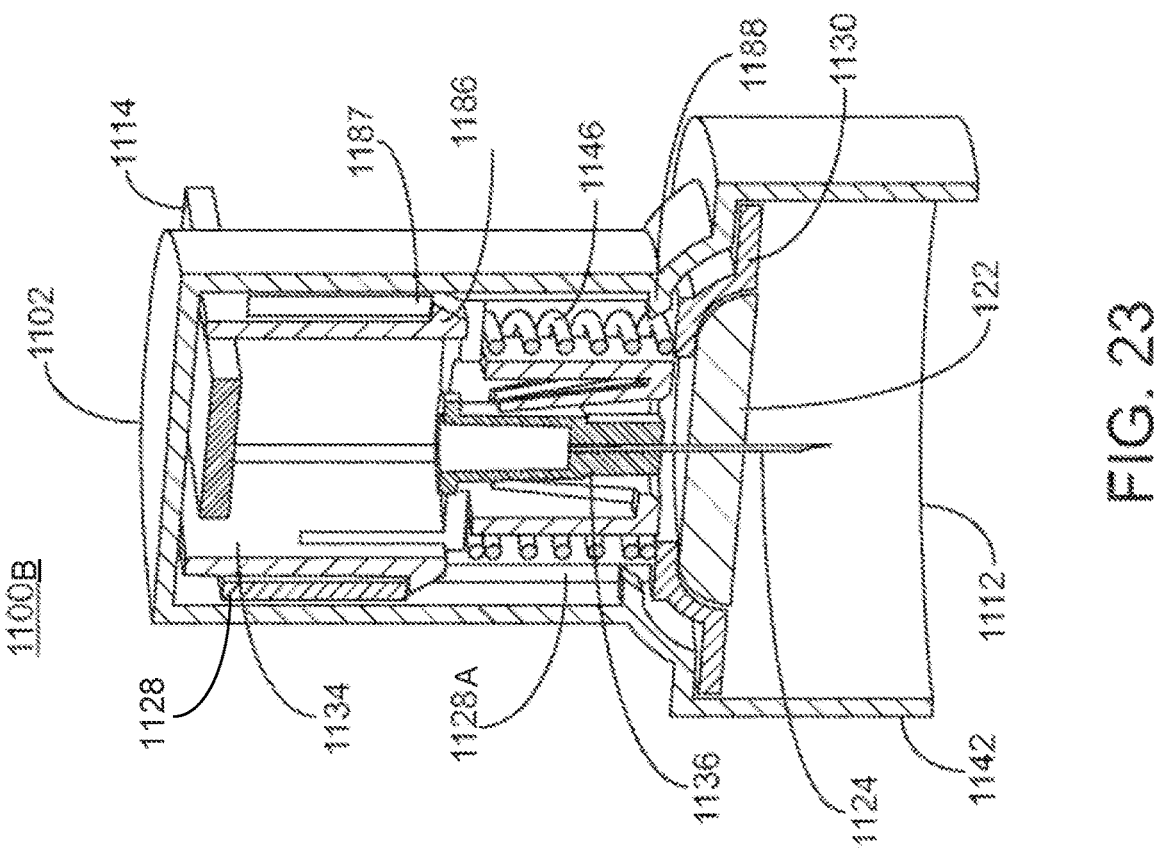
FIGS. 23-25 are sectional, perspective views of the inserter of FIG. 22 in accordance with another embodiment of the disclosed subject matter.

As illustrated in FIG. 23, the inserter 1100B includes an initial configuration in which the sharp 1124 is disposed in a configuration spaced apart from distal portion 1112 of the base 1142. Manual advancement of the actuator may be performed by distal advancement of actuator bar 1114.

Figure 24:
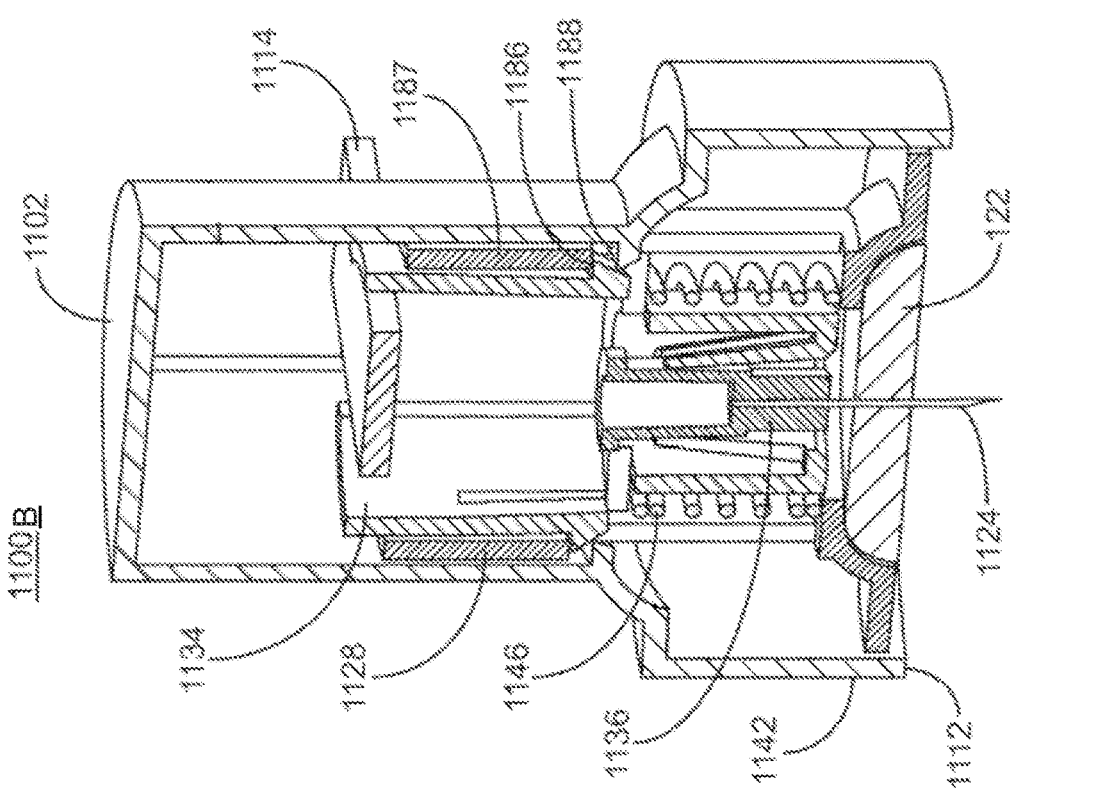
Figure 27:
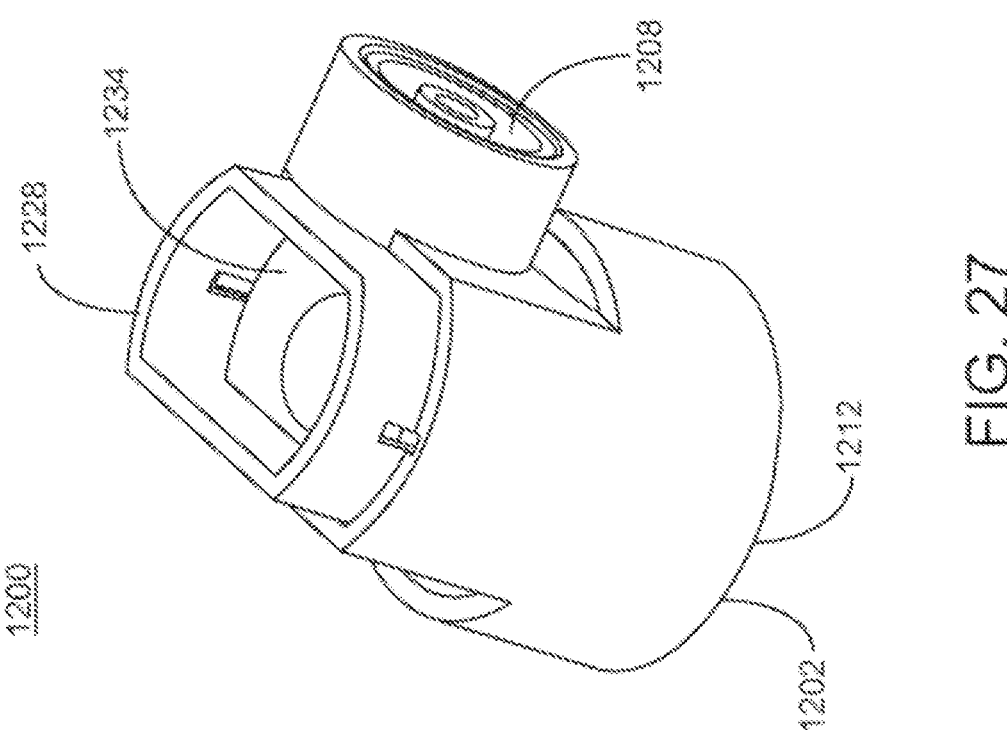
FIG. 27 is a perspective view of the inserter of FIG. 26 in accordance with the disclosed subject matter.
Figure 26:
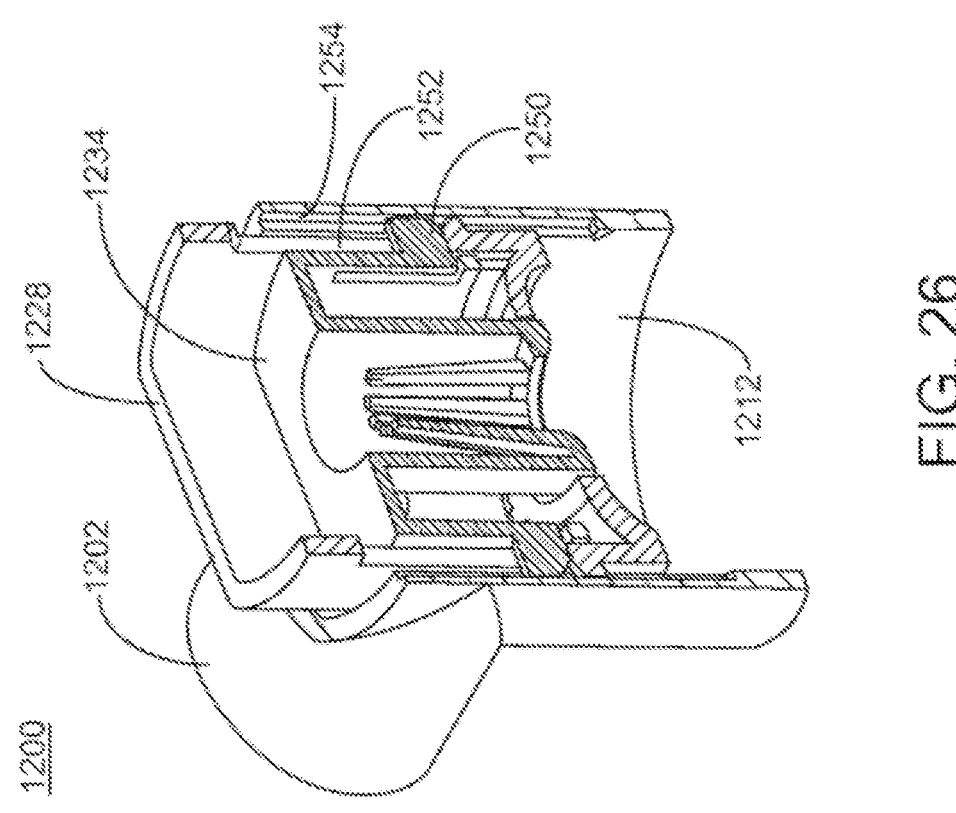
FIG. 26 is a sectional view in section of another embodiment of an inserter in accordance with the disclosed subject matter.
Figure 29:
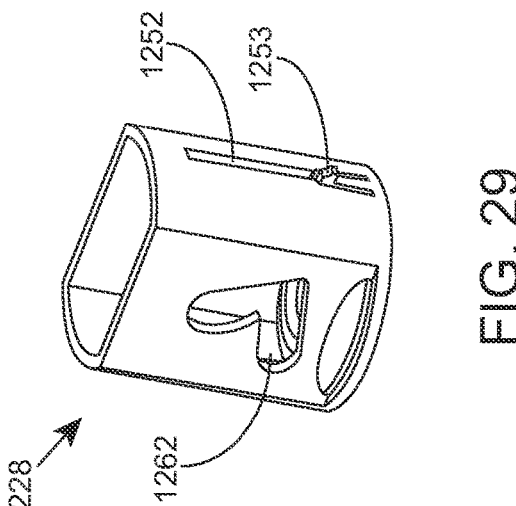
FIGS. 28-31 are perspective views of components of the inserter of FIG. 26 in accordance with the disclosed subject matter.
Figure 31:
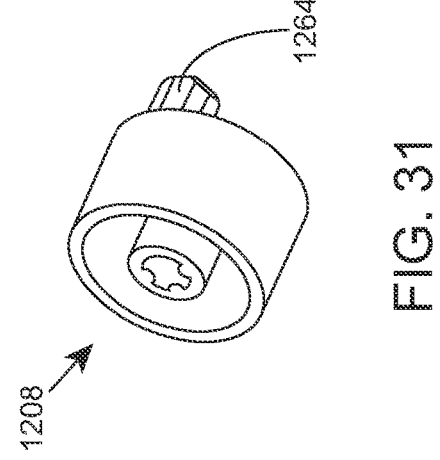
Figure 28:
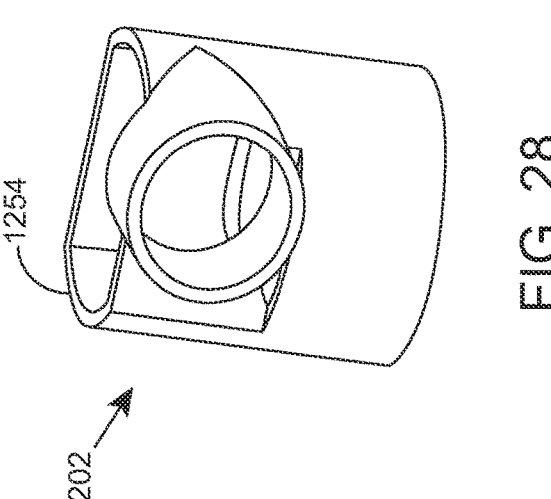
Figure 30:
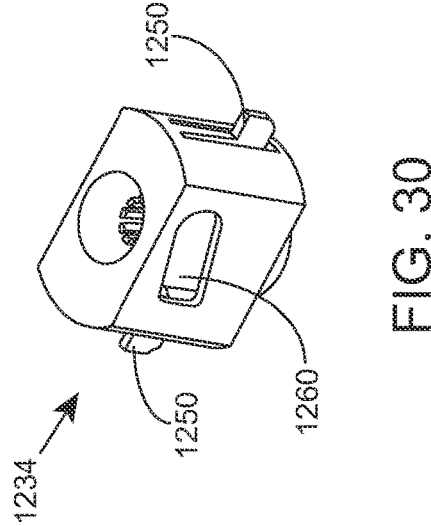

On-body unit inserter 1128A includes carriage 1130 for supporting on body housing 122. Retraction spring 1146 is disposed between needle carrier 1134 and base 1142. Initially, retraction spring 1146 is in a compressed state. As actuator bar 1114 is moved distally, carriage 1130 is moved distally and reaches a distal position, such that flanges 1188 of base 1142 engage fingers 1186 disposed on the shuttle 1134. Fingers 1186 are pivoted outwards by flanges 1188. Such pivoting of fingers 1186 causes fingers 1186 to become disengaged from shoulder 1187 of inner rail 1128. Shuttle 1134 is thereby disengaged from inner rail 1128. The distal surface of the on body housing 122 engages the skin or the upper surface of adhesive pad (not shown), thereby becoming adhered to the skin surface of the subject (FIG. 24).

Figure 25:
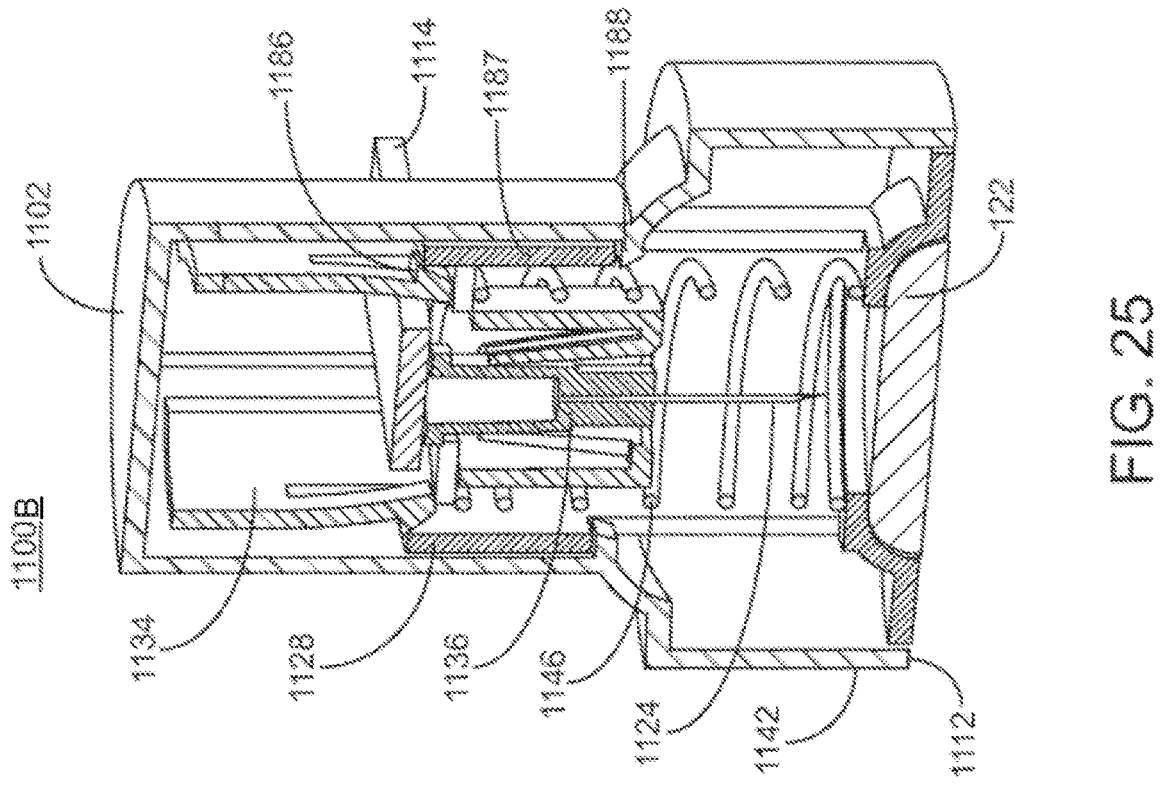

As illustrated in FIG. 25, disengagement of the shuttle 1134 from the inner rail 1128 permits the spring 1146 to expand with the bias, thereby advancing the needle carrier 1136 to a proximal position and withdrawing the sharp 1124 from the skin of the subject, while leaving the sensor 14 in the skin. Once the sharp 1124 has been withdrawn from the subject, it is no longer accessible from the distal portion of the inserter 1100B, and unable to make contact by accident with the subject's skin.

A further embodiment of an inserter is illustrated in FIGS. 26-36. Inserter 1200 is substantially identical to inserters 900, 1000, and 1100B described herein, with the substantial differences noted herein and illustrated in the accompanying figures.

Inserter 1200 includes a housing 1202, an on-body unit inserter 1228, a needle retractor 1234, an inserter base 1212, and a rotor 1208 with a torsion spring (not shown), all of which are depicted separately in FIGS. 28-31. As illustrated in FIGS. 28-31, housing 1202 includes slots 1254; on-body unit inserter 1228 includes slots 1252, tabs 1253, and opening 1262; needle retractor 1234 includes tabs 1250 and opening 1260; and rotor 1208 includes rotor follower 1264.

Figure 32:
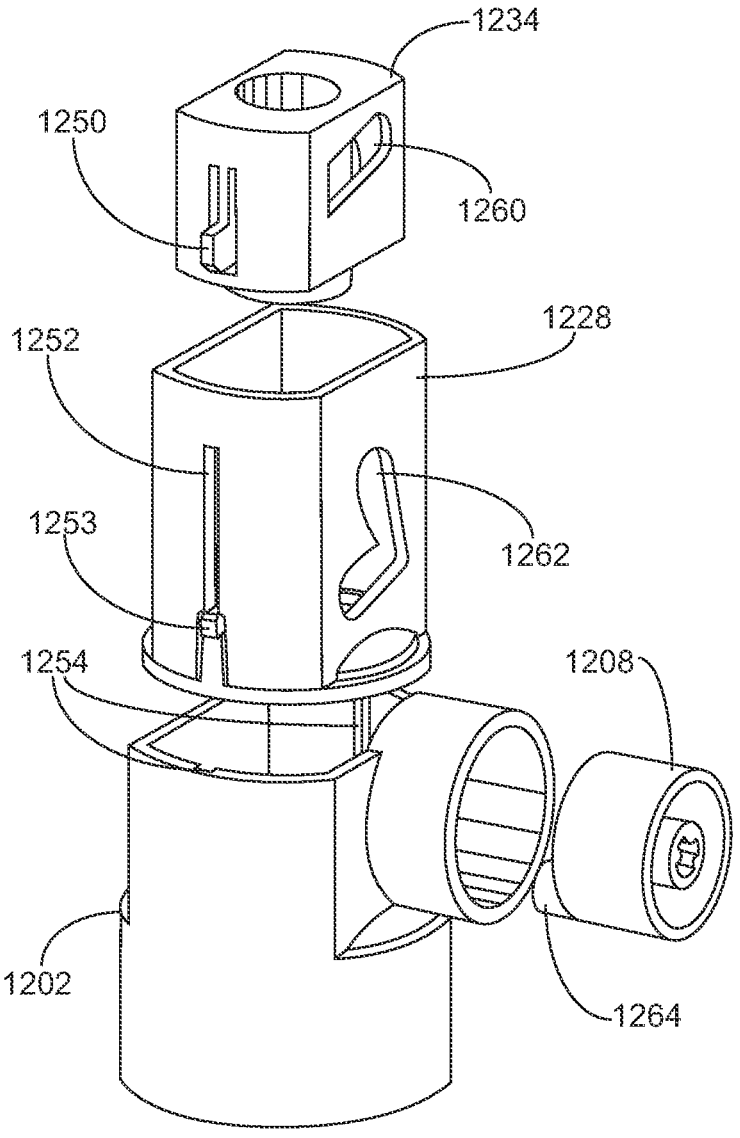
FIG. 32 illustrates an exploded view of the inserter of FIG. 26 in accordance with the disclosed subject matter.
Figure 33:
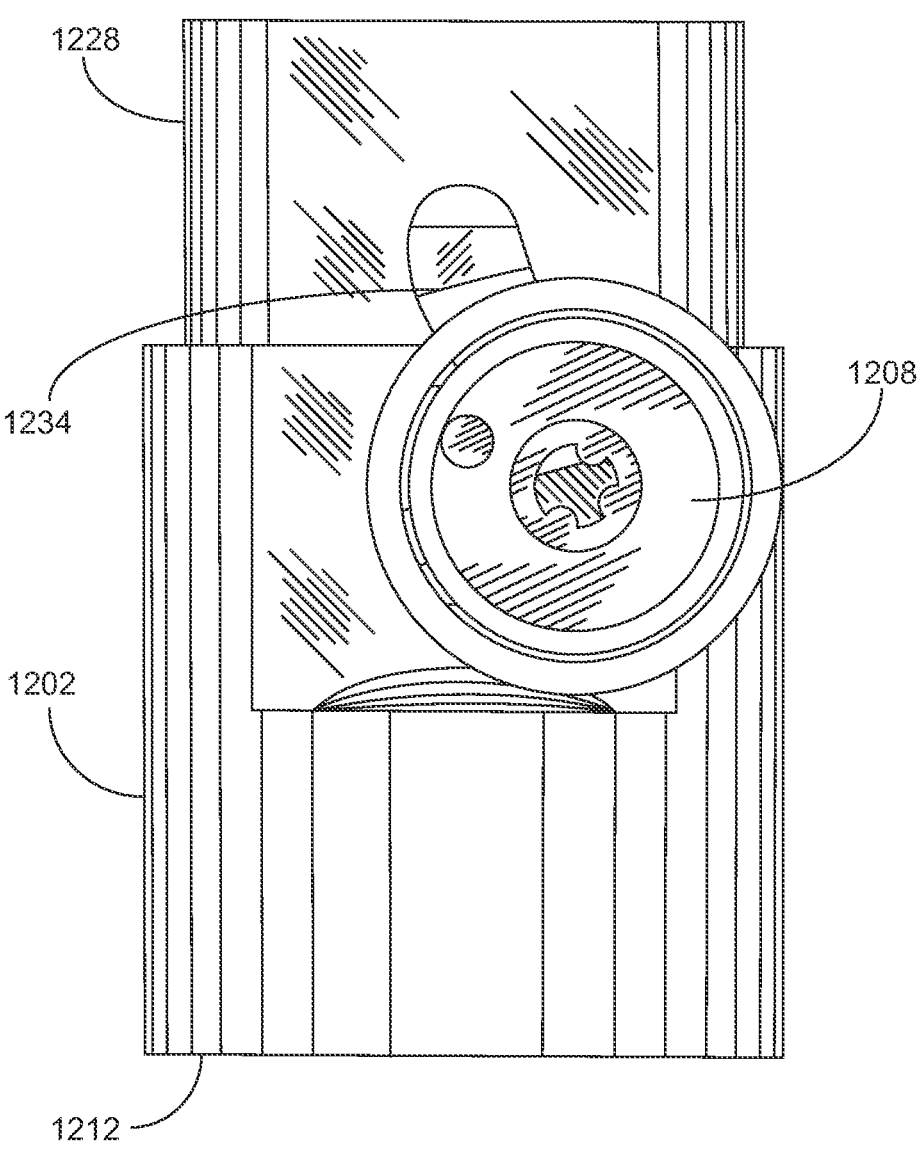
FIG. 33 is a side view of the inserter of FIG. 26 in accordance with the disclosed subject matter.

FIG. 32 illustrates an exploded view of inserter 1200. As illustrated, in some embodiments, inserter 1200 includes housing 1202, on-body unit inserter 1228, needle retractor 1234, and rotor 1208. Tabs 1250 can be disposed on needle retractor 1234 and configured to engage slots 1252 disposed on on-body unit inserter 1228 when assembled as shown in FIG. 33. Tabs 1253 can be disposed on on-body unit inserter 1228 and configured to engage slots 1254 disposed on housing 1202. Needle retractor 1234 and on-body unit inserter 1228 can each contain openings (1260, 1262) to receive rotor follower 1264 disposed on rotor 1208 after rotor 1208 has been inserted into housing 1202. Additionally, on-body unit inserter 1228 can provide support for on body housing 122 (not shown) for installation to the skin of a subject.

Figure 34:
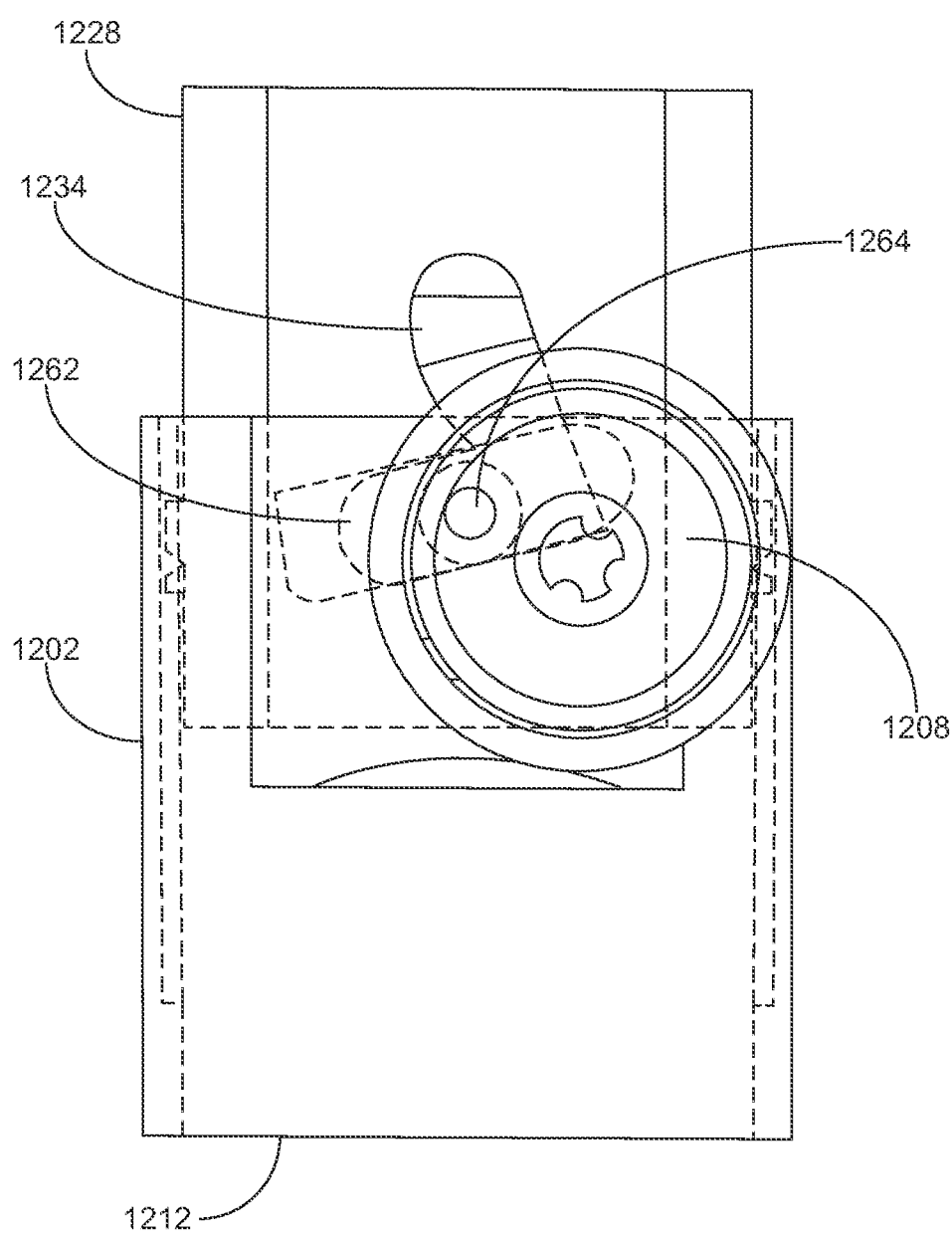
FIGS. 34-36 are side views with transparency of the inserter of FIG. 26 in accordance with the disclosed subject matter.
Figure 36:
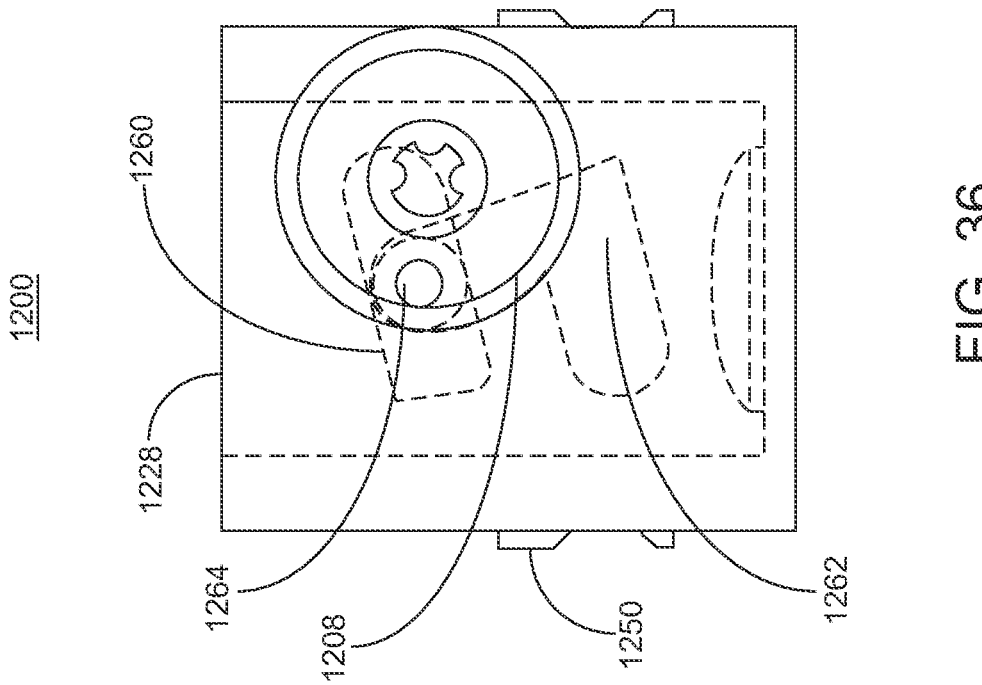
Figure 35:
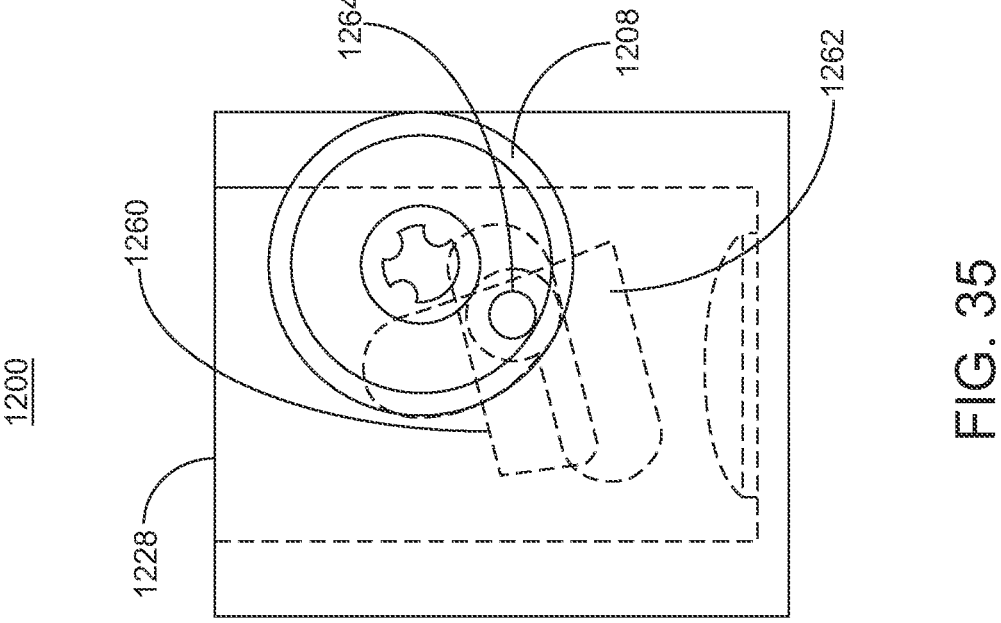
Figure 38:
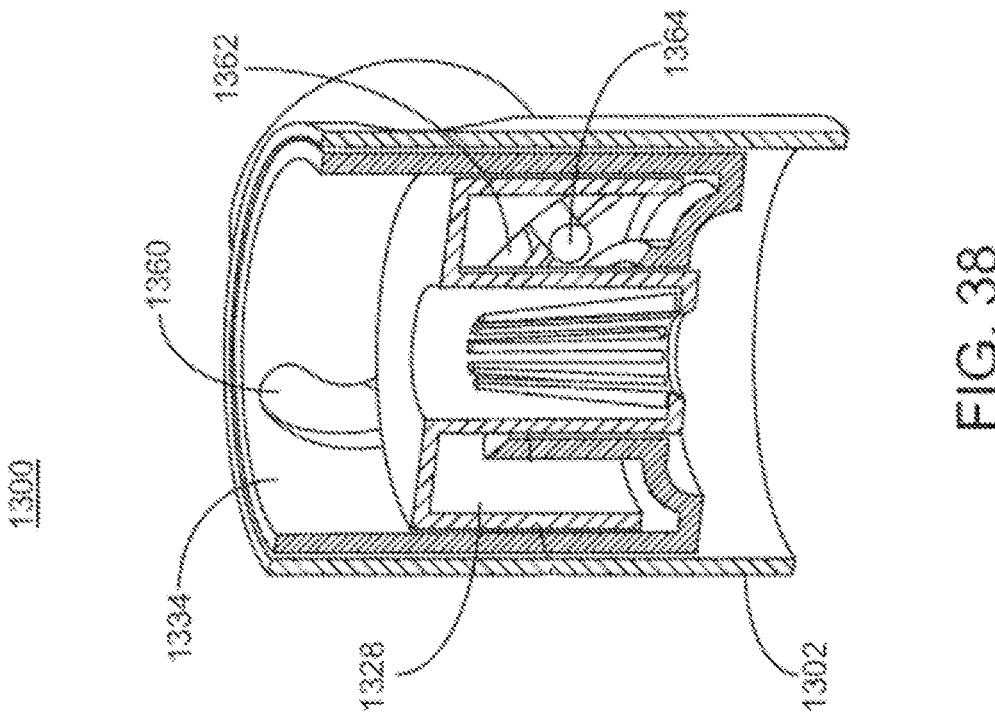
FIG. 38 is a perspective view in section of the inserter of FIG. 37 in accordance with the disclosed subject matter.
Figure 37:
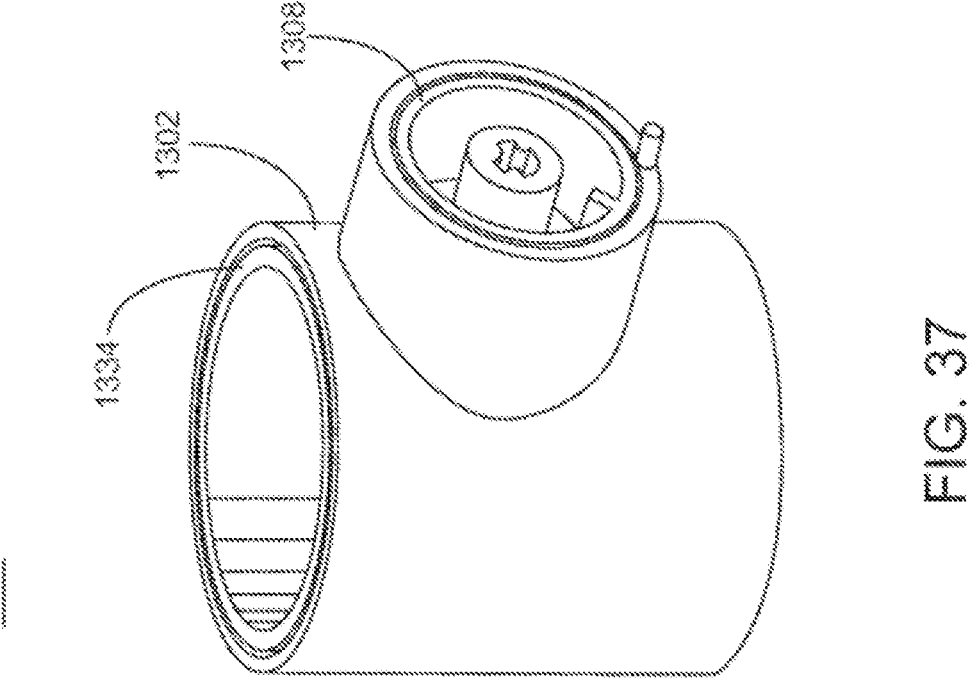
FIG. 37 is an inserter in accordance with another embodiment in accordance with the disclosed subject matter.
Figure 40:
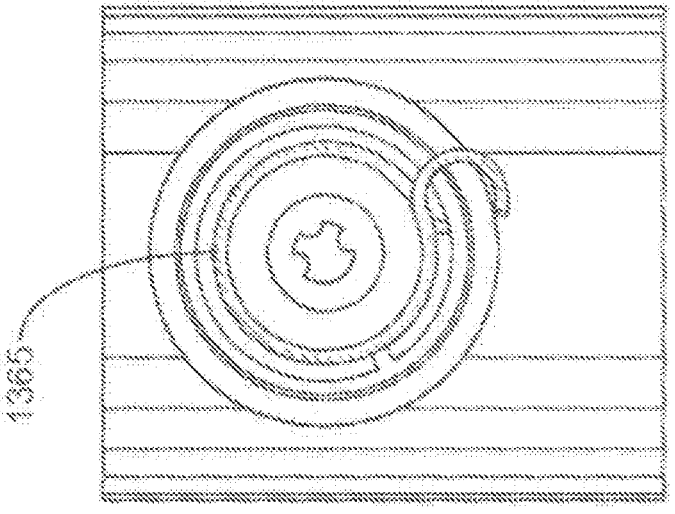
FIG. 40 is a side view of the inserter of FIG. 37 in accordance with the disclosed subject matter.
Figure 39:
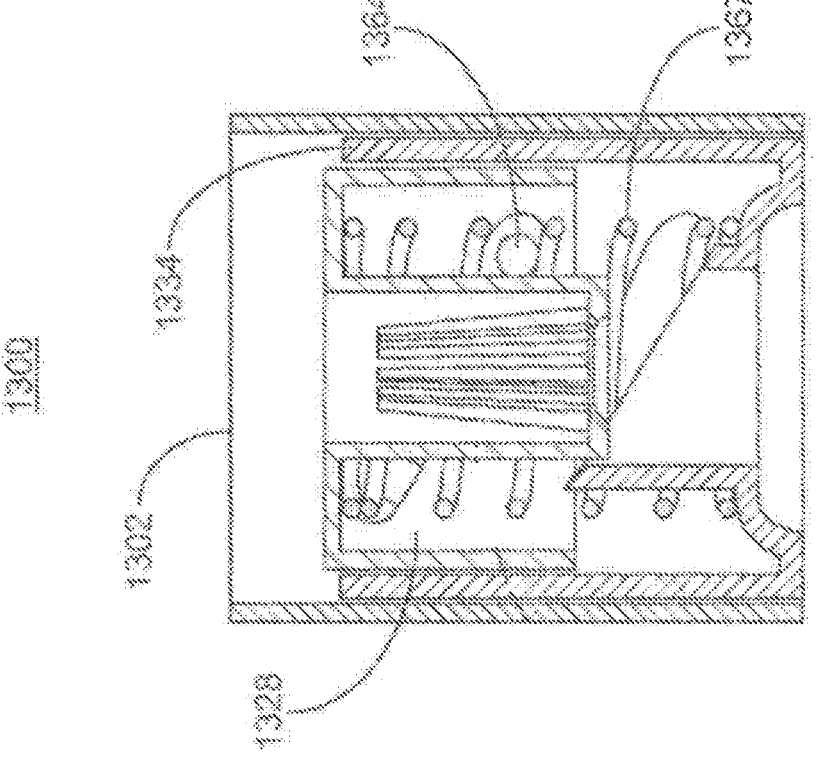
FIG. 39 is a cross-sectional view of the inserter of FIG. 37 in accordance with the disclosed subject matter.
Figure 45:
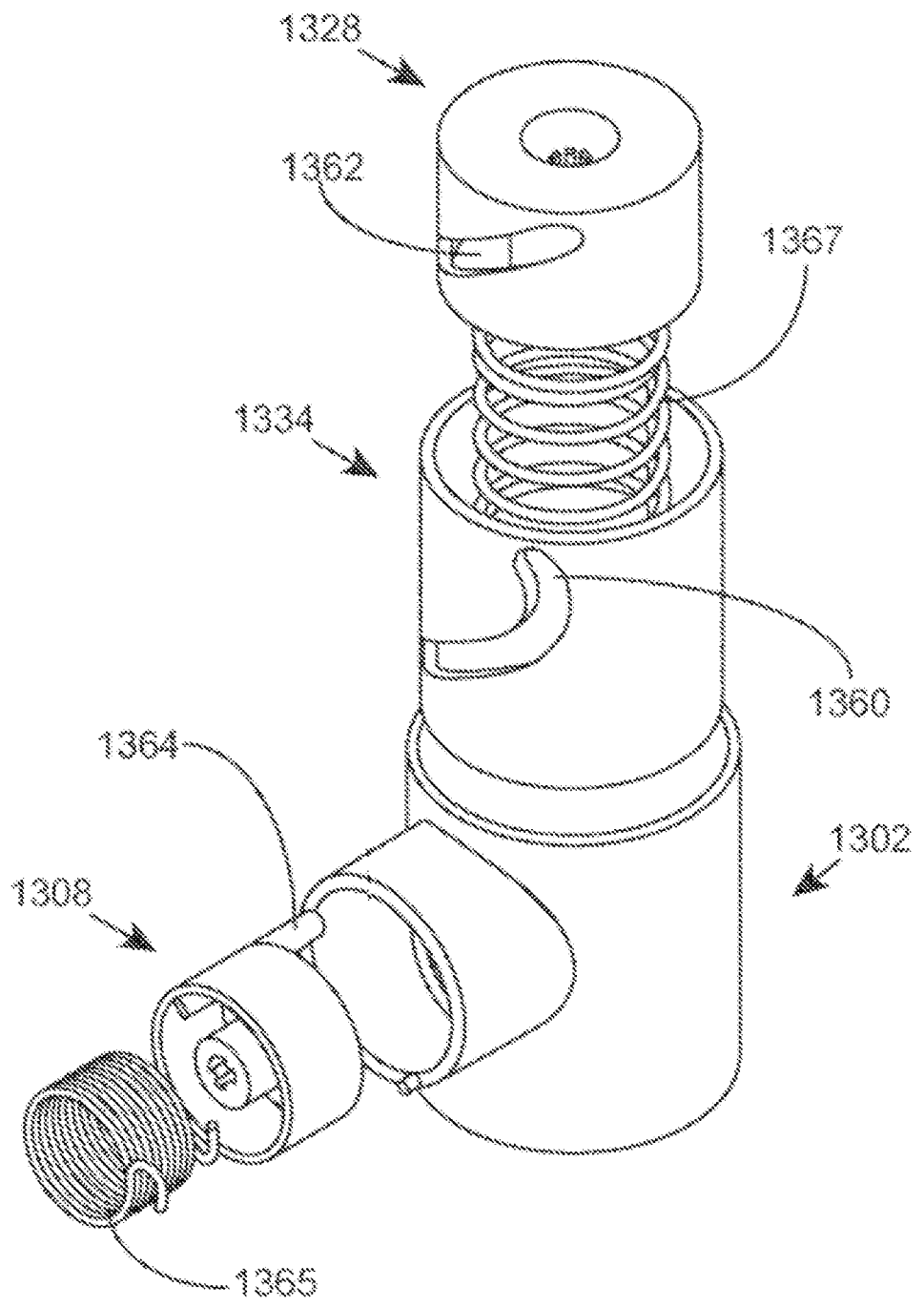
FIG. 45 is an exploded view of the inserter of FIG. 37 in accordance with the disclosed subject matter.
Figure 46:
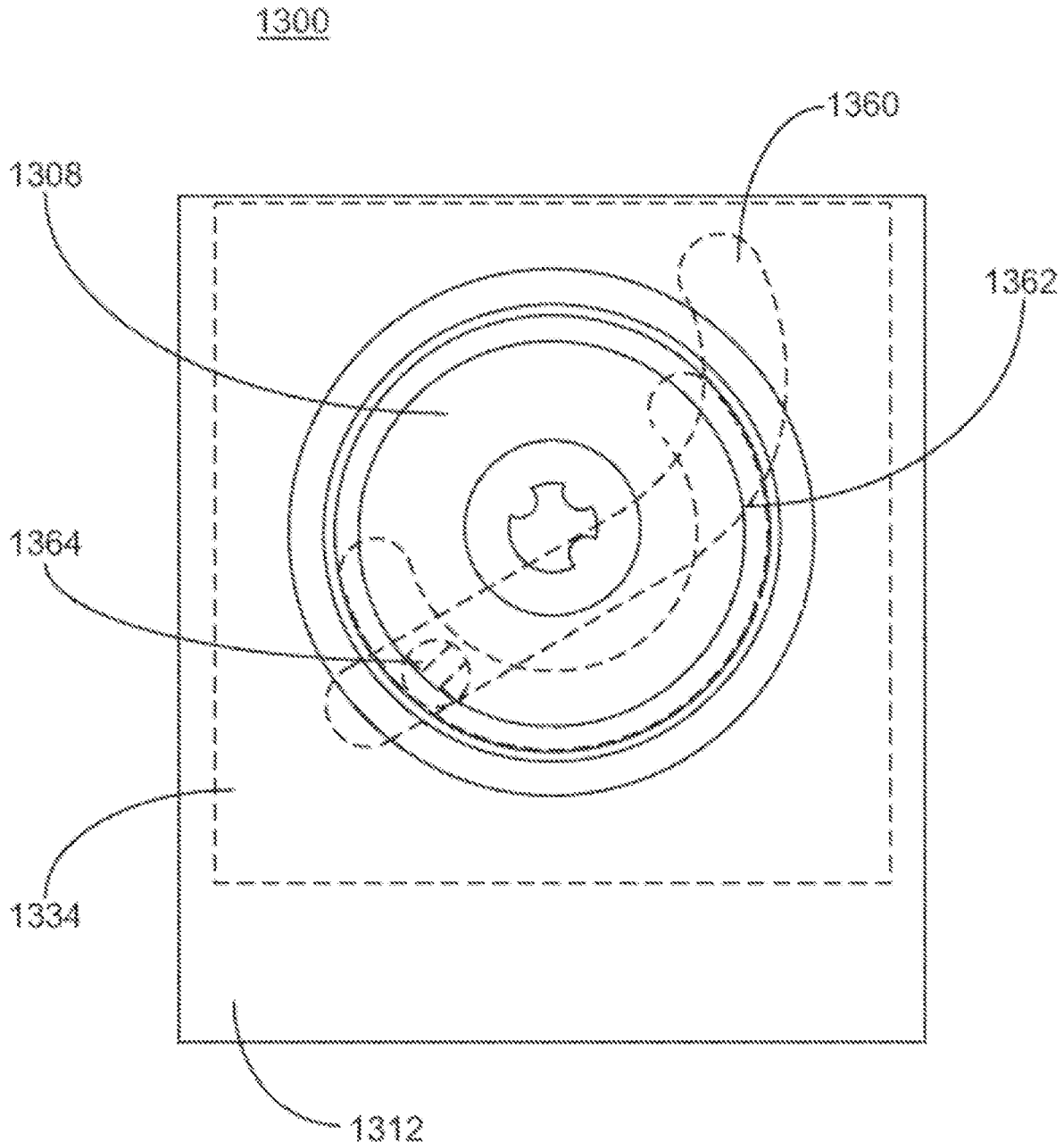
FIG. 46 is a side view with transparency of the inserter of FIG. 37 in accordance with the disclosed subject matter.

As illustrated in FIG. 34, in some embodiments, manually depressing the on-body unit inserter 1228 can cause the torsion spring to wind as the rotor 1208 rotates, guided by the cam path. As illustrated in FIG. 35, continued distal advancement of the on-body unit inserter 1228 causes the rotor follower 1264 to go "over center" within cam. At such point, the torsion spring (not shown) is allowed to unwind. With reference to FIG. 36, further unwinding of the torsion spring pulls up the needle retractor 1234 from the insertion site, while leaving the on-body unit inserter in place.

A further embodiment of an inserter is illustrated in FIGS. 37-46. Inserter 1300 is substantially identical to inserters 900, 1000, 1100B, and 1200 described herein, with the substantial differences noted herein and illustrated in the accompanying figures.

Inserter 1300 includes a housing 1302, an on-body unit inserter 1334, a needle retractor 1328, and a rotor 1308 with torsion spring 1365. As illustrated in FIGS. 37, 38, 39, 45 and 46, the on-body unit inserter 1334 and needle retractor 1328 are disposed within the housing 1302. Rotor 1308 includes a rotor follower 1364 which engages a slot 1362 provided in the needle retractor 1328 and a slot 1360 in the on-body unit inserter 1334. The on-body unit inserter 1334 provides a support portion for supporting on body housing 1302 (not shown).

In operation, torsion spring 1365 is loaded. A release button (not shown) is depressed in order to release torsion spring 1365. Rotor 1308 drives on-body unit inserter 1334 and needle retractor 1328 downwardly simultaneously. A compression spring 1367 holds down on-body unit inserter 1334. As rotor 1308 continues to rotate, slot 1360 allows on-body unit inserter 1334 to travel down and then be held down, while slot 1362 allows needle retractor 1328 to travel down and then back up to lift the needle from insertion site.

A further embodiment of an inserter is illustrated in FIGS. 47-51. Inserter 1400 is substantially identical to inserters

900, 1000, 1100B, 1200, and 1300 described herein, with the substantial differences noted herein and illustrated in the accompanying figures.

Figure 47:
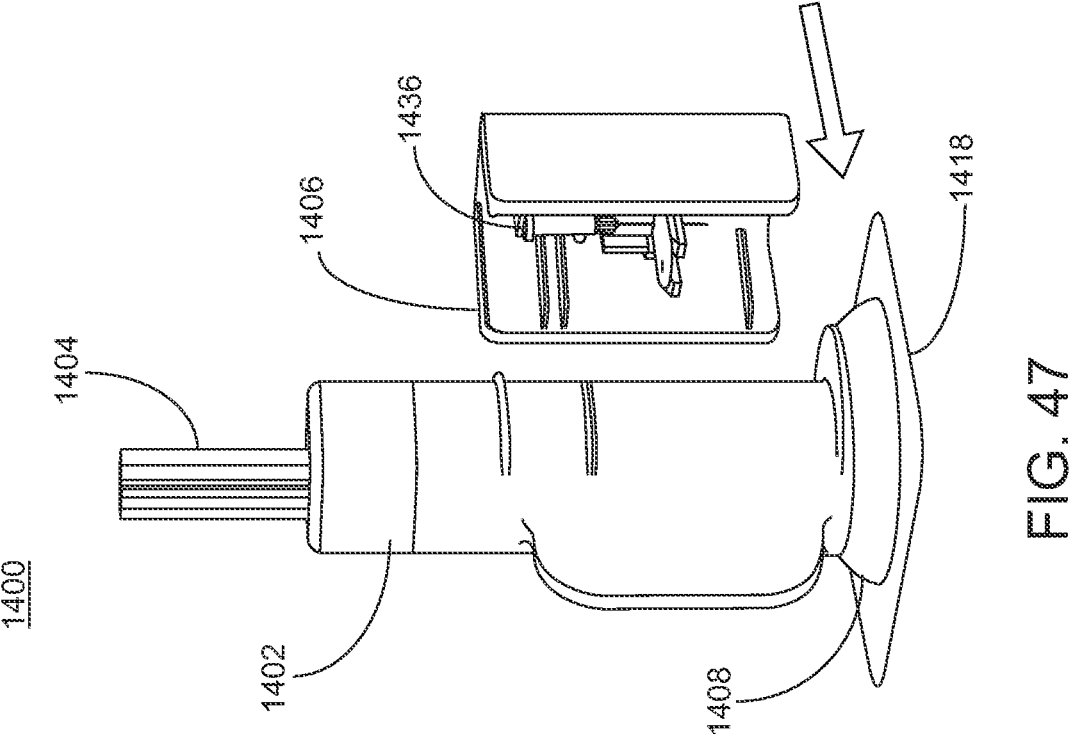

Inserter 1400 may be used for installation of a medical device, e.g., on body housing 122, in connection with a cartridge or carrier 1406. In some embodiments, inserter 1400 includes a body 1402 and an actuator 1404. The carrier 1406 may include a needle hub 1436 including a sharp (not shown) as well as an on body housing 122. In use, the body 1402 is placed on a mount 1408 attached to subject by use of an adhesive pad 1418. As shown in FIG. 47, carrier 1406 is loaded into inserter 1400 laterally as shown.

Figure 48:
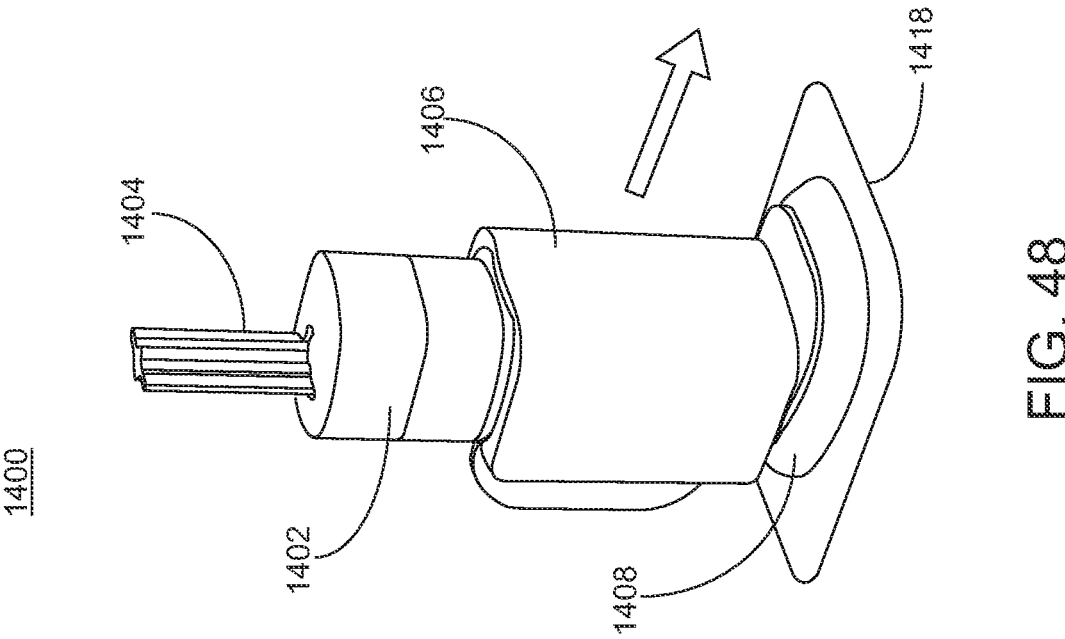
FIGS. 47-51 are perspective views of another inserter in accordance with the disclosed subject matter.

With reference to FIG. 48, a first disposable portion of inserter 1400 includes adhesive pad 1418 and mount 1408. The second disposable portion of inserter 1400 includes carrier 1406 which removably contains needle hub 1436 and sensor hub 1437 (not shown) which is substantially identical to on body housing 122 described herein. Inserter 1400 further includes body 1402, actuator 1404, and return spring 1409 (not shown). Mount 1408 is removably attached to body 1402. Carrier 1406 can be slid on to body 1402 to transfer needle hub 1436 and carrier 1406 to inserter 1400. As shown in FIG. 48, carrier 1406 can then be removed from inserter 1400. Needle hub 1436 and sensor hub 1437 remain in inserter 1400. Adhesive pad 1418 is then adhesively applied to the skin of a subject. Alternatively, adhesive pad 1418 may be applied to the skin of a subject before attaching body 1402 and mount 1408.

Figure 50:
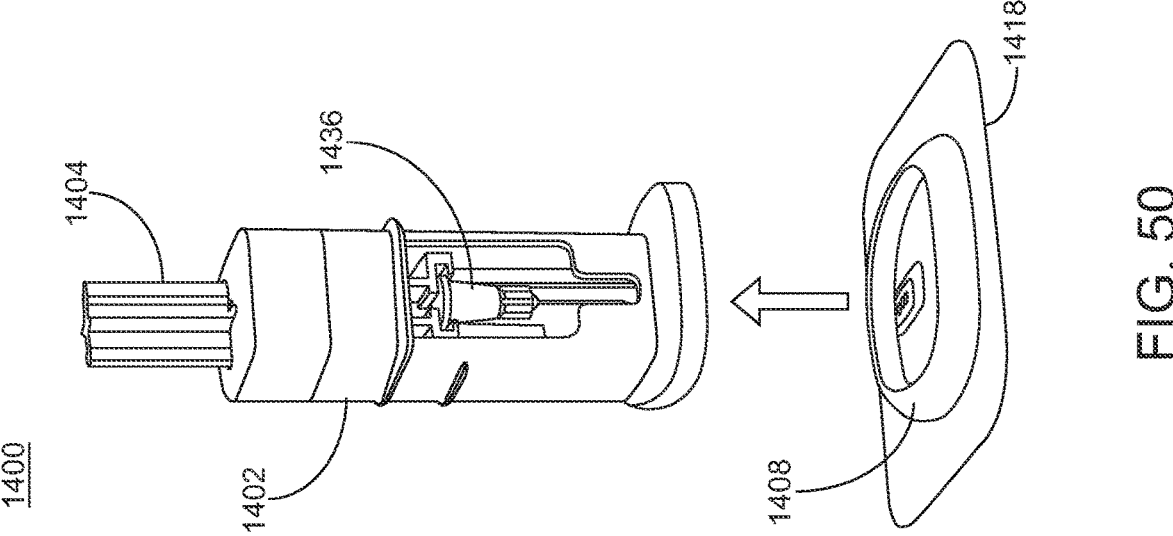
Figure 49:
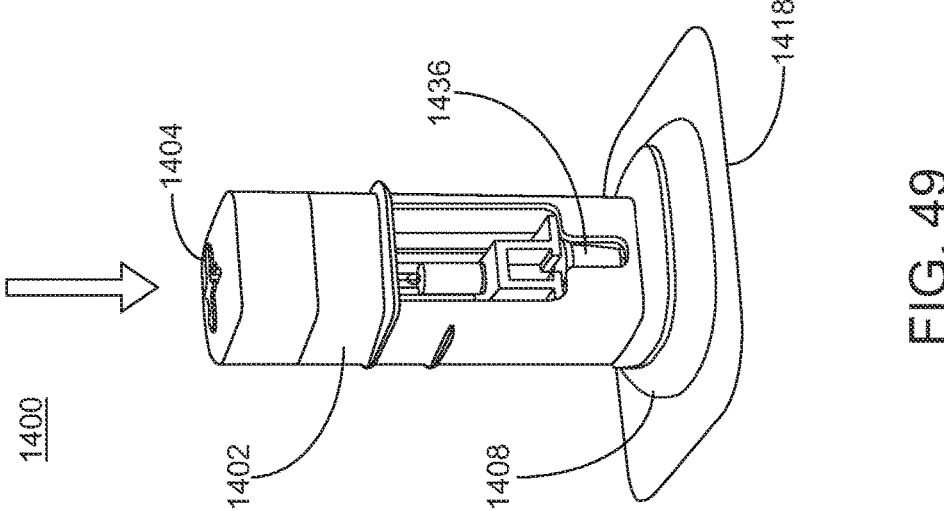
Figure 51:
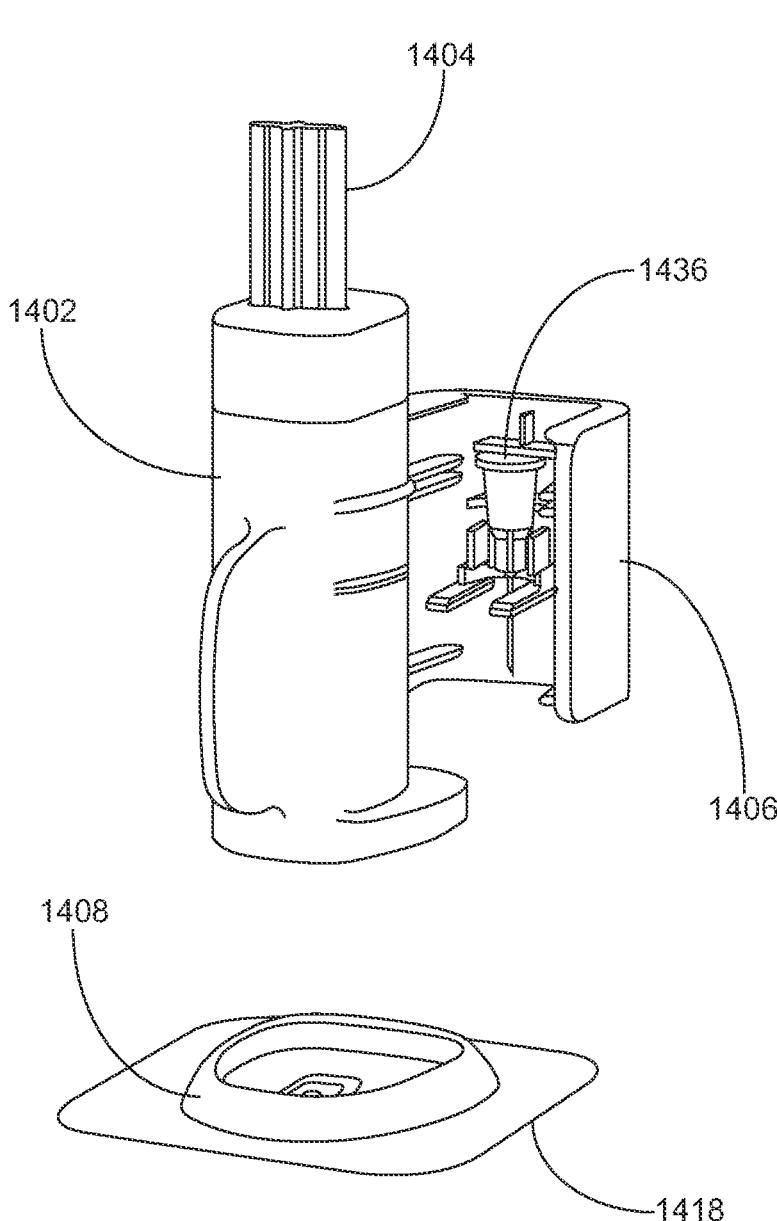

In FIG. 49, actuator 1404 is pressed down, performing a manual insertion of needle hub 1436 and sensor hub 1437, with the needle located in needle hub 1436 and a distal sensor portion penetrating the skin of the subject. When pressure is released from actuator 1404, return spring 1409 (not shown) retracts the needle from the skin of the subject and out of sensor hub 1437. As shown in FIG. 50, body 1402 can be removed from mount 1408, leaving sensor hub 1437 in mounting base 1408. In FIG. 51, in some exemplary embodiments, carrier 1406 is slid on to housing 1402, transferring needle 1436 to carrier 1406. Carrier 1406, with needle 1436, is then removed from housing 1402 and may be disposed of properly, and inserter 1400 is ready to be used again. Communication electronics (not shown) are then attached to mounting base 1408, making electrical contact with sensor hub 1437.

A further embodiment of an inserter is illustrated in FIG. 52. Inserter 1500 is substantially identical to inserters 900, 1000, 1100B, 1200, 1300, and 1400 described herein, with the substantial differences noted herein and illustrated in the accompanying figures.

Inserter 1500 includes a housing 1502, which may be fabricated as a molded plastic tube and may further include a living hinge cap 1504. In some embodiments, a living hinge is a thin flexible plastic junction that connects two mating parts. The hinge keeps the parts attached and may be folded completely without failure to allow the two parts to fully mate.

Cap 1504 may be further provided with a cutout portion to provide access to the index finger and restrict the insertion motion along a desired axis. Cap 1504 is closed up and bonded to the housing through chemical or ultrasonic bonding after the bellow-button assembly (described herein) is provided.

Inserter further includes bellows 1506, which, in some embodiments, is constructed from molded thin wall plastic with an integrated compression spring which collapses during the insertion action, and which provides the force to retract sharp 1524 after insertion. Bellows 1506 also hides sharp 1524 from exposure. The top portion 1520 of the bellows 1506 is secured to button 1514, and bottom portion 1521 is secured to housing 1502.

A button 1514 provides the capability of the user to insert on body housing 122 into the skin of the subject. Button 1514 may be fabricated from plastic and may further include anti-rotation features, e.g., recess 1515 which glides along longitudinal ridge 1517, restricting motion to the desired longitudinal axis. Needle hub 1536 is glued or directly molded onto button 1514. Sharp 1524 is securely held on to on body housing 122, as described herein (See, e.g., FIGS. 11-13).

An adhesive patch 1518 secures on body housing 122 to the skin of the subject. In some embodiments, the adhesive patch 1518 includes a high-tack (i.e., high strength adhesive) region for contact with the skin. A protective liner is provided for removal prior to insertion. On the side of the adhesive patch facing inserter 1500, low-tack region 1530 is provided on the periphery of the patch to allow easy removal of housing 1502 after insertion is completed. A high-tack region 1532 is provided in the center portion of the patch to secure on body housing 122 in place.

Figure 53:
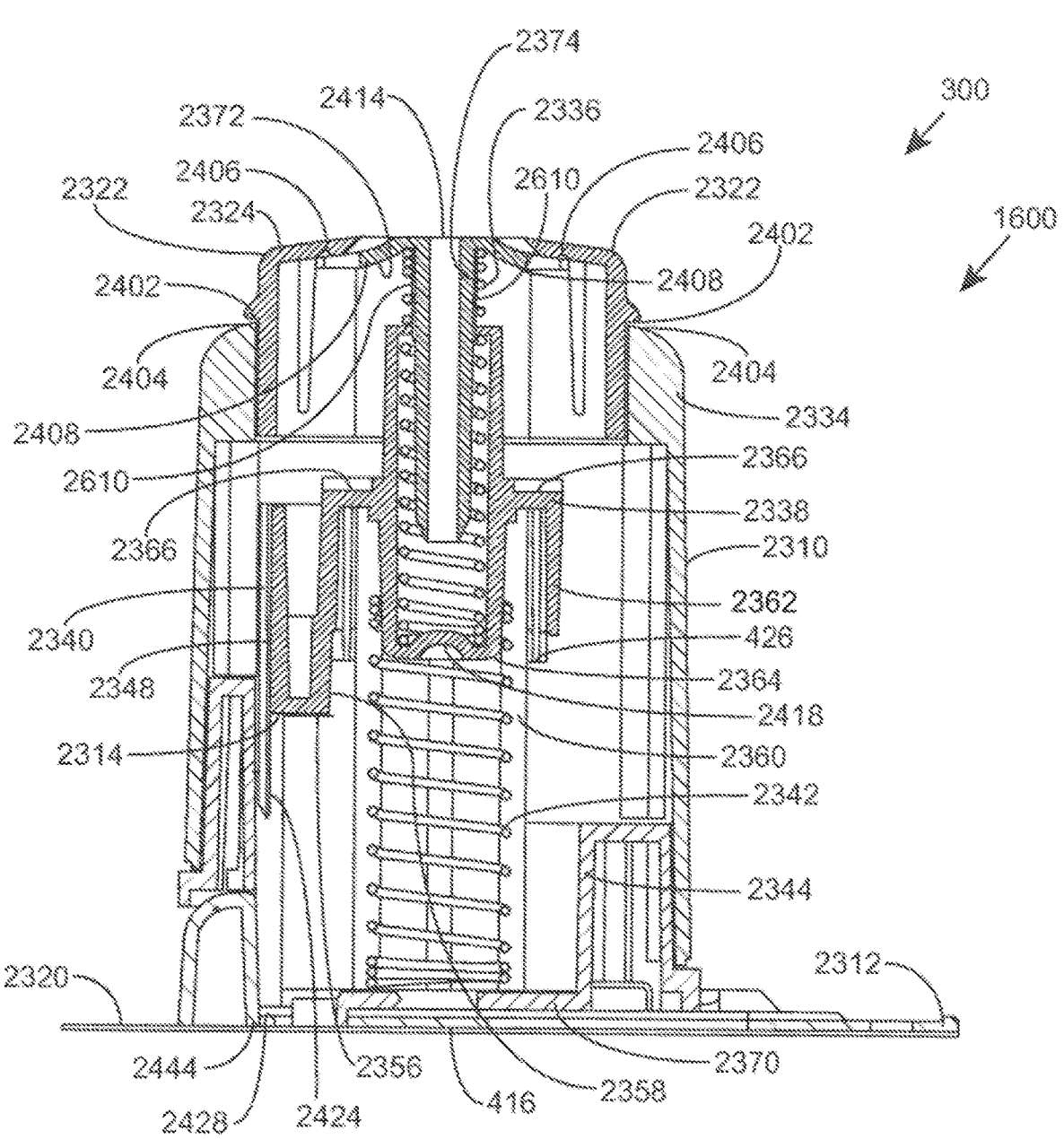
FIG. 53 is a sectional view of an inserter in accordance with the disclosed subject matter.
Figure 55:
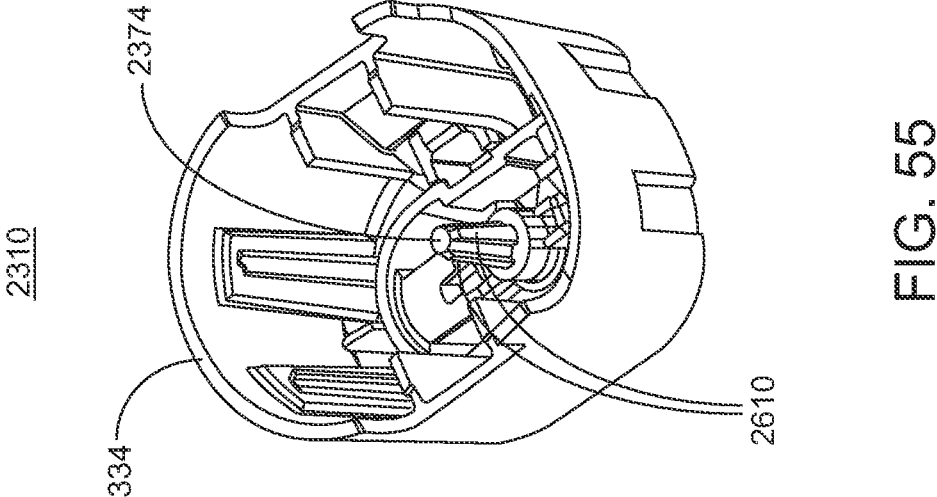
FIGS. 54-55 are perspective views from below of the inserter of FIG. 53.
Figure 54:
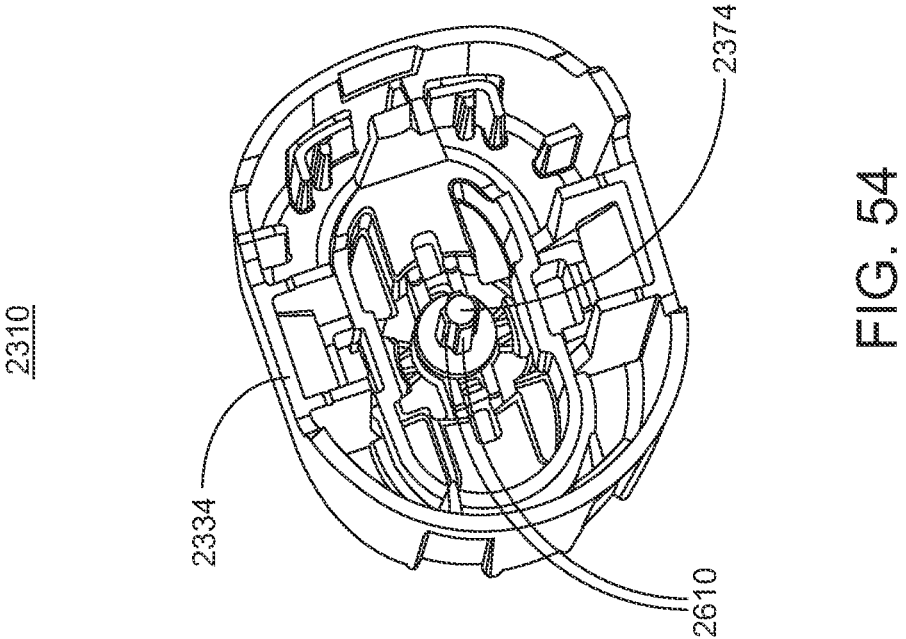
Figure 56:
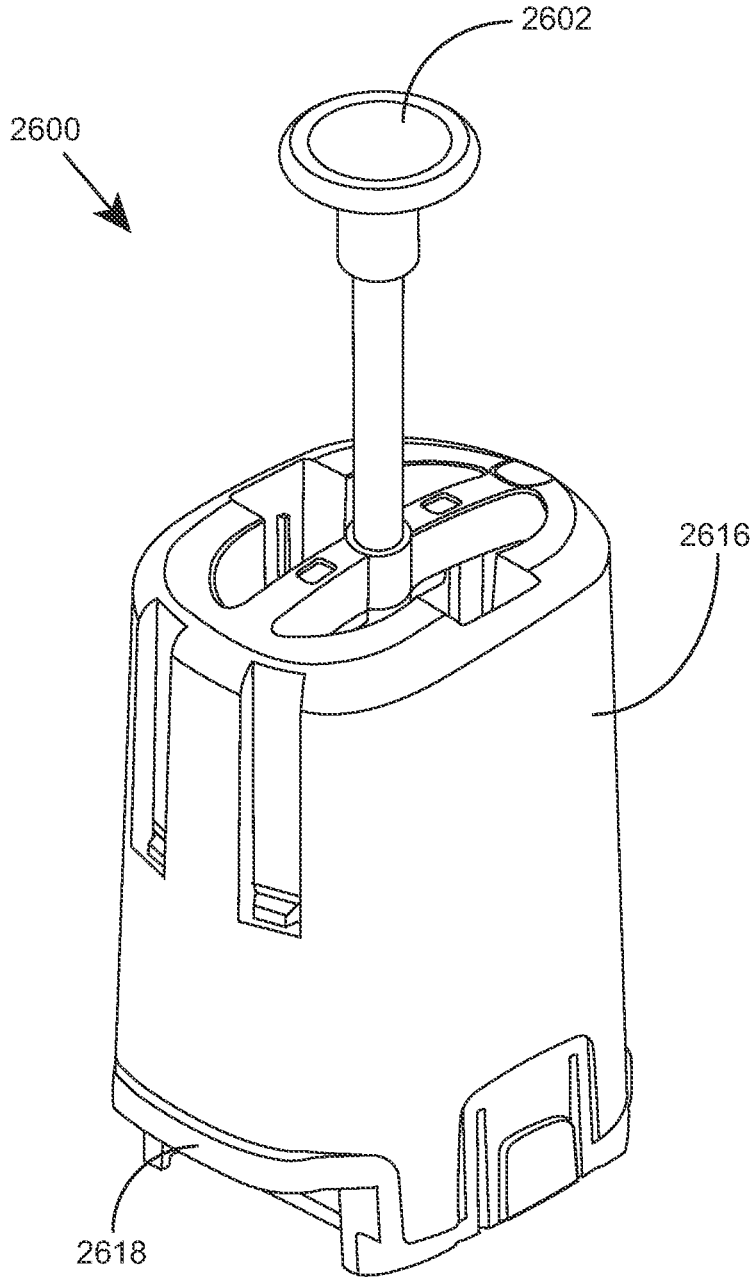
FIG. 56 is a perspective view of another inserter in accordance with the disclosed subject matter.

Referring to FIGS. 53-55, inserter kit 1600 is illustrated with inserter 2310 and an adhesive mount 2312 removably attached to the bottom thereof. Inserter kit 1600 is further described in U.S. Pat. No. 7,381,184, which is incorporated by reference herein for all purposes.

After preparing an insertion site on the skin, typically in the abdominal region, the user removes a liner (not shown) from adhesive mount 2312 to expose the bottom surface and a portion of the top surface of an adhesive tape 2320 located beneath mount 2312. Mount 2312, with inserter 2310 attached, is then applied to the subject's skin at the insertion site. Actuator button 2324 is depressed, causing inserter 2310 to fire, thereby inserting sensor 2314 into the subject's skin with a predetermined velocity and force. Once sensor 2314 has been inserted into the skin, the patient removes inserter 2310 from mount 2312 by pressing release tabs (not shown) on opposite sides of inserter 2310 and lifting inserter 2310 away from mount 2312.

Once inserter 2310 is removed from mount 2312, communications electronics (not shown) can be slid into place. The circuitry of the communications electronics device makes electrical contact with the contact pads on sensor 2314 after the communications electronics is fully seated on mount 2312. Once initialization and synchronization procedures are completed, electrochemical measurements from sensor 2314 can be sent wirelessly from the communications electronics to a receiver unit.

In some embodiments, inserter kit 1600 is assembled from the following components: housing 2334, actuator button 2324, drive spring 2336, shuttle 2338, introducer sharp 2340, sensor 2314, retraction spring 2342, inserter base 2344, upper liner (not shown), adhesive mount 2312, adhesive tape 2320, and lower liner (not shown).

Shuttle 2338 is slidably and non-rotatably constrained on base 2344 by arcuate guides 2360. Shuttle 2338 is generally formed by an outer ring 2362 and an inner cup-shaped post 2364 connected by two bridges 2366. Bridges 2366 slide between the two slots (not shown) formed between guides 2360 and allow shuttle 2338 to travel along guides 2360 without rotating. Retraction spring 2342 is captivated at its outer circumference by guides 2360, at its bottom by the floor 2370 of base 2344, at its top by bridges 2366, and at its inner circumference by the outer surface of shuttle post 2364. Drive spring 2336 is captivated at its bottom and outer circumference by the inside surface of shuttle post 2364, at its top by the ceiling 2372 inside actuator button 2324, and at its inner circumference by stem 2374 depending from ceiling 2372. When drive spring 2336 is compressed between actuator button 2324 and shuttle 2338 it urges shuttle 2338 towards base 2344. When retraction spring 2342 is compressed between shuttle 2338 and base 2344, it urges shuttle 2338 towards actuator button 2324.

Retraction spring 2342 will return shuttle 2338 to the neutral position as shown after firing, but without sensor 2314 which remains inserted in subject's skin. Drive spring 2336 is preferably designed to be stiffer than retraction spring 2342 so that shuttle 2338 oscillations are quickly dampened out, and so introducer sharp 2340 does not return to sensor 2314 or the patient to cause injury. With sensor 2314 inserted in the subject's skin, inserter 2310 can be removed from mount 2312 and then lifting inserter 2310 away from mount 2312. Introducer sharp 2340 remains protected inside housing 2334 during disposal of inserter 2310. Communications electronics can now be slid into place on mount 2312 as previously described.

In some embodiments, a proximal portion of stem 2374 is enlarged to create an interference fit with the coils of spring 2336. For example, one or more laterally extending ribs 2610 are added to stem 2374. The interference fit between ribs 2610 and spring 2336 is typically provided at the proximal (top) coils of spring 2336.

The diameter of the coils of spring 2336 increases slightly when compressed and decreases slightly when extended. Ribs 2610 on stem 2374 provide greatest interference when spring 2336 is extended. The interference fit provides increased stability of shuttle 2338 during insertion. In some embodiments, the interference fit prevents or minimizes distal movement of spring 2336, which may cause impact of spring 2336 against shuttle 2338 and the end of the distal travel of these components.

Figure 62:
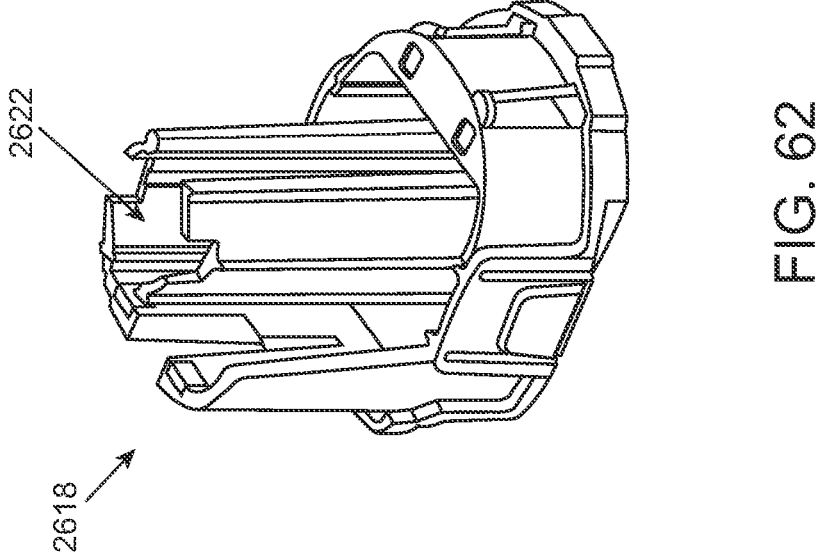
FIG. 61-62 are perspective views of various components of the inserter of FIG. 56.
Figure 61:
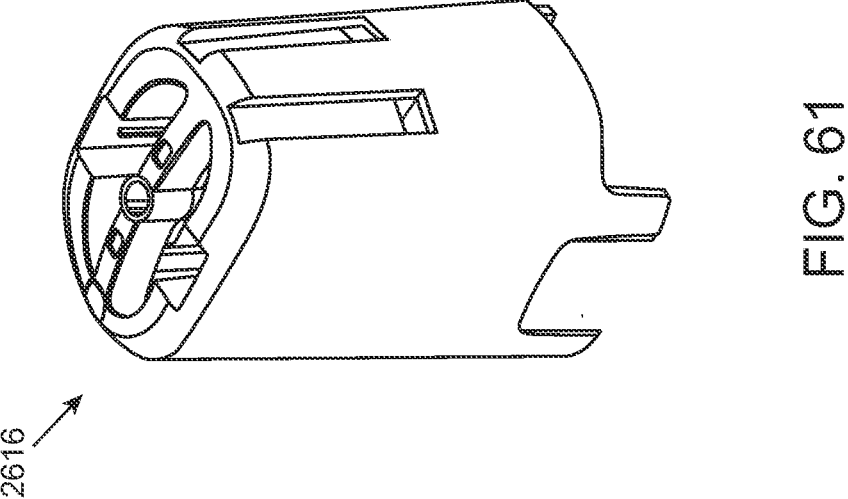
Figure 63:
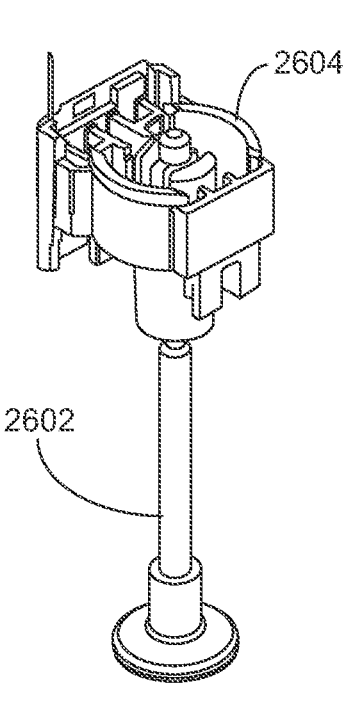
FIGS. 63-65 depict different subassemblies of the components of the inserter of FIG. 56.
Figure 64:
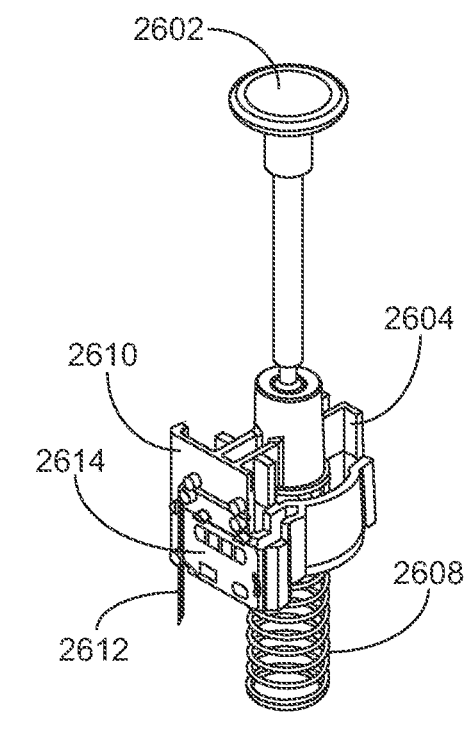
Figure 65:
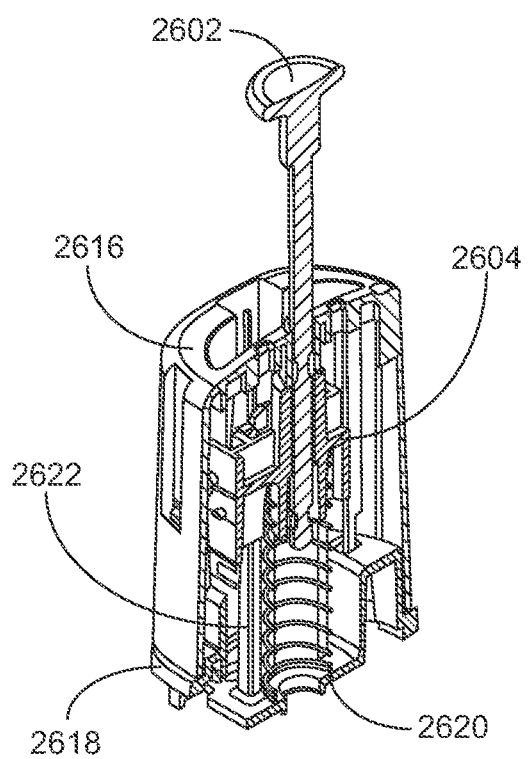

Referring to FIGS. 56-70, in another exemplary embodiment, inserter 2600 generally includes: actuator button 2602 (FIG. 57), shuttle 2604 (FIG. 58), inserter sharp 2610 with skin piercing edge 2612 (FIG. 58), retraction spring 2608 (FIG. 59), sensor 2614 (FIG. 60), housing 2616 (FIG. 61), and base 2618 (FIG. 62). It is understood that inserter 2600 may include additional or fewer components than described herein. Inserter 2600 is substantially identical to inserter 1600 described herein, with the substantial differences noted herein and illustrated in the accompanying figures. The assembly of the different components of inserter 2600 is depicted in FIGS. 63-65. As shown in FIG. 63, actuator button is adapted to be slidably inserted through an opening in shuttle 2604 where it locks into position. Further, as shown in FIG. 64, retraction spring 2608 is adapted to be inserted into a second opening on the opposite side of shuttle 2604. Additionally, in this view, sensor 2614 has been attached to inserter sharp 2610. As shown in FIG. 60, sensor 2614 incorporates a biasing arm 2615 that positively seats the sensor 2614 into the inserter sharp 2610. This allows the inserter sharp 2610 and sensor insertion portion 30 to be smaller, reducing the trauma and pain to the subject. Any number of the aforementioned sensor connection methods can be utilized in conjunction with inserter 2600. For example, inserter sharp 2610 may be provided with rails and dimples, as previously described, in order to retain sensor 2614, the sharp 2610 having a diameter of about 20 to about 26 gauge, e.g., 21 gauge to about 25 gauge, where in certain embodiments the sharp is 21 gauge or 23 gauge or 25 gauge. Such sharp may be used with a sensor having a width or diameter—at least the portion that is carried by the sharp—of about 0.20 mm to about 0.80 mm, e.g., about 0.25 mm to about 0.60 mm, where in some embodiments the width or diameter of at least a portion of a sensor is 0.27 mm or 0.33 mm or 0.58 mm.

Figure 67:
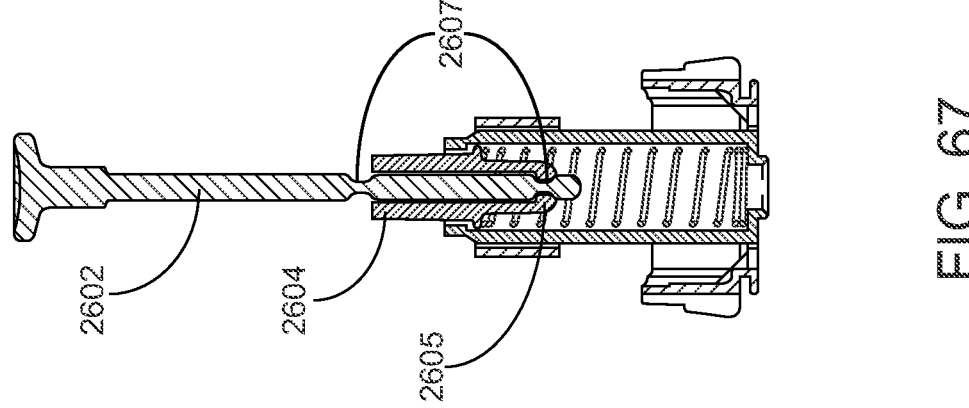
FIGS. 66-67 are cross-sectional views of a subassembly of the components of the inserter of FIG. 56.
Figure 66:
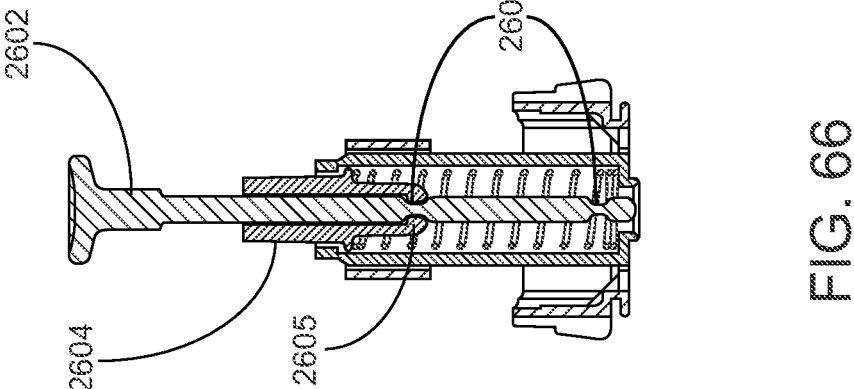

FIG. 66 depicts a cross-sectional view of the assemblage of FIG. 65 after inserter 2600 has been fully assembled (joining housing 2616 to base 2618). As depicted, retraction spring 2608 is surrounded by guides 2622 on its sides and by shuttle 2604 and base 2618 when inserter 2600 is assembled. Additionally, shuttle 2604 is adapted to slidably move on rails (not shown) within base 2618, thereby allowing it to move in a linear direction when actuator button 2602 is depressed. FIG. 66 depicts the actuator button 2602 locked onto the shuttle 2604 using the first of two detent grooves 2607. In this configuration, the shuttle 2604 and actuator button 2602 are in a locked state relative to the housing 2616 and base 2618, preventing accidental deployment of the shuttle during shipping and handling. This configuration also allows for significantly smaller packaging, resulting in lower shipping costs and improved bulk process efficiencies such as sterilization. FIG. 67 depicts the actuator button 2602 locked onto the shuttle 2604 using the second of two detent grooves 2607. In this configuration, the shuttle is ready to be deployed. The actuator button 2602 is moved to the second detent groove 2607 by a user pulling axially on the actuator button 2602 and housing 2616.

Figure 70:
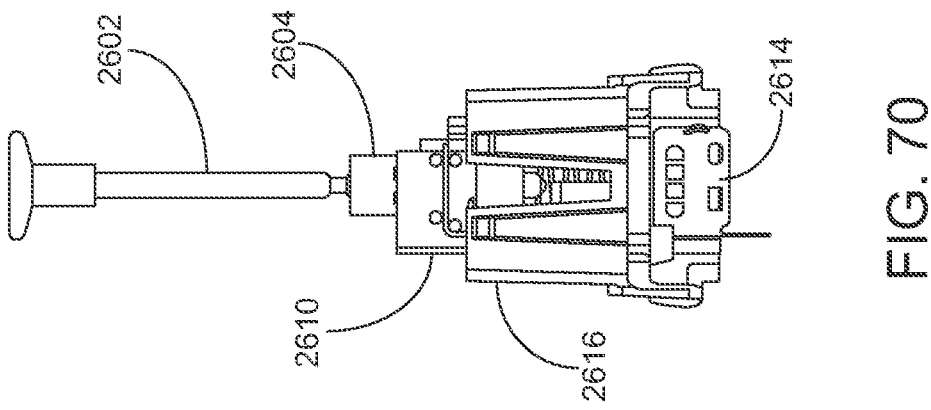
FIGS. 68-70 depict the steps used to actuate the inserter of FIG. 56.
Figure 69:
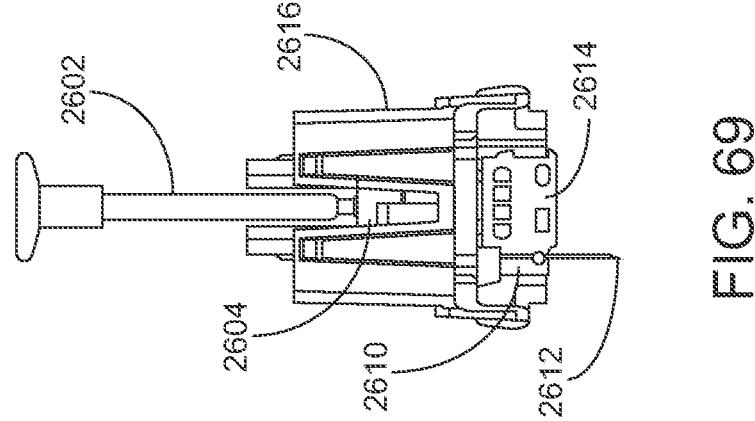
Figure 68:
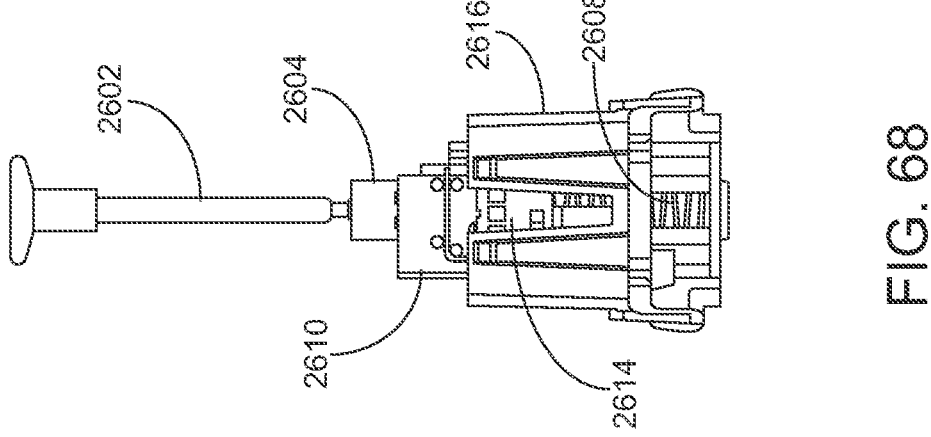

FIGS. 68-70 illustrate the steps utilized to deploy sensor 2614 using inserter 2600. FIG. 68 depicts inserter 2600 in a first configuration. The upward force exerted by retraction spring 2608 on shuttle 2604 (and consequently actuator button 2602) keeps inserter 2600 in its cocked position in the first configuration. As actuator button 2602 is pressed by a user against the bias of retraction spring 2608, it exerts a downward force on shuttle 2604 and retraction spring 2608. Introducer sharp 2610, on which sensor 2614 is mounted, is consequently driven downward and into the skin of the subject (e.g., to a second configuration). Skin piercing edge 2612 pierces the skin of the subject and allows sensor 2614 to be properly inserted, as shown in FIG. 69.

As the force is removed from actuator button 2602, retraction spring 2608 exerts an upward force on shuttle 2604, thereby causing introducer sharp 2610 to return proximally to its original position inside of housing 2616 (e.g., to the first configuration). Sensor 2614 remains implanted in the patient's skin, as shown in FIG. 70. In this position, the plunger is bent approximately 90 degrees by the user, which prevents further use of the device, and provides obvious visual and tactile indications that the device is used and ready to be disposed.

Figure 71:
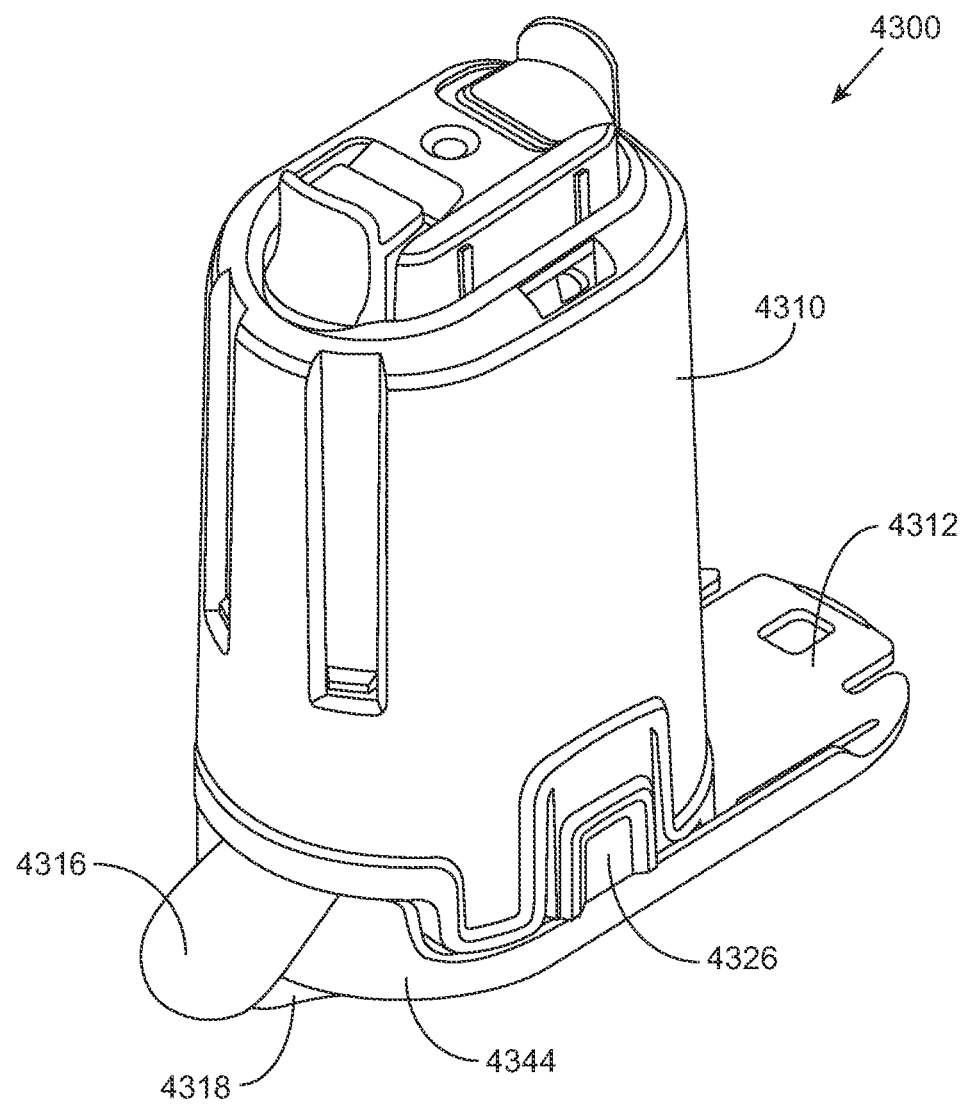
FIG. 71 is a perspective view of an inserter assembly in accordance with the disclosed subject matter.

In another aspect of the disclosed subject matter, an inserter assembly, as illustrated in FIG. 71, is provided which is useful for installing a medical device, such as an analyte sensor, in the skin of a subject. Inserter assembly 4300 may include an inserter, a medical device, such as an analyte sensor, and a mount for positioning the medical device at least partially in or on the skin of the subject. In some embodiments, the mount is a support structure, plate and/or member which is attached, adhered, or otherwise secured to the skin of the subject. The mount may be applied to the skin of the subject simultaneously with the medical device by the inserter. In other embodiments, the mount is installed after or before installation of the medical device. A mount may be applied by the inserter or separately. The mount may include features or structures (e.g., adhesive, guides, barbs, tabs, etc.) to maintain the sensor in position with respect to the skin after insertion and/or maintain the sensor in relative position with respect to the sensor control unit.

Inserter assembly 4300 is useful for analyte measurement systems, e.g., glucose measurement systems which include an on-body unit that may be assembled on the skin of the subject. For example, the on-body unit may include a sensor and a sensor control unit. The sensor is typically installed in the patient. Subsequently, the sensor control unit is installed and coupled to the sensor. In other embodiments, the sensor control unit is installed at the patient first, followed by installation of the sensor, which is then coupled to the sensor control unit. In yet other embodiments, the sensor and sensor control unit are simultaneously installed and coupled. An optional mount may or may not be used to position the sensor and/or the sensor control unit.

Generally, the inserter assembly 4300 is useful to install a sensor in the skin of a subject. A sensor (not shown) may be preloaded within inserter 4310 prior to installation. After preparing an insertion site on the skin of a subject, the user removes an upper liner 4316 and lower liner 4318 from mount 4312 to expose the bottom surface and a portion of the top surface of an adhesive tape located on the bottom surface of the mount 4312. Mount 4312, with inserter 4310 attached, is then applied to the subject's skin at the insertion site. In some embodiments, the mount 4312 is first attached, and then the inserter is coupled to or positioned within and/or adjacent to the mount 4312. The inserter includes an actuator button 4324 (see FIG. 74) to be depressed causing inserter 4310 to fire, thereby inserting a sensor into the user's skin. As will be described herein, certain embodiments install the sensor with a predetermined velocity and force upon actuation. In some embodiments of the disclosed subject matter, the inserter includes a safety member to impede actuation of the inserter as described below.

Figure 72:
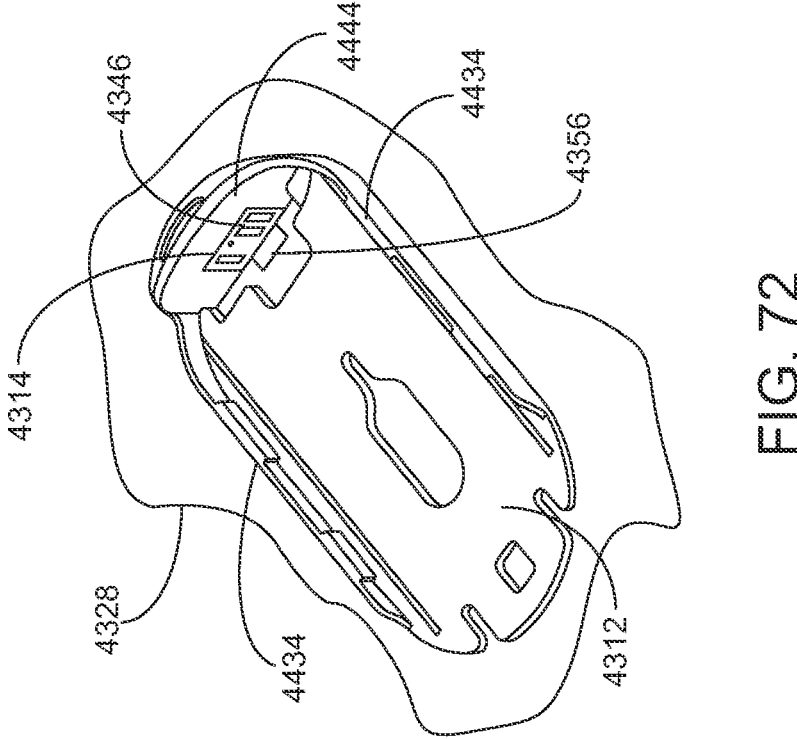
FIG. 72 is a perspective view of a component of an inserter assembly of FIG. 71 in accordance with the disclosed subject matter.

In some embodiments, the sensor 4314 remains positioned at the mount 4312 by one or more positioning techniques. For example, as illustrated in FIG. 72, sensor 4314 has a surface 4356 that extends orthogonally from main surface 4346. Surface 4356 may include an adhesive portion that contacts the subject's skin 4328 or the mount 4312. In some embodiments, the raised end stop 4444 of mount 4312 is provided with a raised bead or bump which is received in an aperture in sensor 4314. Following insertion of the sensor 4314 into the skin, the user may remove the inserter 4310 from mount 4312, e.g., by pressing release tabs 4326 on opposite sides of inserter 4310 and lifting inserter 4310 away from mount 4312. In some embodiments, the inserter 4310 is retained by other techniques, e.g., a friction-fit or a snap-fit with the mount 4312.

Once inserter 4310 is removed from mount 4312, a sensor control unit 4330 can be positioned into place with respect to the mount 4312. The circuitry of sensor control unit 4330 makes electrical contact with the contacts on sensor 4314 after sensor control unit 4330 is seated on mount 4312. For example, as shown in FIG. 72, seal has an exterior wall for surrounding electrical contacts on sensor 4314 (not shown in FIG. 72), and interior walls for isolating electrical contacts from each other. In some embodiments, rails on sensor control unit 4330 are slidable within corresponding rails or grooves 4434 on mount 4312.

Figure 73:
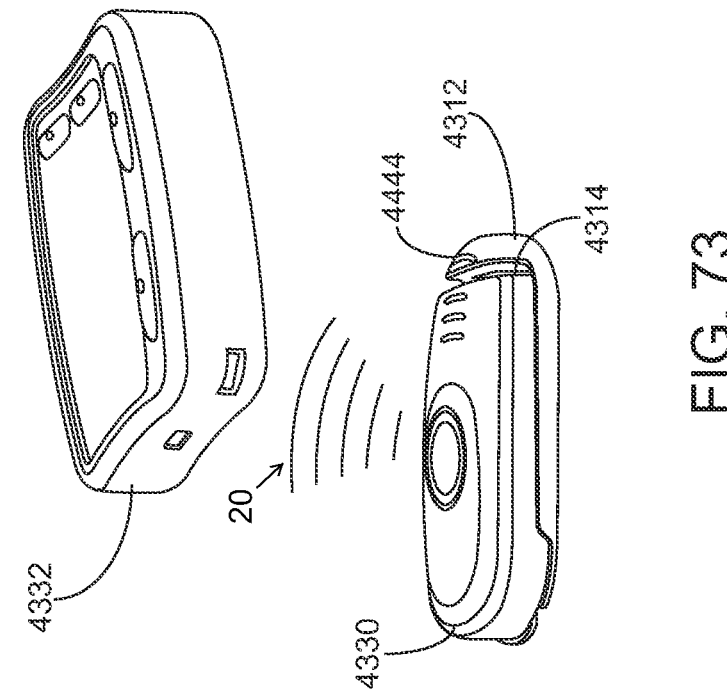
FIG. 73 is a perspective view of a component of an analyte measurement system in accordance with the disclosed subject matter.

In some embodiments, initialization and synchronization procedures are completed, and then electrochemical measurements from sensor 4314 can be provided from sensor control unit 4330 to a monitor unit, such as, e.g., portable monitor unit 4332, shown in FIG. 73. Sensor control unit 4330 and monitor unit 4332 communicate via connection 20 (in this embodiment, a wireless radio frequency (RF) connection). Communication may occur, e.g., via RF communication, infrared communication, Bluetooth® communication, Zigbee® communication, 802.1x communication, or WiFi communication, etc. In some embodiments, the communication may include a radio frequency of 433 MHz, 13.56 MHz, or the like. In some embodiments, communication between sensor control unit 4330 and monitor unit 4332 may include radio frequency identification (RFID) techniques, and may be active RFID or passive RFID, where, in some embodiments, passive RFID technology and the respective system components include the necessary components therefor. For example, in one embodiment, the monitor unit may include a backscatter RFID reader configured to transmit an RF field such that when the sensor control unit is within the transmitted RF field, an antenna is tuned and in turn provides a reflected or response signal (for example, a backscatter signal) to the monitor unit. The reflected or response signal may include sampled analyte level data from the analyte sensor. Additional exemplary details for various embodiments can be found in, e.g., U.S. patent application Ser. No. 12/698,124 filed Feb. 1, 2010, the disclosure of which is incorporated by reference herein for all purposes.

Sensor 4314, mount 4312 and sensor control unit 4330 can remain in place on the subject for a predetermined maximum period of time that may include hours, days, weeks, or a month or more. These components are then removed so that sensor 4314 and mount 4312 can be properly discarded in some embodiments. The entire procedure above can then be repeated with a new inserter 4310, sensor 4314 and mount 4312, reusing sensor control unit 4330 and monitor unit 4332. In other embodiments, inserter 4310 is reusable.

Figure 74:
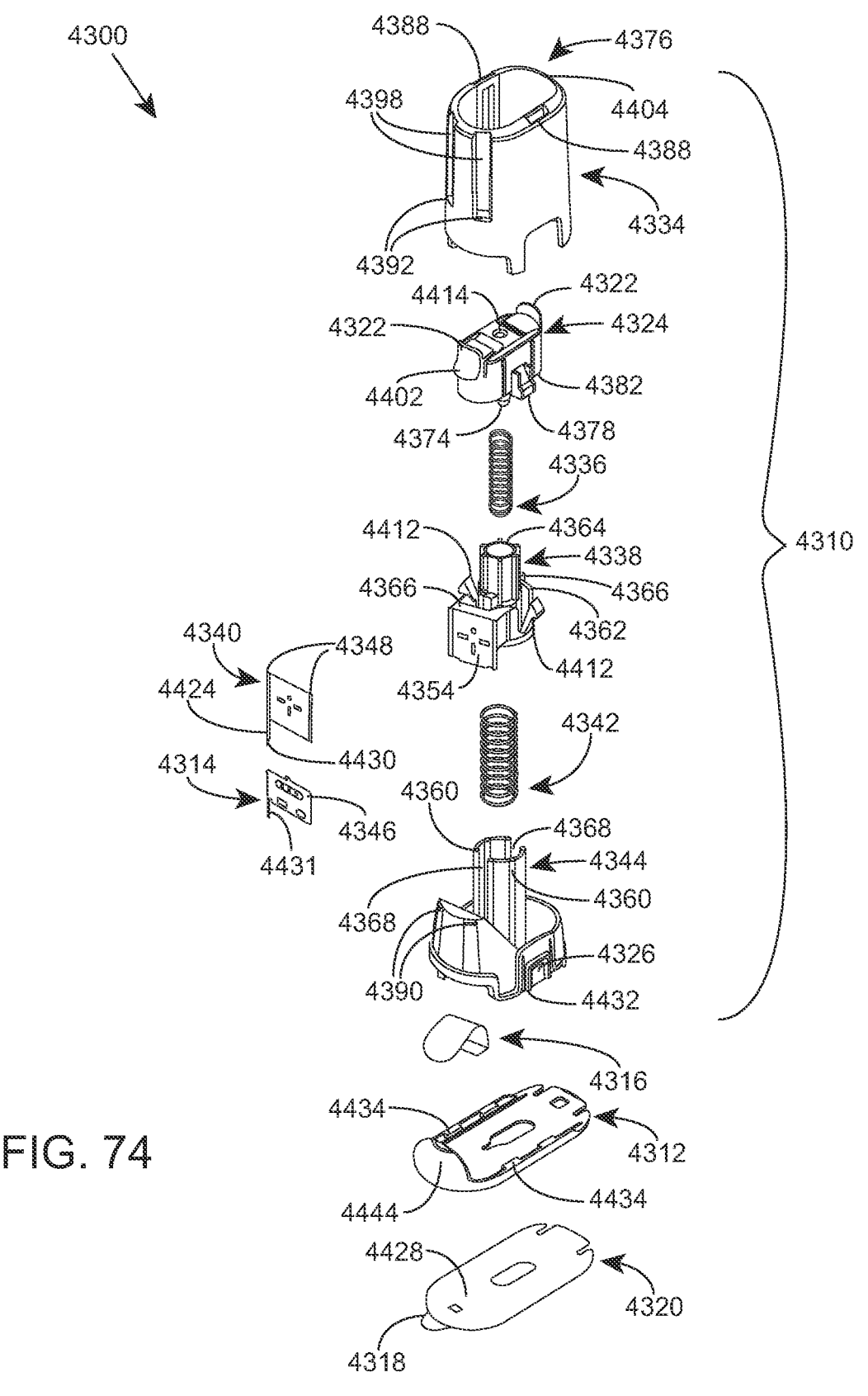
FIG. 74 is a perspective view with parts separated of the inserter assembly of FIG. 71 in accordance with the disclosed subject matter.

Referring to FIG. 74, the inserter assembly 4300 according to one embodiment can be assembled as shown from the following components: housing 4334, actuator button 4324, drive spring 4336, shuttle 4338, introducer sharp 4340, sensor 4314, retraction spring 4342, inserter base 4344, upper liner 4316, adhesive mount 4312, adhesive tape 4320, and lower liner 4318.

In some embodiments, sensor main surface 4346 is slidably mounted between U-shaped rails 4348 of introducer sharp 4340. In addition to the holding members disposed on the introducer, as described above, retention techniques are provided in certain embodiments to retain the sensor 4314 in position on sharp 4340 during storage of the inserter 4300 and/or during insertion of the sensor 4314 into the subject's skin. For example, a sensor dimple (not shown) is provided which engages an introducer dimple (also not shown). Introducer sharp 4340 can be mounted to face 4354 of shuttle 4338, such as with adhesive, heat stake or ultrasonic weld.

In some embodiments, shuttle 4338 can be slidably and non-rotatably constrained on base 4344 by arcuate guides 4360. The shuttle can be generally formed by an outer ring 4362 and an inner cup-shaped post 4364 connected by two bridges 4366. Bridges 4366 can be configured to slide between the two slots 4368 formed between guides 4360 and allow shuttle 4338 to travel along guides 4360 without rotating. In some embodiments, a retraction spring 4342 is provided, which can be captivated at its outer circumference by guides 4360, at its bottom by the floor 4370 (see FIG. 75) of base 4344, at its top by bridges 4366, and at its inner circumference by the outer surface of shuttle post 4364. In some embodiments, a drive spring is provided for advancing the sensor 4314 and the sharp 4340 into the skin of the subject. For example, drive spring 4336 is captivated at its bottom and outer circumference by the inside surface of shuttle post 4364, at its top by the ceiling 4372 (see FIG. 75)

inside actuator button 4324, and at its inner circumference by stem 4374 depending from ceiling 4372. In some embodiments, a drive spring is omitted from the inserter assembly. In such case, for example, sensor 4314 and sharp 4340 are distally advanced by manual force applied by a user.

When drive spring 4336 is compressed between actuator button 4324 and shuttle 4338 it can urge shuttle 4338 towards base 4344. When retraction spring 4342 is compressed between shuttle 4338 and base 4344, it urges shuttle 4338 towards actuator button 4324.

Figure 75:
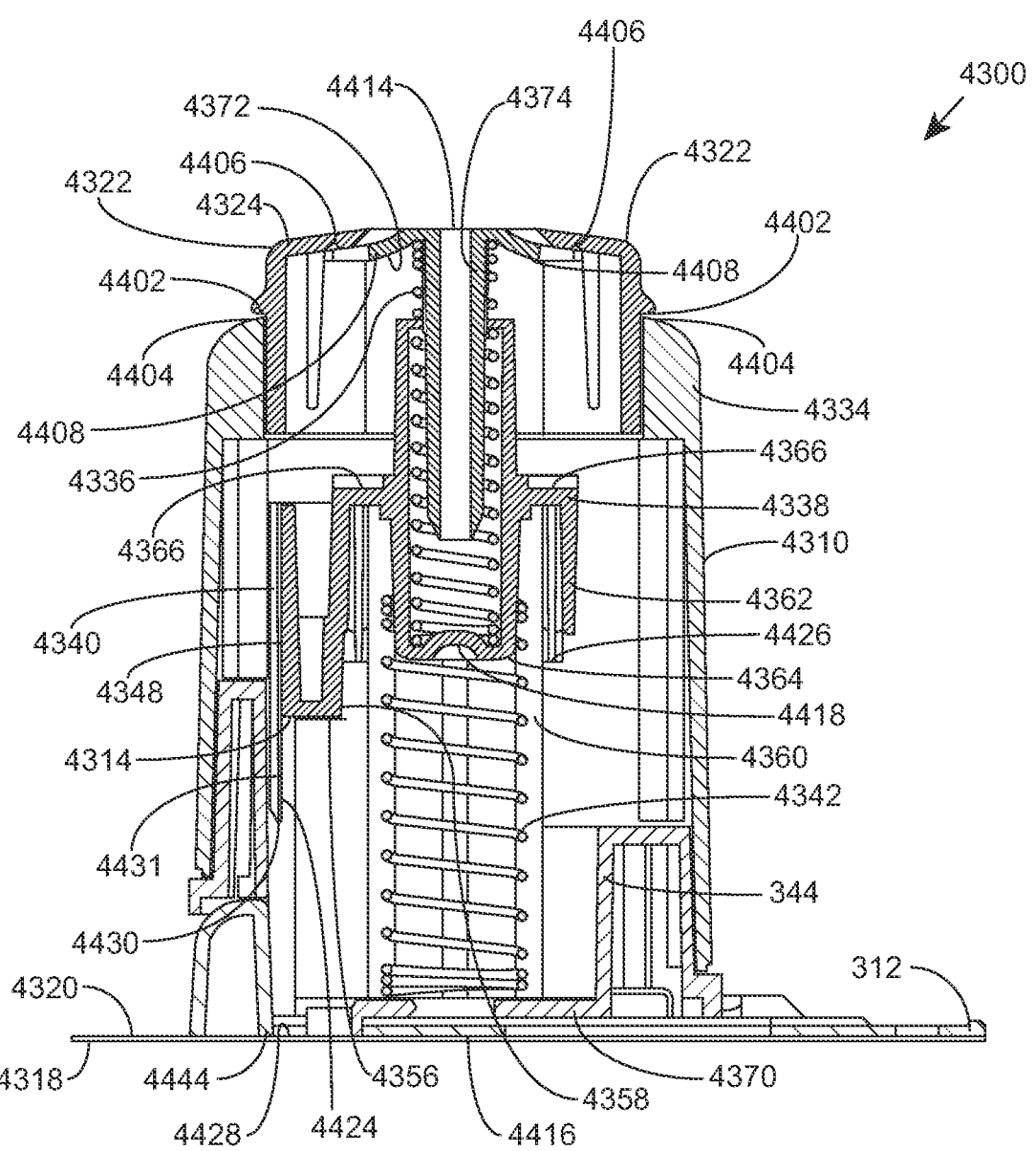
FIG. 75 is a cross-sectional view of the inserter assembly of FIG. 71 in accordance with the disclosed subject matter.

When sensor 4314, introducer sharp 4340, shuttle 4338, retraction spring 4342, drive spring 4336 and actuator button 4324 are assembled between base 4344 and housing 4334 as shown in FIGS. 74-75 and described above, housing 4334 is snapped into place on base 4344. Base 4344 is held onto housing 4334 by upper base barbs 4390 that engage upper openings 4392 in housing 4334, and lower base barbs that engage lower openings in housing 4334. Further details regarding the construction and operation of inserter 4300 is provided in U.S. Pat. No. 7,381,184 which is incorporated by reference herein in its entirety for all purposes.

In some embodiments, retention techniques and/or structures are provided to assist in supporting the sensor 4314 with respect to the sharp 4340 during storage and insertion. As illustrated in FIGS. 76-90, retention mechanisms are provided which are located on the sensor and/or the sharp.

Figure 77:
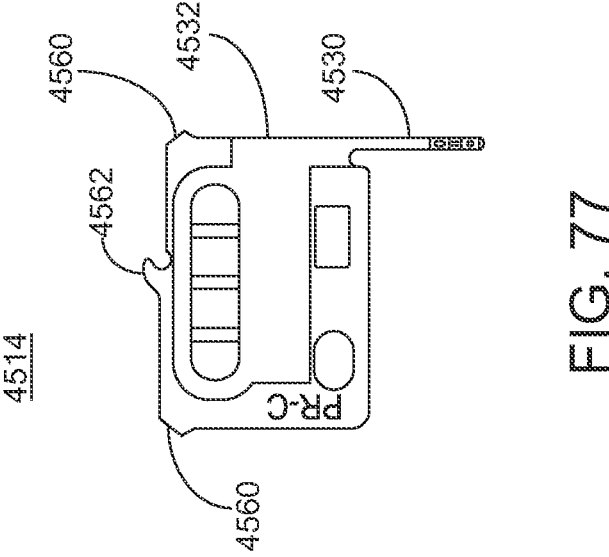
FIG. 77 is a view of an analyte sensor in accordance with the disclosed subject matter.
Figure 76:
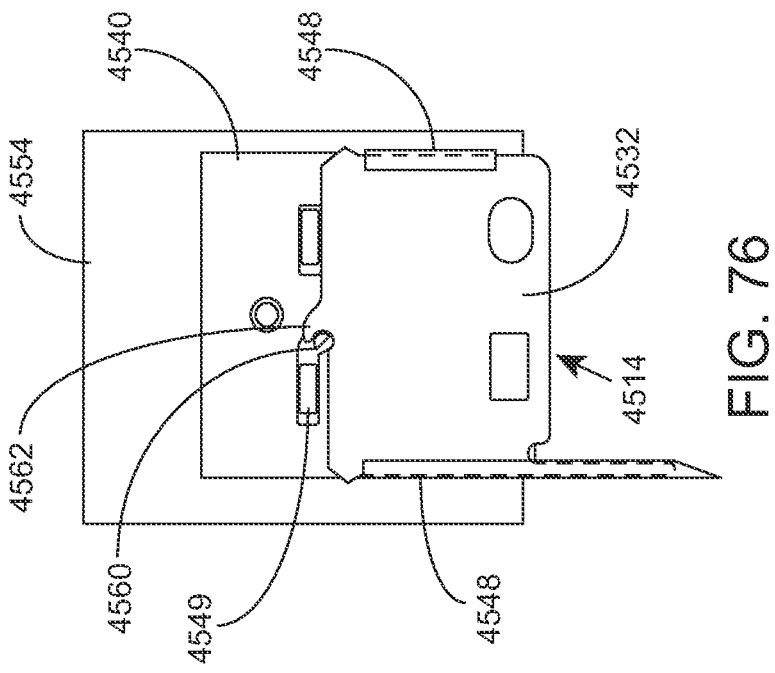
FIG. 76 is a side view of a portion of an inserter assembly in accordance with the disclosed subject matter.

FIGS. 76-77 illustrate a sensor 4514 which is provided with one or two laterally extending tabs 4560. Tabs 4560 engage the rails 4548 of the sharp 4540 for retention. In some embodiments, a radiused edge on the ears allow them to be formed in two punch operations, e.g., a hole punch and a straight cut. A gap between left hard-stop 4549 and the top of sensor 4514 produces, during firing, a moment that biases the sensor tip into the sharp channel. During deployment, the sensor deflects to disengage the sharp.

Figure 79:
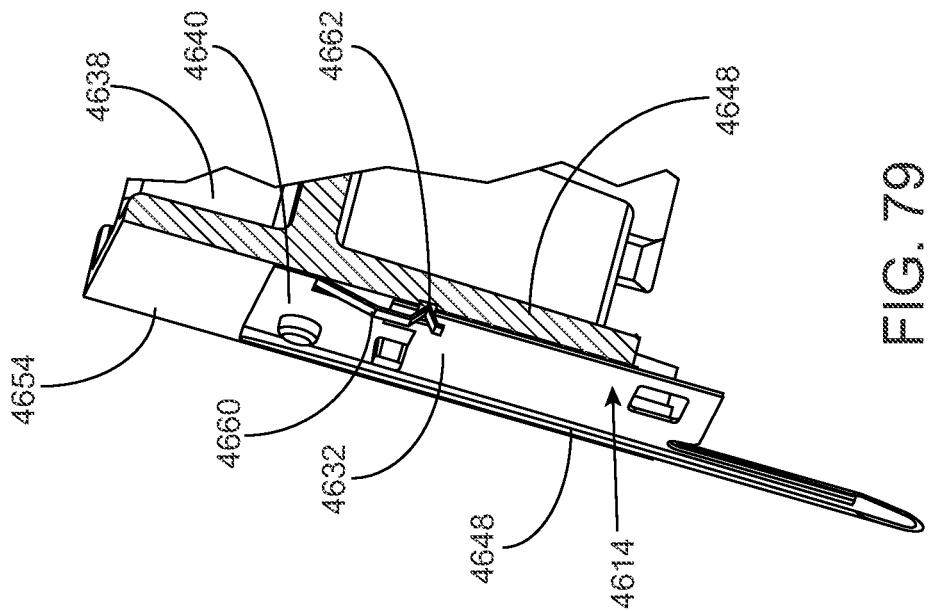
FIGS. 78-79 are perspective views of a portion of an inserter assembly in accordance with the disclosed subject matter.
Figure 78:
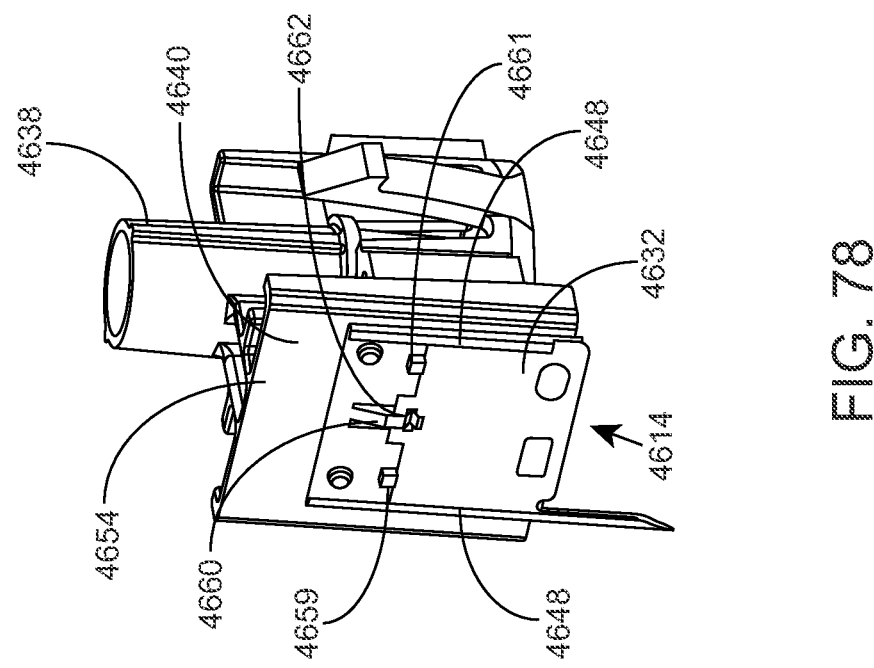

FIGS. 78-79 illustrate an inserter having a sensor retention mechanism in accordance with a further embodiment of the subject disclosure. Sharp 4640 is provided with a clip 4660 that engages a retention window 4662 at the top of sensor 4614 to provide retention of sensor 4614 in sharp 4640, and vertical registration. Two drive blocks 4659 and 4661 on carrier 4654 traverse sharp 4640 to engage the top edge of sensor 4614. There is a gap between the left drive block 4659 and the top edge of sensor 4614. Right drive block 4661 is in contact with the top edge of sensor 4614. During insertion, the upward drive force of the skin on sensor 4614 produces a clock-wise rotational moment on sensor 4614 that biases sharp 4614 into the sharp channel.

The clip feature 4660 and the window 4662 can be moved to the left to bias the tip of the sensor 4614 into the channel during shipping. During deployment, the sensor 4614 and the clip 4662 deflect to transfer the sensor 4614 to the mount 4312.

FIG. 80 illustrates a further embodiment of a sensor retention technique. In particular, sensor 4714 is provided with a retention member 4760, which extends from the contact portion 4732 of the sensor 4714. Retention member 4760 is resiliently biased in the position as shown. When the sensor 4714 is inserted within the sharp (not shown), the retention member engages the inner portion of rails (not shown) of the sharp, and provides a retention force to the sensor 4714.

FIG. 81 illustrates another embodiment of a sensor retention technique. Sensor 4814 is provided with a dimple 4860 which is thermally formed. As shown in FIG. 82, a raised bump 4864 on the sharp 4840 frictionally contacts thermally formed dimple 4860 in order to provide retention force to the sensor 4814. In some embodiments, raised bump is formed using heat. In another embodiment, a raised bump is formed on the sensor and the dimple is formed on the sharp.

FIGS. 83-84 illustrate an aperture 4960 which is formed in the contact portion of the sensor 4914. A raised bump or tab 4962 is provided on the sharp 4940. The interaction of the tab 4962 within the aperture 4960 of the sensor 4914 assists in retaining the sensor 4914 within the inserter.

FIGS. 85-86 illustrate a technique for retention of the sensor 5014 which is similar to the techniques illustrated in FIGS. 81-84. For example, a raised bump 5062 is provided on sharp 5040 which engages the contact portion 5032 of the sensor 5014. In such configuration, the raised bump 5062 creates a bias force against the contact portion 5032. Such force acts as a frictional force to assist retention of the sensor 5014 within the sharp 5040.

Figure 87:
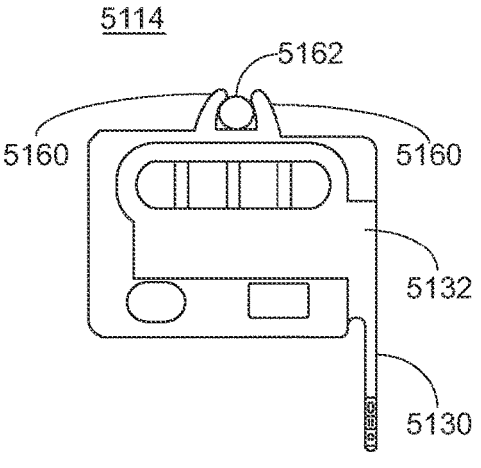
Figure 88:
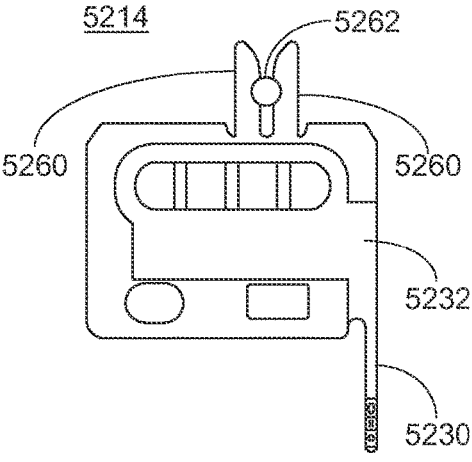

FIGS. 87 and 88 illustrate sensors having retention members which engage a raised post or button on the sharp. FIG. 87 illustrates that contact portion 5132 of sensor 5114 includes a pair of "pincer fingers" 5160 having a substantially arcuate configuration which surround and engage a post 5162 provided on the sharp. Similarly, FIG. 88 illustrates sensor 5214 having a pair of proximally extending arms 5260, which engage a post 5262 on the sharp.

Figure 89:
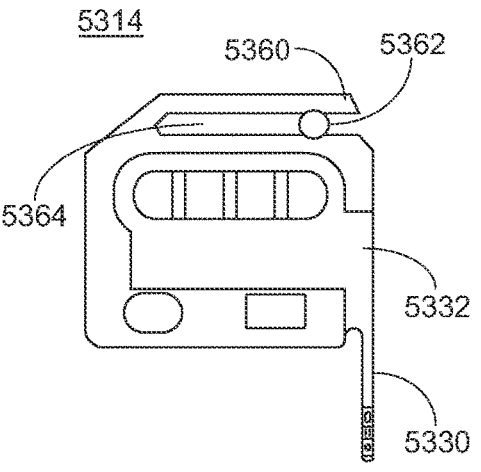

FIG. 89 illustrates a sensor 5314 having a laterally extending arm 5360 which defines a channel 5364 between the arm 5360 and the contact portion 5332 of the sensor 5314. As illustrated in the figure, a post 5360 may be positioned within the channel 5364, and provides frictional resistance to maintain the sensor 5314 within the sharp.

Figure 90:
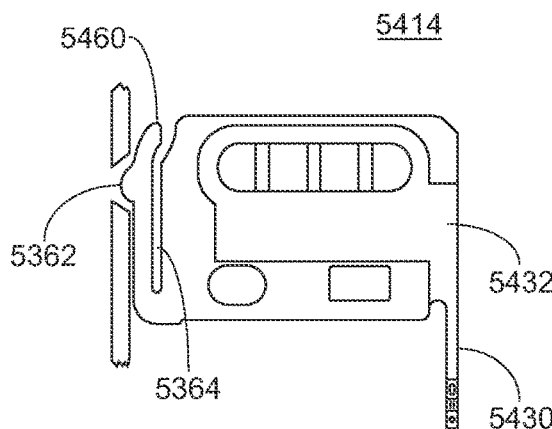

FIG. 90 illustrates a sensor 5414 having a proximally extending arm 5460 which defines a channel 5362 between the arm 5460 and the contact portion 5432 of the sensor 5414. As illustrated in the figure, a tab 5364 is provided on the arm 5460 and is received within a gap provided in the rails of the sharp. This interaction of the tab 5364 with the gap provides frictional resistance to maintain the sensor 5414 within the sharp.

Figure 92:
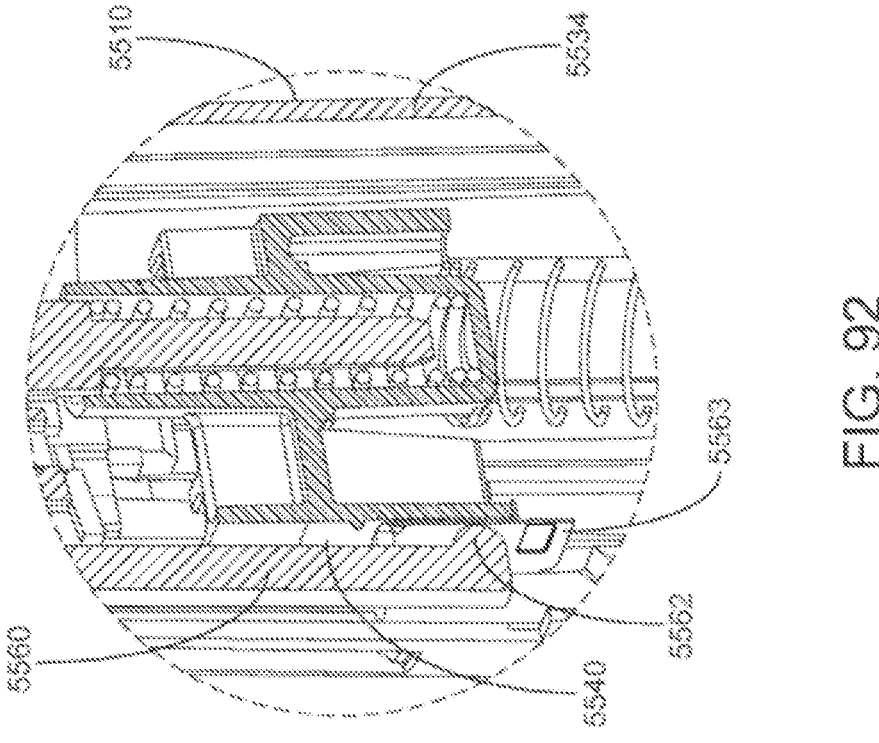
FIGS. 91-92 are cross-sectional views of an inserter assembly in accordance with the disclosed subject matter.
Figure 91:
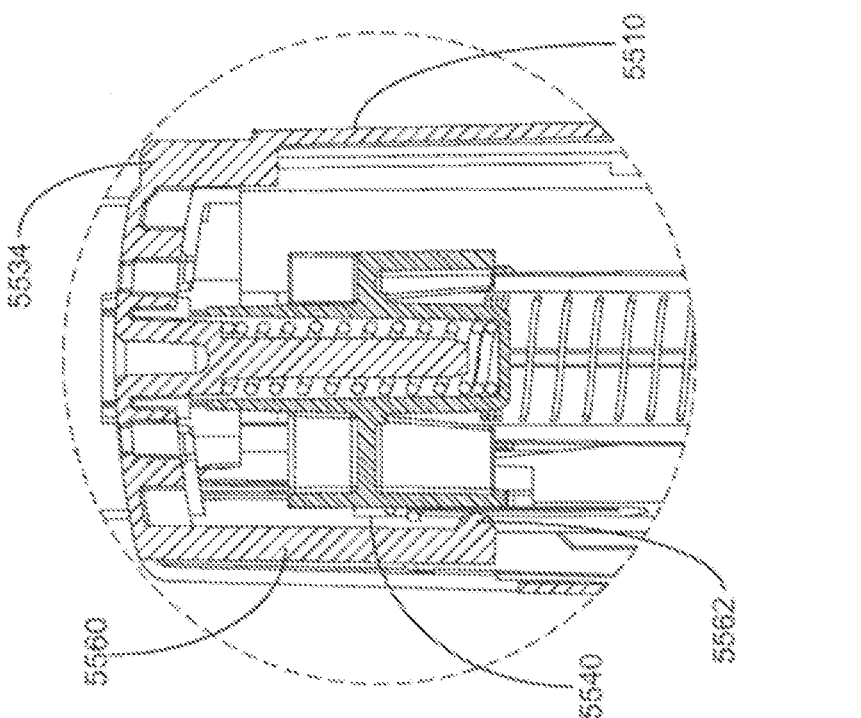

FIGS. 91-92 refer to sensor retention techniques which include a retention member which provides a frictional force substantially normal (perpendicular) to the surface of the sensor. FIGS. 91 and 92 illustrate a retention member which is provided within the housing 5534 of the inserter 5510. For example, the retention member 5560 may extend distally from the housing 5534 and includes a laterally extending tab 5562 which contacts the sensor 5563 and provides a frictional force to assist retention of the sensor within the sharp 5540.

Figures 93, 94:
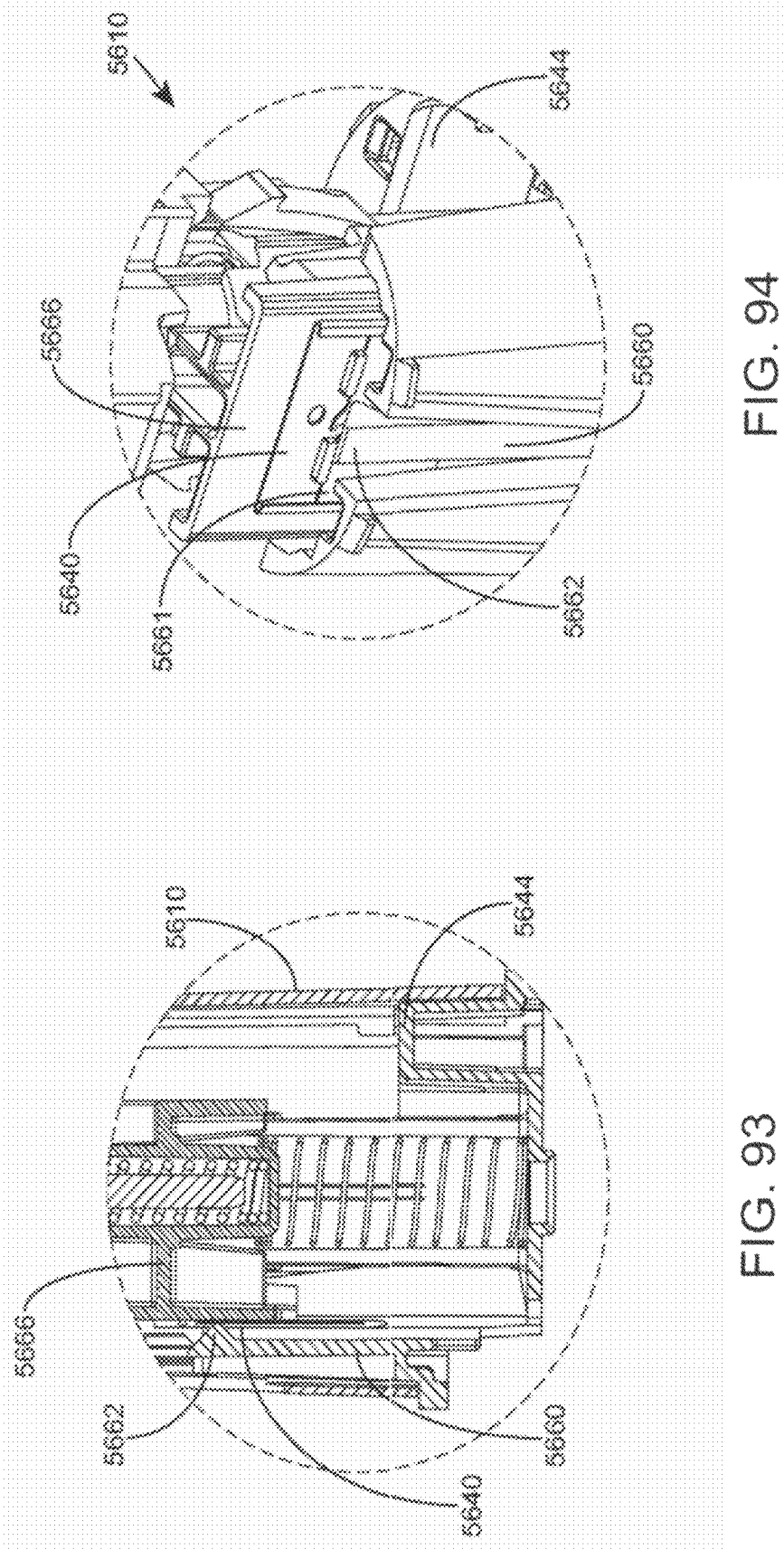
FIGS. 93-94 are cross-sectional views of another inserter assembly in accordance with the disclosed subject matter.

FIGS. 93 and 94 illustrate a retention member which is provided with the base 5644 of the inserter 5610. For example, retention member may include a cantilever 5660 which extends proximally from base 5644 of the inserter 5610. Cantilever 5660 may include a laterally extending member 5662 which contacts the sensor 5661 and provides a frictional force to assist retention of the sensor within the sharp 5640. When the carrier 5666 bottoms down, the cantilever 5660 ceases contact, and release of the sensor occurs.

Figure 96:
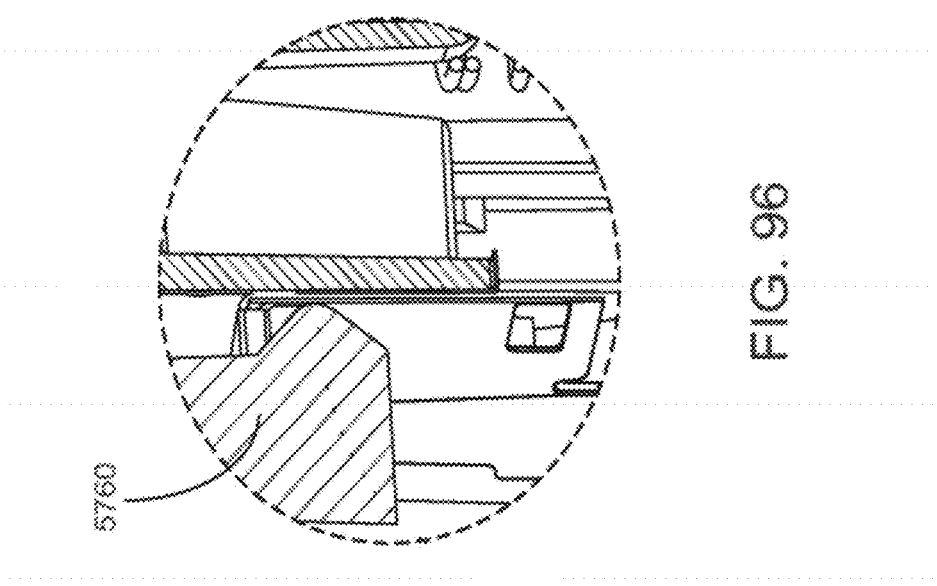
FIGS. 95-96 are cross-sectional views of a further inserter assembly in accordance with the disclosed subject matter.
Figure 95:
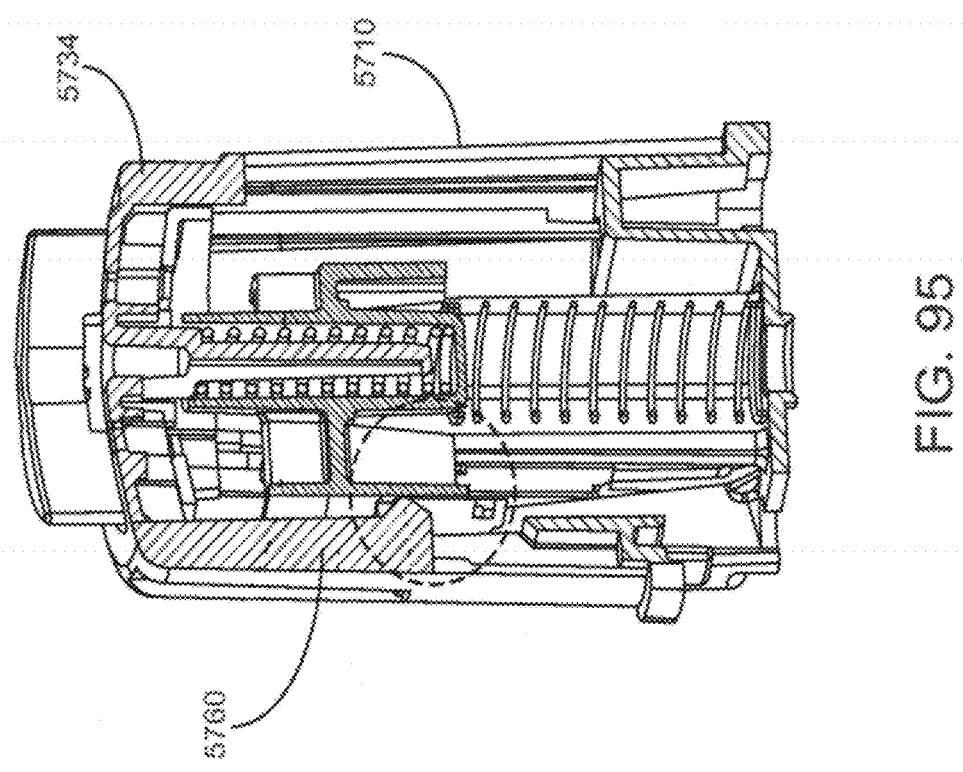

FIGS. 95 and 96 illustrate a resilient or elastomeric member which is disposed within the housing 5734 of the inserter 5710. For example, elastomeric member 5760 is manufactured from TPE and presses against the sensor and the resulting friction keeps the sensor in place. The TPE material creates a higher friction with respect to the sensor, and therefore requires less pressure to produce the sensor holding force. When the inserter 5710 is actuated, the frictional forces are directed upward keeping the sensor inside the sharp. When the carrier bottoms down, the contact with the friction rib ceases and the sensor releases to the mount. In some embodiments, the elastomeric member 5760, or rib, is produced with a second-shot injection molded process or press-fit into housing 5734.

Figure 97:
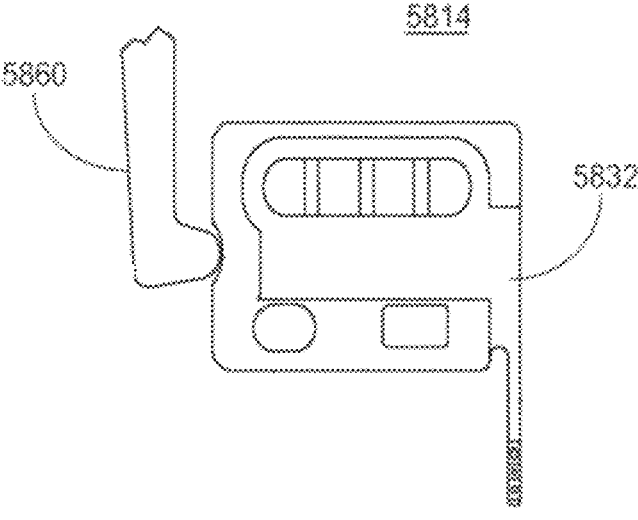
FIGS. 97-98 are views of a portion of an inserter assembly in accordance with the disclosed subject matter.
Figure 98:
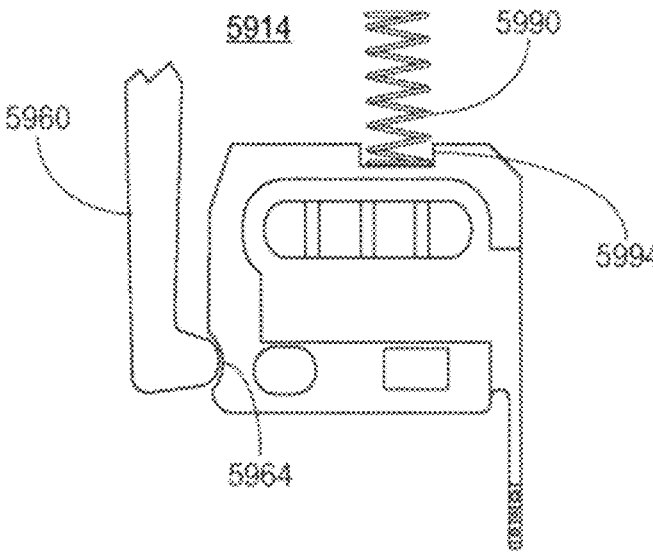

FIGS. 97 and 98 refer to retention members which provide a frictional force in a substantially coplanar direction to the surface of the sensor. FIG. 97 illustrates a retention member or cantilever 5860 which is biased against the side edge of the contact portion 5832 of the sensor 5814. In some embodiments, cantilever 5860 is provided on the carrier or sharp (not shown). FIG. 98 illustrates a sensor retention technique which includes a retention member, or cantilever 5960 which is biased against the sensor, as described in FIG. 97. Cantilever 5960 includes a laterally extending portion which is at least partially received in an optionally provided notch 5964 in sensor 5914. In addition, a second retention member, or retention spring 5990, is provided which is biased to engage the front surface of the sensor. In some embodiments, retention spring 5990 is partially received in cut-out 5994 (or a slot) to capture the sensor.

In some embodiments, an inserter assembly is provided which includes a reusable inserter apparatus. Repeated uses of the inserter include the use of a removable and exchangeable sensor and sharp which may be coupled to the inserter during deployment of the sensor, and in which the sharp is removed and discarded after deployment.

Figures 99, 100, 101:
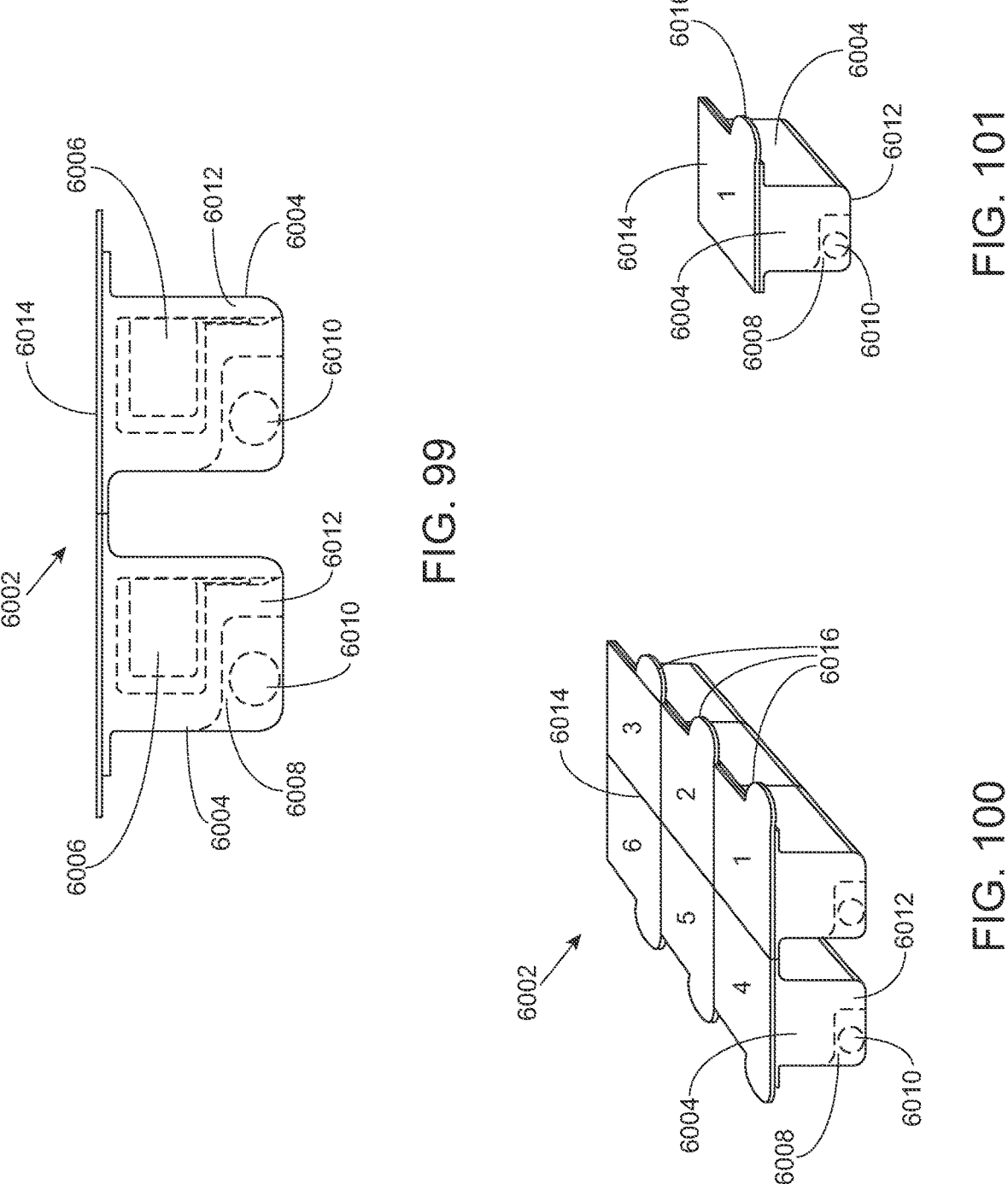
FIG. 99 is a cross-sectional view of a portion of an inserter assembly in accordance with the disclosed subject matter.
FIGS. 100-101 are perspective views of a portion of an inserter assembly in accordance with the disclosed subject matter.

FIGS. 99-101 illustrate a system of sharp/sensor packs 6002 which contain a plurality of sensor/sharp combinations 6006. As illustrated in FIGS. 99 and 101, a support is provided which includes a plurality of trays 6004 which are useful for containing the sensor/sharp configuration 6006, and well as a desiccant 6010 which is contained in a chamber 6008. A well 6012 is provided on one side of the tray 6004 to accommodate the sensor sharp for installation into a patient. A cover, such as a foil lid 6014 is applied to the top of the support to maintain the sterility of the sensor/sharp combination until installation in a subject. FIG. 100 is a perspective view which illustrates an exemplary configuration of pack 6002. The foil lid 6014 for each of trays 6004 may include a tab 6016 to facilitate removal of the lid from the tray 6004 (FIGS. 100, 101).

Figure 102:
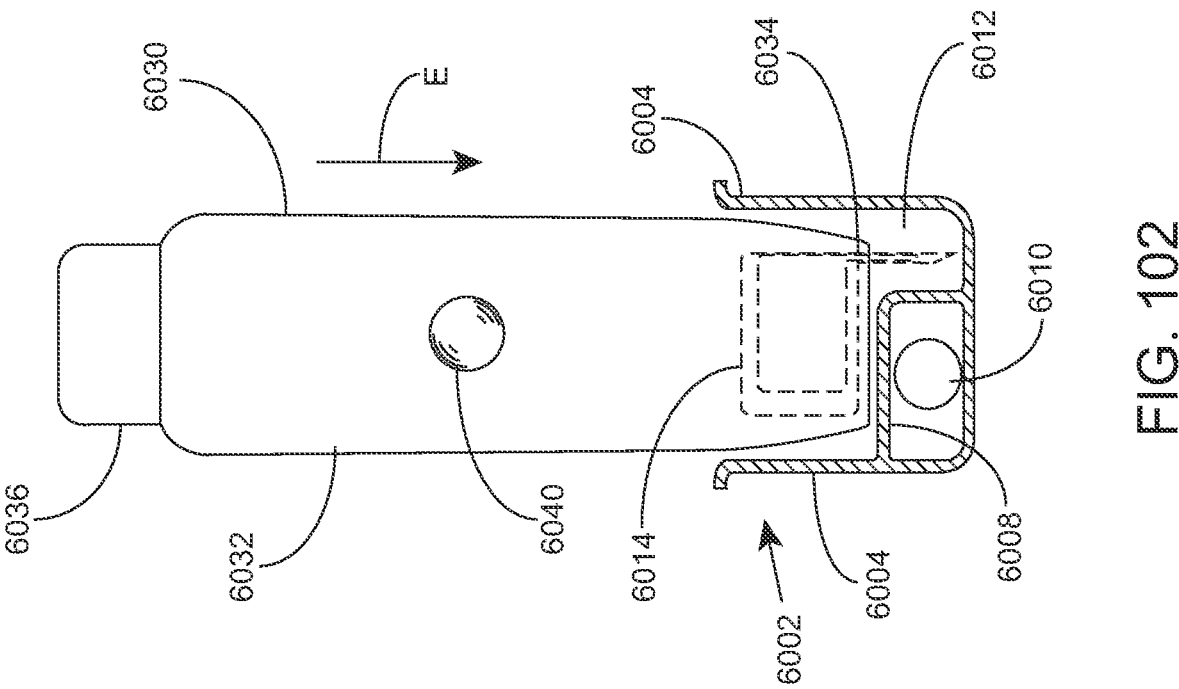

FIGS. 102-105 illustrate a plurality of reusable inserters which are useful in combination with the sharp/sensor packs 6002 described herein. FIG. 102 illustrates an inserter 6030 which includes a body portion 6032, a loading or cocking structure 6036, and an actuator button 6040 for deploying the sensor into the skin of the subject. The advancement structure of inserter 6030 may include a cocking structure which is pulled to arm, e.g., by withdrawing the cocking structure 6036 from the housing 6032; which is pushed to arm, e.g., by depressing the cocking structure 6036 into the housing 6032; or which is rotated to arm, e.g., by rotating the cocking structure 6036 in a rotational movement parallel to the longitudinal axis of the inserter 6030, or perpendicular to the longitudinal axis of the inserter 6030. The driving mechanism of inserter 6030 is substantially similar to the driving mechanisms as disclosed in U.S. Patent Publication 2008/0082166, now U.S. Pat. No. 8,167,934, 6,197,040, or 4,976,724, which are incorporated by reference in their entirety herein for all purposes.

To insert the sharp/sensor combination into the inserter 6030, the foil lid is removed from sharp/sensor pack 6002. The distal end portion 6034 of the inserter 6030 is positioned within the walls 6004 of the tray 6002, as indicated in the direction of arrow E. The distal end portion 6034 comes to rest on the upper surface of desiccant chamber 6008, such that the insertion sharp remains exposed.

Figure 103:
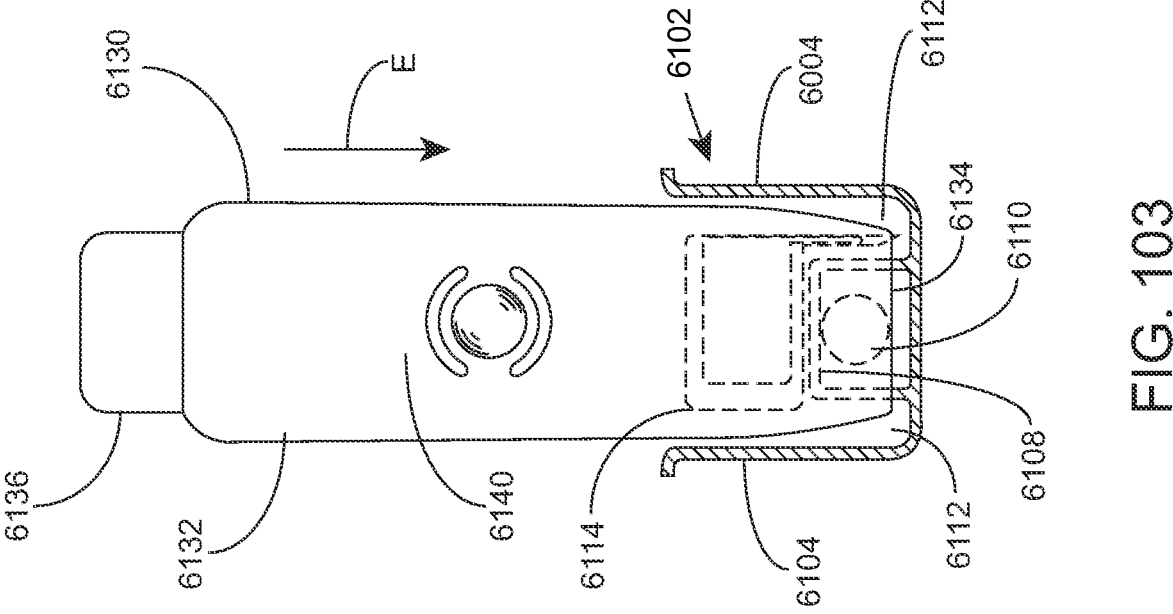
FIGS. 102-105 are side views of various inserter assemblies in accordance with the disclosed subject matter.

FIG. 103 illustrates an inserter 6130 substantially identical to the inserter 6030 described herein. Inserter 6130 is used in connection with sharp/sensor trays 6102. Trays 6102 include a desiccant chamber 6108 which is located in the center portion of the tray 6102. Accordingly, a channel 6112 surrounds the periphery of desiccant chamber 6108. When the inserter 6130 is applied to the sharp/sensor tray 6102, the distal end portion 6134 can be positioned within the channel 6112. As illustrated in FIG. 103, this configuration allows the sensor and sharp to be completely housed within the inserter 6130.

Figure 104:
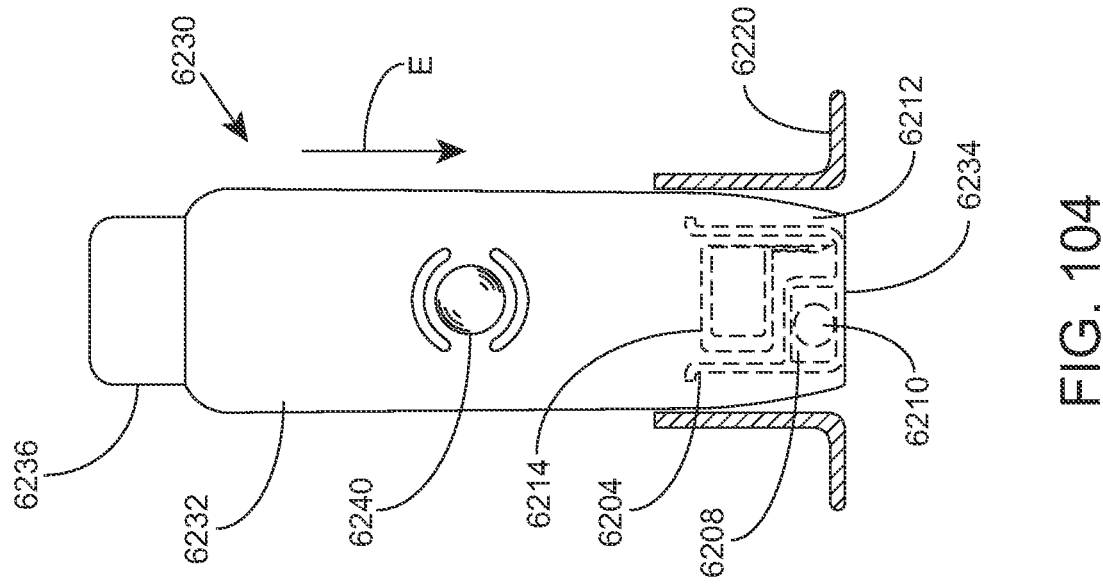

FIG. 104 illustrates an inserter 6230 substantially identical to the inserters 6030 and 6130 described herein, with the differences noted herein and illustrated in the figures. Inserter 6230 may be used in connection with sharp/sensor trays 6204. The tray 6204 and inserter 6230 are sized and configured such that tray 6204 is capable of being positioned entirely within the distal end portion 6234 of inserter 6230. One or more support struts 6220 are provided adjacent the distal end portion 6234 to stabilize the inserter with respect to any surface on which the inserter 6230 and trays 6204 are placed for the insertion step. Support struts 6220 may also secure inserter 6230 to an adhesive mount (not shown) during insertion.

Figure 105:
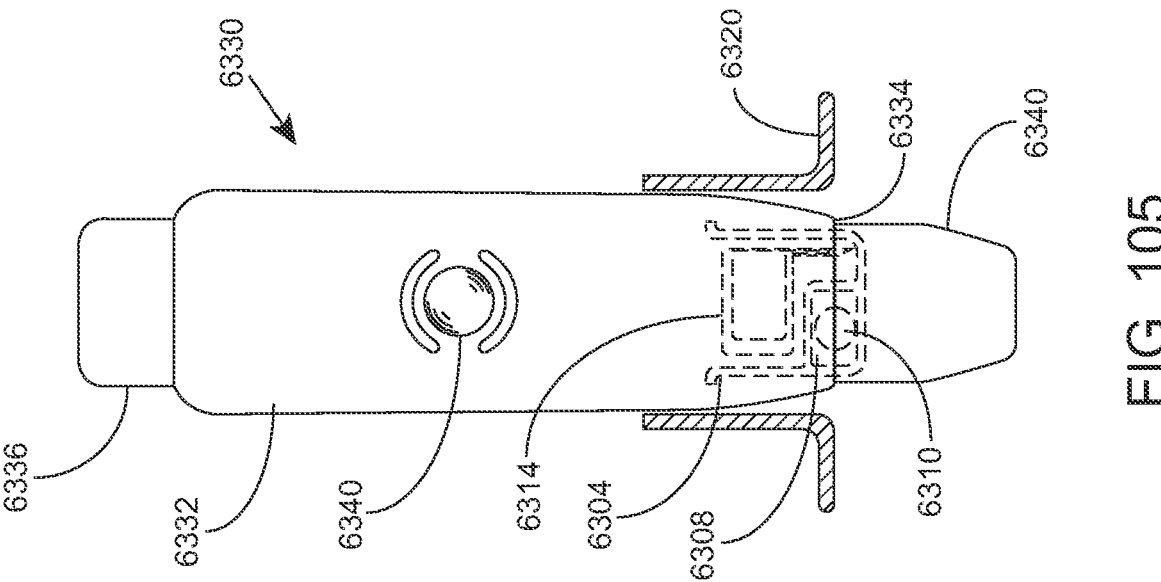

FIG. 105 illustrates an inserter 6330 which is substantially identical to the inserters 6030, 6130, and 6230 described herein, with the differences noted herein and illustrated in the figures. Inserter 6330 may be used in connection with sharp/sensor tray 6304. In some embodiment, tray 6304 includes a distally projecting handle portion 6340 which may be grasped by the user to facilitate insertion of the sharp/sensor into the inserter.

Figure 106:
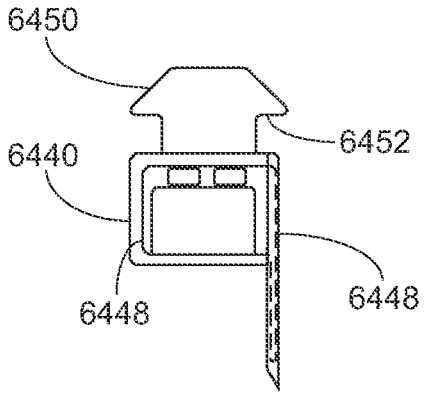
Figure 107:
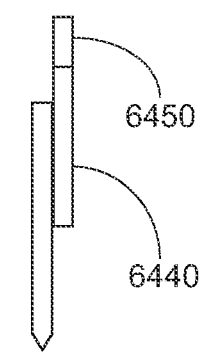
Figure 108:
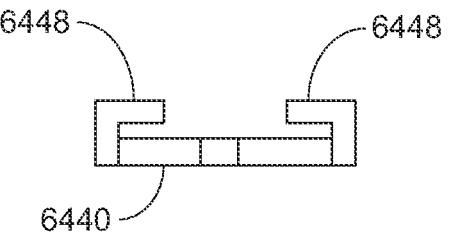
Figure 109:
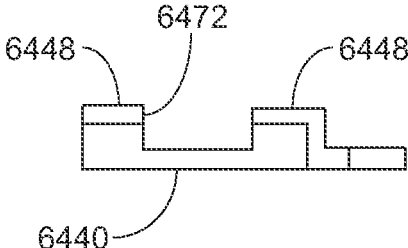

FIGS. 106-107 illustrate an exemplary sharp/sensor combination for use with inserters 6030, 6130, 6230, and 6330 described herein. Sharp 6440 includes side rails 6448 for sliding reception of a sensor therein. A locking tab 6450 is also provided on the proximal portion of the sharp and includes cut-out portion 6452 for interlocking with the carrier of the inserter 6030 (or 6130, 6230, or 6330). As illustrated in FIGS. 108-112 carrier 6466 includes reception structure for mating reception with the sharp 6440. For example, carrier 6466 may include a pair of walls 6480 providing a channel 6478 in which said sharp 6440 may be positioned. Walls 6480 are provided with cutout portions 6482 for reception of undercut portion 6452 in locking tab 6450. A pair of securement members 6484 are movably mounted on the carrier 6466. For example, members 6484 are biased via a spring 6486 towards a center portion of the carrier 6466. As illustrated in FIG. 111, securement members 6484 may be moved outwardly against the spring bias to allow for the insertion of the locking tab 6450 into the cutout portion 6482 of the carrier. Securement member 6484 is subsequently released and returns to a position to engage the undercut portion 6452 to prevent accidental removal of the sharp and sensor from the inserter (FIG. 112). It is understood that coupling of the sharp and carrier may be provided by alternative techniques such as frictional fit, snap-fit, bayonet mounts, magnetic coupling, etc.

Figure 113:
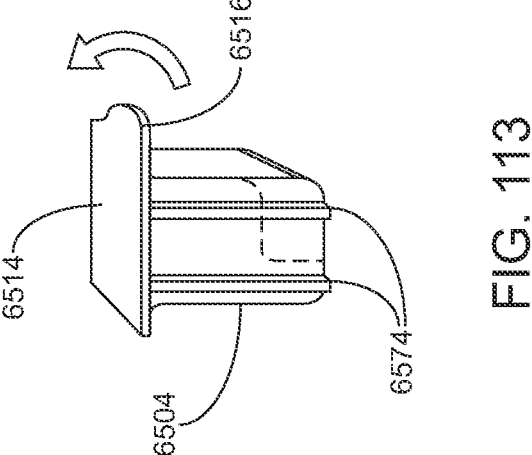
FIG. 113 is a perspective view of a portion of an inserter assembly in accordance with the disclosed subject matter.

FIGS. 113-117 illustrate a further embodiment of the subject disclosure that is reusable, and useful with the sharp/sensor packs discussed herein. FIG. 113 illustrates a sensor pack 6504 which is similar to the sensor packs described herein. Sharp/sensor pack 6504 also includes one or more reinforcing ribs 6574 to prevent accidental deformation of the pack 6504 when the sensor is being inserted into the inserter.

Figure 114:
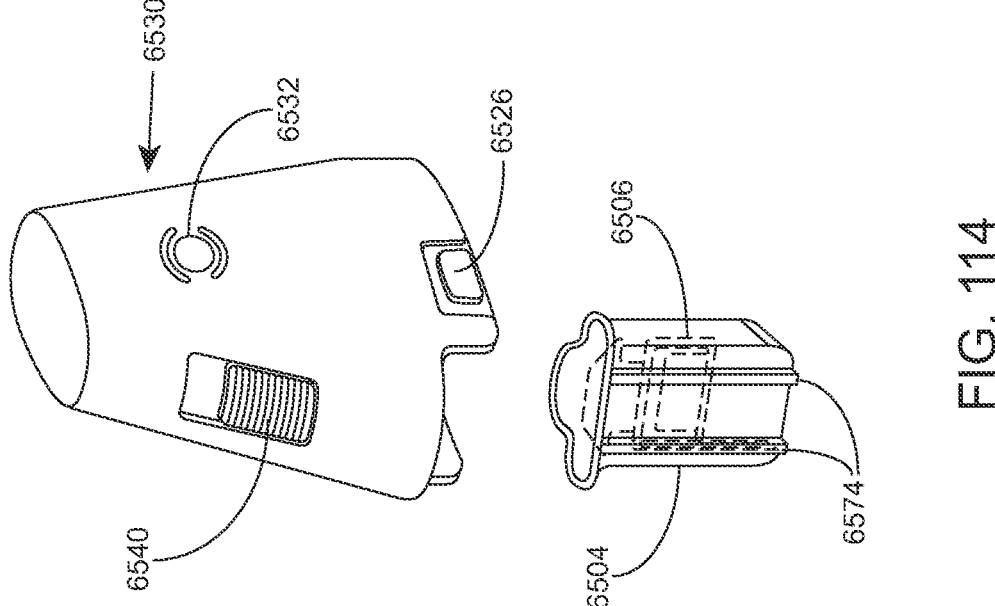
FIGS. 114-117 are perspective views illustrating the operation of an inserter assembly in accordance with the disclosed subject matter.
Figure 115:
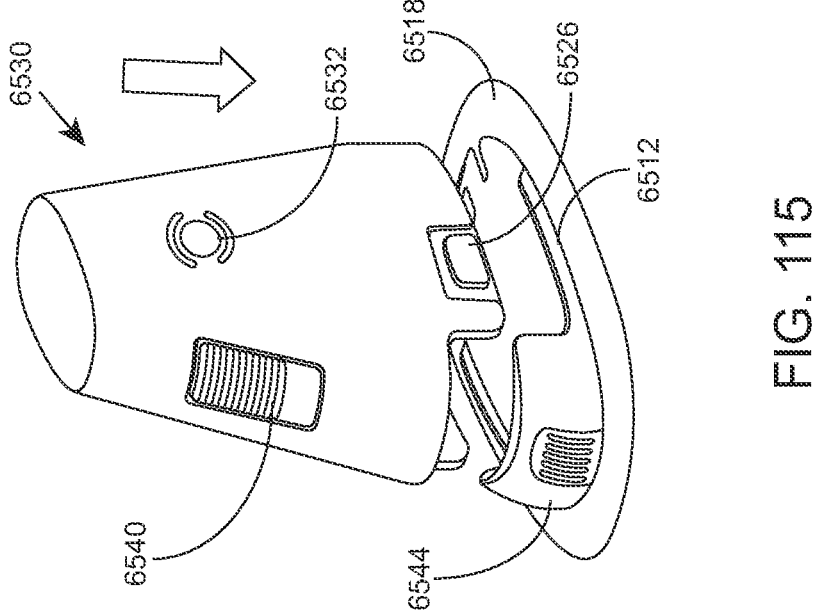
Figure 117:
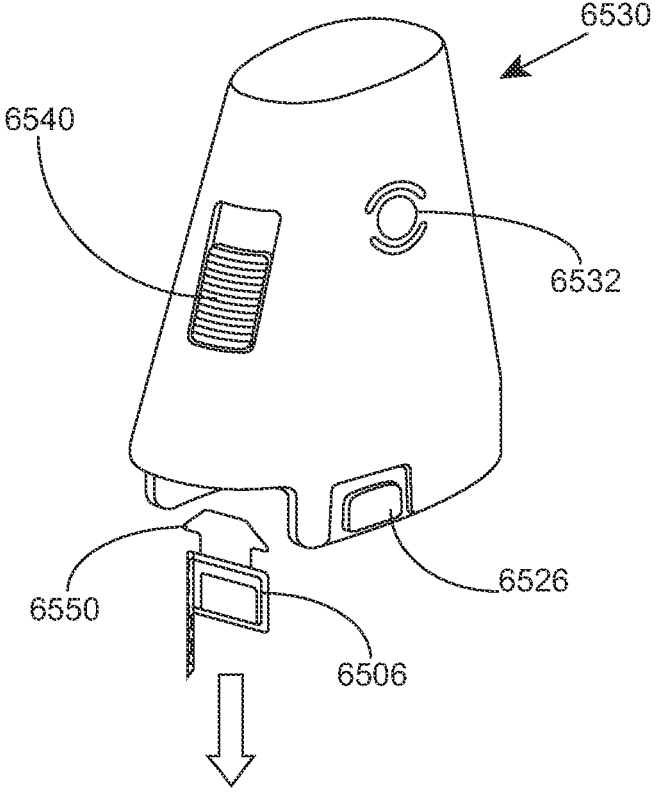

As illustrated in FIG. 114, inserter 6530 is provided which is substantially similar to inserters 6030, 6130, 6230, and 6330 described herein, with the differences noted herein or illustrated in the figures. Inserter 6530 includes a carrier (not shown) for coupling with a sharp/sensor combination. As illustrated in the figure, inserter 6530 is lowered onto sharp/sensor pack 6504 in order to couple the sharp 6506 with the carrier. As illustrated in FIG. 115, inserter 6530 which now contains the sharp/sensor 6506 is positioned over the mount 6512. Mount 6512 may include an adhesive for securement to the skin of the subject. Inserter 6530 includes a locking structure 6526 which allows for temporary engagement of the inserter 6530 with the mount 6512.

Figure 116:
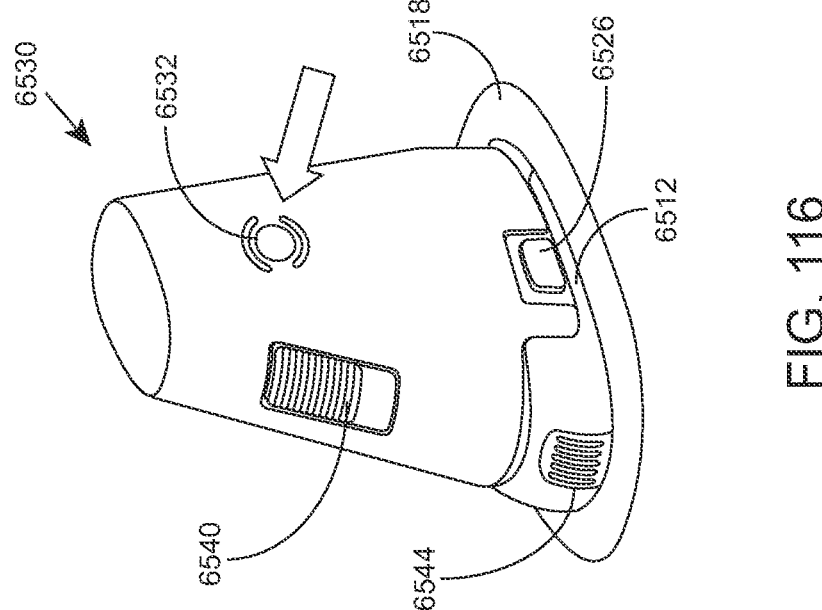

As illustrated in FIG. 116, the sensor is deployed by depressing actuation button 6532 on the inserter 6530 to advance the sensor into the skin by use of an internal drive mechanism, such as, e.g., a spring. It is understood that the above-described process may alternatively be carried out by using an inserter which allows the user to provide a manual distal force for deployment of the sensor.

Following installation of the sensor, inserter 6530 is decoupled from the mount, e.g., by depressing locking buttons 6526 on inserter 6530. Once the inserter 6530 is separated from the mount, the user may remove and discard the sharp. In some embodiments, inserter 6530 includes a sliding lever 6540 which allows for removal of the sharp. It is understood that disengagement of the sharp from carrier may be executed in one of several ways, e.g., sliding switch allows securement member (discussed herein) to slide outwardly and allow disengagement of the contact portions 6483 of the securement members 6484 from the undercut portions 6452 of locking tab 6450.

Figure 118:
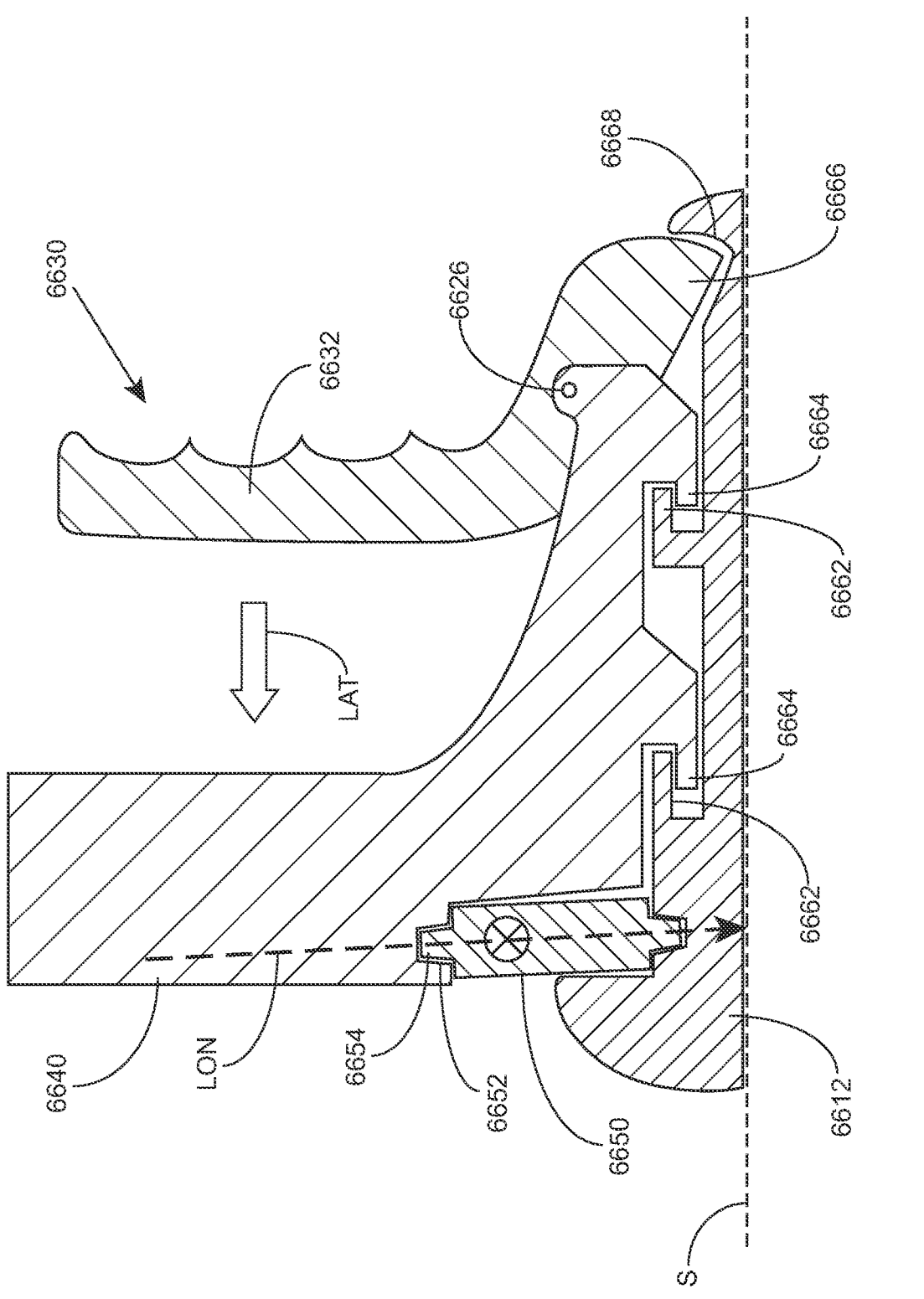
FIG. 118 is a side view of an inserter assembly in accordance with the disclosed subject matter.

FIG. 118 illustrates an inserter 6630 and engagement structure for mounting on mount 6612. Inserter 6630 includes a body portion 6640 which is configured to advance a sharp/sensor cartridge into the skin S of a subject along longitudinal axis LON. The longitudinal axis LON may be substantially perpendicular to the skin surface. In some embodiments, axis LON forms an acute angle with the skin surface. Mount 6612 and inserter 6630 are each provided with complementary locking structures 6662 on the mount 6612 and 6664 on the inserter. Inserter is advanced laterally (direction LAT) over mount 6612. Inserter 6630 may be locked in place by pivoting locking structure 6632 about pivot 6626. Following such pivoting action, the engagement portion 6666 of locking structure 6632 is received in recess 6668 in mount 6612. Securement of the inserter to the mount is further provided by insertion of the sharp/sensor cartridge 6650 between the inserter 6630 and the mount 6612. For example, cartridge 6650 includes raised tabs 6654 which are slidable within complementary grooves 6652 provided on the inserter 6630 and mount 6612. Insertion of the cartridge is carried out in a direction perpendicular to the direction in which the inserter is attached to the mount, e.g., a direction perpendicular to the plane of the page.

Figure 119:
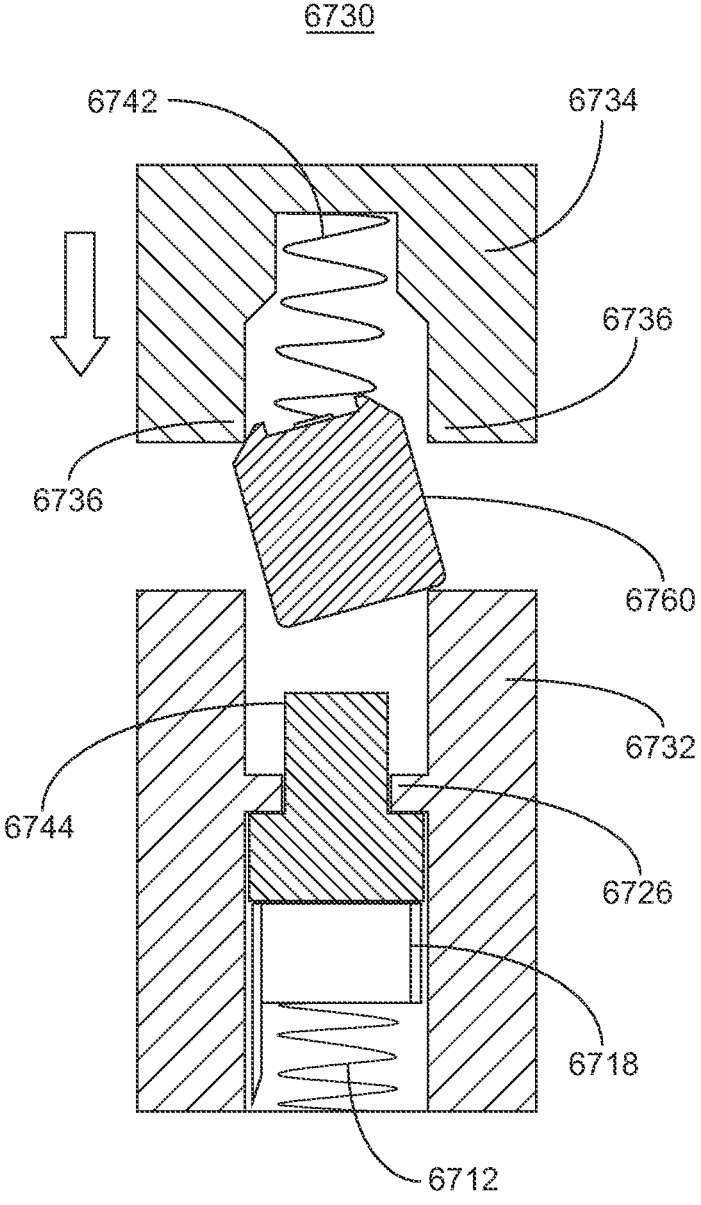
FIGS. 119-121 are cross-sectional views of an inserter assembly in accordance with the disclosed subject matter.
Figure 120:
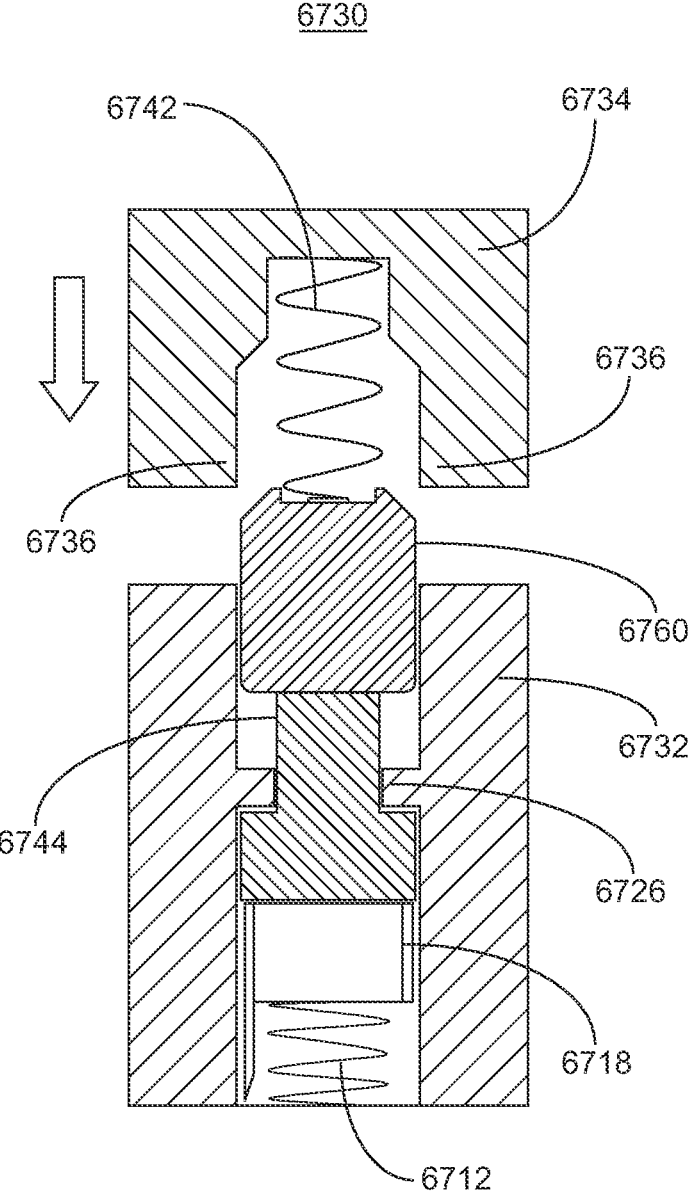
Figure 121:
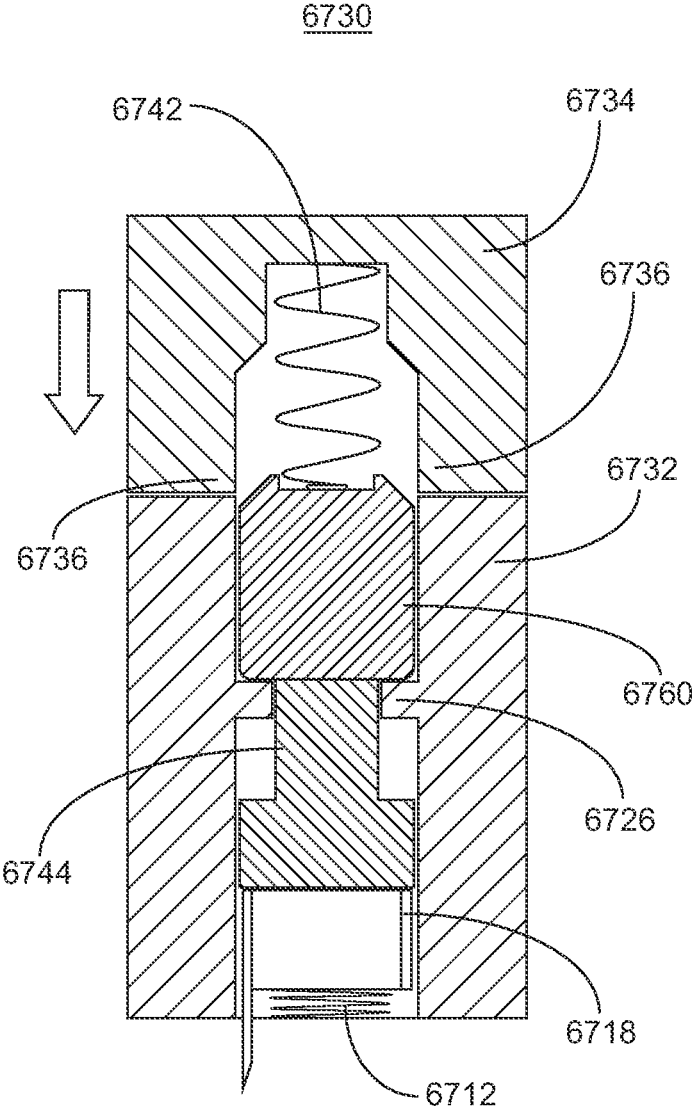

FIGS. 119-121 illustrate another embodiment of an inserter in accordance with the disclosed subject matter. Inserter 6730 is useful for advancing a medical device, such as an analyte sensor, into the skin of a subject. Inserter 6730 includes a hammer member 6760 which accumulates advancement energy to provide a more rapid and powerful advancement stroke. As illustrated in FIG. 119, hammer member 6760 is initially positioned somewhat askew with respect to the longitudinal axis of the device. As the alignment trigger 6734 is advanced distally, alignment sleeves 6736 gradually pivot the hammer member 6760 into a longitudinal configuration. As the hammer member 6760 is being pivoted into position, the advancement spring continues to be compressed. With reference to FIG. 120, the hammer member 6760 is pivoted into alignment with the central bore of the inserter 6730, e.g., along the longitudinal axis represented by the arrow. Consequently, the tension of advancement spring 6742 is immediately released, which permits rapid distal movement of the hammer member 6760. Hammer member 6760 contacts carrier 6744, which in turn contacts sharp/sensor combination 6718 to provide distal movement.

As illustrated in FIG. 121, a ledge or lateral member 6726 is provided with the internal bore of the inserter. As the hammer member 6760 advances distally, the distal surface of the hammer member contacts the ledge 6726. Interengagement of the hammer member 6760 and the ledge 6726 inhibits further distal travel of the hammer member 6760.

FIG. 122 illustrates an exemplary embodiment of a simplified unit, or cartridge 6800, which holds certain components for sterility and subsequent interaction with the subject. In some embodiments, the components include the sharp 6840, the housing 6860, the sensor 6814. The cartridge 6800 may be used in connection with any of the inserters 6030, 6130, 6230, 6330, 6530 and/or 6730 described herein. In some embodiments, the cartridge includes a housing and a lid which contain the sharp and sensor therein. In some embodiments, a resilient member or other cantilever structure is used to maintain the alignment of the sharp and sensor within the cartridge. Interaction of the cartridge with the inserter advances the sensor and sharp such that the sensor is installed at the subject.

Figure 124:
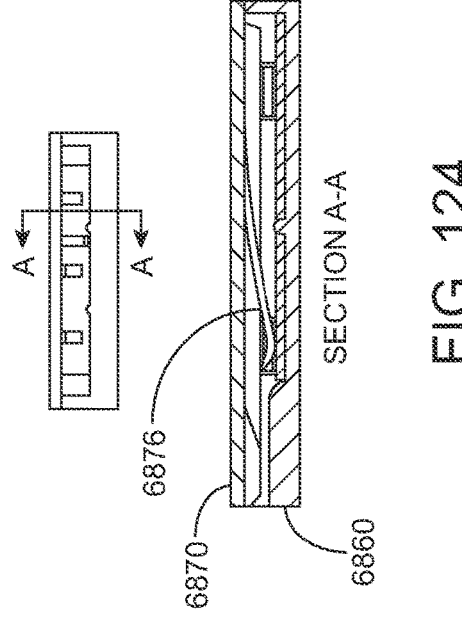
FIG. 124 is a cross-sectional view of the cartridge of FIG. 122 in a neutral state in accordance with the disclosed subject matter.
Figure 123:
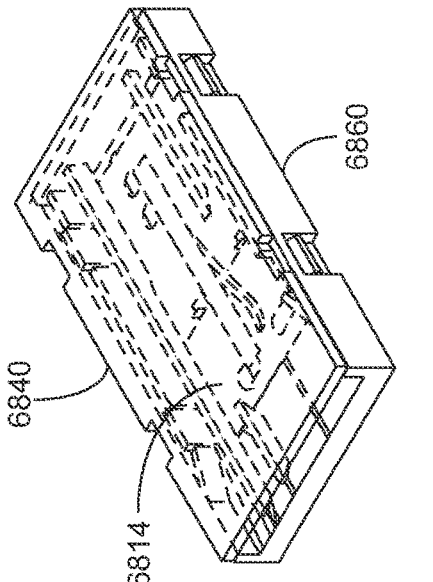
FIG. 123 is a perspective view of the cartridge of FIG. 122 in a first stage of deployment in accordance with the disclosed subject matter.

As illustrated in FIGS. 123-124, the sharp 6840 and sensor 6814 may sit in a recessed portion of the disposable cartridge 6800. A spring finger or cantilever 6876 on the housing lid maintains a load on the sharp 6840 and sensor 6814 to keep it depressed in the cavity. Attachment for a lid to the base of the cartridge housing 6860 is not shown in the figure above, but methods such as snaps, heat stake, or ultrasonic welding may be used to join the two housings in assembly. The sensor 6814 is contained within the sharp 6840, laterally by the two rounded ends 6848 of the sharp, and in the orthogonal lateral direction (in relation to the views shown above), by two bent tabs 6849 on the sharp 6840 and the cartridge housing base cavity. The sharp is held in its lateral position by not only the cavity, but also by the raised pyramid feature 6878 shown on the housing base 6870. In the figure above, the locating pyramid sits in the opening 6882 created from the bent tab in the sharp. The engagement features to locate/attach/engage the cartridge to the inserter portion of the device are not shown in the figures above, but may include such features as illustrated in FIGS. 106-112 above.

Figure 126:
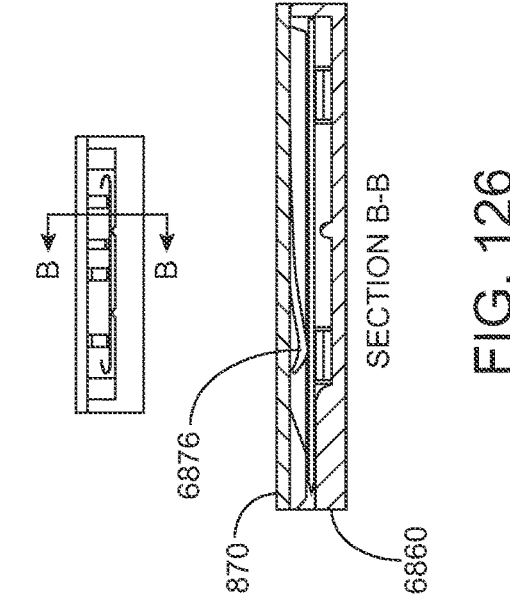
FIG. 126 is a cross-sectional view of the cartridge of FIG. 122 in a first stage of deployment in accordance with the disclosed subject matter.
Figure 125:
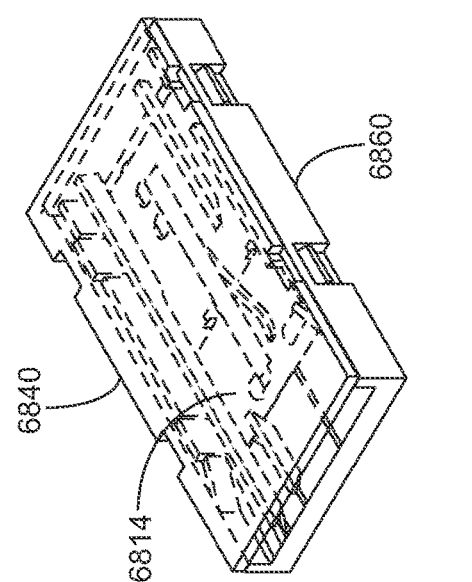
FIG. 125 is a perspective view of the cartridge of FIG. 122 in a neutral state in accordance with the disclosed subject matter.

As illustrated in FIGS. 125 and 126, when the cartridge 6800 is loaded onto the reusable inserter part of the device, the sharp is raised out of its cavity by stationary elements built onto the inserter (not shown). Features from the reusable portion of the inserter enter through the two shorter slots shown FIG. 122. These features will remain stationary throughout the sensor delivery action of the inserter device.

In the longer middle slot 6866, a stepped feature from the inserter, mates with the opening on the sharp (shown as two holes 6864 in the figure above). The stepped portion of the feature provides a force on the back portion of the sharp to keep it raised against the force of the sprung cantilever 6876 on the housing. This feature of the inserter will move in relation to the cartridge and provide the drive and retraction movement for the sharp through insertion and delivery of the sensor. In some embodiments, the force is transmitted through driving pins which are part of the movable portion of the inserter device. The driving pins protrude through holes 6864. In case of minor misalignment of the driving pins (not shown), ribs on the cartridge housing lid will constrain the sharp from tilting up.

Once the sharp and sensor are raised from the cavity portion of the cartridge, they are no longer constrained by the recessed cavity portion of the housing base and the pyramid feature maintaining the sharp position. The sharp is held in its raised position by the stationary and stepped drive feature of the inserter, balanced with the force of the cantilever finger on the lid housing. The sensor is kept in place by being pinched against the cantilever finger on the housing lid. The sharp is constrained in its retracted position by the mated drive feature of the inserter.

Figures 127, 128, 129, 130:
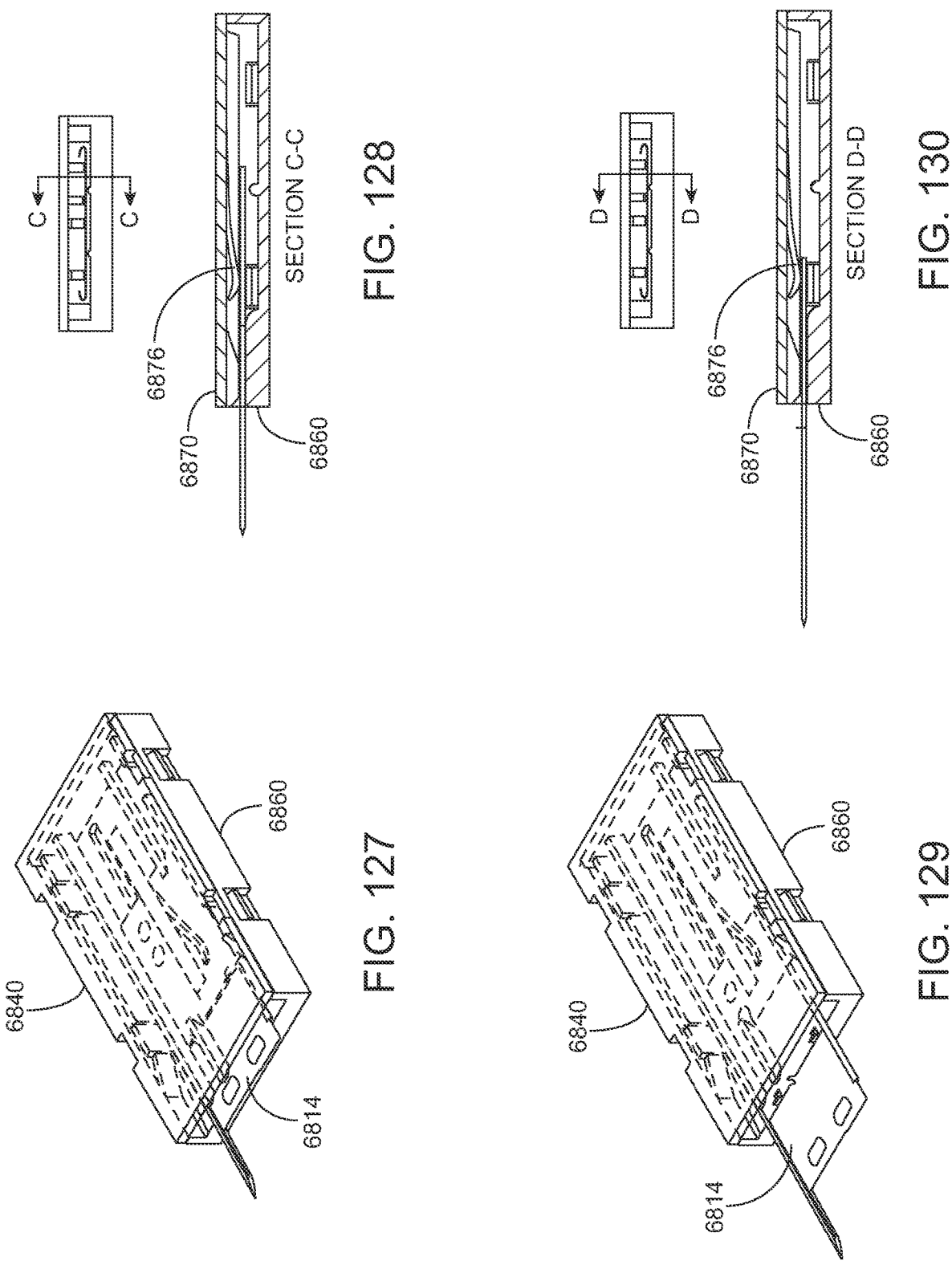
FIG. 127 is a perspective view of the cartridge of FIG. 122 in a second stage of deployment in accordance with the disclosed subject matter.
FIG. 128 is a cross-sectional view of the cartridge of FIG. 122 in a second stage of deployment in accordance with the disclosed subject matter.
FIG. 129 is a perspective view of the cartridge of FIG. 122 in a third stage of deployment in accordance with the disclosed subject matter.
FIG. 130 is a cross-sectional view of the cartridge of FIG. 122 in a third stage of deployment in accordance with the disclosed subject matter.

As the inserter is actuated, the mated inserter drive feature drives the sharp downward as it moves through the longer slot shown in the figure above (see FIGS. 127-129). The driven sharp slides along the stationary ribs of the inserter, ribbed features built into the cartridge housing, and the housing lid cantilever finger. The friction force of the cantilever keeps the sensor up against the 'drive block' and bends in the sharp sheet metal to assure the tail is not exposed from the sharp channel during insertion. In some embodiments, the 'drive block' features are longitudinal constraints either built into the sharp or the carrier which constrain the sensor from proximal movement with respect to the sharp. In another embodiment, the drive block features are protrusions on the carrier or bends on the sharp which push the sensor as the sharp is propelled distally.

The sensor is kept from popping over the drive block features by the stationary ribs built into the housing lid. As the cantilever slides over the top edge of the sensor, the retention force is relieved from the sensor, and it can be captured onto the mount portion of the device with relatively little force. Alternately, if geometry permits, and the finger is positioned appropriately, the pinching of the cantilever on the sharp may provide enough resistance on the return motion of the sharp to keep the sensor in its inserted position even without a capture device on the mount. The inserter drive feature then retracts the sharp, leaving the sensor in place on the mount portion (that is attached to the skin) of the device.

The cartridge can be removed from the inserter. As the cartridge is removed, the force from the housing lid cantilever presses the sharp back into the recess on the cartridge base housing. The base housing is removed and can be discarded.

Figure 131:
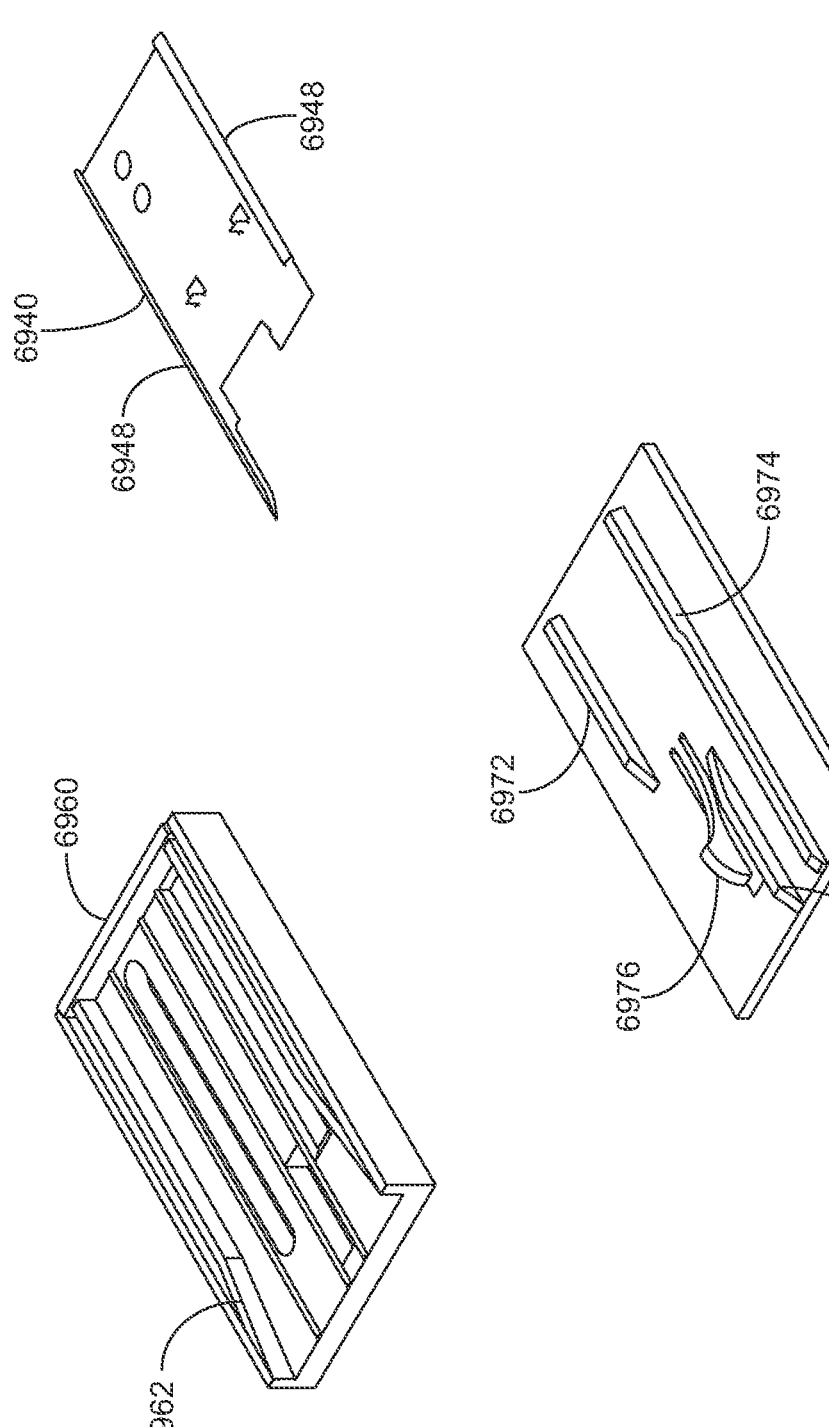
FIG. 131 is a perspective view with parts separated of another embodiment of a component of an inserter in accordance with the disclosed subject matter.

Another embodiment of the cartridge is illustrated in FIGS. 131-137. As illustrated in FIG. 131, the sharp 6940 and sensor 6914 in this embodiment abuts ribs 6972 and 6974 and on insertion plane to which the sharp 6940 will be driven and retracted by the inserter into the skin. The sharp and sensor are held in place by a central cantilever feature 6976 built onto the cartridge lid housing. This cantilever 6976 has geometry such that a vertical portion of the end of the cantilever is butted against the sharp 6940 and sensor 6914.

Figures 132, 133, 134, 135:
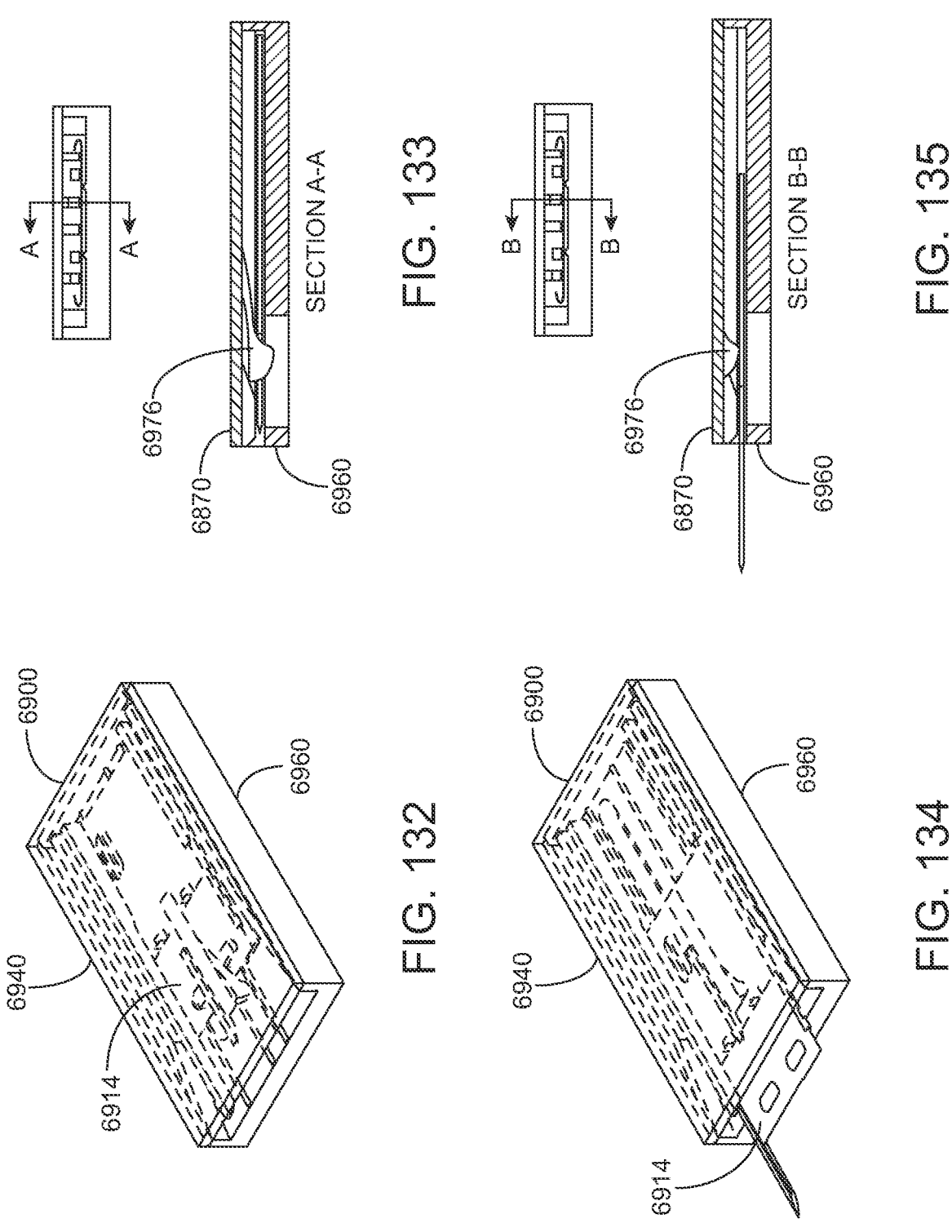
FIG. 132 is a perspective view of the cartridge of FIG. 131 in a neutral state in accordance with the disclosed subject matter.
FIG. 133 is a cross-sectional view of the cartridge of FIG. 131 in a neutral state in accordance with the disclosed subject matter.
FIG. 134 is a perspective view of the cartridge of FIG. 131 in a second stage of deployment in accordance with the disclosed subject matter.
FIG. 135 is a cross-sectional view of the cartridge of FIG. 131 in a second stage of deployment in accordance with the disclosed subject matter.

As illustrated in FIGS. 132 and 133, the cartridge 6900 is loaded onto the inserter, in which a stationary feature on the inserter (not shown) raises the cartridge cantilever so that the ramped portion of the cantilever end feature is now in line with the insertion plane of the sharp. Also, a driving element of the inserter (not shown) fits through the slot opening on the sharp. In the embodiment described herein, a step is not required on the driving element on this design.

As the sharp is driven downward (see, FIGS. 134-135), the cantilever arm 6976 is pushed up, keeping the sensor in position against the sharp 6940. Stationary ribs on the housing lid assure that the sharp 6940 maintains its insertion plane during insertion, and also assures that the pinching force of the cantilever does not cause the sensor to hop the drive block elements integrated into the sharp. The stationary ribs keep the sensor flat against the sharp through the insertion motion.

Figure 136:
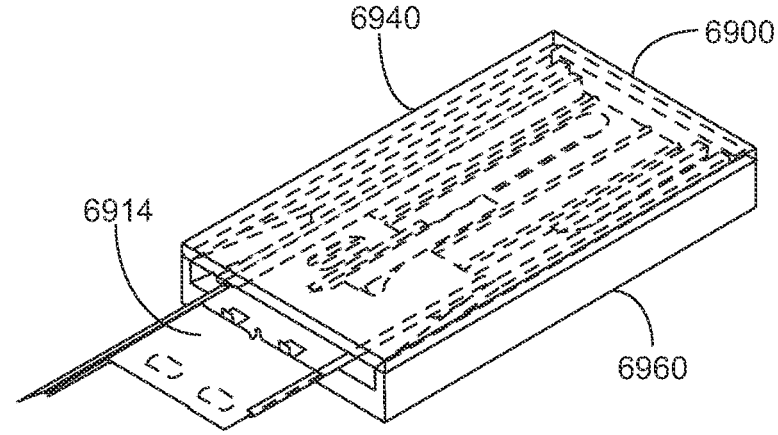
FIG. 136 is a perspective view of the cartridge of FIG. 131 in a third stage of deployment in accordance with the disclosed subject matter.
Figure 137:
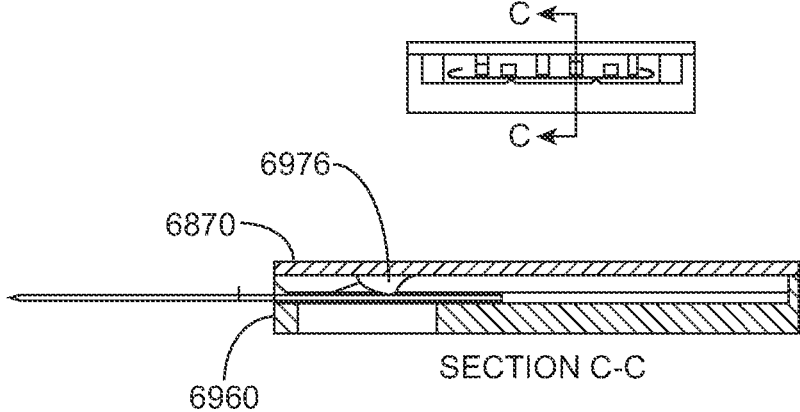
FIG. 137 is a cross-sectional view of the cartridge of FIG. 131 in a third stage of deployment in accordance with the disclosed subject matter.

As illustrated in FIGS. 136-137, the sensor 6914 is captured at the bottom of its motion on the mount, as discussed hereinabove. The drive elements on the inserter retract the sharp 6940 back to its starting position. The cantilever arm 6976 returns to its original unbiased configuration. The cartridge 6900 is removed from the inserter and can be discarded.

It is understood that the subject matter described herein is not limited to particular embodiments described, as such may, of course, vary. It is also understood that the terminology used herein is for the purpose of describing particular embodiments only, and is not intended to be limiting, since the scope of the present subject matter is limited only by the appended claims.

The invention claimed is:

1. An inserter assembly for partially inserting a glucose sensor into a subject, the inserter assembly comprising:
   an inserter housing;
   a carrier coupled with a sharp, the sharp configured to be inserted into a skin of the subject;
   the glucose sensor releasably coupled with the sharp, the glucose sensor comprising:
      a distal portion configured to be positioned under the skin of the subject and in contact with an interstitial fluid of the subject, and
      a proximal portion configured to be positioned above the skin and coupled with sensor electronics;
   a retention member disposed within the inserter housing, wherein the retention member is a separate structure from the glucose sensor, the carrier, and the sharp, and wherein the retention member is not integral with any of the glucose sensor, the carrier, or the sharp;
   a drive spring configured to advance the carrier, the sharp, and the glucose sensor from a proximal position to a distal position; and
   a retraction spring configured to retract the carrier and the sharp from the distal position to a retracted position entirely within the inserter housing,
   wherein the retention member is configured to retain a part of the glucose sensor within the sharp while the carrier, the sharp, and the glucose sensor are in the proximal position by providing a force in a direction substantially perpendicular to a surface of the glucose sensor, and
   wherein the glucose sensor is configured to have a predetermined monitoring time period of ten days.

2. The inserter assembly of claim 1, wherein the retention member is an elastomeric member.

3. The inserter assembly of claim 1, wherein the force provided by the retention member is a pressing force.

4. The inserter assembly of claim 1, wherein the retention member is further configured to retain the part of the glucose sensor within the sharp during storage of the inserter assembly.

5. The inserter assembly of claim 1, wherein the retention member is further configured to retain the part of the glucose sensor within the sharp during advancement of the glucose sensor and the sharp from the proximal position to the distal position.

6. The inserter assembly of claim 1, wherein the retention member is further configured such that the retention member does not provide the force to the glucose sensor after the carrier, the sharp, and the glucose sensor reach the distal position.

7. The inserter assembly of claim 1, wherein the retention member is further configured such that the retention member does not provide the force to the glucose sensor after the sharp releases the glucose sensor.

8. The inserter assembly of claim 1, further comprising an actuator button configured to, upon depression, cause the drive spring to advance the carrier, the sharp, and the glucose sensor from the proximal position to the distal position.

9. The inserter assembly of claim 1, further comprising an adhesive layer configured for placement on the skin of the subject, wherein the adhesive layer comprises an aperture, and wherein the sharp and the glucose sensor are configured to extend through the aperture when the carrier, the sharp, and the glucose sensor are in the distal position.

10. An inserter assembly for partially inserting a glucose sensor into a subject, the inserter assembly comprising:
   an inserter housing;
   an actuator button;
   a carrier coupled with a sharp, the sharp configured to be inserted into a skin of the subject;
   the glucose sensor releasably coupled with the sharp, the glucose sensor comprising:
      a distal portion configured to be positioned under the skin of the subject and in contact with an interstitial fluid of the subject, and
      a proximal portion configured to be positioned above the skin and coupled with sensor electronics;
   an elastomeric retention member disposed within the inserter housing, wherein the elastomeric retention member is a separate structure from the glucose sensor, the carrier, and the sharp, and wherein the elastomeric retention member is not integral with any of the glucose sensor, the carrier, or the sharp;
   a drive spring configured to, upon depression of the actuator button, advance the carrier, the sharp, and the glucose sensor from a proximal position to a distal position; and
   a retraction spring configured to retract the carrier and the sharp from the distal position to a retracted position entirely within the inserter housing,
   wherein the elastomeric retention member is configured to retain a part of the glucose sensor within the sharp while the carrier, the sharp, and the glucose sensor are in the proximal position, and
   wherein the glucose sensor is configured to have a predetermined monitoring time period of fourteen days.

11. The inserter assembly of claim 10, wherein the elastomeric retention member is further configured to provide a force in a direction substantially perpendicular to a surface of the glucose sensor while the carrier, the sharp, and the glucose sensor are in the proximal position.

12. The inserter assembly of claim 11, wherein the elastomeric retention member is further configured such that the elastomeric retention member does not provide the force to the glucose sensor after the carrier, the sharp, and the glucose sensor reach the distal position.

13. The inserter assembly of claim 11, wherein the elastomeric retention member is further configured such that the elastomeric retention member does not provide the force to the glucose sensor after the sharp releases the glucose sensor.

14. The inserter assembly of claim 11, wherein the force is a pressing force.

15. The inserter assembly of claim 10, wherein the elastomeric retention member is further configured to retain the part of the glucose sensor within the sharp during storage of the inserter assembly.

16. The inserter assembly of claim 10, wherein the elastomeric retention member is further configured to retain the part of the glucose sensor within the sharp during advancement of the glucose sensor and the sharp from the proximal position to the distal position.

\* \* \* \* \*